United States Patent
Ji et al.

(10) Patent No.: US 11,639,492 B2
(45) Date of Patent: May 2, 2023

(54) METHODS FOR FERMENTATIVE PRODUCTION OF MASSOIA LACTONE

(71) Applicant: TEMASEK LIFE SCIENCES LABORATORY LIMITED, Singapore (SG)

(72) Inventors: Lianghui Ji, Singapore (SG); Si Te Ngoh, Singapore (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 421 days.

(21) Appl. No.: 16/712,672

(22) Filed: Dec. 12, 2019

(65) Prior Publication Data

US 2020/0157488 A1    May 21, 2020

Related U.S. Application Data

(62) Division of application No. 15/750,584, filed as application No. PCT/SG2016/050395 on Aug. 16, 2016, now abandoned.

(60) Provisional application No. 62/205,996, filed on Aug. 17, 2015.

(51) Int. Cl.
  *C12N 1/14* (2006.01)
  *C12P 17/06* (2006.01)
  *C12R 1/645* (2006.01)

(52) U.S. Cl.
  CPC .............. *C12N 1/14* (2013.01); *C12N 1/145* (2021.05); *C12P 17/06* (2013.01); *C12N 2500/22* (2013.01); *C12N 2500/24* (2013.01); *C12N 2500/42* (2013.01); *C12R 2001/645* (2021.05)

(58) Field of Classification Search
  CPC ................................ C12P 17/06; C12N 1/145
  See application file for complete search history.

(56) References Cited

U.S. PATENT DOCUMENTS

2010/0267012 A1   10/2010   Bergeron et al.

FOREIGN PATENT DOCUMENTS

| CN | 102653531 | * | 8/2014 |
|---|---|---|---|
| WO | 2007025181 A2 | | 3/2007 |
| WO | 2015128552 A1 | | 9/2015 |

OTHER PUBLICATIONS

International Search Report and Written Opinion issued in Application No. PCT/SG2016/050395 dated Nov. 10, 2016, 18 pages.
Cene Gostinčar et al. "Genome sequencing of four Aureobasidium pullulans varieties: biotechnological potential, stress tolerance, and description of new species". BMC Genomics, 2014, vol. 15:164-15/549, 29 pages.
Julien Cescut et al. "Carbon accumulation in Rhodotorula glutinis induced by nitrogen limitation", Biotechnology for Biofuels, 2014. vol. 7:164, 11 pages.
Takafumi Kurosawa et al. "Extracellular Accumulation of the Polyol Lipids, 3,5-Dihydroxydecanoyl and 5-Hydroxy-2-decanoyl Esters of Arabitol and Mannitol, by *Aureobasidium* sp." Bioscience, Biotechnology, and Biiochemistry, Jun. 1994, vol. 58, pp. 2057-2060.
Jerry L. Slightom et al. "Cloning and molecular characterization of the gene encoding the Aureobasidin A biosynthesis complex in Aurobasidium pulluians BP-1938", Gene, 2009, vol. 431, pp. 67-79.
Singapore Written Opinion issued in Application No. 11201801204U dated Mar. 21, 2019, 9 pages.
Pan, J. G., et al., "High density cell culture of Rhodotorula Glutinis using oxygen-enriched air," Biotechnology Letters, vol. 8, No. 10, 1986, pp. 715-718.
Extended European Search Report for EP 16837405.6 dated May 21, 2019, 12 pages.
The partial supplementary European Search Report issued in application No. 16837405.6 dated Jan. 15, 2019, 10 pages.

* cited by examiner

*Primary Examiner* — Ruth A Davis
(74) *Attorney, Agent, or Firm* — Rothwell, Figg, Ernst & Manbeck, P.C.

(57) ABSTRACT

The present invention relates to the field of fermentation biotechnology, more particularly to methods for the fermentative production of massoia lactone by *Aureobasidium* species.

10 Claims, 14 Drawing Sheets

Specification includes a Sequence Listing.

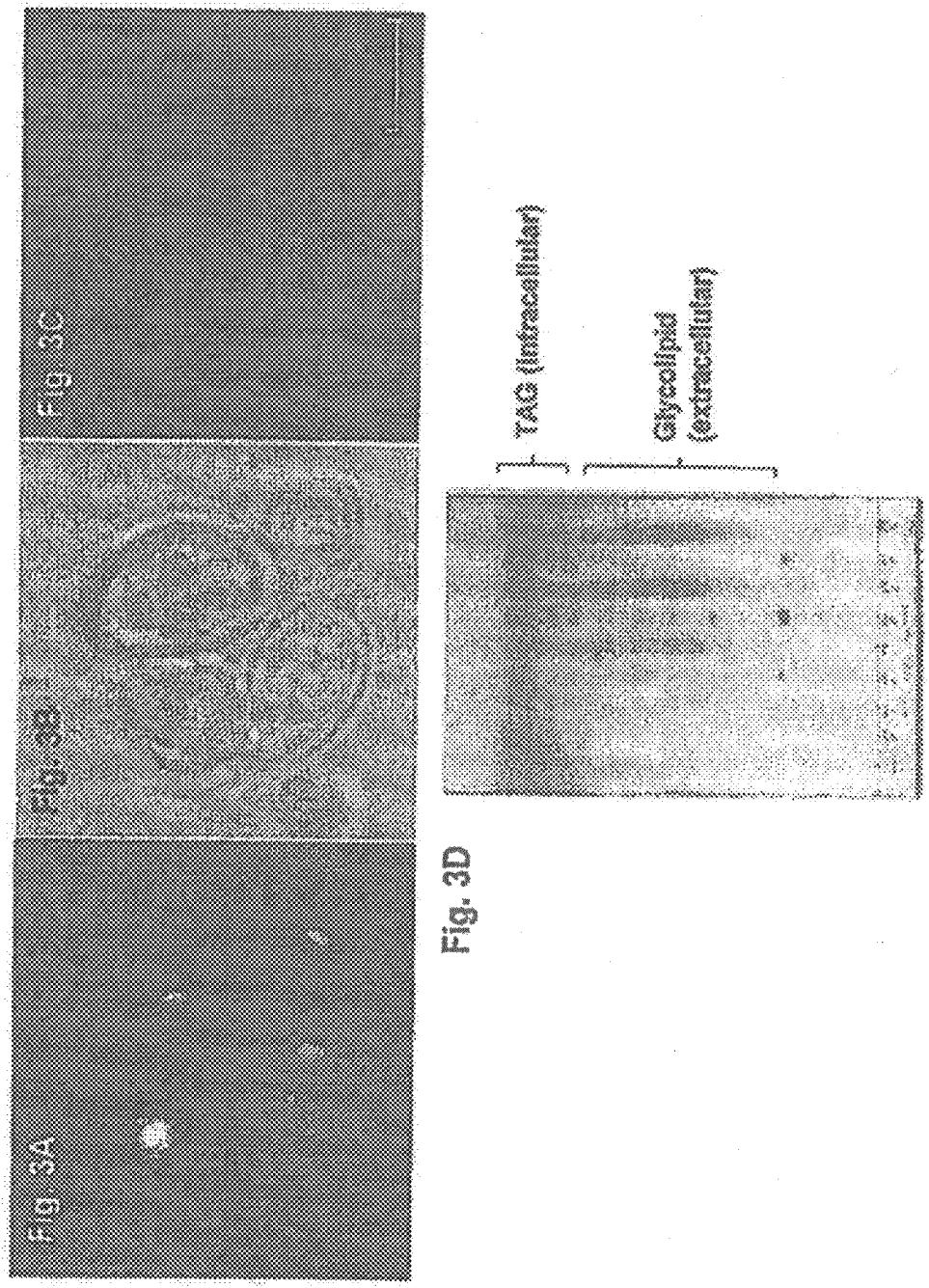

Fig. 12C

Similarity Search Results

Report  View  Compound Info  Process  Help

| Hit | Similar | Regi | Compound Name | Mol Wt | Formula | Library |
|---|---|---|---|---|---|---|
| 1 | 96 | ☒ | Massoia lactone $$ 2H-Pyran-2-one 5,6-dihydro-6-pentyl- | 168 | C10H16O2 | FFNSC1.3.lib |
| 2 | 95 | ☐ | 2H-Pyran-2-one, 5,6-dihydro-6-pentyl- $$ 6-Pentyl-5,6-dihydro-2H-pyran-2-one $$ trans-2-Oxabicyclo[4.4.0]decane $$ Octahydro-2H-chromene # $$ | 168 | C10H16O2 | NIST08.LIB |
| 3 | 82 | ☐ | Cyclopentane, 1,1'-ethylidenebis- $$ Ethane, 1,1'-dicyclopentyl- $$ 1,1-Dicyclopentylethane $$ (1-Cyclopentylethyl)cyclopentane # $$ | 140 | C9H16O | NIST08s.LIB |
| 4 | 82 | ☐ | Cyclopentane, 1,1'-ethylidenebis- $$ Ethane, 1,1'-dicyclopentyl- $$ 1,1-Dicyclopentylethane $$ (1-Cyclopentylethyl)cyclopentane # $$ | 166 | C12H22 | NIST08s.LIB |
| 5 | 82 | ☐ | Cyclopentane, 1,1'-ethylidanebis- $$ Ethane, 1,1-dicyclopentyl- $$ 1,1-Dicyclopentylmethane $$ (1-Cyclopentylethyl)cyclopentane # $$ | 166 | C12H22 | NIST08.LIB |
| 6 | 81 | ☐ | 2(5H)-Furanone, 4-methyl-5-(2-methyl-2-propenyl)- $$ 4-Methyl-5-(2-methyl-2-propenyl)-2(5H)furanone # $$ | 152 | C9H12O2 | NIST08.LIB |
| 7 | 81 | ☐ | cis-2-Oxabicyclo[4.4.0]decane $$ Octahydro-2H-chromene # $$ | 140 | C9H16O | NIST08.LIB |
| 8 | 81 | ☐ | 2H-Pyran-2-one, 5,6-dihydro-6-pentyl-, (R)- $$ (R)-(+)-Massoilactone $$ Massoia lactone $$ 6-Pentyl-5,6-dihydro-2H-pyran-2-one # $$ | 168 | C10H16O2 | NIST08.LIB |
| 9 | 81 | ☐ | Bicyclo[3.2.0]heptan-2-one, 6-hydroxy-5-methyl-6-vinyl- | 166 | C10H14O2 | NIST08.LIB |
| 10 | 81 | ☐ | 2H-Pyrrol-2-one, 1,5-dihydro-1-methyl- $$ 3-Pyrrolin-2-one, 1-methyl- $$ 1-Methyl-3-pyrrolin-2-one $$ 1-Methyl-1,5-dihydro-2H-pyrrol-2-one # $$ | 97 | C5H7NO | NIST08.LIB |
| 11 | 80 | ☐ | Cyclohexane, 1-ethyl-1-methyl- $$ 1-Methyl-1-ethylcyclohexane $$ 1-Ethyl-1-methylcyclohexane $$ | 126 | C9H18 | NIST08s.LIB |
| 12 | 80 | ☐ | Cyclohexane, 1-ethyl-1-methyl- $$ 1-Methyl-1-ethylcyclohexane $$ 1-Ethyl-1-methylcyclohexane $$ | 126 | C9H18 | NIST08.LIB |
| 13 | 80 | ☐ | Cyclohexane, 1-ethyl-2-methyl- $$ 1-Ethyl-2-methylcyclohexane $$ | 126 | C9H18 | NIST08.LIB |

METHODS FOR FERMENTATIVE PRODUCTION OF MASSOIA LACTONE

CROSS-REFERENCE TO RELATED APPLICATIONS

The present application is a division of U.S. patent application Ser. No. 15/750,584, filed on 6 Feb. 2018 as a national stage filing under 35 U.S.C. § 371 of PCT/SG2016/050395, filed on 16 Aug. 2016, which is related to and claims the benefit of priority to U.S. Provisional Patent Application Ser. No. 62/205,996 filed 17 Aug. 2015. Each application is incorporated herein by reference in its entirety.

SUBMISSION OF SEQUENCE LISTING

The present application is being filed along with a Sequence Listing in electronic format. The Sequence Listing is entitled 2577249US3SequenceListing.txt, created on 12 Dec. 2019 and is 295 kb in size. The information in the electronic format of the Sequence Listing is incorporated herein by reference in their entirety.

BACKGROUND OF THE INVENTION

The present invention relates to the field of fermentation biotechnology, more particularly to methods for the fermentative production of massoia lactone by *Aureobasidium* species.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

C-10 massoia lactone [C-10 (5,6-dihydro-6-pentyl-2H-pyran-2-one)] and C-12 massoia lactone [C-12 (5,6-dihydro-6-heptyl-2H-pyran-2-one)] are the major constituent of bark oil of massoia (*Cryptocarya massoia*) [1]. Massoia lactones can also be found in cane sugar molasses, cured tobacco and the essential oil of Sweet Osmanthus (*Osmanthus fragrans*) and jasmine [2]. At 20 ppm, it has a taste described as creamy, coconut, green and slightly fruity. Massoia bark oil is used in the flavor industry as an additive in butter and milk flavors (international FEMA code 3744). Current global supply of massoia bark oil comes from Indonesia, using primitive and costly extraction process that destroy precious native forest.

Massoia lactone is the substrate for the production of saturated delta-decanolide or delta-dodecanolide, which is the key molecule for peach flavor. It can be made by biohydrogenation using a wide range of microorganisms, e.g., yeast (*Saccharomyces, Candida, Pichia*), molds (*Cladosporium*), and bacteria (*Pseudomonas, Sarcina*), [3,4].

Although methods for the chemical synthesis of massoia lactone have been available, the process is a rather complicated and requires multi-step reactions using costly raw materials and catalysts [5]. Previously, massoia lactone was found in the alkali-hydrolyzed glycolipid secreted by *Aureobasidium pullalan* A-21 that was cultured under a calcium-deficient condition. It has been reported that, in the presence of calcium, polymalic acid was produced instead [6]. The interaction between various trace elements on the production of massoia lactone has not been reported.

Certain strains of *A. pullulans* are known to produce extracellular "heavy oils", or polyol lipids, when $CaCO_3$ is not present in the medium. The oils have been described as 3,5-dihydroxydecanoyl and 5-hydroxy-2-decenoyl esters of arabitol and mannitol. Medium for oil production is composed of 50 g/l sucrose, 0.6 g/l (w/v) peptone, 0.4 g/l yeast extract, 5 g/l $K_2HPO_4$, 0.4% g/l $MgSO_4.7H_2O$, and 1 g/l NaCl [7]. Another reported medium uses nitrate as the sole nitrogen source with low phosphate content and is composed of 120 g/l glucose, 1.5 g/l $NaNO_3$, 1 g/l $KNO_3$, 0.05 g/l $KH_2PO_4$, 0.2 g/l $MgSO_4.7H_2O$, 2 ppm $ZnSO_4.7H_2O$, and 0.2 g/l yeast extract [6].

It is desired to develop new fermentation methods for the production of massoia lactone.

SUMMARY OF THE INVENTION

The present invention relates to the field of fermentation biotechnology, more particularly to methods for the fermentative production of massoia lactone by *Aureobasidium* species.

In one aspect, the present invention provides a method for the fermentative production of massoia lactone by *Aureobasidium* species. In one embodiment, the *Aureobasidium* species is *Aureobasidium melanogenum*. In another embodiment, the *A. melanogenum* is a strain of *A. melanogenum* that does not express a functional Aureobasidin A (AbA) biosynthesis complex (aba1) gene mRNA when cultured. In one embodiment, the functional mRNA is not expressed in the culture medium described herein. In a further embodiment, the *A. melanogenum* that does not express a functional aba1 gene mRNA when cultured is the W5-2 strain of *A. melanogenum* as described herein. In one embodiment, the *Aureobasidium* species described herein is cultured in a culture medium described in further detail herein to produce a fermentation product containing massoia lactone. In one embodiment, the culturing is performed for about 4 days to about 12 days, preferably for about 5 days to about 12 days, more preferably for about 7 days to about 10 days. In another embodiment, the culturing is performed at about 25° C. to about 35° C., preferably about 28° C. to about 32° C. In some embodiments, the massoia lactone is purified from the fermentation product using conventional techniques and/or as described in further detail herein.

In a second aspect, the present invention provides a culture medium for the fermentative production of massoia lactone. In one embodiment, the culture medium comprises high levels of phosphate ions, ammonium ions and calcium ions as described in further detail herein. In some embodiments, the culture medium comprises $KH_2PO_4$, $Na_2HPO_4$, $(NH4)_2SO_4$, $MgSO_4$ and $CaCl_2$. In another embodiment, the culture medium further comprises at least two trace elements as described in further detail herein. In some embodiments, the trace elements may be selected from $Fe^{2+}$, $Cu^{2+}$, $Zn^{2+}$ and $MoO_4^{2-}$. In other embodiments, each trace element that may be present in the culture medium may be present in an amount from about 0.1 µM to about 1.0 mM. In a further embodiment, the culture medium comprises urea as a nitrogen source. In another embodiment, the culture medium comprises glucose, mannose, xylose or mixtures thereof as a carbon source. In one embodiment, glucose is used as the sole carbon source. In one embodiment, the culture medium has a pH from about 5.5 to about 6.5, preferably about 6.0. The fermentation method produces high levels of glycolipids. Biochemically, hydroxyl fatty acids conjugate to produce sugars and eventually produce massoia lactone. Thus, the method produces high levels of massoia lactone—a commercially desirable feature of the present invention.

In a third aspect, the present invention provides a novel strain of *A. melanogenum* designated W5-2. In some embodiments, *A. melanogenum* W5-2 does not express a functional Aureobasidin A biosynthesis complex gene mRNA when cultured. In one embodiment, a functional mRNA is not expressed in the culture medium described herein. In other embodiments, *A. melanogenum* W5-2 has been deposited with the Agricultural Research Culture Collection (NRRL), 1815 N. University Street, Peoria, Ill. 61604, USA on 28 May 2015 and assigned accession number NRRL 67063.

BRIEF DESCRIPTION OF THE FIGURES

FIGS. 3A-3D show the characterization of Nile Red staining substance in W5-2 cells. Cell were cultured in HMDC medium with 10% glucose in shaking flasks for 5 day. Cells were stained with Nile Red and imaged by Confocal microscopy. FIG. 3A: Red channel. FIG. 3B: bright field image. FIG. 3C: Over-lay of FIG. 3A and FIG. 3B. Scale bar=10 µM. FIG. 3D: TLC image of total ethyl acetate extract. The positions for triacylglyceride (TAG) and glycolipid are indicated on the right.

FIG. 4A: GCMS spectra of methanol-esterified products of methanol and chloroform extract of freeze-dried cell biomass. Arrows indicate the peaks for major fatty acid methyl esters and massoia lactone. FIG. 4B: Database search and the comparison of MS spectrum of the peak shown in upper panel to that of standard massoia lactone, 6-Pentyl-5,6-dihydro-2H-pyran-2-one, shown in lower panel.

FIG. 7A: Factorial Design was used to evaluate the effects of FeSO4, MnSO4, ZnSO4, CuCl2 and AlCl3. Run #6 (T2) and Run #12 (T3) were selected for further optimization. FIG. 7B: Factorial Design was used to evaluate the effects of H3BO4, CoCl2 and NaMoO4 based on Medium 2 of step 5.

FIG. 9A: Massoia lactone. FIG. 9B: Dry biomass yield. FIG. 9C: Residual $NH_4^+$ in the medium.

FIGS. 12A-12C show production of massoia lactone. FIG. 12A: GCMS chromatograph of W5-2 Sample cultured in R15 Medium in shake flask. FIG. 12B: GCMS chromatograph of W5-2 Sample cultured in T3 medium in 2 L fermenter. FIG. 12C: database search of ML massoia lactone peak of (FIG. 12B).

DETAILED DESCRIPTION OF THE INVENTION

Figure 1:
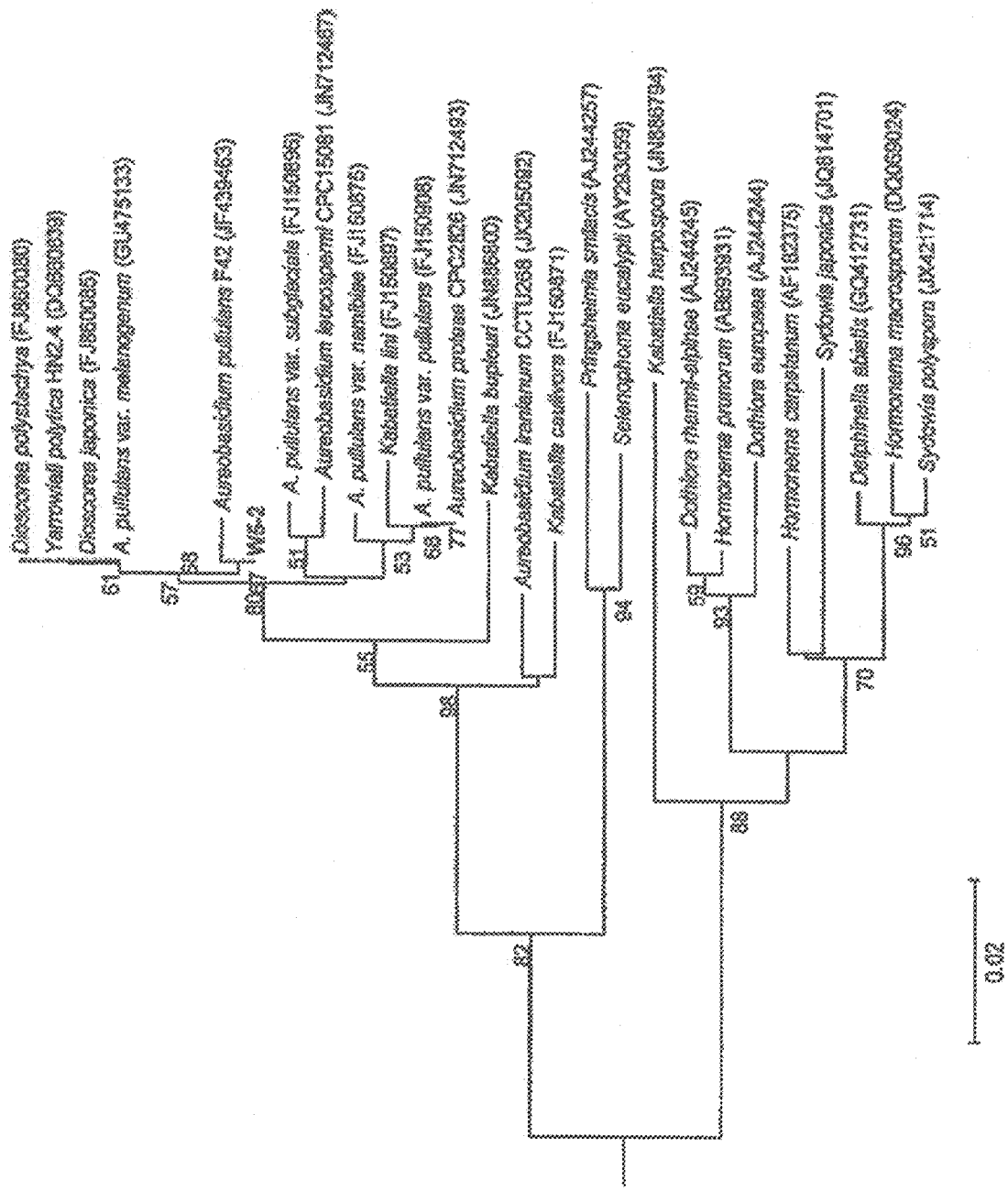
FIG. 1 shows a phylogenetic dendrogram, based on 18S rRNA gene, the first internal transcribed spacer (ITS1), the 5.8S rRNA gene, the second ITS region and the 5' end of the 28S rRNA gene sequences and constructed from evolutionary distances, showing the position of *Aureobasidium* strain W5-2 within the radiation of members of the family Dothioraceae, order Dothideales [36]. Numbers at branching points refer to bootstrap percentages (based on 1000 resamplings); only values above 50% are shown. GenBank accession number of each sequence is shown in parentheses.

The present invention relates to the field of fermentation biotechnology, more particularly to methods for the fermentative production of massoia lactone by *Aureobasidium* species.

Unless defined otherwise, all technical and scientific terms used herein have the same meaning as is commonly understood by one of skill in the art to which the invention belongs.

The term "about" or "approximately" means within a statistically meaningful range of a value. Such a range can be within an order of magnitude, preferably within 50%, more preferably within 20%, more preferably still within 10%, and even more preferably within 5% of a given value or range. The allowable variation encompassed by the term "about" or "approximately" depends on the particular system under study, and can be readily appreciated by one of ordinary skill in the art.

The term "as described in further detail herein" means the description of the embodiments set forth in the detailed description of the invention and in the Examples. In this context, the Examples comprise additional details of the general nature of the invention, as well as certain specific aspects not found elsewhere in the specification.

The term "massoia lactone" as used herein means C-10 massoia lactone [C-10 (5,6-dihydro-6-pentyl-2H-pyran-2-one)] and/or C-12 massoia lactone [C-12 (5,6-dihydro-6-heptyl-2H-pyran-2-one)].

The term "*Aureobasidium melanogenum* W5-2" or "*A. melanogenum* W5-2" or "W5-2" refers to a novel strain of *A. melanogenum* isolated and characterized as described herein and a culture of which has been deposited as described herein.

In one aspect, the present invention provides a method for the fermentative production of massoia lactone by *Aureobasidium* species. In one embodiment, the *Aureobasidium* species is *Aureobasidium melanogenum*. In another embodiment, the *A. melanogenum* is a strain of *A. melanogenum* that does not express a functional Aureobasidin A (AbA) biosynthesis complex (aba1) gene mRNA when cultured. In one embodiment, the functional mRNA is not expressed in the culture medium described herein. The sequence of a functional aba1 gene is set forth in Genbank Accession No. EU886741 (SEQ ID NO:5). In a further embodiment, the *A. melanogenum* that does not express a functional aba1 gene mRNA when cultured is the W5-2 strain of *A. melanogenum* as described herein. In one embodiment, the *Aureobasidium* species described herein is cultured in a culture medium described in further detail herein to produce a fermentation product containing massoia lactone. In one embodiment, the culturing is performed for about 4 days to about 12 days, preferably for about 5 days to about 12 days, preferably for about 5 days to about 11 days, preferably for about 6 days to about 11 days, more preferably for about 7 days to about 10 days. In another embodiment, the culturing is performed at about 25° C. to about 35° C., preferably at about 27° C. to about 32° C., more preferably at about 28° C. to about 32° C. In a further embodiment, the culturing is performed in shake flasks agitated with a speed from about 175 rpm to about 225 rpm, preferably about 200 rpm. In some embodiments, the massoia lactone is purified from the fermentation product using conventional techniques and/or as described in further detail herein.

In some embodiments, the massoia lactone is purified from the fermentation product using conventional techniques, e.g., by alkaline hydrolysis and solvent extraction [6]. In other embodiments, a strong inorganic acid is added to the fermentation product to hydrolyze the fermentation product. In one embodiment, the strong organic acid is sulfuric acid or hydrochloric acid. In a further embodiment, the massoia lactone is purified by solvent extraction or distillation. In some embodiments, the solvent is ethyl acetate or hexane.

In a second aspect, the present invention provides a culture medium for the fermentative production of massoia lactone. In one embodiment, the culture medium comprises high levels of phosphate ions, ammonium ions and calcium ions as described in further detail herein. In some embodiments, the culture medium comprises $KH_2PO_4$, $Na_2HPO_4$, $(NH_4)_2SO_4$, $MgSO_4$ and $CaCl_2$. In some embodiments, the culture medium comprises about 10.0 g/l to about 15 g/l, preferably about 12.5 g/l $KH_2PO_4$, about 0.5 g/l to about 2.0 g/l, preferably about 1.0 g/l $Na_2HPO_4$, about 3.5 g/l to about 6.5 g/l, preferably about 5.0 g/l $(NH_4)_2SO_4$, about 1.0 g/l to about 4.0 g/l, preferably about 2.5 g/l $MgSO_4.7H_2O$ and about 0.10 g/l to about 0.40 g/l, preferably about 0.25 g/l $CaCl_2.2H_2O$. In another embodiment, the culture medium further comprises at least two trace elements. In a further embodiment, the culture medium comprises at least three trace elements. In an additional embodiment, the culture medium comprises four trace elements. In some embodiments, the trace elements may be selected from $Fe^{2+}$, $Cu^{2+}$, $Zn^{2+}$ and $MoO_4^{2-}$. In other embodiments, each trace element that may be present in the culture medium may be present in an amount from about 0.1 µM to about 1.0 mM, from about 1.0 µM to about 1.0 mM, from about 10.0 µM to about 1.0 mM, or from about 100 µM to about 1.0 mM. In a further embodiment, the culture medium comprises urea or ammonium as a nitrogen source. In some embodiments, the urea is present in the culture medium in an amount from about 1.5 g/l to about 2.5 g/l, preferably from about 1.8 g/l to about 2.2 g/l, more preferably about 2 g/l. In some embodiments, ammonium is present in the culture medium in an amount to provide the same amount of nitrogen as provided by the noted urea amounts. In another embodiment, the culture medium comprises glucose, mannose, xylose or mixtures thereof as a carbon source. In some embodiments, the carbon source is present in the culture medium in an amount from about 4% to about 12%, preferably from about 5% to about 12%, preferably from about 5% to about 11%, more preferably from about 5% to about 10%. In some embodiments, glucose is the sole carbon source. In one embodiment, the culture medium has a pH from about 5.5 to about 6.5, preferably about 6.0.

In a third aspect, the present invention provides a novel strain of *A. melanogenum* designated W5-2, including a pure culture of the novel strain or the isolated novel strain or the isolated and biologically pure culture of the novel strain. In some embodiments, *A. melanogenum* W5-2 does not express a functional Aureobasidin A synthase gene mRNA when cultured. In one embodiment, the functional mRNA is not expressed in the culture medium described herein. In other embodiments, *A. melanogenum* W5-2 was deposited on 28 May 2015 under terms of the Budapest Treating with the Agricultural Research Culture Collection (NRRL) located at 1815 N. University Street, Peoria, Ill. 61604, USA and assigned Accession Number NRRL 67063.

In some embodiments, *Aureobasidium melanogenum* and/or *Aureobasidium* melanogenum strain W5-2 is characterized by the sequence of its genome. In one embodiment, the *Aureobasidium melanogenum* GDP1 genomic sequence shares at least 97.5% identity over at least 98.5% of SEQ ID NO:2, preferably 99%-100% identity to over at least 98% of SEQ ID NO:2. In another embodiment, the *Aureobasidium melanogenum* TEF1A genomic sequence shares at least 98% identity over at least 94% of SEQ ID NO:8, preferably 99%-100% identity to over at least 99% of SEQ ID NO:8. In an additional embodiment, the *Aureobasidium* melanogenum RBP1 genomic sequence shares at least 91% identity over at least 92% of SEQ ID NO:10, preferably 96%-100% identity to over at least 98% of SEQ ID NO:10. In a further embodiment, the *Aureobasidium melanogenum* GDP1 genomic sequence shares at least 97.5% identity over at least 98.5% of SEQ ID NO:2, preferably 99%-100% identity to over at least 98% of SEQ ID NO:2, the *Aureobasidium melanogenum* TEF1A genomic sequence shares at least 98% identity over at least 94% of SEQ ID NO:8, preferably 99%-100% identity to over at least 99% of SEQ ID NO:8 and the *Aureobasidium melanogenum* RBP1 genomic sequence shares at least 91% identity over at least 92% of SEQ ID NO:10, preferably 96%-100% identity to over at least 98% of SEQ ID NO:10.

In other embodiments, the *Aureobasidium melanogenum* and/or *Aureobasidium* melanogenum strain W5-2 is characterized by the amount of fatty acids stored in the fungal cells. In one embodiment, the *Aureobasidium melanogenum* and/or *Aureobasidium* melanogenum strain W5-2 fungal cells can store fatty acids at about 40% of its dry weight.

In accordance with the present invention, it has surprisingly been found that the fermentation of *A. melanogenum* W5-2 in the culture medium that contains all of the components described herein for the culture medium produces a very high yield of massoia lactone. For example, as shown in the Examples, batch fermentation of *A. melanogenum* W5-2 in this culture medium produced massoia lactone at a 7 day peak of 10.268 g/l in a 2 L bioreactor, with a volume productivity of 61.11 mg/hr/l. Thus, in one embodiment, the batch fermentation of *A. melanogenum* W5-2 in this culture medium yields 10.268 g/l of crude massoia lactone. In another embodiment, the batch fermentation of *A. melanogenum* W5-2 in this culture medium yields more than 10 g/l of crude massoia lactone. In some embodiments, the yield of crude massoia lactone is at least 11 g/l, or at least 12 g/l, or at least 13 g/l, or at least 14 g/l or at least 15 g/l. In other embodiments, the yield of crude massoia lactone is from about 10 g/l to about 25 g/l, or from about 10 g/l to about 24 g/l, or from about 10 g/l to about 23 g/l, or from about 10 g/l to about 22 g/l, or from about 10 g/l to about 21 g/l, or from about 10 g/l to about 20 g/l, or from about 10 g/l to about 19 g/l, or from about 10 g/l to about 18 g/l, or from about 10 g/l to about 17 g/l, or from about 10 g/l to about 16 g/l, or from about 10 g/l to about 15 g/l, or from about 10 g/l to about 14 g/l.

In some embodiments, the yield of purified massoia lactone from the crude extract is at least 50%. In other embodiments, the yield of purified massoia lactone from the crude extract is more than 5 g/l. In some embodiments, the yield of purified massoia lactone from the crude extract is at least 5.5 g/l, or at least 6 g/l, or at least 6.5 g/l, or at least 7 g/l or at least 7.5 g/l. In other embodiments, the yield of purified massoia lactone from the crude extract from about 5 g/l to about 12.5 g/l, or from about 5 g/l to about 12 g/l, or from about 5 g/l to about 11.5 g/l, or from about 5 g/l to about 11 g/l, or from about 5 g/l to about 10.5 g/l, or from about 5 g/l to about 10 g/l, or from about 5 g/l to about 9.5 g/l, or from about 5 g/l to about 9 g/l, or from about 5 g/l to about 8.5 g/l, or from about 5 g/l to about 8 g/l, or from about 5 g/l to about 7.5 g/l, or from about 10 g/l to about 7 g/l.

It has surprisingly been found that the fermentation method using strain W5-2, as described herein, has several advantages.

The method produces high levels of glycolipids. Biochemically hydroxyl fatty acids conjugate to produce sugars and eventually produce massoia lactone. Thus, the method produces high levels of massoia lactone—a commercially desirable feature of the invention.

Massoia lactone is exuded into the medium and about 80% of the supernatant contains massoia lactone—reflecting the ability to obtain high amounts of massoia lactone.

The method can produce more than 10 g/l massoia lactone within 5 days at lab scale using glucose as a sole carbon source.

The crude extract has more than 10 g/l of massoia lactone. Upon purification the yield is more than 5 g/l of the crude extract, which is at least about 50% distillation recovery.

Use of 2 liter bioreactor yields high amounts of massoia lactone.

The method is highly efficient—the crude extract has less of impurities, including negligible or minimum intermediates. The method is highly time and cost efficient.

The massoia lactone is capable of producing multiple odors and/or flavorsflavors, e.g., coconut, waxy, oily aroma, creamy, green and slightly fruity flavors and/or odors. The massoia lactone can be converted into delta-decanolide or delta-dodecanolide to produce a peachy flavor and/or odor.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, DNA Cloning (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols* (*Methods in Molecular Biology*), Human Press, Totowa, N.J., 2004; Sohail, *Gene Silencing by RNA Interference: Technology and Application*, C R C, 2004.

EXAMPLES

The present invention is described by reference to the following Examples, which are offered by way of illustration and are not intended to limit the invention in any manner. Standard techniques well known in the art or the techniques specifically described below were utilized.

Example 1

Materials and Methods

Isolation of Microbial Strains:

Microbial samples were collected from various regions in Singapore. Samples were mixed with 100 ml autoclaved sea water and incubated overnight at 28° C. A 100 µl of the overnight culture was withdrawn and streaked on modified seawater-YPD (Yeast Peptone Dextrose) medium (containing 1 g/l peptone, 2 g/l yeast extract, 4 g/l glucose, and 8 g/l agar, pH 7), which was further supplemented with 0.5 µg/ml Nile red and an antibiotic selected from ampicillin (25 µg/ml), kanamycin (25 µg/ml) and streptomycin (100 µg/ml). Potato dextrose agar (PDA) was also used for the initial screening. The plates were incubated at 28° C. for 48 hr and the strongly Nile red staining strains were identified by examining the plates under a Nikon C-DSS230 stereomicroscope microscope (Nikon, Japan) equipped with Digital Sight DS-L1 camera. Candidate strains were purified by 2 rounds of single colony isolation on seawater-YPD plates followed by verification of Nile red staining in small scale liquid cultures. Florescence was measured using the TECAN infinite M200 fluorometer with the excitation wave-length and emission wave-length set at of 530 nm and 575 nm respectively (TECAN, USA).

Phylogenetic Analysis of the Microbial Strains by ITS Sequencing:

Yeast isolates were cultured in YPD medium at 30° C. Genomic DNAs were extracted from 2 ml of 48 hr cultures using the MasterPure™ Yeast DNA Purification Kit (Epicentre Biotechnologies, USA) according to the manufacturer's instructions. PCR amplification reactions were performed in 40 µl 1× buffer with 2.5 mM dNTP, 50 µM each primer, 50 ng of total DNA and 3 units of Taq DNA polymerase (i-DNA Biotechnology, Singapore). PCR cycling conditions were as followed: 95° C./10 min, 30 cycles of 95° C./1 min, 61.8° C./1 min and 72° C./1 min and final extension for 5 min/72° C. The ITS1(5'-tccgtaggt-gaacctgcgg; SEQ ID NO:3) and ITS4 (5'-tcctccgcttattgatatgc SEQ ID NO:4) [8] primers were used to amplify the ITS region of the nuclear rRNA operon spanning the 3' end of the 18S rRNA gene, the first internal transcribed spacer (ITS1), the 5.8S rRNA gene, the second ITS region and the 5' end of the 28S rRNA gene. [9]. Gel-purified PCR products were sequenced with the Big-Dye sequencing method in Applied Biosystems 3730xl DNA Analyzer (Life technologies, USA). Sequences were analyzed by BLAST against the NCBI database and aligned using the CLUSTAL W tool in MEGA version 5.05 [10]. Phylogenetic analyses were performed by the Neighbour-Joining [11], Maximum-Likelihood [12] and Maximum-Parsimony methods [13] using the MEGA version 5.05 with the bootstrap values set at 1000 replications.

Small Scale Culture and Fed-Batch Fermentation:

*Aureobasidium* strain W5-2 was cultured in 100 ml liquid medium in 250 ml shake flasks, agitated with a speed of 200 rpm and constant temperature of 30° C. The High Density Culture Medium (HDCM) developed for *Rhodotorula giutinis* [14] was used as the basic culture medium. It contains 90 g/l glucose, 12.5 g/l $KH_2PO_4$, 1.0 g/l $Na_2HPO_4$, 5.0 g/l $(N14)_2SO_4$, 1.9 g/l yeast extract, 2.5 g/l $MgSO_4.7H_2O$, 0.25 g/l $CaCl_2.2H_2O$ and 0.25 ml/l trace element mix (pH 5.5). Trace elements mix was made in 5N HCl and contains 40 g/l $FeSO_4.7H_2O$, 40 g/l $CaCl_2.2H_2O$, 10 g/l $MnSO_4.7H_2O$, 10 g/l $AlCl_3.6H_2O$, 4 g/l $CoCl_2$, 2 g/l $ZnSO_4.7H_2O$, 2 g/l $Na_2MoO_4$, 1 g/l $CuCl_2.2H_2O$ and 0.5 g/l $H_3BO_3$. Where indicated, levels of trace elements and various nitrogen sources were varied. For comparison purpose, the strain was also cultured in the A-21M medium reported previously [6], which contains 120 g/l glucose, 1.5 g/l $NaNO_3$, 1.0 g/l $KNO_3$, 0.05 g/l $KH_2PO_4$, 0.2 g/l $MgSO_4.7H_2O$, 2 ppm $ZnSO_4$, 0.2 g/l yeast extract (pH 5.5).

Fed-batch fermentation was carried out in a 2 L Biostat B plus bioreactor (Sartorius Stedim Biotech, Germany). Dissolved oxygen level ($pO_2$) and air flow was maintained at 30% and 1.5 vvm, respectively. 25 ml samples were taken daily to monitor glucose, ammonium, $NO^{2-}$ and $NO^{3-}$ levels.

Optimization of Massaio Lactone Production by Design of Experiment (DOE):

Optimization of massaio lactone production by Design of Experiment (DOE) was aided with the Design-Expert® V8 Software (Stat-Ease, USA) using both the Optimised Factorial Design and Central Composite Design (CCD). Seed cultures prepared in the HDCM medium were harvested by centrifugation, washed with sterile distilled water and suspended in sterile distilled water. A fraction of which (2 ml) was inoculated into 100 ml of the respective designed medium in a 250 ml shake flask, which was cultured in a 30° C. shaking platform agitated at 200 rpm. Culture samples (15 ml) were taken daily for the analyses of cell biomass, $OD_{600}$ and metabolites.

Extraction and Quantification of Glycolipids:

Ethyl acetate was added to cell culture at a volumetric ratio of 1:1 in a 15 ml Falcon tube. The mixture was vortexed vigorously for 20 seconds; centrifuged at 3,500 g for 10 minutes and 1 ml of the upper phase was transferred to a 1.5 ml Eppendorf tube and left to air dry overnight at room temperature in an exhaust hood. The resultant dried residue was weighed with a microbalance before being added with 10 µl menthol in methanol (10% w/v) (as the internal standard) and 300 µl of 2M NaOH. The suspended mixture was allowed to hydrolyze overnight in a shaking platform at room temperature. After mixing with 150 µl of 5M $H_2SO_4$, 450 µl ethyl acetate was added and vortexed vigorously. After centrifugation, the upper phase was used for GCMS analysis directly. Alternatively, glycolipids were extracted directly from wet cell biomass collected by centrifugation from 10 ml culture. 2 ml of 72% $H_2SO_4$ was added to the cell pellet, mixed well and allowed to stand for half an hour and then mixed with 4 ml water. After boiling for one hour, 4 ml of the mixture was added with equal volume of ethyl acetate; vortexed vigorously for 20 seconds; centrifuged at 3,500 g for 10 minutes and 1 ml of the upper phase was analyzed by GCMS or thin-layer chromatography (TLC). Conditions used TLC were as described previously [15]. Hexane can be used in place of ethyl acetate in this procedure. HCl can be used in place of $H_2SO_4$ in this procedure.

Preparation and Quantification of Massoia Lactone:

Equal volume of $H_2SO_4$ was added to 2 ml of cell culture in a 15 ml Falcon tube. Samples were vortexed briefly and left in room temperature for 30 mins. After adding 4 ml of water, Falcon tubes were boiled in a water-bath for 60 min; cooled for 10 mins at room temperature, and then 4 ml of ethyl acetate was added into the tubes, which were mixed vigorously with a vortex for 20 seconds. Samples were centrifuged for 10 mins at 3,500 rcf and 1 ml of the top organic layer was transferred to a 2 ml glass vial containing 50 mg of $Na_2SO_4$ and 10 µl menthol solution in methanol (10%). Massoia lactone was quantified using GCMS using menthol as the internal standard. HCl can be used in place of $H_2SO_4$ in this procedure.

Quantification of Fatty Acid:

Cell biomass was collected from 20 ml culture by centrifugation and dried in a 60° C. oven until constant weight is reached. The resultant dried pellets were frozen in liquid nitrogen and grinded to a fine powder using mortar and pestle. A 250 mg sample was transferred to a 15 ml Falcon tube and then mixed with 2 ml of 72% $H_2SO_4$ and 10 µl of 10% (w/v) pentadeconoic acid in methanol (as the internal standard). The samples were hydrolyzed at room temperature for 30 mins and then mixed with 4 ml water. After boiling for 1 hour, a 500 µl fraction was transferred to a 2 ml Eppendorf tube and fatty acids were extracted by mixing with 1 ml methanol/chloroform mixture (1:1 v/v). After centrifugation, the bottom layer was collected by pipetting and washed once with PBS buffer in an Eppendorf tube. The methanol/chloroform bottom layer was collected after centrifugation and left to dry at room temperature in an exhaust hood. 300 µl petroleum ester (Fisher Chemicals, CAS: 64742-49-0)/benzene (QREC Asia SDN BDH, CAS 71-43-2) mixture (1:1 v/v) and 300 µl 0.4 M KOH in methanol was added to solubilize the dried residues. Esterification was performed at room temperature for 3 hours. After separation by centrifugation, 50 µl of the top layer was diluted with 450 µl of methanol and subjected to analysis by GC-MS.

GC-Ms Analysis:

GC-MS analysis was performed using GCMS-QP2010 Ultra (Shimadzu Corporation, Japan). Samples (1 µl) were injected into a HP-88 column (30 m×0.25 mm ID×0.20 µm) (Agilent Technologies, USA) and run with helium as the carrier gas maintained at 10 psi. A split-less injection time of 0.5 min was used. The GC started at an initial temperature of 50° C. for 1 minute, ramped at 15° C. per minute up to 150° C. and 3° C. per minute to a final temperature 240° C. The spectrometer was scanned from 41-400 amu. The compounds were identified by searching against the NIST 08 mass spectral library. Quantification of fatty acid ester and massoia lactone was done by comparing the peak area between the target compounds and the respective internal standards.

Other Quantification Methods:

Glucose levels were quantified using a Shimadzu Prominence UFLC (Shimadzu, Japan). Samples were run through an Aminex HPX-87H column (Bio-rad, USA) maintained at 50° C. 5 mM $H_2SO_4$ was used as the mobile phase and run at a flow rate of 0.7 ml/min. Total nitrates, nitrites and ammonia levels were determined using the method as described [16, 17].

RNA Sampling and RNA-Sequencing:

Cell cultures (1 ml) were collected at day 1, 2, 3 and RNAs were immediately extracted with RiboPure™ RNA Purification Kit, yeast (Life Technologies, USA). After determination of the RNA quantity and quality by Nanodrop and agarose gel electrophoresis, the RNA samples were sent to Macrogen Inc. (Korea) for cDNA shotgun library construction and sequencing using Illumina Hiseq 2000.

Computational Analysis:

Computational analysis was performed in the Galaxy platform (http://galaxyproject.org/) installed locally [18]. Raw reads (100 bp paired-end) were analyzed with NGS QC toolkit [19] for their quality. Then, Tophat and Cufflinks [20-22] were used to identify differential gene/transcript expression based on published genome sequences as the references. de novo assembly was performed with Trinity [23, 24], which produced ~18 k isoforms or transcripts. Differentially expressed (DE) transcripts and expression profile clusters were done with Bioconductor with rsem and edgeR packages [25, 26].

Example 2

Identification of Massoia Lactone-Producing Microbial Strains

Nile red is an uncharged hydrophobic molecule whose fluorescence is strongly influenced by the polarity of its environment and it is often used as a marker for hydrophobic substances, such as lipid, glycolipids and hydrophobic proteins [27-29]. By screening water and soil samples obtained from local costal environment using Nile red as a marker, 32 candidates were identified that showed significant red fluorescence, among which strain W5-2 was identified as fungus closely related to Aureobasidium species based on the sequence comparison of the rDNA ITS region (SEQ ID NO.1) (FIG. 1). W5-2 colonies turned black after 7 days of culture on solid medium (not shown).

Because Aureobasidium species are identified by phylogenetic analysis of their whole genome sequences as well as certain phylogenetically important genes, such as housekeeping genes encoding Actin, β-tubulin, calmodulin, chytin synthase, NAD-dependent glycerol-3-phosphate dehydrogenase and translation elongation factor 1α (TEF1A), the whole transcriptome of W5-2 was chosen to compare those of the type Aureobasidium strains [30].

The overall alignment rates of raw reads to the 4 reference genomes of Aurebasidium species [31] were low, ~55.7% to A. melanogenum and ~15-19% to the rest Aureobasidium species (Table 1). Therefore, de novo assembly of RNA-seq data was performed using the Trinity program [32], producing a sequence library of ~18 k isoforms/transcripts. The overall alignment rate of raw reads to this local reference was increased to above 95%.

TABLE 1

Mapping Rates to Reference Genomes of Aurebasidium Species

| | T0-1d | T0-2d | T0-3d | T2-1d | T2-2d | T2-3d | Average |
| --- | --- | --- | --- | --- | --- | --- | --- |
| A. melanogenum | 60.47% | 52.76% | 52.10% | 58.24% | 56.73% | 54.06% | 55.72% |
| A. pullulans | 21.68% | 15.71% | 15.81% | 16.80% | 15.06% | 13.86% | 16.49% |
| A. subglaciale | 19.80% | 14.23% | 14.41% | 15.46% | 13.48% | 12.41% | 14.97% |
| A. namibiae | 24.90% | 18.11% | 18.23% | 20.08% | 18.04% | 16.32% | 19.28% |

Note:
Raw reads were mapped to reference genome using TopHat software[33]. RNA samples were extracted from W5-2 cell culture in Medium T0 and Medium T2 at Day, 1, 2 and 3 respectively.

Figure 2:
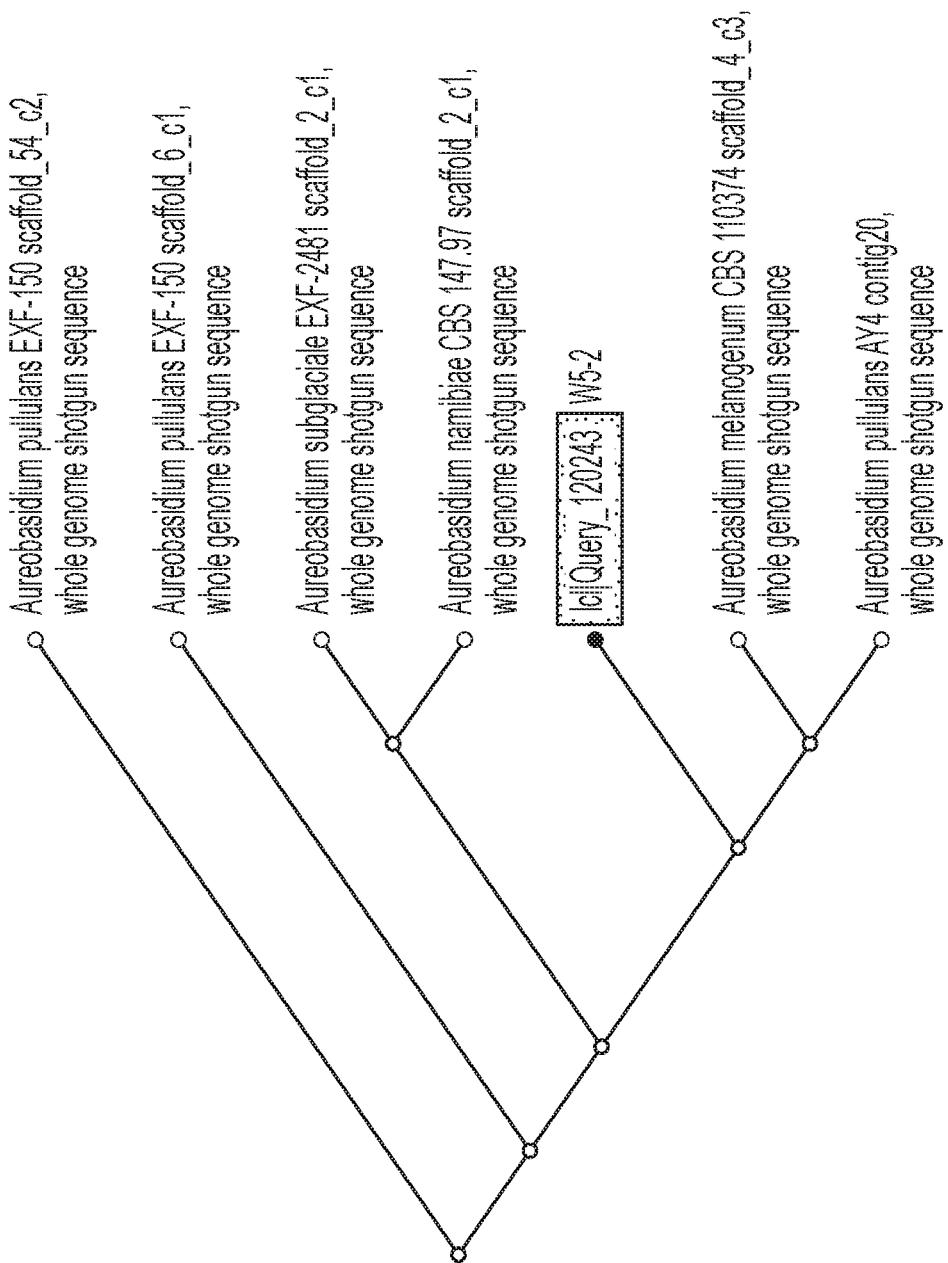
FIG. 2 shows results of a GPD1 CDS search by BLASTn against the Whole Genome Shortgun Motifs of *Aureobasidium* species. This search identified two highly related genomic sequences from *Aureobasidium melanogenum* CBS 110374 scaffold_4_c3 and *Aureobasidium pullulans* AY4 contig20 (which is in fact *A. melanogenum*). *Aureobasidium namibiae* CBS, *Aureobasidium subglaciale* EXF-2481 and *Aureobasidium pullulans* EXF-150 had only partial sequences in the region. The phylogenic tree is generated Blast Tree View at NCBI using fast minimal evolution method.

DNA sequence divergence in GPD1 gene is used as an important indicator for phylogenetic analysis in Aureobasidium species [30]. GPD1 CDS sequence (SEQ ID NO:2) was searched by BLASTn against the Whole Genome Shortgun sequences of Aureobasidium species at NCBI. Six highly related sequences were identified. Phylogenic tree generated Blast Tree View using fast minimal evolution method is shown in FIG. 2, which clearly places the W5-2 GPD1 sequence between A. melanogenum CBS 110374/A. pullulans AY4, which has been re-classified as A. melanogenum [30], and A. namibiae CBS 147.97/A. subglaciale EXF-2481. W5-2 showed highest divergence from A. pullulans EXF-150 and lowest divergence to A. melanogenum.

A. pullulans is known to produce antibiotic aureobasidin A [34], which is made by a huge polyketide synthase Aba1[35]. A search of ABA1 CDS (Genbank no. EU886741) against the W5-2 whole transcriptome failed to identify any homologs in the genome. Therefore, strain W5-2 does not encode a functional ABA1 gene and is not likely to produce any antibiotics.

Figure 4A:
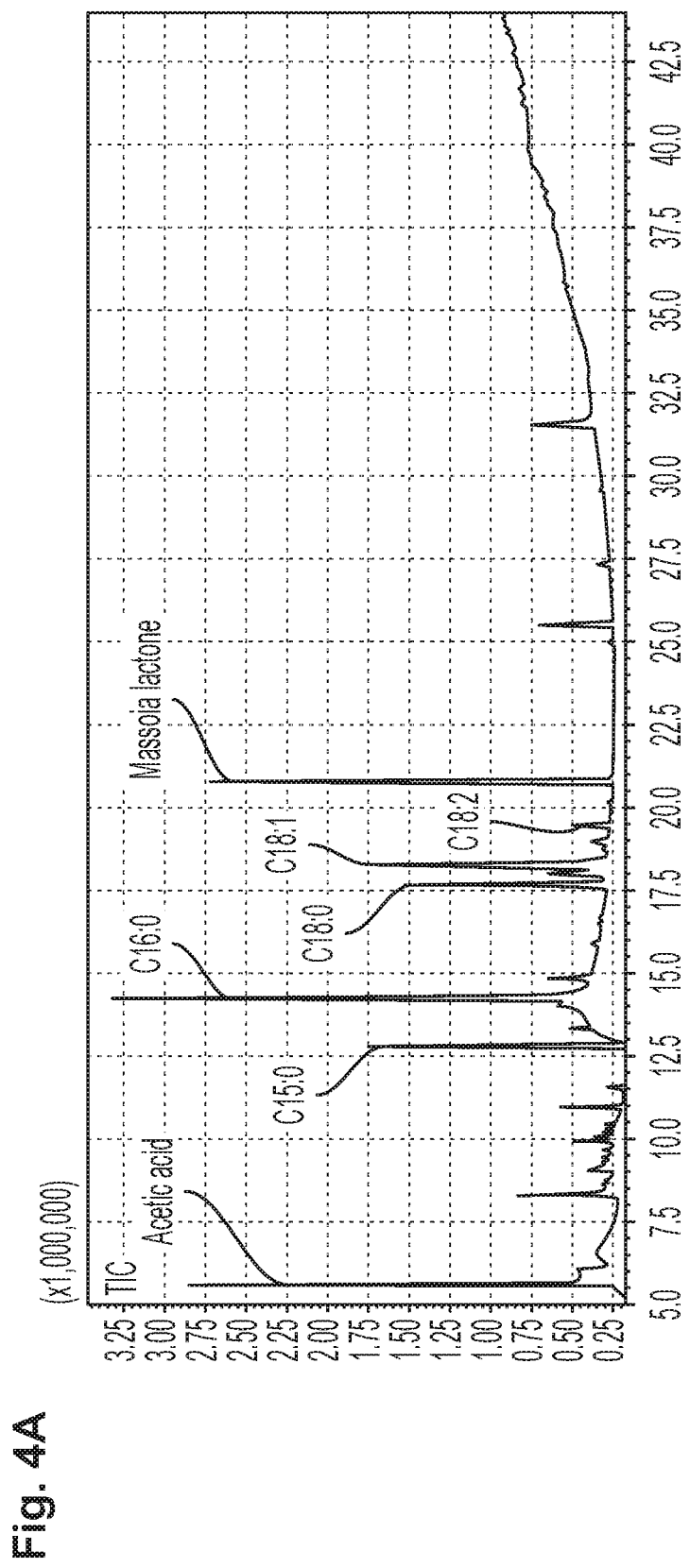
FIGS. 4A and 4B show GCMS analysis of *Aureobasidium* isolate W5-2.
Figure 4B:
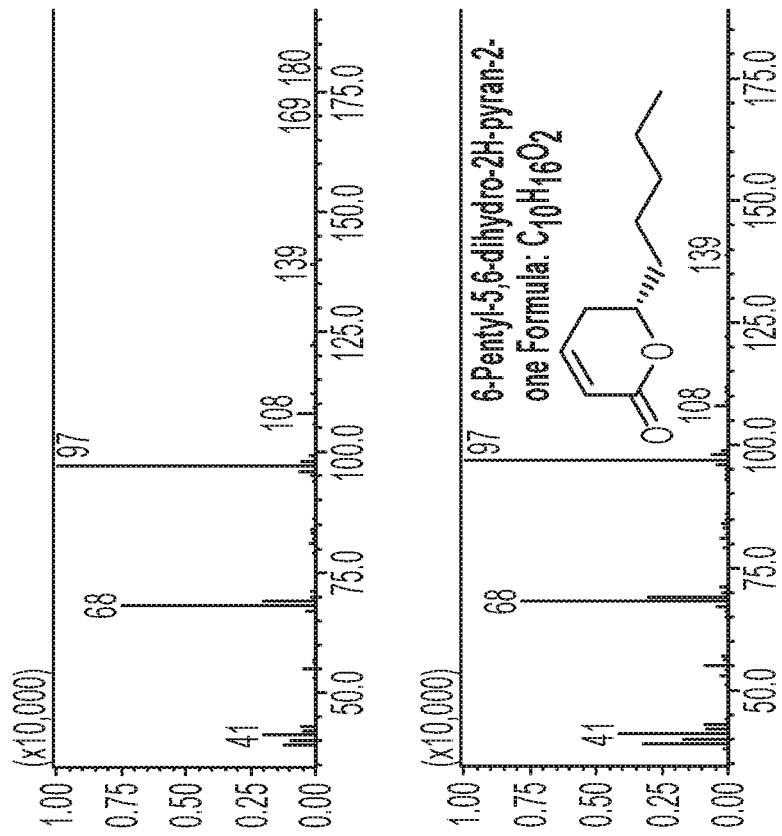

Confocal imaging confirmed that Nile red stained the cytoplasm intensely with little signal in the cytoplasmic membrane, suggesting the high accumulation of hydrophobic substance in the cells (FIG. 3C). Fatty acid profiling by GCMS revealed that the total ethyl acetate extract contained 52.28% oleic acid, 33.9% palmitic acid, 3.98% linoleic acid, 1.31% palmatolic acid and about 1.3% of long chain (C24 and above) fatty acids (Table 2). Thin layer chromatography (TLC) confirmed the production of triacylglyceride (TAG) and glycolipids (FIG. 3D). Unexpectedly, the GCMS profile showed a significant peak with a retention time of approximately 25.7 min, which had >93% similarity to massoia lactone, i.e., 6-pentyl-5,6-dihydro-2H-pyran-2-one (FIGS. 4A and 4B). Sensory test of the dried cell pellet confirmed the presence a strong coconut-like aroma.

TABLE 2

Fatty Acid Profile of W5-2

| | C16 | C16:1 | C18 | C18:1 | C18:2 | C24 |
|---|---|---|---|---|---|---|
| W5-2 | 33.91% | 1.31% | 7.24% | 52.28% | 3.98% | 1.29% |

Example 3

Medium Optimization Using Central Composite Designs (CCD)

Figure 5:
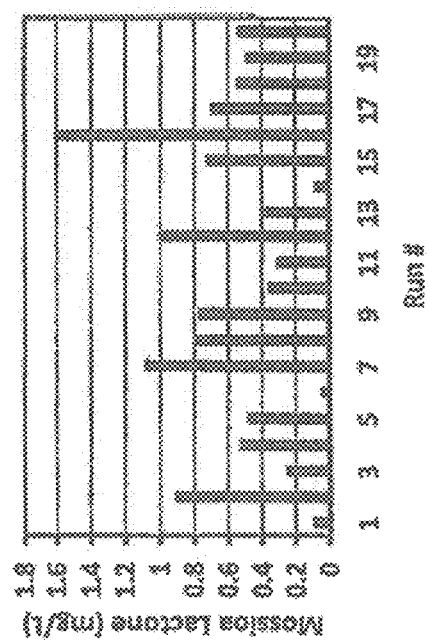
FIG. 5 shows using Central Composite Design (CCD) to optimize concentration of urea, trace elements and glucose.
Figure 6:
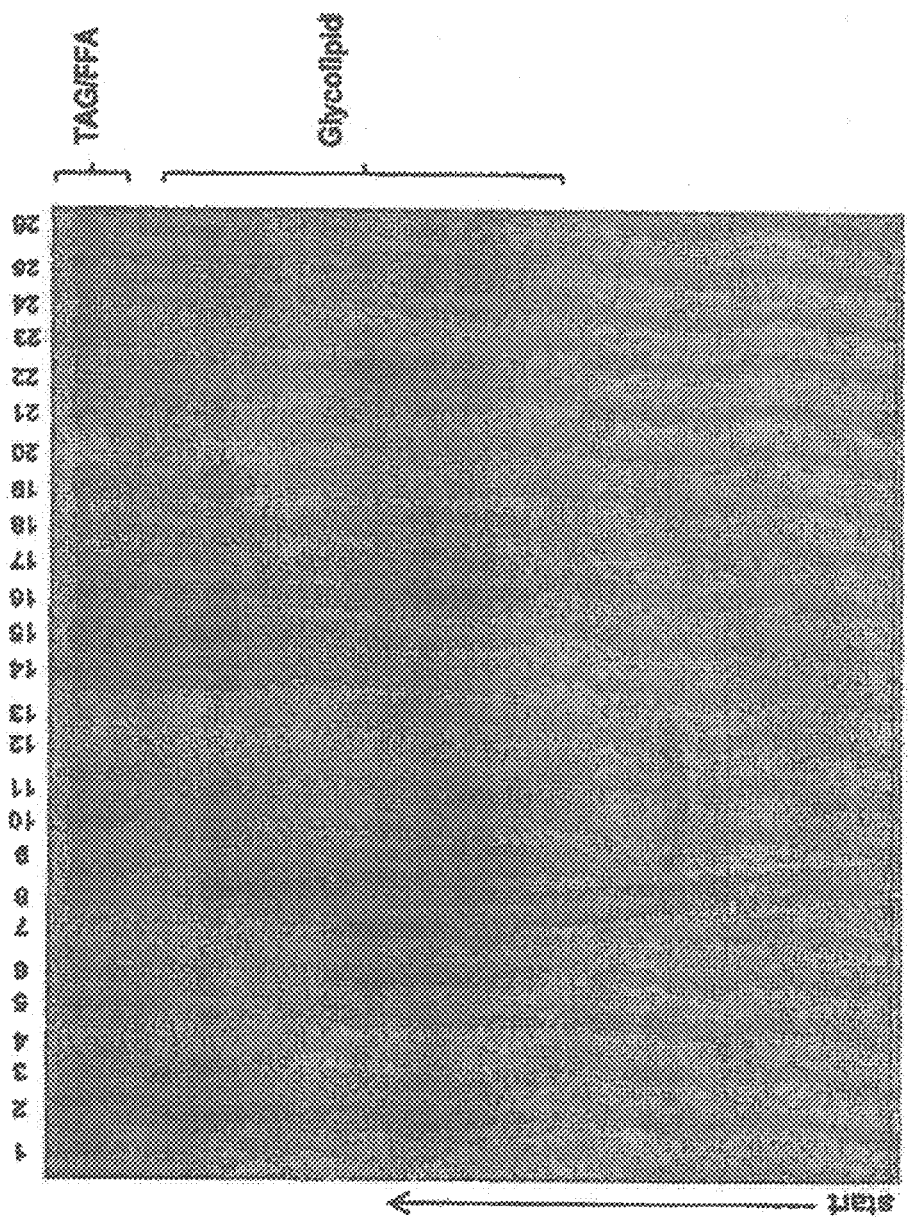
FIG. 6 shows glycolipid profiles of various media. Medium composition is shown in Table 2. Seed culture was prepared by inoculating 1.5 ml of frozen 7% DMSO culture into 100 ml of the original HDCM in a 250 ml flask and cultured for 48 hrs at 30° C. The cells were harvested by centrifugation, re-suspended in water and inoculated at 2% into each medium in 250 ml flasks. Cells were cultured at 30° C. with 200 rpm agitation. Samples shown are taken from the 6th day.

To improve massoia lactone production, the *Rhodotorula glutinis* high density (HMDC) medium [14] was modified by changing the levels of nitrogen source (urea), carbon source (glucose) and trace element mix, which contains $FeSO_4.7H_2O$, $CaCl_2.2H_2O$, $MnSO_4$, $AlCl_3.6H_2O$, $CoCl_2$, $ZnSO_4.7H_2O$, $Na_2MoO_4.2H_2O$, $CuCl_2.2H_2O$ and $H_3BO_4$. Medium compositions are shown in Table 3. Massoia lactone production was low, ranging from 0.05 mg/l (Run 6) to 1.61 mg/l (Run 16) (FIG. 5). While there were obvious differences amongst the runs, none of the parameters appeared to significantly influence the production by ANOVA analysis (p<0.05) (Table 4). Since massoia lactone produced in *A. pullulans* has been reported to derive from glycolipid [6], we monitored glycolipid levels by TLC. Again, CCD was employed to optimize the nitrogen source and carbon source in HMDC medium, with urea and yeast extract set as category factors while glucose level was set at 7.5, 20, 50, 80, 92.4 g/l respectively. In addition, the trace element mix was set at 0.034, 0.2, 0.6, 1.0, 1.17 ml per litre medium respectively (Table 5). High variations in glycolipid profiles were observed: Run No. 15 appeared to be the best combination for glycolipid production (FIG. 6), with 285 mg/l massoia lactone present in the acid hydrolyzed glycolipid products. Therefore, we chose a medium containing high level of glucose (~100 g/l), 2 g/l urea as the sole nitrogen source and 0.6 ml original HMDC trace element mix for subsequent medium optimizations. For convenience, this medium is referred as the Run 15 (R15) medium.

TABLE 3

Optimization of Nitrogen source, Carbon Source and Trace Elements by CCD

| Run No. | Urea (g/L) | Glucose (g/l) | Trace (ml/l) |
|---|---|---|---|
| 1 | 2.89 | 36.21 | 0.95 |
| 2 | 1.11 | 83.78 | 0.24 |
| 3 | 2 | 60 | 1.2 |
| 4 | 2 | 60 | 0.6 |
| 5 | 0.5 | 60 | 0.6 |
| 6 | 2 | 60 | 0 |
| 7 | 2.89 | 36.21 | 0.24 |
| 8 | 2 | 60 | 0.6 |
| 9 | 2 | 60 | 0.6 |
| 10 | 2 | 60 | 0.6 |
| 11 | 3.5 | 60 | 0.6 |
| 12 | 1.11 | 83.78 | 0.957 |
| 13 | 1.11 | 36.21 | 0.96 |
| 14 | 2 | 20 | 0.6 |
| 15 | 2 | 60 | 0.6 |
| 16 | 2 | 60 | 1.00 |
| 17 | 2.89 | 83.78 | 0.24 |
| 18 | 1.11 | 36.21 | 0.24 |
| 19 | 2 | 100 | 0.6 |
| 20 | 2.89 | 83.78 | 0.96 |

TABLE 4

Anova Analysis of Table 3

| Source | Sum of Squares | df | Mean Square | F Value | p-value Prob > F | Remarks |
|---|---|---|---|---|---|---|
| Model | 0.75 | 3.00 | 0.25 | 1.98 | 0.1580 | not |
| A-Trace elements | 0.23 | 1.00 | 0.23 | 1.86 | 0.1919 | significant |
| B-Urea | 0.00 | 1.00 | 0.00 | 0.02 | 0.8813 | |
| C-Glucose | 0.51 | 1.00 | 0.51 | 4.05 | 0.0612 | |
| Residual | 2.02 | 16.00 | 0.13 | | | |
| Lack of Fit | 1.87 | 11.00 | 0.17 | 5.95 | 0.0308 | significant |
| Pure Error | 0.14 | 5.00 | 0.03 | | | |
| Cor Total | 2.77 | 19.00 | | | | |
| Std. Dev. | 0.36 | | R-Squared | 0.27 | | |
| Mean | 0.59 | | Adj R-Squared | 0.13 | | |
| C.V. % | 60.42 | | Pred R-Squared | −0.30 | | |
| PRESS | 3.60 | | Adeq Precision | 4.27 | | |

TABLE 5

Medium Compositions of Central Composite Design 1 (CCD1)

| Run | Nitrogen source | Glucose (g/l) | Trace element mix (ml/l) | lactone titre (mg/l) |
|---|---|---|---|---|
| 1 | Urea | 7.57 | 0.6 | 0.256 |
| 2 | Yeast extract | 50 | 0.03 | 4.192 |
| 3 | Yeast extract | 50 | 0.6 | 2.384 |
| 4 | Yeast extract | 7.57 | 0.6 | 1.386 |
| 5 | Yeast extract | 80 | 0.2 | 2.594 |
| 6 | Yeast extract | 20 | 0.2 | 3.257 |
| 7 | Yeast extract | 20 | 1 | 4.130 |
| 8 | Urea | 80 | 0.2 | 3.082 |
| 9 | Urea | 50 | 1.17 | 4.978 |
| 10 | Yeast extract | 50 | 0.6 | 3.100 |
| 11 | Yeast extract | 80 | 1 | 3.366 |
| 12 | Urea | 20 | 1 | 1.853 |
| 13 | Urea | 20 | 0.2 | 4.103 |
| 14 | Urea | 80 | 1 | 4.935 |
| 15 | Urea | 92.43 | 0.6 | 6.731 |
| 16 | Urea | 50 | 0.6 | 2.300 |
| 17 | Urea | 50 | 0.6 | 5.272 |
| 18 | Urea | 50 | 0.6 | 3.011 |
| 19 | Yeast extract | 50 | 0.6 | 4.325 |
| 20 | Yeast extract | 50 | 1.17 | 2.510 |
| 21 | Yeast extract | 50 | 0.6 | 2.651 |
| 22 | Urea | 50 | 0.6 | 5.715 |
| 23 | Urea | 50 | 0.03 | 4.990 |
| 24 | Yeast extract | 92.43 | 0.6 | 0.934 |
| 25 | Urea | 50 | 0.6 | 3.700 |
| 26 | Yeast extract | 50 | 0.6 | 4.855 |

Note:
urea and yeast extract were both set at 1.9 g/l.

Example 4

Figure 7A:
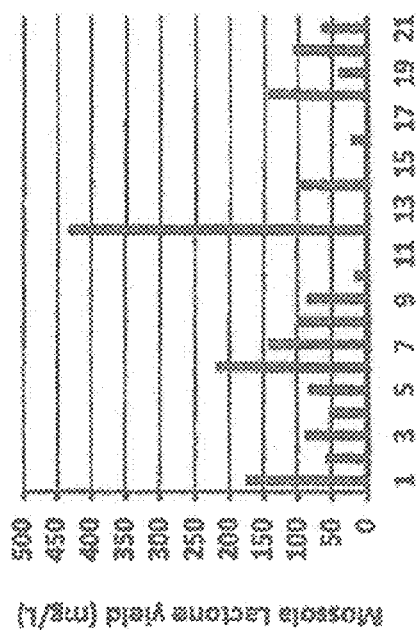
FIGS. 7A and 7B show the effects of trace elements. Media were inoculated with water-washed cell stock cultured in HMDC medium to 0.1 $OD_{600}$ and cultured at 30° C. with 200 rpm shaking for 8 days.

Optimization of Trace Elements Using Factorial Designs $FeSO_4$, $MnSO_4$, $ZnSO_4$, $CuCl_2$, $AlCl_3$ were supplemented to the R15 medium using Factorial Optimal Design at the same concentration [14], either individually or in combinations (Table 6). Results showed that Run #12 which was supplemented with $Fe^{2+}$, $Zn^{2+}$ and $Cu^{2+}$ (named as T3 medium hereafter) produced the highest level of massoia lactone, reaching 433 mg/l on day 8. Run #6 in which $Mn^{2+}$ and $Zn^{2+}$ were both supplemented (named as T2 medium hereafter) ranked $2^{nd}$, yielding 218 mg/l massoia lactone (FIG. 7A; Table 6). In contrast, Basal medium (Run 2, referred to as T0 medium) with $CoCl_2$, $HBO_3$ and $NaMoO_4$ only produced only 58 mg/l massoia lactone, more than 14 folds lower than with T3 medium (FIG. 7A, Table 6). Anova analysis showed that $ZnSO_4$, $CuCl_2$, $FeSO_4$, $ZnSO_4$, $FeSO_4$—$CuCl_2$, $FeSO_4$—$AlCl_3$, and $CuCl_2$—$AlCl_3$ significantly affected massoia lactone production (Tables 6 and 7).

TABLE 6

Trace Elements Part 1

| Run # | $FeSO_4$ | $MnSO_4$ | $ZnSO_4$ | $CuCl_2$ | $AlCl_3$ |
|---|---|---|---|---|---|
| 1  | Y | N | Y | Y | Y |
| 2  | N | N | N | N | N |
| 3  | Y | Y | N | Y | Y |
| 4  | N | Y | N | N | Y |
| 5  | N | N | N | N | Y |
| 6  | N | Y | Y | N | N |
| 7  | N | N | Y | N | Y |
| 8  | Y | N | Y | N | N |
| 9  | N | N | Y | Y | N |
| 10 | Y | N | N | N | Y |
| 11 | Y | N | N | Y | N |
| 12 | Y | N | Y | Y | N |
| 13 | Y | N | N | N | N |
| 14 | N | Y | Y | Y | Y |
| 15 | Y | N | N | Y | N |
| 16 | Y | Y | N | N | Y |
| 17 | Y | Y | N | N | N |
| 18 | Y | Y | Y | Y | Y |
| 19 | N | Y | N | Y | N |
| 20 | Y | Y | Y | Y | N |
| 21 | N | N | N | Y | Y |

Note:
Basal medium (T0 medium) contained 100 g/l glucose, 12.5 g/l $KH_2PO_4$, 1.0 g/l $Na_2HPO_4$, 5.0 g/l $(NH_4)_2SO_4$, 2 g/l urea, 2.5 g/l $MgSO_4 \cdot 7H_2O$, 0.25 g/l $CaCl_2 \cdot 2H_2O$, 2.4 mg/l $CoCl_2$, 0.3 mg/l $HBO_3$ and 1.2 mg/l $NaMoO_4$, pH 5.5. 0.6 ml of trace element mix was added to each litre of medium. Where indicated by N, the trace element was omitted in the trace element mix. The final medium contained various combinations of $FeSO_4 7H_2O$ (24 mg/l), $MnSO_4$ (6 mg/l), $ZnSO_4$ (1.2 mg/l) and $CuCl2$ (0.6 mg/l).

TABLE 7

Anova Analysis of Table 6

| Source | Sum of Squares | df | Mean Square | F Value | p-value Prob > F | Remarks |
|---|---|---|---|---|---|---|
| Model | 469.03 | 15.00 | 31.27 | 17.67 | 0.0025 | significant |
| A—$FeSO_4$ | 6.58 | 1.00 | 6.58 | 3.72 | 0.1118 | |
| B—$MnSO_4$ | 5.67 | 1.00 | 5.67 | 3.20 | 0.1335 | |
| C—$ZnSO_4$ | 305.29 | 1.00 | 305.29 | 172.50 | <0.0001 | significant |
| D—$CuCl_2$ | 22.61 | 1.00 | 22.61 | 12.78 | 0.0160 | significant |
| E—$AlCl_3$ | 3.46 | 1.00 | 3.46 | 1.95 | 0.2211 | |
| AB | 0.87 | 1.00 | 0.87 | 0.49 | 0.5151 | |
| AC | 69.62 | 1.00 | 69.62 | 39.34 | 0.0015 | significant |
| AD | 22.14 | 1.00 | 22.14 | 12.51 | 0.0166 | significant |
| AE | 16.67 | 1.00 | 16.67 | 9.42 | 0.0278 | significant |
| BC | 2.88 | 1.00 | 2.88 | 1.63 | 0.2579 | |
| BD | 0.44 | 1.00 | 0.44 | 0.25 | 0.6408 | |
| BE | 5.87 | 1.00 | 5.87 | 3.32 | 0.1282 | |
| CD | 0.18 | 1.00 | 0.18 | 0.10 | 0.7598 | |
| CE | 0.29 | 1.00 | 0.29 | 0.16 | 0.7043 | |
| DE | 19.93 | 1.00 | 19.93 | 11.26 | 0.0202 | significant |
| Residual | 8.85 | 5.00 | 1.77 | | | |
| Cor Total | 477.88 | 20.00 | | | | |
| Std. Dev. | 1.33 | | R-Squared | 0.98 | | |
| Mean | 21.66 | | Adj R-Squared | 0.93 | | |
| C.V. % | 6.14 | | Pred R-Squared | 0.29 | | |
| PRESS | 339.46 | | Adeq Precision | 16.34 | | |

Figure 7B:
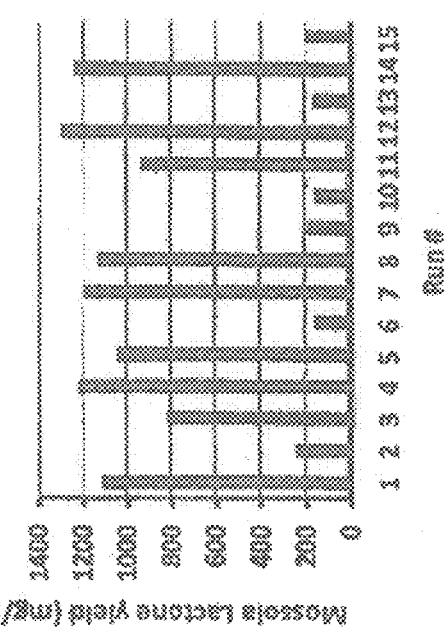

In another experiment, the effects of the remaining trace elements, i.e., $CoCl_2$, $HBO_3$ and $NaMoO_4$ were tested. Results showed that $CoCl_2$ (2.4 mg/l) strongly inhibited massoia lactone production (p<0.0001) while $NaMoO_4$ (1.2 mg/l) significantly improved the production (p<0.05). $HBO_3$ (0.3 mg/l) did not appear to have significant effect (Tables 8 and 9). The best medium was Run 12, with a massoia lactone yield of 1300 mg/l (FIG. 7B). Notably, this medium contains high level of $CaCl_2$ (0.25 g/l $CaCl_2.2H_2O$).

TABLE 8

Trace Elements Part 2

| Run # | $CoCl_2$ | $NaMoO_4$ | $H3BO_4$ |
|---|---|---|---|
| 1  | N | Y | Y |
| 2  | Y | Y | N |
| 3  | N | N | N |
| 4  | N | Y | N |
| 5  | N | N | N |
| 6  | Y | N | Y |
| 7  | N | Y | Y |
| 8  | N | N | Y |
| 9  | Y | Y | Y |
| 10 | Y | N | N |
| 11 | N | N | Y |
| 12 | N | Y | N |
| 13 | Y | Y | Y |

Note:
Media were inoculated to 0.1 $OD_{600}$ with water-washed cell stock cultured in HMDC medium and cultured at 30° C. with 200 rpm shaking for 8 days. Basal medium was T0 medium (Table 6) with various combinations of $CoCl_2$ (2.4 mg/l), $HBO_3$ (0.3 mg/l) and $NaMoO_4$ (1.2 mg/l).

TABLE 9

Anova Analysis of Table 8

| Source | Sum of Squares | df | Mean Square | F Value | p-value Prob > F | Remarks |
|---|---|---|---|---|---|---|
| Model | 2702668.48 | 6.00 | 450444.75 | 47.99 | <0.0001 | significant |
| A—$CoCl_2$ | 2431273.40 | 1.00 | 2431273.40 | 259.0 | <0.0001 | significant |
| B—$NaMoO_4$ | 60353.96 | 1.00 | 60353.96 | 6.43 | 0.0443 | significant |
| C—$H_3BO_4$ | 769.68 | 1.00 | 769.68 | 0.08 | 0.7842 | |
| AB | 21411.70 | 1.00 | 21411.70 | 2.28 | 0.1817 | |
| AC | 320.50 | 1.00 | 320.50 | 0.03 | 0.8595 | |
| BC | 18462.23 | 1.00 | 18462.23 | 1.97 | 0.2103 | |
| Residual | 56320.37 | 6.00 | 9386.73 | | | |
| Lack of Fit | 3671.82 | 1.00 | 3671.82 | 0.35 | 0.5805 | not significant |
| Pure Error | 52648.56 | 5.00 | 10529.71 | | | |
| Cor Total | 2758988.86 | 12.00 | | | | |
| Std. Dev. | 96.89 | R-Squared | 0.98 | | | |
| Mean | 741.48 | Adj R-Squared | 0.96 | | | |
| C.V. % | 13.07 | Pred R-Squared | 0.91 | | | |
| PRESS | 243152.35 | Adeq Precision | 15.75 | | | |

Example 5

Utilization of Various Carbon Sources by *A. melanogenum* W5-2

Figure 8:
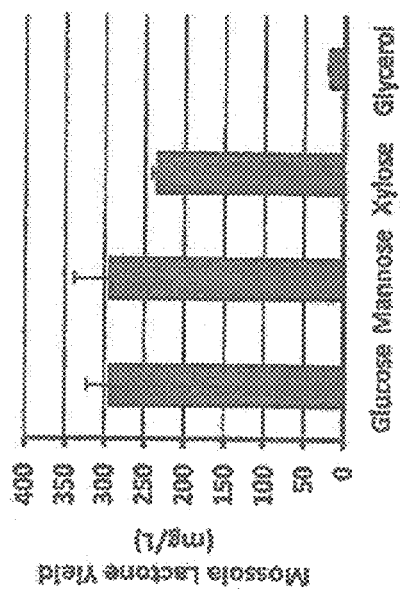
FIG. 8 shows production of massoia lactone with various carbon sources. W5-2 was cultured in T2 medium with glucose, mannose, xylose or glycerol as carbon sole source for 4 days. Each data set derived from 3 biological replicates. Error bars indicates SD.

To see if strain W5-2 is able to utilize other carbon sources for the production of massoia lactone, glucose in T2 medium was replaced with the same concentrations of D-(+)-mannose, D-(+)-xylose and glycerol. Mannose was essentially as efficiently utilized as glucose. The strain also efficiently converted xylose to massoia lactone although the yield was about 20% lower than with glucose under the conditions tested. Glycerol was a poor carbon source (FIG. 8).

Example 6

Fed-Batch Fermentation

Figure 9:
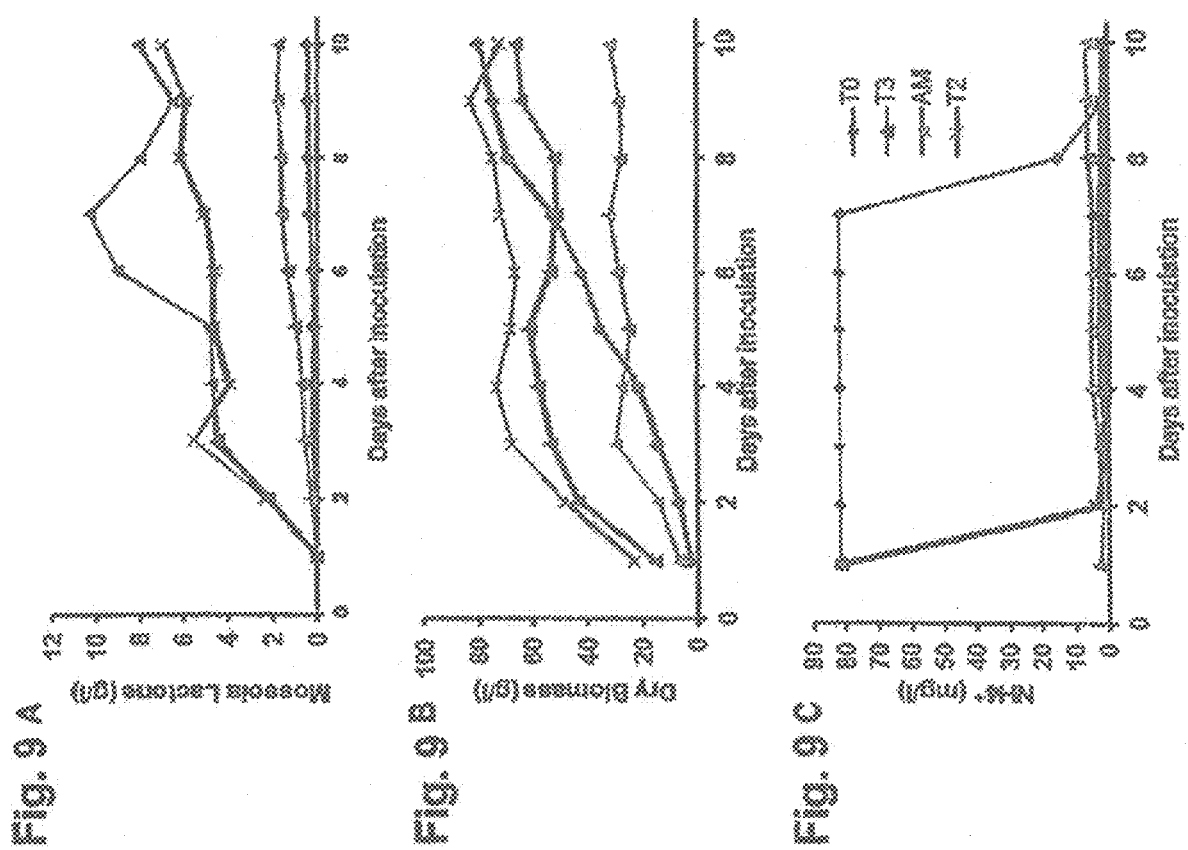
FIGS. 9A-9C show a comparison of massoia lactone yields in 4 media. The symbols for the media are shown in FIG. 9C. AM refers to a modified A-21M medium (MA-21M) containing 120 g/l glucose, 1.5 g/l NaNO3, 1.0 g/l KNO3, 0.05 g/l KH2PO4, 0.2 g/l MgSO4, 0.0056 g/l FeSO4, 0.2 g/l Yeast Extract (pH 5.5). Seed culture was made in HMDC medium with complete trace elements.
Figure 10:
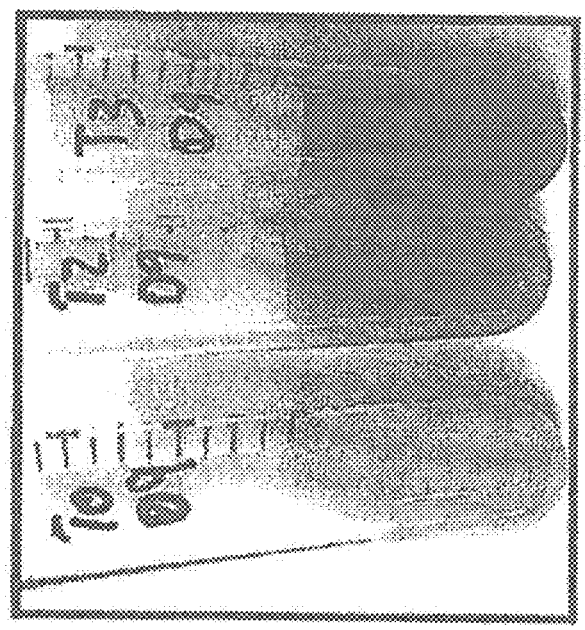
FIG. 10 shows a comparison of cells cultured in T0, T2 and T3 media. Cells were cultured in 2 L fermentor for 9 days.

To verify the performance of the optimized media, fed-batch fermentation was performed in 2 L bioreactors using T0, T2 and T3 media. As the original A-21M medium barely supports the growth of W-52, a modified A-21M medium (MA-21M) was used as a reference. MA-21M contained 120 g/l glucose, 1.5 g/l $NaNO_3$, 1.0 g/l $KNO_3$, 0.05 g/l $KH_2PO_4$, 0.2 g/l $MgSO_4$, 0.0056 g/l $FeSO_4$, 0.2 g/l Yeast Extract (pH 5.5). Indeed, both T2 and T3 media showed drastically improved massoia lactone production compared to the T0 medium (FIG. 9A). Best result was observed with T3 medium, in which massoia lactone level peaked at Day 7, reaching 10.268 g/l, with a volumetric productivity of 61.11 mg/hr/l. In T2 medium, massoia lactone production was significantly lower than T3 medium throughout the time course. Maximal production was delayed at least 3 days with a titre of 6.924 g/l and volumetric productivity of 28.85 mg/hr/l. In contrast, maximal titre for T0 medium was only 0.441 g/l observed at Day 10, with a volumetric productivity of 1.84 mg/hr/l. The MA-21M medium performed better than T0 medium, peaking Day 9 with a titre of 1.777 g/l and volumetric productivity of 8.23 mg/hr/l. Thus, the volumetric productivity in T3 and T2 medium were 7.43-fold and 3.51-fold higher than that of A-21M medium, respectively.

In T0 and T2 medium, cells produced much higher biomass at the cost of the desired metabolite (FIG. 9B). Nitrogen source in both T2 and T3 media were rapidly consumed and became depleted after Day 2. In contrast, $NH^{4+}$ level remained high in T0 medium until Day 8 (FIG. 9C). The cells showed very different colors: cells contained strong black pigments, presumably melanin, in T2 and T3 media. In stark contrast with previous report [6], the result suggests that the production of black pigment was associated with high massoia lactone production.

Example 7

Effect of Medium pH

Figure 11:
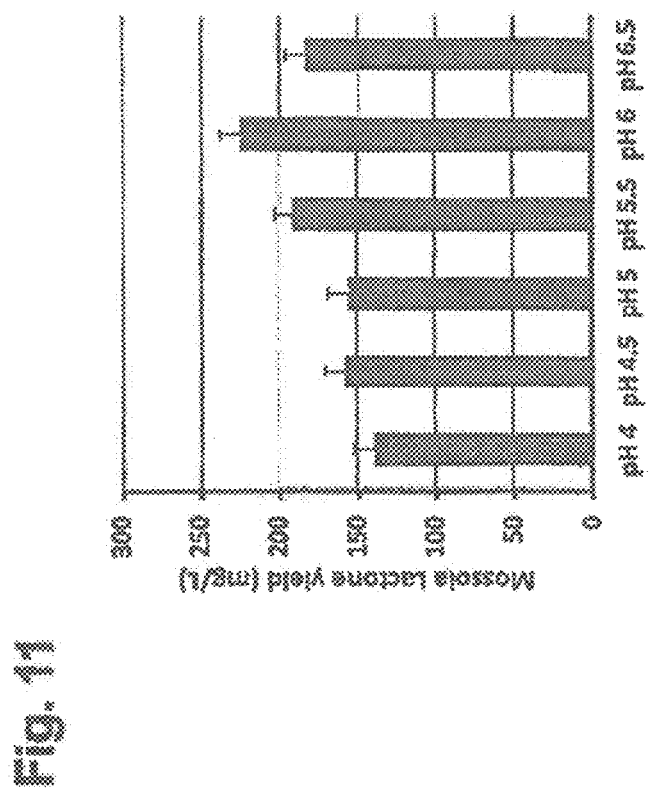
FIG. 11 shows the effect of medium pH on massoia lactone yield. T2 medium was adjusted to various pH from pH 4 to pH 6.5. Cells were cultured for 5 days.

W5-2 cells cultured in YPD medium was cultured in T2 medium adjusted to various pH values ranging from pH 4 to pH 6.5. The maximal titre was observed with pH6.0. Slight reduction of yield was seen for pH 5.5 and 6.5 (FIG. 11).

Example 8

Purity of Massoia Lactone

Figure 12A:
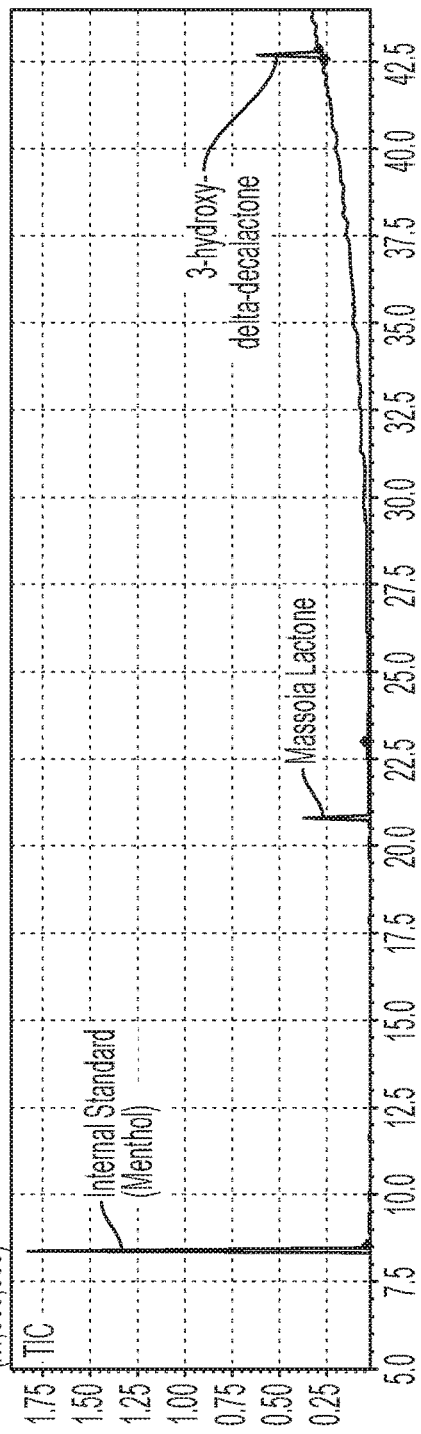
Figure 12B:
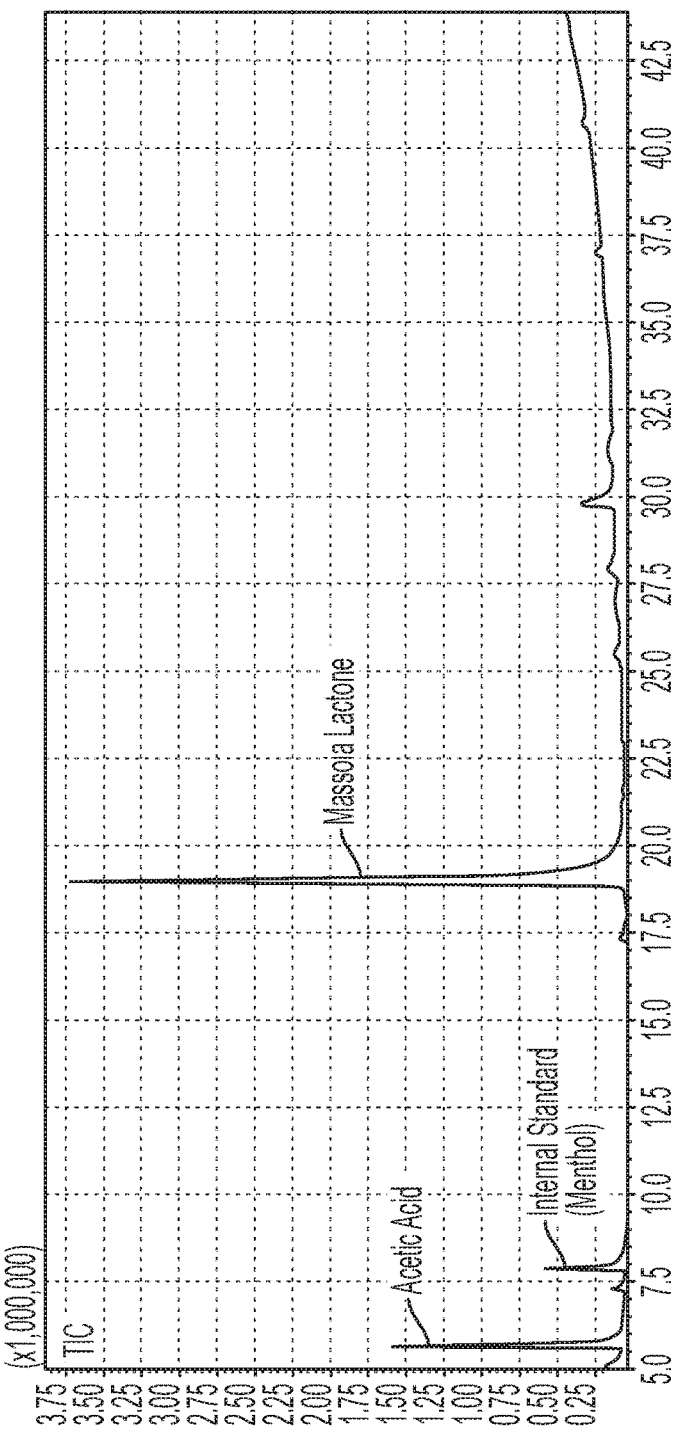

Fed-batch fermentation was performed in 2 L bioreactors using T3 media. The total fermentation broth was hydrolyzed with $H_2SO_4$. GCMS analysis of the showed the high production of a single peak of massoia lactone (FIGS. 12A and 12B). This is in contrast to earlier work with *Aureobasidium pullalan* A-21M, which produced 3-hydroxyl delta-decalactone at ratio of about 1:1.7 [6].

Example 9

Comparison of House-Keeping Genes

The coding sequences (CDS) of five house-keeping genes of W5-2 strain were identified using known protein sequences of *Ustilago maydis* as the query to search against the W5-2 whole transcriptome database. SEQ ID NOs:2, 7, 8, 9 and 10 are the CDS sequence for GPD1, Actin, TEF1A, Tubulin1 and RPB1 (RNA polymerase 2, the largest subunit), respectively. There were high variations in the levels of sequence identity to homologs of different *Aureobasidium* species (Tables 10-14). Note that *A. pullulans* AY4 has been re-classified as *A. melanogenum* AY4. For example, GDP1 genomic sequence shares at least 99% identity to homologs of *A. melanogenum* species at least over 98% of SEQ ID NO:2 while the inter-species homology for GPD1 CDS is below 97% over 98% of SEQ ID NO:2 (Table 10). Similarly, TEFA genomic sequence shares at least 99% identity to homologs of *A. melanogenum* species over 99% of SEQ ID NO:8 while the inter-species homology for TEF1A CDS is below 98% over 94% of SEQ ID NO:8 (Table 12). RPB1 (SEQ ID NO:10) sequence is the most divergent.

RPB1 genomic sequence shares at least 96% identity to homologs of *A. melanogenum* species over 98% of SEQ ID NO:10 while the inter-species homology for RPB1 CDS is below 90% over 92% of SEQ ID NO:10 (Table 14).

TABLE 10

BLASTn Search Results of GPD1 (SEQ ID NO: 2)

| Description | Max score | Total score | Query cover | E value | Ident | Accession |
|---|---|---|---|---|---|---|
| *Aureobasidium melanogenum* CBS 110374 scaffold_4_c3, whole genome shotgun sequence | 1459 | 1812 | 98% | 0.0 | 99% | AYEN01000011.1 |
| *Aureobasidium pullulans* AY4 contig20, whole genome shotgun sequence | 1448 | 1795 | 98% | 0.0 | 99% | AMCU01000020.1 |
| *Aureobasidium namibiae* CBS 147.97 scaffold_2_c1, whole genome shotgun sequence | 1371 | 1692 | 98% | 0.0 | 97% | AYEM01000004.1 |
| *Aureobasidium pullulans* isolate Santander contig_514, whole genome shotgun sequence | 1321 | 1635 | 98% | 0.0 | 96% | LVWM01000514.1 |
| *Aureobasidium subglaciale* EXF-2481 scaffold_2_c1, whole genome shotgun sequence | 1315 | 1636 | 98% | 0.0 | 96% | AYYB01000004.1 |
| *Aureobasidium pullulans* EXF-150 scaffold_6_c1, whole genome shotgun sequence | 1293 | 1605 | 98% | 0.0 | 95% | AYEO01000008.1 |

TABLE 11

BLASTn Search Results of Actin (SEQ ID NO: 7)

| Description | Max score | Total score | Query cover | E value | Ident | Accession |
|---|---|---|---|---|---|---|
| *Aureobasidium pullulans* AY4 contig120, whole genome shotgun sequence | 1216 | 2960 | 99% | 0.0 | 92% | AMCU01000120.1 |
| *Aureobasidium melanogenum* CBS 110374 scaffold_3_c1, whole genome shotgun sequence | 1210 | 2960 | 99% | 0.0 | 92% | AYEN01000004.1 |
| *Aureobasidium namibiae* CBS 147.97 scaffold_18_c1, whole genome shotgun sequence | 917 | 1016 | 44% | 0.0 | 86% | AYEM01000024.1 |
| *Aureobasidium pullulans* isolate Santander contig_225, whole genome shotgun sequence | 828 | 1993 | 96% | 0.0 | 84% | LVWM01000225.1 |
| *Aureobasidium pullulans* EXF-150 scaffold_2_c1, whole genome shotgun sequence | 811 | 1872 | 93% | 0.0 | 84% | AYEO01000002.1 |
| *Aureobasidium subglaciale* EXF-2481 scaffold_19_c1, whole genome shotgun sequence | 614 | 735 | 39% | 4e-174 | 82% | AYYB01000022.1 |

TABLE 12

BLASTn Search Results of TEF1A (SEQ ID NO: 8)

| Description | Max score | Total score | Query cover | E value | Ident | Accession |
|---|---|---|---|---|---|---|
| *Aureobasidium melanogenum* CBS 110374 scaffold_11_c1, whole genome shotgun sequence | 2041 | 2472 | 99% | 0.0 | 99% | AYEN01000021.1 |
| *Aureobasidium pullulans* AY4 contig64, whole genome shotgun sequence | 2041 | 2472 | 99% | 0.0 | 99% | AMCU01000064.1 |
| *Aureobasidium namibiae* CBS 147.97 scaffold_4_c1, whole genome shotgun sequence | 2015 | 2368 | 94% | 0.0 | 98% | AYEM01000007.1 |
| *Aureobasidium pullulans* EXF-150 scaffold_17_c1, whole genome shotgun sequence | 1881 | 2112 | 92% | 0.0 | 96% | AYEO01000027.1 |
| *Aureobasidium subglaciale* EXF-2481 scaffold_23_c1, whole genome shotgun sequence | 1753 | 1985 | 93% | 0.0 | 94% | AYYB01000027.1 |

TABLE 13

BLASTn Search Results of TubulinI (SEQ ID NO: 9)

| Description | Max score | Total score | Query cover | E value | Ident | Accession |
|---|---|---|---|---|---|---|
| *Aureobasidium melanogenum* CBS 110374 scaffold_23_c2, whole genome shotgun sequence | 1284 | 2316 | 97% | 0.0 | 98% | AYEN01000040.1 |
| *Aureobasidium pullulans* AY4 contig32, whole genome shotgun sequence | 1284 | 2305 | 97% | 0.0 | 98% | AMCU01000032.1 |
| *Aureobasidium namibiae* CBS 147.97 scaffold_17_c1, whole genome shotgun sequence | 1194 | 2187 | 97% | 0.0 | 96% | AYEM01000023.1 |
| *Aureobasidium pullulans* isolate Santander contig_153, whole genome shotgun sequence | 1160 | 1981 | 92% | 0.0 | 95% | LVWM01000153.1 |
| *Aureobasidium pullulans* EXF-150 scaffold_3_c1, whole genome shotgun sequence | 1158 | 1984 | 92% | 0.0 | 95% | AYEO01000003.1 |
| *Aureobasidium subglaciale* EXF-2481 scaffold_0_c1, whole genome shotgun sequence | 1140 | 2033 | 97% | 0.0 | 95% | AYYB01000001.1 |

TABLE 14

BLASTn Search Results of RPB1 (SEQ ID NO:10)

| Description | Max score | Total score | Query cover | E value | Ident | Accession |
|---|---|---|---|---|---|---|
| *Aureobasithum melanogenum* CBS 110374 scaffold_1_c2, whole genome shotgun sequence | 7915 | 9706 | 98% | 0.0 | 96% | AYEN01000002.1 |
| *Aureobasidium pullulans* AY4 contig81, whole genome shotgun sequence | 7866 | 9631 | 99% | 0.0 | 96% | AMCU01000081.1 |
| *Aureobasidium namibiae* CBS 147.97 scaffold_1_c2, whole genome shotgun sequence | 6032 | 6855 | 91% | 0.0 | 89% | AYEM01000002.1 |
| *Aureobasidium subglaciale* EXF-2481 scaffold_15_c1, whole genome shotgun sequence | 5389 | 6038 | 91% | 0.0 | 87% | AYYB01000017.1 |
| *Aureobasidium pullulans* contig_319, whole genome shotgun sequence | 5334 | 5999 | 92% | 0.0 | 86% | LVWM01000319.1 |
| *Aureobasidium pullulans* contig_233, whole genome shotgun sequence | 5334 | 5999 | 92% | 0.0 | 86% | LVWM01000233.1 |
| *Aureobasidium pullulans* contig_45, whole genome shotgun sequence | 5334 | 5999 | 92% | 0.0 | 86% | LVWM01000045.1 |

TABLE 14-continued

BLASTn Search Results of RPB1 (SEQ ID NO:10)

| Description | Max score | Total score | Query cover | E value | Ident | Accession |
|---|---|---|---|---|---|---|
| *Aureobasidium pullulans* EXF-150 scaffold_18_c1, whole genome shotgun sequence | 5323 | 5993 | 92% | 0.0 | 86% | AYE001000028.1 |

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

1. Rali T, Wossa S W, Leach D N (2007) Comparative chemical analysis of the essential oil constituents in the bark, heartwood and fruits of *Cryptocarya massoy* (Oken) Kosterm. (Lauraceae) from Papua New Guinea. Molecules 12: 149-154.
2. Mineeva I (2012) Asymmetric synthesis of (−)-(R)-massoia lactone, (R)-δ-decalactone, and (+)-(3R, 5R)-3-hydroxydecano-5-lactone. Formal synthesis of verbalactone. Russian Journal of Organic Chemistry 48: 977-981.
3. Gocho S, Rumi K, Tsuyoshi K (1998) Process for the production of delta decalactone. Google Patents.
4. Muys G T, Van Der Ven B, De Jonge A (1963) Preparation of Optically Active γ- and δ-Lactones by Microbiological Reduction of the Corresponding Keto Acids. Applied microbiology 11: 389-393.
5. Ramachandran P V, Reddy M V R, Brown H C (2000) Asymmetric synthesis of goniothalamin, hexadecanolide, massoia lactone, and parasorbic acid via sequential allylboration-esterification ring-closing metathesis reactions. Tetrahedron Letters 41: 583-586.
6. Kurosawa T, Sakai K, Nakahara T, Oshima Y, Tabuchi T (1994) Extracellular accumulation of the polyol lipids, 3, 5-dihydroxydecanoyl and 5-hydroxy-2-decenoyl esters of arbitol and mannitol, by *Aureobasidium* sp. Bioscience, biotechnology, and biochemistry 58: 2057-2060.
7. Manitchotpisit P, Price N P J, Leathers T D, Punnapayak H (2011) Heavy oils produced by *Aureobasidium pullulans*. Biotechnology Letters 33: 1151-1157.
8. White T J, Bruns T, Lee S, Taylor J (1990) Amplification and direct sequencing of fungal ribosomal RNA genes for phylogenetics. PCR protocols: a guide to methods and applications 18: 315-322.
9. Bellemain E, Carlsen T, Brochmann C, Coissac E, Taberlet P, et al. (2010) ITS as an environmental DNA barcode for fungi: an in silico approach reveals potential PCR biases. Bmc Microbiology 10: 189.
10. Tamura K, Peterson D, Peterson N, Stecher G, Nei M, et al. (2011) MEGA5: molecular evolutionary genetics analysis using maximum likelihood, evolutionary distance, and maximum parsimony methods. Molecular biology and evolution 28: 2731-2739.
11. Saitou N, Nei M (1987) The neighbor-joining method: a new method for reconstructing phylogenetic trees. Molecular biology and evolution 4: 406-425.
12. Felsenstein J (1981) Evolutionary trees from DNA sequences: a maximum likelihood approach. Journal of molecular evolution 17: 368-376.
13. Fitch W M (1971) Toward defining the course of evolution: minimum change for a specific tree topology. Systematic Biology 20: 406-416.
14. Pan J G, Kwak M Y, Rhee J S (1986) High density cell culture of *Rhodotorula glutinis* using oxygen-enriched air. Biotechnology letters 8: 715-718.
15. Liu Y, Koh C M J, Ji L (2011) Bioconversion of crude glycerol to glycolipids in *Ustilago maydis*. Bioresource technology 102: 3927-3933.
16. Carvalho A, Meireles L, Malcata F (1998) Rapid spectrophotometric determination of nitrates and nitrites in marine aqueous culture media. Analusis 26: 347-351.
17. Solorzano L (1969) Determination of ammonia in natural waters by the phenolhypochlorite method. Limnol Oceanogr 14: 799-801.
18. Cock P J, Gruning B A, Paszkiewicz K, Pritchard L (2013) Galaxy tools and workflows for sequence analysis with applications in molecular plant pathology. PeerJ 1: e167.
19. Patel R K, Jain M (2012) NGS QC Toolkit: a toolkit for quality control of next generation sequencing data. PLoS One 7: e30619.

20. Trapnell C, Roberts A, Goff L, Pertea G, Kim D, et al. (2012) Differential gene and transcript expression analysis of RNA-seq experiments with TopHat and Cufflinks. Nat Protoc 7: 562-578.
21. Trapnell C, Pachter L, Salzberg S L (2009) TopHat: discovering splice junctions with RNA-Seq. Bioinformatics 25: 1105-1111.
22. Trapnell C, Williams B A, Pertea G, Mortazavi A, Kwan G, et al. (2010) Transcript assembly and quantification by RNA-Seq reveals unannotated transcripts and isoform switching during cell differentiation. Nat Biotech 28: 511-515.
23. Grabherr M G, Haas B J, Yassour M, Levin J Z, Thompson D A, et al. (2011) Full-length transcriptome assembly from RNA-Seq data without a reference genome. Nat Biotechnol 29: 644-652.
24. Haas B J, Papanicolaou A, Yassour M, Grabherr M, Blood P D, et al. (2013) De novo transcript sequence reconstruction from RNA-seq using the Trinity platform for reference generation and analysis. Nat Protoc 8: 1494-1512.
25. Robinson M D, McCarthy D J, Smyth G K (2010) edgeR: a Bioconductor package for differential expression analysis of digital gene expression data. Bioinformatics 26: 139-140.
26. Li B, Dewey C N (2011) RSEM: accurate transcript quantification from RNA-Seq data with or without a reference genome. BMC Bioinformatics 12: 323.
27. Greenspan P, Mayer E P, Fowler S D (1985) Nile red: a selective fluorescent stain for intracellular lipid droplets. The Journal of cell biology 100: 965-973.
28. Sackett D L, Wolff J (1987) Nile red as a polarity-sensitive fluorescent probe of hydrophobic protein surfaces. Analytical biochemistry 167: 228-234.
29. Morita T, Konishi M, Fukuoka T, Imura T, Kitamoto D (2006) Discovery of Pseudozyma rugulosa NBRC 10877 as a novel producer of the glycolipid biosurfactants, mannosylerythritol lipids, based on rDNA sequence. Applied microbiology and biotechnology 73: 305-313.
30. Gostin C, Ohm R A, Kogej T, Sonjak S, Turk M, et al. (2014) Genome sequencing of four *Aureobasidium pullulans* varieties: biotechnological potential, stress tolerance, and description of new species. BMC genomics 15: 549.
31. Gostincar C, Ohm R A, Kogej T, Sonjak S, Turk M, et al. (2014) Genome sequencing of four *Aureobasidium pullulans* varieties: biotechnological potential, stress tolerance, and description of new species. BMC Genomics 15: 549.
32. Haas B J, Papanicolaou A, Yassour M, Grabherr M, Blood P D, et al. (2013) De novo transcript sequence reconstruction from RNA-seq using the Trinity platform for reference generation and analysis. Nature protocols 8: 1494-1512.
33. Trapnell C, Pachter L, Salzberg SL (2009) TopHat: discovering splice junctions with RNA-Seq. Bioinformatics 25: 1105-1111.
34. Takesako K, Kuroda H, Inoue T, Haruna F, Yoshikawa Y, et al. (1993) Biological properties of aureobasidin A, a cyclic depsipeptide antifungal antibiotic. The Journal of antibiotics 46: 1414-1420.
35. Slightom J L, Metzger B P, Luu H T, Elhammer A P (2009) Cloning and molecular characterization of the gene encoding the Aureobasidin A biosynthesis complex in *Aureobasidium pullulans* BP-1938. Gene 431: 67-79.
36. Lindau in Nat Pflansenfam 1(1):373, Engler & Prantl (eds.)

---

What is claimed is:

1. A method of fermentative production of massoia lactone comprising culturing an *Aureobasidium melanogenum* strain that expresses no functional Aureobasidin A synthase gene mRNA when culture medium for a period of time to yield more than 10 g of crude massoia lactone in a fermentation product, and purifying the massoia lactone from the fermentation product, wherein the culture medium comprises:

10.0 g/l to 15 g/l, 0.5 g/l to 2.0 g/l $Na_2HPO_4$, 3.5 g/l to 6.5 g/l, $(NH_4)_2SO_4$, 1.0 g/l to 4.0 g/l $MgSO_4 \cdot 7H_2O$ and 0.10 g/l to 0.40 g/l $CaCl_2 \cdot 2H_2O$;

at least two trace elements selected from the group consisting of $Fe^{2+}$, $Cu^{2+}$, $Zn^{2+}$ and $MoO_4^{2-}$, wherein each trace element present in the culture medium is present in an amount from 0.1 μM to 1.0 mM;

1.5 g/l to 2.5 g/l, urea; and a carbon source selected from the group consisting of glucose, mannose, xylose and mixtures thereof, wherein the carbon source present in the culture medium from 9.2% to 12%, wherein the pH of the culture medium is from 5.5 to 6.5, and wherein the yield of purified massoia lactone from the fermentation product is at least 50%.

2. The method of claim 1, wherein the period of time for culturing is 4 days to 12 days.

3. The method of claim 1, wherein the yield of crude massoia lactone in the fermentation product is at least 11 g/l.

4. The method of claim 1, wherein the yield of crude massoia lactone in the fermentation product is from 10 g/l to 25 g/l.

5. The method of claim 1, wherein the *Aureobasidium melanogenum* strain is *Aureobasidium melanogenum* W5-2 deposited with Agricultural Research Culture Collection (NRRL) and assigned Accession Number NRRL 67063.

6. The method of claim 1, wherein the fermentation product is substantially free of contaminant 3-hydroxyl delta-decalactone (3-hydroxydecan-5-olide).

7. The method of claim 5, wherein the fermentation product is substantially free of contaminant 3-hydroxyl delta-decalactone (3-hydroxydecan-5-olide).

8. The method of claim 1, wherein the purification step comprises hydrolyzing the fermentation product by a strong inorganic acid.

9. The method of claim 5, wherein the purification step comprises hydrolyzing the fermentation product by a strong inorganic acid.

10. The method of claim 1, wherein the *Aureobasidium melanogenum* strain shares 100% identity with at least 98% of the nucleotide sequence of SEQ ID NO: 2, or wherein the *Aureobasidium melanogenum* strain shares 100% identity with at least 99% of the nucleotide sequence of SEQ ID NO: 8, or wherein the *Aureobasidium melanogenum* strain shares 100% identity with at least 98% of the nucleotide sequence of SEQ ID NO: 10.

\* \* \* \* \*

SEQUENCE LISTING

<160> NUMBER OF SEQ ID NOS: 10

<210> SEQ ID NO 1
<211> LENGTH: 666
<212> TYPE: DNA
<213> ORGANISM: Aureobasidium melanogenum strain W5-2
<220> FEATURE:
<221> NAME/KEY: misc_feature
<222> LOCATION: (36)..(36)
<223> OTHER INFORMATION: n is a, c, g, or t

<400> SEQUENCE: 1

```
agcgtcccgc caaagcaaca agtagtttta acaacnaagg gttcttggtc atttagagga      60
agtaaaagtc gtaaacaagg cttccgtaag gtgaacctgc ggaaggatca ttaaagagta     120
agggtgctca gcgcccgacc tccaacccct tgttgttaaa actaccttgt tgctttggcg     180
ggaccgctcg gtctcgagcc gctggggatt cgtcccaggc gagcgcccgc cagagttaaa     240
ccaaactctt gttatttaac cggtcgtctg agttaaaatt ttgaataaat caaaactttc     300
aacaacggat ctcttggttc tcgcatcgat gaagaacgca gcgaaatgcg ataagtaatg     360
tgaattgcag aattcagtga atcatcgaat ctttgaacgc acattgcgcc ccttggtatt     420 ccgagggca tgcctgttcg agcgtcatta caccactcaa gctatgcttg gtattgggtg     480
ccgtccttag ttgggcgcgc cttaaagacc tcggcgaggc ctcaccggct ttaggcgtag     540
tagaatttat tcgaacgtct gtcaaggag aggacttctg ccgactgaaa ccttttattt     600
ttctaggttg acctcggatc aggtagggat acccgctgaa cttaagcata tcaataagcg     660
```

```
                                                  gaggaa                                              666

<210> SEQ ID NO 2
<211> LENGTH: 1014
<212> TYPE: DNA
<213> ORGANISM: Aureobasidium species

<400> SEQUENCE: 2
atgcctgtca acgtcggtat taacggcttc ggtcgcattg gtcgcattgt cttccgcaat        60
gccatcgagc tcgacaacgt ccacgtcgtt gccgtcaacg accccttcat tgagcccgag       120
tacgctgcct acatgctcaa gtacgactcc gtccacggcc agttcaaggg taccattgag       180
gtctccggca aggacctgat cgtcaacggc aagaaggtca ccttctacac cgagagagac       240
cccgccaaca tcccctgggc tgagactggc gcctactacg tcgtcgagtc caccggtgtc       300
ttcaccacca ccgagaaggc ctccgctcac ttgaagggtg gcgccaagaa ggtcgtcatc       360
tctgctccct ccgctgacgc ccccatgttc gtcatgggtg tcaacgagaa gagctacaag       420
tccgacatcc aggtcctgtc caacgcctct tgcaccacca actgccttgc tcccctcgcc       480
aaggtcatca cgacaagtt cggtatcgtt gagggtctca tgaccaccat ccactcctac       540
accgccaccc agaagaccgt cgacggtcct tccggcaagg actggcgcgg tggccgtgct       600
gctgcccaga acatcatccc cagcagcact ggtgccgcca aggctgtcgg caaggtcatt       660
cctcagctca cggcaagct gaccggtatg tccatgcgtg tccccaccgc caacgtctcc       720
gttgtcgacc ttactgcccg tctcgagaag ggtgcctctt acgacaccat caagaaggcc       780
atcaaggagg cctccgaggg tgagcttaag ggcattctcg gctacaccga ggacgacatt       840
gtctcctccg acatgtgcgg tgccaacgag tcctccatct tcgacgccaa ggccggtatc       900
tcgctcaacg acaacttcgt caagcttgtc tcctggtacg acaacgagtg gggttactcc       960
cgccgtgtcc tcgacctcct ggcttacatt gccaaggtcg acggtaacgc ataa          1014

<210> SEQ ID NO 3
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 3
tccgtaggtg aacctgcgg                                                     19

<210> SEQ ID NO 4
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 4
tcctccgctt attgatatgc                                                    20

<210> SEQ ID NO 5
<211> LENGTH: 35683
<212> TYPE: DNA
<213> ORGANISM: Aureobasidium pullulans strain BP-1938
<220> FEATURE:
<221> NAME/KEY: CDS
<222> LOCATION: (506)..(35485)

<400> SEQUENCE: 5
```

```
cgatggcaac tgttgccaac aaagcggaaa atttctctat gcggaggtgt gttacgaatc    60
tgcctaactt ttgcctcatc cactgacgac tgactaatca cagggaggtt agtgttcgct   120
gccgagggcg ccatgtcagg cgtcgcccgg cagagttgat catgcaaatt cgaagtgagc   180
accgatcaga tgagtcaagt caatatgcat tgtcttatag ccagacgata tgcgcgccac   240
aacgattctt gctgacatca cccatataca gtcataagtg tagttcgctt acggagctca   300
catgaccgca atgtctatca gagtaagcat gtctgtcgtg gctgacgctg ctctaacaat   360
gatgcgtgaa gcatcagtca atcagcaagc gaggaatact tctgccacat tgaccagact   420
atcaaccctc tgcatcgag caacagcgac agcaaacgtt tgactacaac aacagccacc    480
gtatagcaac attcaacaaa caaag atg tcg cga atg cca cag ggc gca gca     532
                            Met Ser Arg Met Pro Gln Gly Ala Ala
                              1               5 aga cgc aac gac tgt gtc tcg gag cac caa ggc act acc gat ctg gag     580
Arg Arg Asn Asp Cys Val Ser Glu His Gln Gly Thr Thr Asp Leu Glu
 10              15                  20                  25 gat att gtg cga ttc tgg gaa cga cac tta gac ggt gtg aat gca tct     628
Asp Ile Val Arg Phe Trp Glu Arg His Leu Asp Gly Val Asn Ala Ser
                 30                  35                  40 gca ttc cct gct ctg tca tct agc ttg gtt gta cct aaa ccc aaa ttg     676
Ala Phe Pro Ala Leu Ser Ser Ser Leu Val Val Pro Lys Pro Lys Leu
             45                  50                  55 cag aca gag cat cgc atc agc ctc gga acc gcc gtg tct gat cag tgg     724
Gln Thr Glu His Arg Ile Ser Leu Gly Thr Ala Val Ser Asp Gln Trp
         60                  65                  70 tca gat gca gtc atc tgt cga gct gca ctt gct gtc att ttg gcc cgt     772
Ser Asp Ala Val Ile Cys Arg Ala Ala Leu Ala Val Ile Leu Ala Arg
 75                  80                  85 tat acg cac gct act gaa gcg ctc tac ggc att gtg gtc gag cag cct     820
Tyr Thr His Ala Thr Glu Ala Leu Tyr Gly Ile Val Val Glu Gln Pro
 90                  95                 100                 105 tca gtc tcc aat gcc cag aaa cga tcc gcc gat gat gca tcc tcc att     868
Ser Val Ser Asn Ala Gln Lys Arg Ser Ala Asp Asp Ala Ser Ser Ile
             110                 115                 120 gtt gta ccg att cgt gtg caa tgt gca tct ggt caa ttt ggg aac gat     916
Val Val Pro Ile Arg Val Gln Cys Ala Ser Gly Gln Phe Gly Asn Asp
         125                 130                 135 att ttg gct gca att gct act cac gac gct tct tgt cgt agc ctc agc     964
Ile Leu Ala Ala Ile Ala Thr His Asp Ala Ser Cys Arg Ser Leu Ser
     140                 145                 150 gcg atc ggc ctg gat ggc att cgc tgt ctt gat gat gct aaa act gtg    1012
Ala Ile Gly Leu Asp Gly Ile Arg Cys Leu Asp Asp Ala Lys Thr Val
155                 160                 165 gct cgg gga tta cag act gta ttg act gta acc agc agg aag tcg gtg    1060
Ala Arg Gly Leu Gln Thr Val Leu Thr Val Thr Ser Arg Lys Ser Val
170                 175                 180                 185 gac gca tca agc cca aac att ctc gac ttg gag aac atc gca tct tct    1108
Asp Ala Ser Ser Pro Asn Ile Leu Asp Leu Glu Asn Ile Ala Ser Ser
                190                 195                 200 cac ggt cga gct ctc atg ata gaa tgt caa atg agc acc acc tcg gca    1156
His Gly Arg Ala Leu Met Ile Glu Cys Gln Met Ser Thr Thr Ser Ala
            205                 210                 215 tgc ttg cgt gca cag tac gac gcg ggc atc ttg cgt aat gaa cag gta    1204
Cys Leu Arg Ala Gln Tyr Asp Ala Gly Ile Leu Arg Asn Glu Gln Val
        220                 225                 230 gtt cgt ctt ctc aaa cag ctc gcg ctt tcg atc cag cac ttt cga ggt    1252
Val Arg Leu Leu Lys Gln Leu Ala Leu Ser Ile Gln His Phe Arg Gly
    235                 240                 245
```

```
aac gct gcc aac gac ctg cta cgc gac ttc tgc ttt atc tcg cca ggc    1300
Asn Ala Ala Asn Asp Leu Leu Arg Asp Phe Cys Phe Ile Ser Pro Gly
250                 255                 260                 265 gaa gag atg gaa att gca tac tgg aat cgt cga agc att cgc aca aat    1348
Glu Glu Met Glu Ile Ala Tyr Trp Asn Arg Arg Ser Ile Arg Thr Asn
                270                 275                 280 gag gtt tgt atc cat gat gtg atc ttt aag agg gcg acc tac atg ccg    1396
Glu Val Cys Ile His Asp Val Ile Phe Lys Arg Ala Thr Tyr Met Pro
            285                 290                 295 act gat acg gcg gtt tcc gcc tgg gat ggg gag tgg aca tac gca gat    1444
Thr Asp Thr Ala Val Ser Ala Trp Asp Gly Glu Trp Thr Tyr Ala Asp
        300                 305                 310 cta gat gtc gta tct tca tgt ctt gcc gat tac gtt cgg tcc ttg gat    1492
Leu Asp Val Val Ser Ser Cys Leu Ala Asp Tyr Val Arg Ser Leu Asp
315                 320                 325 ctg agg tct gga caa gcc ata cca cta tgc ttc gag aag tca aga aac    1540
Leu Arg Ser Gly Gln Ala Ile Pro Leu Cys Phe Glu Lys Ser Arg Asn
330                 335                 340                 345 acc atc gcc gct atg gtg gcc gtt ctc aaa gct ggt cat ccg ttt tgc    1588
Thr Ile Ala Ala Met Val Ala Val Leu Lys Ala Gly His Pro Phe Cys
                350                 355                 360 ctg att gac ccg tct act cca tct gcg aga atc act cag atg tgc gag    1636
Leu Ile Asp Pro Ser Thr Pro Ser Ala Arg Ile Thr Gln Met Cys Glu
            365                 370                 375 cag atg tcc gct acc gtc gct ttc gct tcg aga gca ctt tgt agc atc    1684
Gln Met Ser Ala Thr Val Ala Phe Ala Ser Arg Ala Leu Cys Ser Ile
        380                 385                 390 atg caa gca gga gtc tct aga tgt att gca gtt gat gac gat ctc ttt    1732
Met Gln Ala Gly Val Ser Arg Cys Ile Ala Val Asp Asp Asp Leu Phe
395                 400                 405 caa tcc ttg tca tca gtc atc ggg tgt cca cag atg tcc atg acg aga    1780
Gln Ser Leu Ser Ser Val Ile Gly Cys Pro Gln Met Ser Met Thr Arg
410                 415                 420                 425 ccc cag gac ctt gcc tat gtc ata ttt aca tcc gga agt act gga atc    1828
Pro Gln Asp Leu Ala Tyr Val Ile Phe Thr Ser Gly Ser Thr Gly Ile
                430                 435                 440 ccg aag ggc agc atg atc gag cat cga ggt ttt gca agc tgc gca ctt    1876
Pro Lys Gly Ser Met Ile Glu His Arg Gly Phe Ala Ser Cys Ala Leu
            445                 450                 455 gaa ttc gga cct caa ttg tta atc gat cgc aac acg cgt gca tta cag    1924
Glu Phe Gly Pro Gln Leu Leu Ile Asp Arg Asn Thr Arg Ala Leu Gln
        460                 465                 470 ttc gcc tct cac gct ttt ggc gca tgc ttg tta gag gtt ctg gtg acg    1972
Phe Ala Ser His Ala Phe Gly Ala Cys Leu Leu Glu Val Leu Val Thr
475                 480                 485 ctt atg ctt gga ggt tgt gta tgc gtc ccg tcc gaa aac gat cgc ttg    2020
Leu Met Leu Gly Gly Cys Val Cys Val Pro Ser Glu Asn Asp Arg Leu
490                 495                 500                 505 aac aac ctg tca ggt ttc att gaa caa agc ggc gtg aac tgg acc cta    2068
Asn Asn Leu Ser Gly Phe Ile Glu Gln Ser Gly Val Asn Trp Thr Leu
                510                 515                 520 ttt acg cct tct ttt att gga gct ctc acg ccc gag act att cgt ggg    2116
Phe Thr Pro Ser Phe Ile Gly Ala Leu Thr Pro Glu Thr Ile Arg Gly
            525                 530                 535 gtg cac act gtc gtg ctg ggt gga gag cca atg aca cca ttc atc aga    2164
Val His Thr Val Val Leu Gly Gly Glu Pro Met Thr Pro Phe Ile Arg
        540                 545                 550 gac gta tgg gca tca aaa gtg caa ctc ttg tcc ata tat gga caa agt    2212
Asp Val Trp Ala Ser Lys Val Gln Leu Leu Ser Ile Tyr Gly Gln Ser
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
|     |     | 555 |     |     |     |     | 560 |     |     |     |     | 565 |     |     |     |      |
| gag | agc | tcg | act | gtg | tgt | agt | gtg | gtt | aaa | atc | aag | cct | gat | acc | acc | 2260 |
| Glu | Ser | Ser | Thr | Val | Cys | Ser | Val | Val | Lys | Ile | Lys | Pro | Asp | Thr | Thr |      |
| 570 |     |     |     | 575 |     |     |     |     | 580 |     |     |     |     | 585 |     |      |
| gat | ctg | agt | agc | ctg | ggc | cac | gct | ata | gga | gct | cgc | ttc | tgg | atc | gtt | 2308 |
| Asp | Leu | Ser | Ser | Leu | Gly | His | Ala | Ile | Gly | Ala | Arg | Phe | Trp | Ile | Val |      |
|     |     |     | 590 |     |     |     |     | 595 |     |     |     |     | 600 |     |     |      |
| gat | gct | gaa | aat | ccg | agt | cga | ttg | gca | cca | atc | ggc | tgc | atc | ggc | gag | 2356 |
| Asp | Ala | Glu | Asn | Pro | Ser | Arg | Leu | Ala | Pro | Ile | Gly | Cys | Ile | Gly | Glu |      |
|     |     | 605 |     |     |     |     | 610 |     |     |     |     | 615 |     |     |     |      |
| ctc | atg | gta | gag | agt | cct | gga | att | gca | cgc | gaa | tac | cta | tct | gct | caa | 2404 |
| Leu | Met | Val | Glu | Ser | Pro | Gly | Ile | Ala | Arg | Glu | Tyr | Leu | Ser | Ala | Gln |      |
| 620 |     |     |     |     | 625 |     |     |     |     | 630 |     |     |     |     |     |      |
| gaa | gca | cag | atg | tcc | cca | ttc | ata | acg | aag | aca | cct | gct | tgg | tat | cct | 2452 |
| Glu | Ala | Gln | Met | Ser | Pro | Phe | Ile | Thr | Lys | Thr | Pro | Ala | Trp | Tyr | Pro |      |
| 635 |     |     |     | 640 |     |     |     |     | 645 |     |     |     |     |     |     |      |
| atg | aag | cag | cgt | tgc | agt | cct | gtc | aag | ttc | tac | atg | acc | ggc | gat | ctt | 2500 |
| Met | Lys | Gln | Arg | Cys | Ser | Pro | Val | Lys | Phe | Tyr | Met | Thr | Gly | Asp | Leu |      |
| 650 |     |     |     | 655 |     |     |     |     | 660 |     |     |     |     | 665 |     |      |
| gct | tgt | tat | gga | cgt | gat | ggc | acc | gtc | atg | aat | ctt | gga | cgc | aaa | gat | 2548 |
| Ala | Cys | Tyr | Gly | Arg | Asp | Gly | Thr | Val | Met | Asn | Leu | Gly | Arg | Lys | Asp |      |
|     |     |     | 670 |     |     |     |     | 675 |     |     |     |     | 680 |     |     |      |
| tcg | caa | gtc | aag | atc | cga | ggc | caa | cgc | gtg | gag | ctt | ggc | gat | gtg | gag | 2596 |
| Ser | Gln | Val | Lys | Ile | Arg | Gly | Gln | Arg | Val | Glu | Leu | Gly | Asp | Val | Glu |      |
|     |     |     | 685 |     |     |     |     | 690 |     |     |     |     | 695 |     |     |      |
| act | aat | ctg | cga | tca | gtc | tta | cct | aaa | cac | atc | ata | cct | gtt | gtc | gag | 2644 |
| Thr | Asn | Leu | Arg | Ser | Val | Leu | Pro | Lys | His | Ile | Ile | Pro | Val | Val | Glu |      |
|     |     | 700 |     |     |     |     | 705 |     |     |     |     | 710 |     |     |     |      |
| gcg | att | gat | tcg | atc | cat | gca | tcc | gga | agc | aaa | ttt | ctg | gtt | gcg | atc | 2692 |
| Ala | Ile | Asp | Ser | Ile | His | Ala | Ser | Gly | Ser | Lys | Phe | Leu | Val | Ala | Ile |      |
|     | 715 |     |     |     |     | 720 |     |     |     |     | 725 |     |     |     |     |      |
| ctg | att | ggc | gca | aac | cat | gga | atg | aaa | aat | gaa | ttc | gat | aca | gag | cca | 2740 |
| Leu | Ile | Gly | Ala | Asn | His | Gly | Met | Lys | Asn | Glu | Phe | Asp | Thr | Glu | Pro |      |
| 730 |     |     |     |     | 735 |     |     |     |     | 740 |     |     |     |     | 745 |      |
| aga | cgt | gaa | gtc | tct | ata | ctg | gat | gaa | acc | gcg | gtg | atc | cgt | ata | agg | 2788 |
| Arg | Arg | Glu | Val | Ser | Ile | Leu | Asp | Glu | Thr | Ala | Val | Ile | Arg | Ile | Arg |      |
|     |     |     |     | 750 |     |     |     |     | 755 |     |     |     |     | 760 |     |      |
| aag | agt | atg | cag | gat | ctt | gtt | cca | tct | tac | tgc | ata | ccc | aca | cag | tat | 2836 |
| Lys | Ser | Met | Gln | Asp | Leu | Val | Pro | Ser | Tyr | Cys | Ile | Pro | Thr | Gln | Tyr |      |
|     |     | 765 |     |     |     |     | 770 |     |     |     |     | 775 |     |     |     |      |
| atc | tgc | atg | gaa | cga | ctc | ctg | acc | acg | aca | aca | ggg | aag | gcg | gat | cgc | 2884 |
| Ile | Cys | Met | Glu | Arg | Leu | Leu | Thr | Thr | Thr | Thr | Gly | Lys | Ala | Asp | Arg |      |
|     |     |     | 780 |     |     |     |     | 785 |     |     |     |     | 790 |     |     |      |
| aag | aga | cta | cgc | gcg | att | tgc | gtg | gac | ctt | ctc | aag | cct | tca | agg | aga | 2932 |
| Lys | Arg | Leu | Arg | Ala | Ile | Cys | Val | Asp | Leu | Leu | Lys | Pro | Ser | Arg | Arg |      |
|     |     + 795 |     |     |     |     | 800 |     |     |     |     | 805 |     |     |     |      |
| gca | atg | gta | cca | gaa | tct | tcg | gac | ggg | ccc | acg | cta | aaa | ctc | acg | gca | 2980 |
| Ala | Met | Val | Pro | Glu | Ser | Ser | Asp | Gly | Pro | Thr | Leu | Lys | Leu | Thr | Ala |      |
| 810 |     |     |     |     | 815 |     |     |     |     | 820 |     |     |     |     | 825 |      |
| gga | caa | gtt | ttg | gat | gag | gca | tgg | cat | cga | tac | ctg | cgt | ttt | gat | tct | 3028 |
| Gly | Gln | Val | Leu | Asp | Glu | Ala | Trp | His | Arg | Tyr | Leu | Arg | Phe | Asp | Ser |      |
|     |     |     |     | 830 |     |     |     |     | 835 |     |     |     |     | 840 |     |      |
| gtt | ctc | gat | ggt | tct | aag | tcg | aag | ttc | ttt | gat | ctg | aat | gga | gac | tcc | 3076 |
| Val | Leu | Asp | Gly | Ser | Lys | Ser | Lys | Phe | Phe | Asp | Leu | Asn | Gly | Asp | Ser |      |
|     |     |     | 845 |     |     |     |     | 850 |     |     |     |     | 855 |     |     |      |
| atc | aca | gcg | atc | aag | ata | gca | aat | gcg | gcg | agg | aaa | cac | ggg | gta | atg | 3124 |
| Ile | Thr | Ala | Ile | Lys | Ile | Ala | Asn | Ala | Ala | Arg | Lys | His | Gly | Val | Met |      |
|     |     | 860 |     |     |     |     | 865 |     |     |     |     | 870 |     |     |     |      |
| ctc | aaa | gta | gca | gac | att | ctt | gct | aat | cct | act | ctc | gcc | gac | ctg | aga | 3172 |

```
                Leu Lys Val Ala Asp Ile Leu Ala Asn Pro Thr Leu Ala Asp Leu Arg
                    875                 880                 885 gct caa ttt cag att gat ttc aca cct caa aac tcc ata ctt cgc acc        3220
Ala Gln Phe Gln Ile Asp Phe Thr Pro Gln Asn Ser Ile Leu Arg Thr
890                 895                 900                 905 tcg tac cgt gga cca atc caa caa tcc ttt gcg caa aac agg ttg tgg        3268
Ser Tyr Arg Gly Pro Ile Gln Gln Ser Phe Ala Gln Asn Arg Leu Trp
                910                 915                 920 ttt ctg gac cag ctg aac gtt ggc gcg tca tgg tac ata gta cca gtc        3316
Phe Leu Asp Gln Leu Asn Val Gly Ala Ser Trp Tyr Ile Val Pro Val
                    925                 930                 935 gcg gtg cgc ttg caa gga aca gtc cat gtc gac gcg ctt gtc acc gca        3364
Ala Val Arg Leu Gln Gly Thr Val His Val Asp Ala Leu Val Thr Ala
                940                 945                 950 cta tgt gcc ctg gaa caa cgt cat gaa acg ttg cgt acg acc ttt gaa        3412
Leu Cys Ala Leu Glu Gln Arg His Glu Thr Leu Arg Thr Thr Phe Glu
    955                 960                 965 gaa tcc gat ggc gag ggc ata caa cgg att cag cca agt ggg ctt gag        3460
Glu Ser Asp Gly Glu Gly Ile Gln Arg Ile Gln Pro Ser Gly Leu Glu
970                 975                 980                 985 cag ctt agg ttg atc gac gtg gat tgc gtg gac tct agg gac tac  cag       3508
Gln Leu Arg Leu Ile Asp Val Asp Cys Val Asp Ser Arg Asp Tyr  Gln
                    990                 995                 1000 cga gta ttg gaa  gaa gag cag acg act  ccc ttc gag ctg agc  cgc         3553
Arg Val Leu Glu  Glu Glu Gln Thr Thr  Pro Phe Glu Leu Ser  Arg
                 1005                 1010                1015 gag cct gga tgg  agg gta gcg ctg ctg  cgt ctg gga gat gac  gac         3598
Glu Pro Gly Trp  Arg Val Ala Leu Leu  Arg Leu Gly Asp Asp  Asp
                 1020                 1025                1030 cac gtc ctc tcc  atc gtc atg cat cac  atc atc tcc gac ggt  tgg         3643
His Val Leu Ser  Ile Val Met His His  Ile Ile Ser Asp Gly  Trp
                 1035                 1040                1045 tct gtg gac gtg  ctg cgc cac gag cta  ggt cag ttc tac tcg  gcc         3688
Ser Val Asp Val  Leu Arg His Glu Leu  Gly Gln Phe Tyr Ser  Ala
                 1050                 1055                1060 gcg ctc cgg ggg  cag gac ccg ttg tcg  cag ata agt cct ctg  ccg         3733
Ala Leu Arg Gly  Gln Asp Pro Leu Ser  Gln Ile Ser Pro Leu  Pro
                 1065                 1070                1075 atc cag tat cgt  gac ttc gct ctc tgg  cag aga caa gac gag  caa         3778
Ile Gln Tyr Arg  Asp Phe Ala Leu Trp  Gln Arg Gln Asp Glu  Gln
                 1080                 1085                1090 gtt gcg gag cat  cag cgc cag ctg gag  cat tgg aca gag cag  ttg         3823
Val Ala Glu His  Gln Arg Gln Leu Glu  His Trp Thr Glu Gln  Leu
                 1095                 1100                1105 gca gac agt tca  ccc gcc gag ttg ttg  agc gac cac ccg agg  cca         3868
Ala Asp Ser Ser  Pro Ala Glu Leu Leu  Ser Asp His Pro Arg  Pro
                 1110                 1115                1120 tcg att ctt tct  ggc cag gcg ggc gct  att ccc gtc aat gtt  caa         3913
Ser Ile Leu Ser  Gly Gln Ala Gly Ala  Ile Pro Val Asn Val  Gln
                 1125                 1130                1135 ggc tct ctg tat  cag gcg ctt cgg gcg  ttc tgc cgc gct cac  cag         3958
Gly Ser Leu Tyr  Gln Ala Leu Arg Ala  Phe Cys Arg Ala His  Gln
                 1140                 1145                1150 gtc acc tct ttc  gta gtc ctg ctc acg  gcg ttc cgc ata gca  cac         4003
Val Thr Ser Phe  Val Val Leu Leu Thr  Ala Phe Arg Ile Ala  His
                 1155                 1160                1165 tat cgt ctg acg  ggt gcg gag gac gca  acc att gga act ccc  att         4048
Tyr Arg Leu Thr  Gly Ala Glu Asp Ala  Thr Ile Gly Thr Pro  Ile
                 1170                 1175                1180
```

-continued

| | | |
|---|---|---|
| gca aat cgc aac cgg cca gag ctc gag aac atg atc ggt ttc ttc<br>Ala Asn Arg Asn Arg Pro Glu Leu Glu Asn Met Ile Gly Phe Phe<br>                1185                     1190                      1195 | 4093 |
| gtc aat aca caa tgc atg cgc atc gtc att ggc agt gac gac aca<br>Val Asn Thr Gln Cys Met Arg Ile Val Ile Gly Ser Asp Asp Thr<br>        1200                     1205                     1210 | 4138 |
| ttt gaa ggg ctg gtg cag caa gta cgc tcg ata act gca gct gcc<br>Phe Glu Gly Leu Val Gln Gln Val Arg Ser Ile Thr Ala Ala Ala<br>             1215                   1220                 1225 | 4183 |
| cac gag aac cag gac gtt cca ttc gag cgc atc gtg tca gca ctg<br>His Glu Asn Gln Asp Val Pro Phe Glu Arg Ile Val Ser Ala Leu<br>           1230                     1235                   1240 | 4228 |
| ctt ccc ggt tct aga gac aca tca cgc aat cct ctg gtt cag ctc<br>Leu Pro Gly Ser Arg Asp Thr Ser Arg Asn Pro Leu Val Gln Leu<br>            1245                    1250                   1255 | 4273 |
| atg ttt gct gtc cac tcg caa aga aac ctt ggt cag atc agt cta<br>Met Phe Ala Val His Ser Gln Arg Asn Leu Gly Gln Ile Ser Leu<br>        1260                    1265                    1270 | 4318 |
| gaa ggc ctg cag ggt gaa ttg ctg gga gtg gca tcg cca acg aga<br>Glu Gly Leu Gln Gly Glu Leu Leu Gly Val Ala Ser Pro Thr Arg<br>             1275                    1280                 1285 | 4363 |
| ttc gat gta gag ttc cac ctc ttc caa gag gag aat atg cta agc<br>Phe Asp Val Glu Phe His Leu Phe Gln Glu Glu Asn Met Leu Ser<br>            1290                    1295                   1300 | 4408 |
| gga agg gtg ctg ttt tca gac gat ctt ttc gag cag aag act atg<br>Gly Arg Val Leu Phe Ser Asp Asp Leu Phe Glu Gln Lys Thr Met<br>        1305                    1310                    1315 | 4453 |
| caa ggc atg gtc gac gtg ttc cag gaa gtg ctc agc cgg ggc ctt<br>Gln Gly Met Val Asp Val Phe Gln Glu Val Leu Ser Arg Gly Leu<br>             1320                    1325                 1330 | 4498 |
| gag cag ccc cag ata cct ctg gcg acc ctc ccg ctc acg cac gga<br>Glu Gln Pro Gln Ile Pro Leu Ala Thr Leu Pro Leu Thr His Gly<br>            1335                    1340                   1345 | 4543 |
| ctg gag gag ctc agg acc atg ggt ctt ctc gac gtg gag aag aca<br>Leu Glu Glu Leu Arg Thr Met Gly Leu Leu Asp Val Glu Lys Thr<br>        1350                    1355                    1360 | 4588 |
| gac tac cct cga gag tcg agc gtg gtg gac gtg ttc cgt gag caa<br>Asp Tyr Pro Arg Glu Ser Ser Val Val Asp Val Phe Arg Glu Gln<br>             1365                    1370                 1375 | 4633 |
| gcg gct gcc tgc tcc gag gcg att gcg gtc aaa gac tcg tcg gcg<br>Ala Ala Ala Cys Ser Glu Ala Ile Ala Val Lys Asp Ser Ser Ala<br>            1380                    1385                   1390 | 4678 |
| cag ctc acc tac tcg gag ctc gat cga cag tcg gac gag ctt gcc<br>Gln Leu Thr Tyr Ser Glu Leu Asp Arg Gln Ser Asp Glu Leu Ala<br>        1395                    1400                    1405 | 4723 |
| ggc tgg ctg cgc cag caa cgt ctt cct gcg gag tcg ttg gtt gca<br>Gly Trp Leu Arg Gln Gln Arg Leu Pro Ala Glu Ser Leu Val Ala<br>             1410                    1415                 1420 | 4768 |
| gtg ctg gca ccc agg tcg tgc cag acc att gtc gcg ttc ctg ggc<br>Val Leu Ala Pro Arg Ser Cys Gln Thr Ile Val Ala Phe Leu Gly<br>        1425                    1430                    1435 | 4813 |
| atc ctc aag gcg aat ctg gca tac ctg ccg cta gac gtc aac gtg<br>Ile Leu Lys Ala Asn Leu Ala Tyr Leu Pro Leu Asp Val Asn Val<br>             1440                    1445                 1450 | 4858 |
| ccc gct act cgc ctc gag tcg ata ctg tct gcc gtc ggc ggc cgg<br>Pro Ala Thr Arg Leu Glu Ser Ile Leu Ser Ala Val Gly Gly Arg<br>        1455                    1460                    1465 | 4903 |
| aag ctg gtc ttg ctt gga gct gac gtg gcc gac cct ggc ctt cgc<br>Lys Leu Val Leu Leu Gly Ala Asp Val Ala Asp Pro Gly Leu Arg<br>             1470                    1475                 1480 | 4948 |

```
ctg gcg gat gtg gag ctc gtg cgg atc ggc gac aca ctc ggc cgc       4993
Leu Ala Asp Val Glu Leu Val Arg Ile Gly Asp Thr Leu Gly Arg
            1485                1490                1495 tgt gta ccc ggg gcg ccc ggc gac aac gag gca cct gtg gtg cag       5038
Cys Val Pro Gly Ala Pro Gly Asp Asn Glu Ala Pro Val Val Gln
        1500                1505                1510 cct tct gcc aca agc ctt gcc tac gtc atc ttc act tcc ggc tcg       5083
Pro Ser Ala Thr Ser Leu Ala Tyr Val Ile Phe Thr Ser Gly Ser
            1515                1520                1525 acc ggc aag ccg aag ggt gtc atg gtc gag cac cgg ggt gta gtg       5128
Thr Gly Lys Pro Lys Gly Val Met Val Glu His Arg Gly Val Val
        1530                1535                1540 cga ctt gtc aag cag agc aat gtt gtc tac cat ctc ccg tcc aca       5173
Arg Leu Val Lys Gln Ser Asn Val Val Tyr His Leu Pro Ser Thr
            1545                1550                1555 tct cgc gtg gcc cac ctg tcg aat ctc gcc ttt gat gcc tcg gcg       5218
Ser Arg Val Ala His Leu Ser Asn Leu Ala Phe Asp Ala Ser Ala
        1560                1565                1570 tgg gag atc tat gcg gca ctg ctt aat ggc ggt aca ctc atc tgc       5263
Trp Glu Ile Tyr Ala Ala Leu Leu Asn Gly Gly Thr Leu Ile Cys
            1575                1580                1585 att gac tat ttc aca act cta gac tgc tct gct ctc ggc gcc aaa       5308
Ile Asp Tyr Phe Thr Thr Leu Asp Cys Ser Ala Leu Gly Ala Lys
        1590                1595                1600 ttc atc aag gag aag atc gtc gcg acc atg att ccg cca gcg ctt       5353
Phe Ile Lys Glu Lys Ile Val Ala Thr Met Ile Pro Pro Ala Leu
            1605                1610                1615 ctg aag caa tgt ctg gcg atc ttc ccg acc gct ctt agt gaa ctg       5398
Leu Lys Gln Cys Leu Ala Ile Phe Pro Thr Ala Leu Ser Glu Leu
        1620                1625                1630 gtc ctg ctg ttt gct gcc gga gat cga ttc agc agt ggc gat gcc       5443
Val Leu Leu Phe Ala Ala Gly Asp Arg Phe Ser Ser Gly Asp Ala
            1635                1640                1645 gtc gaa gtg cag cgc cac acc aaa ggc gct gtt tgt aac gcg tac       5488
Val Glu Val Gln Arg His Thr Lys Gly Ala Val Cys Asn Ala Tyr
        1650                1655                1660 gga ccg aca gaa aac acc att ctt agt acg atc tac gaa gtc aag       5533
Gly Pro Thr Glu Asn Thr Ile Leu Ser Thr Ile Tyr Glu Val Lys
            1665                1670                1675 cag aat gag aac ttc ccg aac ggt gtg cct atc ggc cgc gct gtg       5578
Gln Asn Glu Asn Phe Pro Asn Gly Val Pro Ile Gly Arg Ala Val
        1680                1685                1690 agc aac tca ggg gca tat gtc atg gac ccg cag cag caa ctg gtg       5623
Ser Asn Ser Gly Ala Tyr Val Met Asp Pro Gln Gln Gln Leu Val
            1695                1700                1705 cct ctc ggg gtg atg ggc gag ctc gtc gtc acc ggc gac ggc ctg       5668
Pro Leu Gly Val Met Gly Glu Leu Val Val Thr Gly Asp Gly Leu
        1710                1715                1720 gcc cgt ggt tac acc gac ccg tca ctg gat gcg gac cgc ttt gtg       5713
Ala Arg Gly Tyr Thr Asp Pro Ser Leu Asp Ala Asp Arg Phe Val
            1725                1730                1735 cag gtc tcc gtc aac ggg cag ctc gtg aga gcg tac cga aca ggc       5758
Gln Val Ser Val Asn Gly Gln Leu Val Arg Ala Tyr Arg Thr Gly
        1740                1745                1750 gat cgc gtg cgc tgc agg cct tgc gat ggc cag atc gag ttc ttt       5803
Asp Arg Val Arg Cys Arg Pro Cys Asp Gly Gln Ile Glu Phe Phe
            1755                1760                1765 gga cgt atg gac cgg caa gtc aag atc cga gga cat cgc atc gag       5848
Gly Arg Met Asp Arg Gln Val Lys Ile Arg Gly His Arg Ile Glu
```

-continued

| | | | | | | | | | | | | | |
|---|---|---|---|---|---|---|---|---|---|---|---|---|---|
| | | | 1770 | | | 1775 | | | 1780 | | | | |
| ctc | gca | gag | gta | gag | cat | gcg | gtg | ctt | ggc | ttg | gaa | gac | gtg caa | 5893 |
| Leu | Ala | Glu | Val | Glu | His | Ala | Val | Leu | Gly | Leu | Glu | Asp | Val Gln |
| | | | 1785 | | | 1790 | | | 1795 | | | | |
| gac | gct | gcc | gtt | atc | gca | ttt | gac | aat | gtg | gac | agc | gaa | gag cca | 5938 |
| Asp | Ala | Ala | Val | Ile | Ala | Phe | Asp | Asn | Val | Asp | Ser | Glu | Glu Pro |
| | | | 1800 | | | 1805 | | | 1810 | | | | |
| gaa | atg | gtt | ggg | ttt | gtc | act | att | acc | gaa | gac | aat | cct | gtc cgt | 5983 |
| Glu | Met | Val | Gly | Phe | Val | Thr | Ile | Thr | Glu | Asp | Asn | Pro | Val Arg |
| | | | 1815 | | | 1820 | | | 1825 | | | | |
| gag | gac | gaa | acc | agc | ggt | caa | gta | gaa | gac | tgg | gcg | aac | cac ttc | 6028 |
| Glu | Asp | Glu | Thr | Ser | Gly | Gln | Val | Glu | Asp | Trp | Ala | Asn | His Phe |
| | | | 1830 | | | 1835 | | | 1840 | | | | |
| gag | ata | agt | acc | tac | acc | gat | atc | gcg | gcg | atc | gat | cag | ggt agc | 6073 |
| Glu | Ile | Ser | Thr | Tyr | Thr | Asp | Ile | Ala | Ala | Ile | Asp | Gln | Gly Ser |
| | | | 1845 | | | 1850 | | | 1855 | | | | |
| att | gga | agt | gac | ttt | gta | ggt | tgg | act | tct | atg | tac | gac | gga agc | 6118 |
| Ile | Gly | Ser | Asp | Phe | Val | Gly | Trp | Thr | Ser | Met | Tyr | Asp | Gly Ser |
| | | | 1860 | | | 1865 | | | 1870 | | | | |
| gag | atc | gac | aag | gca | gag | atg | caa | gaa | tgg | ctt | gcc | gat | acc atg | 6163 |
| Glu | Ile | Asp | Lys | Ala | Glu | Met | Gln | Glu | Trp | Leu | Ala | Asp | Thr Met |
| | | | 1875 | | | 1880 | | | 1885 | | | | |
| gcc | tct | atg | ctc | gac | ggg | cag | gcg | ccg | ggc | aat | gtg | tta | gag ata | 6208 |
| Ala | Ser | Met | Leu | Asp | Gly | Gln | Ala | Pro | Gly | Asn | Val | Leu | Glu Ile |
| | | | 1890 | | | 1895 | | | 1900 | | | | |
| ggt | aca | ggc | act | ggc | atg | gtc | ctc | ttc | aat | ctc | ggc | gac | gga ctg | 6253 |
| Gly | Thr | Gly | Thr | Gly | Met | Val | Leu | Phe | Asn | Leu | Gly | Asp | Gly Leu |
| | | | 1905 | | | 1910 | | | 1915 | | | | |
| cag | agc | tat | gtc | ggc | ctc | gaa | cca | tca | aga | tcg | gcg | gcc | gct ttt | 6298 |
| Gln | Ser | Tyr | Val | Gly | Leu | Glu | Pro | Ser | Arg | Ser | Ala | Ala | Ala Phe |
| | | | 1920 | | | 1925 | | | 1930 | | | | |
| gtc | aac | cag | acg | att | aag | tcg | ctc | ccc | acc | ctt | gct | ggc | aac gct | 6343 |
| Val | Asn | Gln | Thr | Ile | Lys | Ser | Leu | Pro | Thr | Leu | Ala | Gly | Asn Ala |
| | | | 1935 | | | 1940 | | | 1945 | | | | |
| gaa | gta | cac | att | ggc | act | gcg | acc | gac | gtg | gcc | cgt | cta | gat ggc | 6388 |
| Glu | Val | His | Ile | Gly | Thr | Ala | Thr | Asp | Val | Ala | Arg | Leu | Asp Gly |
| | | | 1950 | | | 1955 | | | 1960 | | | | |
| ctc | cgc | ccc | gac | tta | gtg | gta | gtc | aat | tcg | gta | gtc | cag | tac ttc | 6433 |
| Leu | Arg | Pro | Asp | Leu | Val | Val | Val | Asn | Ser | Val | Val | Gln | Tyr Phe |
| | | | 1965 | | | 1970 | | | 1975 | | | | |
| cca | tca | cca | gag | tac | cta | atg | gaa | gtc | gtg | gag | gct | ctt | gca cgt | 6478 |
| Pro | Ser | Pro | Glu | Tyr | Leu | Met | Glu | Val | Val | Glu | Ala | Leu | Ala Arg |
| | | | 1980 | | | 1985 | | | 1990 | | | | |
| ctg | ccg | ggc | gtc | gag | cga | att | ttc | ttc | gga | gac | gta | cgt | tcg tac | 6523 |
| Leu | Pro | Gly | Val | Glu | Arg | Ile | Phe | Phe | Gly | Asp | Val | Arg | Ser Tyr |
| | | | 1995 | | | 2000 | | | 2005 | | | | |
| gcc | atc | aac | aga | gat | ttc | ctg | gct | gcc | aga | gct | cta | cac | gaa ctt | 6568 |
| Ala | Ile | Asn | Arg | Asp | Phe | Leu | Ala | Ala | Arg | Ala | Leu | His | Glu Leu |
| | | | 2010 | | | 2015 | | | 2020 | | | | |
| ggc | gac | aga | gcg | act | aag | cac | gag | att | cgg | cga | aag | atg | cta gag | 6613 |
| Gly | Asp | Arg | Ala | Thr | Lys | His | Glu | Ile | Arg | Arg | Lys | Met | Leu Glu |
| | | | 2025 | | | 2030 | | | 2035 | | | | |
| atg | gaa | gaa | cgc | gaa | gag | gag | ctg | ctc | gtc | gac | cca | gct | ttc ttc | 6658 |
| Met | Glu | Glu | Arg | Glu | Glu | Glu | Leu | Leu | Val | Asp | Pro | Ala | Phe Phe |
| | | | 2040 | | | 2045 | | | 2050 | | | | |
| acc | atg | ttg | acc | agc | agt | ctc | cct | ggc | ctg | att | cag | cat | gtc gag | 6703 |
| Thr | Met | Leu | Thr | Ser | Ser | Leu | Pro | Gly | Leu | Ile | Gln | His | Val Glu |
| | | | 2055 | | | 2060 | | | 2065 | | | | |
| atc | ttg | ccg | aag | ctg | atg | aga | gcc | act | aat | gag | ctc | agc | gcg tat | 6748 |

| | | | | | | | | | | | | | |
|---|---|---|---|---|---|---|---|---|---|---|---|---|---|
|Ile|Leu|Pro|Lys|Leu|Met|Arg|Ala|Thr|Asn|Glu|Leu|Ser|Ala|Tyr|
| | |2070| | | |2075| | | |2080| | | |

```
cga  tac  act  gct  gta  gta  cac  gtg  tgc  cgt  gcc  ggt  caa  gag  cct      6793
Arg  Tyr  Thr  Ala  Val  Val  His  Val  Cys  Arg  Ala  Gly  Gln  Glu  Pro
          2085                2090                2095 cgt  tcc  gtg  cat  acg  atc  gac  gac  gat  gcc  tgg  gtg  aat  ctt  gga      6838
Arg  Ser  Val  His  Thr  Ile  Asp  Asp  Asp  Ala  Trp  Val  Asn  Leu  Gly
          2100                2105                2110 gct  tct  cgg  ttg  agt  cgc  cct  acc  ctt  tca  agc  ctt  ttg  caa  act      6883
Ala  Ser  Arg  Leu  Ser  Arg  Pro  Thr  Leu  Ser  Ser  Leu  Leu  Gln  Thr
          2115                2120                2125 tcc  gag  ggc  gca  tcg  gcc  gtc  gca  gta  agc  aat  att  cct  tac  agc      6928
Ser  Glu  Gly  Ala  Ser  Ala  Val  Ala  Val  Ser  Asn  Ile  Pro  Tyr  Ser
          2130                2135                2140 aag  acc  atc  aca  gag  cga  gcg  ctc  gtt  agt  gcg  ctc  gat  gag  gat      6973
Lys  Thr  Ile  Thr  Glu  Arg  Ala  Leu  Val  Ser  Ala  Leu  Asp  Glu  Asp
          2145                2150                2155 gat  atg  caa  gac  tca  tcg  gac  tgg  ctg  ctg  gcc  gtg  cgc  gag  aca      7018
Asp  Met  Gln  Asp  Ser  Ser  Asp  Trp  Leu  Leu  Ala  Val  Arg  Glu  Thr
          2160                2165                2170 ggc  aga  tct  tgt  tcc  tcc  ttc  tcc  gca  aca  gac  ctt  gtc  gag  ctt      7063
Gly  Arg  Ser  Cys  Ser  Ser  Phe  Ser  Ala  Thr  Asp  Leu  Val  Glu  Leu
          2175                2180                2185 gct  cga  gag  acg  ggc  tgg  cgt  gtg  gag  ctc  agc  tgg  gca  cga  cag      7108
Ala  Arg  Glu  Thr  Gly  Trp  Arg  Val  Glu  Leu  Ser  Trp  Ala  Arg  Gln
          2190                2195                2200 tac  tca  cag  aaa  ggc  gca  ctc  gat  gct  gtc  ttc  cac  aga  cac  cct      7153
Tyr  Ser  Gln  Lys  Gly  Ala  Leu  Asp  Ala  Val  Phe  His  Arg  His  Pro
          2205                2210                2215 gtt  tcc  gct  ggg  agc  ggg  cgt  gtc  atg  ttc  cag  ttt  cca  gtt  gag      7198
Val  Ser  Ala  Gly  Ser  Gly  Arg  Val  Met  Phe  Gln  Phe  Pro  Val  Glu
          2220                2225                2230 acc  gaa  gat  cga  ccg  cac  atc  tca  cgc  acg  aac  cga  cct  tta  cag      7243
Thr  Glu  Asp  Arg  Pro  His  Ile  Ser  Arg  Thr  Asn  Arg  Pro  Leu  Gln
          2235                2240                2245 cga  ttg  cag  aag  aag  cga  acc  gag  aca  cat  gtt  cat  gag  cag  ttg      7288
Arg  Leu  Gln  Lys  Lys  Arg  Thr  Glu  Thr  His  Val  His  Glu  Gln  Leu
          2250                2255                2260 cgg  gct  ttg  ctt  cca  cga  tac  atg  gtt  cct  acg  cgg  att  gtg  gcg      7333
Arg  Ala  Leu  Leu  Pro  Arg  Tyr  Met  Val  Pro  Thr  Arg  Ile  Val  Ala
          2265                2270                2275 ctt  gat  aag  ctg  ccc  gtc  aat  gca  aac  ggc  aag  gtt  gat  cgt  caa      7378
Leu  Asp  Lys  Leu  Pro  Val  Asn  Ala  Asn  Gly  Lys  Val  Asp  Arg  Gln
          2280                2285                2290 cag  ctc  gct  agg  aca  gcc  cag  gtt  ctc  cca  gcg  agc  aag  gcg  ccg      7423
Gln  Leu  Ala  Arg  Thr  Ala  Gln  Val  Leu  Pro  Ala  Ser  Lys  Ala  Pro
          2295                2300                2305 tct  gca  tgc  gtg  gcc  cca  cgc  aac  gaa  ttg  gaa  atg  aca  ctg  tgt      7468
Ser  Ala  Cys  Val  Ala  Pro  Arg  Asn  Glu  Leu  Glu  Met  Thr  Leu  Cys
          2310                2315                2320 gaa  gag  ttc  tcg  cag  gtt  ctt  ggc  gtc  gag  gtc  ggc  att  act  gac      7513
Glu  Glu  Phe  Ser  Gln  Val  Leu  Gly  Val  Glu  Val  Gly  Ile  Thr  Asp
          2325                2330                2335 aat  ttc  ttc  cac  ctg  ggt  ggc  cac  tct  ctc  atg  gca  aca  aag  ttc      7558
Asn  Phe  Phe  His  Leu  Gly  Gly  His  Ser  Leu  Met  Ala  Thr  Lys  Phe
          2340                2345                2350 gcc  gct  cgt  atc  agc  cgc  cgg  ctg  aat  gct  atc  gtt  tcg  gtc  aag      7603
Ala  Ala  Arg  Ile  Ser  Arg  Arg  Leu  Asn  Ala  Ile  Val  Ser  Val  Lys
          2355                2360                2365
```

```
aat gtc ttc gac cac ccc gta cct atg gat ctt gca gcg aca atc       7648
Asn Val Phe Asp His Pro Val Pro Met Asp Leu Ala Ala Thr Ile
            2370            2375            2380 caa gaa ggc tca aag ctt cat act cca atc cct cgc acg gct tac       7693
Gln Glu Gly Ser Lys Leu His Thr Pro Ile Pro Arg Thr Ala Tyr
            2385            2390            2395 agc ggt cct gtc gaa cag tct ttc gca caa gga cgt ctt tgg ttc       7738
Ser Gly Pro Val Glu Gln Ser Phe Ala Gln Gly Arg Leu Trp Phe
            2400            2405            2410 ctt gac caa ttc aat cct agc tcg att ggg tat gtg atg cct ttc       7783
Leu Asp Gln Phe Asn Pro Ser Ser Ile Gly Tyr Val Met Pro Phe
            2415            2420            2425 gct gcg cgt ctt cat ggt caa cta caa atc gaa gcg ctc aca gca       7828
Ala Ala Arg Leu His Gly Gln Leu Gln Ile Glu Ala Leu Thr Ala
            2430            2435            2440 gca ttg ttc gct ttg gaa cag cga cat gag atc ctg cga aca acg       7873
Ala Leu Phe Ala Leu Glu Gln Arg His Glu Ile Leu Arg Thr Thr
            2445            2450            2455 ttg gac gca cac gat ggt gta ggc atg cag atc gtt cac gcg gaa       7918
Leu Asp Ala His Asp Gly Val Gly Met Gln Ile Val His Ala Glu
            2460            2465            2470 cat ccg caa cag ttg aga atc att gat gtg tca gca aag gcg tcg       7963
His Pro Gln Gln Leu Arg Ile Ile Asp Val Ser Ala Lys Ala Ser
            2475            2480            2485 agc agt tat gct cag aca ctg cgt gac gag cag gcg tca cct ttc       8008
Ser Ser Tyr Ala Gln Thr Leu Arg Asp Glu Gln Ala Ser Pro Phe
            2490            2495            2500 gac cta agc aag gaa cca ggt tgg aga gtc tcg ttg ctg cag ctc       8053
Asp Leu Ser Lys Glu Pro Gly Trp Arg Val Ser Leu Leu Gln Leu
            2505            2510            2515 agt gag ata gat tat gtt ctt tcc att gta atg cat cac acc atc       8098
Ser Glu Ile Asp Tyr Val Leu Ser Ile Val Met His His Thr Ile
            2520            2525            2530 tat gac ggt tgg tct ctc gac gta ctc cgg cgg gag cta agt cag       8143
Tyr Asp Gly Trp Ser Leu Asp Val Leu Arg Arg Glu Leu Ser Gln
            2535            2540            2545 ttt tat gcc gct gcc atc cgt ggt cga gaa cct cta tcg aca atc       8188
Phe Tyr Ala Ala Ala Ile Arg Gly Arg Glu Pro Leu Ser Thr Ile
            2550            2555            2560 gag cca ttg cct atc caa tac cgc gac ttt tct gtc tgg caa aag       8233
Glu Pro Leu Pro Ile Gln Tyr Arg Asp Phe Ser Val Trp Gln Lys
            2565            2570            2575 cag gaa gac caa gtc gca gag cat cga cga cag ctc cat tat tgg       8278
Gln Glu Asp Gln Val Ala Glu His Arg Arg Gln Leu His Tyr Trp
            2580            2585            2590 ata gag cag cta gat ggc agc tct cct gct gag ttc cta aac gat       8323
Ile Glu Gln Leu Asp Gly Ser Ser Pro Ala Glu Phe Leu Asn Asp
            2595            2600            2605 aaa cca cgg cct acg ttg ctt tct ggc aag gca gga gtt gtg gaa       8368
Lys Pro Arg Pro Thr Leu Leu Ser Gly Lys Ala Gly Val Val Glu
            2610            2615            2620 att gct gtg aag ggc act gta tat caa cgt ctg cta gag ttc tgc       8413
Ile Ala Val Lys Gly Thr Val Tyr Gln Arg Leu Leu Glu Phe Cys
            2625            2630            2635 agg ctt cat cag gtc acc tcg ttc atg gtg ctg ctt gcg gca ttc       8458
Arg Leu His Gln Val Thr Ser Phe Met Val Leu Leu Ala Ala Phe
            2640            2645            2650 cga gcg aca cac tat cgt ctg aca ggc aca gag gac gcg act gtc       8503
Arg Ala Thr His Tyr Arg Leu Thr Gly Thr Glu Asp Ala Thr Val
            2655            2660            2665
```

```
                                            -continued gga  aca  ccc  atc  gcc  aat  cgc  aat  cga  cct  gag  ctg  gag  aac  atg           8548
Gly  Thr  Pro  Ile  Ala  Asn  Arg  Asn  Arg  Pro  Glu  Leu  Glu  Asn  Met
                    2670                    2675                    2680 att  gga  ttg  ttc  gtg  aat  act  cag  tgt  ata  cgc  ctc  aag  atc  gag           8593
Ile  Gly  Leu  Phe  Val  Asn  Thr  Gln  Cys  Ile  Arg  Leu  Lys  Ile  Glu
               2685                    2690                    2695 gac  aat  gat  act  ctc  gag  gag  cta  gta  cag  cac  gtt  cgt  gcc  acg           8638
Asp  Asn  Asp  Thr  Leu  Glu  Glu  Leu  Val  Gln  His  Val  Arg  Ala  Thr
               2700                    2705                    2710 atc  aca  gca  tca  atc  tcg  aac  cag  gat  gta  ccc  ttt  gaa  cag  gta           8683
Ile  Thr  Ala  Ser  Ile  Ser  Asn  Gln  Asp  Val  Pro  Phe  Glu  Gln  Val
               2715                    2720                    2725 gtg  tct  gca  ttg  cta  cca  gga  tca  cgc  gac  acc  tct  agg  aac  cca           8728
Val  Ser  Ala  Leu  Leu  Pro  Gly  Ser  Arg  Asp  Thr  Ser  Arg  Asn  Pro
          2730                    2735                    2740 cta  gtt  cag  ctg  act  ttt  gcg  gtg  cat  tct  cag  cga  aat  ttg  gct           8773
Leu  Val  Gln  Leu  Thr  Phe  Ala  Val  His  Ser  Gln  Arg  Asn  Leu  Ala
          2745                    2750                    2755 gac  att  cag  cta  gaa  aac  gtg  gag  acc  aat  gct  atg  cca  att  tgc           8818
Asp  Ile  Gln  Leu  Glu  Asn  Val  Glu  Thr  Asn  Ala  Met  Pro  Ile  Cys
          2760                    2765                    2770 ccc  tcg  aca  cgt  ttc  gac  gct  gaa  ttc  cac  ctc  ttc  caa  gag  gag           8863
Pro  Ser  Thr  Arg  Phe  Asp  Ala  Glu  Phe  His  Leu  Phe  Gln  Glu  Glu
          2775                    2780                    2785 aat  atg  cta  agc  gga  agg  gtg  ctg  ttt  tca  gac  gat  ctt  ttc  gag           8908
Asn  Met  Leu  Ser  Gly  Arg  Val  Leu  Phe  Ser  Asp  Asp  Leu  Phe  Glu
          2790                    2795                    2800 cag  aag  act  atg  caa  ggc  atg  gtc  gac  gtg  ttc  cag  gaa  gtg  ctc           8953
Gln  Lys  Thr  Met  Gln  Gly  Met  Val  Asp  Val  Phe  Gln  Glu  Val  Leu
          2805                    2810                    2815 agc  cgg  ggc  ctt  gag  cag  ccc  cag  ata  cct  ctg  gcg  acc  ctc  ccg           8998
Ser  Arg  Gly  Leu  Glu  Gln  Pro  Gln  Ile  Pro  Leu  Ala  Thr  Leu  Pro
          2820                    2825                    2830 ctc  acg  cac  gga  ctg  gag  gag  ctc  agg  acc  atg  ggt  ctt  ctc  gac           9043
Leu  Thr  His  Gly  Leu  Glu  Glu  Leu  Arg  Thr  Met  Gly  Leu  Leu  Asp
          2835                    2840                    2845 gtg  gag  aag  aca  gac  tac  cct  cga  gag  tcg  agc  gtg  gtg  gac  gtg           9088
Val  Glu  Lys  Thr  Asp  Tyr  Pro  Arg  Glu  Ser  Ser  Val  Val  Asp  Val
          2850                    2855                    2860 ttc  cgt  gag  caa  gcg  gct  gcc  tgc  tcc  gag  gcg  att  gcg  gtc  aaa           9133
Phe  Arg  Glu  Gln  Ala  Ala  Ala  Cys  Ser  Glu  Ala  Ile  Ala  Val  Lys
          2865                    2870                    2875 gac  tcg  tcg  gcg  cag  ctc  acc  tac  tcg  gag  ctc  gat  cga  cag  tcg           9178
Asp  Ser  Ser  Ala  Gln  Leu  Thr  Tyr  Ser  Glu  Leu  Asp  Arg  Gln  Ser
          2880                    2885                    2890 gac  gag  ctt  gcc  ggc  tgg  ctg  cgc  cag  caa  cgt  ctt  cct  gcg  gag           9223
Asp  Glu  Leu  Ala  Gly  Trp  Leu  Arg  Gln  Gln  Arg  Leu  Pro  Ala  Glu
          2895                    2900                    2905 tcg  ttg  gtt  gca  gtg  ctg  gca  ccc  agg  tcg  tgc  cag  acc  att  gtc           9268
Ser  Leu  Val  Ala  Val  Leu  Ala  Pro  Arg  Ser  Cys  Gln  Thr  Ile  Val
          2910                    2915                    2920 gcg  ttc  ctg  ggc  atc  ctc  aag  gcg  aat  ctg  gca  tac  ctg  ccg  cta           9313
Ala  Phe  Leu  Gly  Ile  Leu  Lys  Ala  Asn  Leu  Ala  Tyr  Leu  Pro  Leu
          2925                    2930                    2935 gac  gtc  aac  gtg  ccc  gct  act  cgc  ctc  gag  tcg  ata  ctg  tct  gcc           9358
Asp  Val  Asn  Val  Pro  Ala  Thr  Arg  Leu  Glu  Ser  Ile  Leu  Ser  Ala
          2940                    2945                    2950 gtc  ggc  ggc  cgg  aag  ctg  gtc  ttg  ctt  gga  gct  gac  gtg  gcc  gac           9403
Val  Gly  Gly  Arg  Lys  Leu  Val  Leu  Leu  Gly  Ala  Asp  Val  Ala  Asp
```

-continued

|  |  |  |  |  |  |  |  |  |  |  |  |  |
|---|---|---|---|---|---|---|---|---|---|---|---|---|
|  |  | 2955 |  |  | 2960 |  |  |  | 2965 |  |  |  |
| cct | ggc | ctt | cgc | ctg | gcg | gat | gtg | gag | ctc | gtg | cgg | atc | ggc | gac | 9448 |
| Pro | Gly | Leu | Arg | Leu | Ala | Asp | Val | Glu | Leu | Val | Arg | Ile | Gly | Asp |  |
|  |  | 2970 |  |  |  | 2975 |  |  |  |  | 2980 |  |  |  |  |
| aca | ctc | ggc | cgc | tgt | gta | ccc | ggg | gcg | ccc | ggc | gac | aat | gag | gca | 9493 |
| Thr | Leu | Gly | Arg | Cys | Val | Pro | Gly | Ala | Pro | Gly | Asp | Asn | Glu | Ala |  |
|  |  | 2985 |  |  |  | 2990 |  |  |  |  | 2995 |  |  |  |  |
| cct | gtg | gtg | cag | cct | tct | gcc | aca | agc | ctt | gcc | tac | gtc | atc | ttc | 9538 |
| Pro | Val | Val | Gln | Pro | Ser | Ala | Thr | Ser | Leu | Ala | Tyr | Val | Ile | Phe |  |
|  |  | 3000 |  |  |  | 3005 |  |  |  |  | 3010 |  |  |  |  |
| act | tcc | ggc | tcg | acc | ggc | aag | ccg | aag | ggt | gtc | atg | gtc | gag | cac | 9583 |
| Thr | Ser | Gly | Ser | Thr | Gly | Lys | Pro | Lys | Gly | Val | Met | Val | Glu | His |  |
|  |  | 3015 |  |  |  | 3020 |  |  |  |  | 3025 |  |  |  |  |
| cgt | agt | atc | gtc | cgc | ttg | atg | agg | cac | agc | aat | gtc | tcg | agt | cgc | 9628 |
| Arg | Ser | Ile | Val | Arg | Leu | Met | Arg | His | Ser | Asn | Val | Ser | Ser | Arg |  |
|  |  | 3030 |  |  |  | 3035 |  |  |  |  | 3040 |  |  |  |  |
| ctt | ctg | cta | cat | ccc | cgc | atg | acc | cac | ctg | tcg | aat | ctc | gcc | ttc | 9673 |
| Leu | Leu | Leu | His | Pro | Arg | Met | Thr | His | Leu | Ser | Asn | Leu | Ala | Phe |  |
|  |  | 3045 |  |  |  | 3050 |  |  |  |  | 3055 |  |  |  |  |
| gat | gcg | tcg | gtg | tgg | gag | att | ttc | ttg | acg | ctg | ctc | aac | ggt | gga | 9718 |
| Asp | Ala | Ser | Val | Trp | Glu | Ile | Phe | Leu | Thr | Leu | Leu | Asn | Gly | Gly |  |
|  |  | 3060 |  |  |  | 3065 |  |  |  |  | 3070 |  |  |  |  |
| aca | ttg | att | tgt | att | gac | tac | ctc | tcg | tca | cta | gac | tgt | cgt | gct | 9763 |
| Thr | Leu | Ile | Cys | Ile | Asp | Tyr | Leu | Ser | Ser | Leu | Asp | Cys | Arg | Ala |  |
|  |  | 3075 |  |  |  | 3080 |  |  |  |  | 3085 |  |  |  |  |
| ctt | ggg | gta | agt | atc | ctg | gaa | cac | cag | gtt | gac | gca | tcg | gta | ctt | 9808 |
| Leu | Gly | Val | Ser | Ile | Leu | Glu | His | Gln | Val | Asp | Ala | Ser | Val | Leu |  |
|  |  | 3090 |  |  |  | 3095 |  |  |  |  | 3100 |  |  |  |  |
| cct | cct | gct | ttg | ctc | aaa | caa | tgc | cta | gca | aat | gtc | cct | gag | gca | 9853 |
| Pro | Pro | Ala | Leu | Leu | Lys | Gln | Cys | Leu | Ala | Asn | Val | Pro | Glu | Ala |  |
|  |  | 3105 |  |  |  | 3110 |  |  |  |  | 3115 |  |  |  |  |
| ctt | gcg | agc | ctg | caa | gtg | ctc | ttg | tcc | gct | gga | gat | cga | ctc | gac | 9898 |
| Leu | Ala | Ser | Leu | Gln | Val | Leu | Leu | Ser | Ala | Gly | Asp | Arg | Leu | Asp |  |
|  |  | 3120 |  |  |  | 3125 |  |  |  |  | 3130 |  |  |  |  |
| agt | cgt | gat | gct | ata | gag | agt | tgc | gca | ctc | gtg | cgc | gga | agt | gtc | 9943 |
| Ser | Arg | Asp | Ala | Ile | Glu | Ser | Cys | Ala | Leu | Val | Arg | Gly | Ser | Val |  |
|  |  | 3135 |  |  |  | 3140 |  |  |  |  | 3145 |  |  |  |  |
| tac | aat | ggg | tat | ggt | ccc | acg | gag | aat | ggc | atc | cag | agc | aca | atc | 9988 |
| Tyr | Asn | Gly | Tyr | Gly | Pro | Thr | Glu | Asn | Gly | Ile | Gln | Ser | Thr | Ile |  |
|  |  | 3150 |  |  |  | 3155 |  |  |  |  | 3160 |  |  |  |  |
| tat | gaa | gtc | aaa | gcg | gac | gct | gag | ttt | gtc | aat | ggt | gtg | cct | atc | 10033 |
| Tyr | Glu | Val | Lys | Ala | Asp | Ala | Glu | Phe | Val | Asn | Gly | Val | Pro | Ile |  |
|  |  | 3165 |  |  |  | 3170 |  |  |  |  | 3175 |  |  |  |  |
| ggc | cgc | gct | gtg | agc | aac | tca | ggg | gca | tat | gtc | atg | gac | ccg | cag | 10078 |
| Gly | Arg | Ala | Val | Ser | Asn | Ser | Gly | Ala | Tyr | Val | Met | Asp | Pro | Gln |  |
|  |  | 3180 |  |  |  | 3185 |  |  |  |  | 3190 |  |  |  |  |
| cag | caa | ctg | gtg | cct | ctc | ggg | gtg | atg | ggc | gag | ctc | gtc | gtc | acc | 10123 |
| Gln | Gln | Leu | Val | Pro | Leu | Gly | Val | Met | Gly | Glu | Leu | Val | Val | Thr |  |
|  |  | 3195 |  |  |  | 3200 |  |  |  |  | 3205 |  |  |  |  |
| ggc | gac | ggc | ctg | gcc | cgt | ggt | tac | acc | gac | ccg | tca | ctg | gat | gcg | 10168 |
| Gly | Asp | Gly | Leu | Ala | Arg | Gly | Tyr | Thr | Asp | Pro | Ser | Leu | Asp | Ala |  |
|  |  | 3210 |  |  |  | 3215 |  |  |  |  | 3220 |  |  |  |  |
| gac | cgc | ttt | gtg | cag | gtc | tcc | gtc | aac | ggg | cag | ctc | gtg | aga | gcg | 10213 |
| Asp | Arg | Phe | Val | Gln | Val | Ser | Val | Asn | Gly | Gln | Leu | Val | Arg | Ala |  |
|  |  | 3225 |  |  |  | 3230 |  |  |  |  | 3235 |  |  |  |  |
| tac | cga | aca | ggc | gat | cgc | gtg | cgc | tgc | agg | cct | tgc | gat | ggc | cag | 10258 |
| Tyr | Arg | Thr | Gly | Asp | Arg | Val | Arg | Cys | Arg | Pro | Cys | Asp | Gly | Gln |  |
|  |  | 3240 |  |  |  | 3245 |  |  |  |  | 3250 |  |  |  |  |
| atc | gag | ttc | ttt | gga | cgt | atg | gac | cgg | caa | gtc | aag | atc | cga | gga | 10303 |

-continued

| | |
|---|---|
| Ile Glu Phe Phe Gly Arg Met Asp Arg Gln Val Lys Ile Arg Gly<br>3255              3260              3265 | |
| cat cgc atc gag ctc gca gag gta gag cat gcg gtg ctt ggc ttg<br>His Arg Ile Glu Leu Ala Glu Val Glu His Ala Val Leu Gly Leu<br>3270              3275              3280 | 10348 |
| gaa gac gtg caa gac gct gcc gtt ctc ata gct caa aca gcc gaa<br>Glu Asp Val Gln Asp Ala Ala Val Leu Ile Ala Gln Thr Ala Glu<br>3285              3290              3295 | 10393 |
| aat gaa gag cta gtt ggc ttc ttc acg ctt cga caa acc cag gct<br>Asn Glu Glu Leu Val Gly Phe Phe Thr Leu Arg Gln Thr Gln Ala<br>3300              3305              3310 | 10438 |
| gtg cag tca aat ggt gcc gct ggt gtt gtg cca gag cac agc gac<br>Val Gln Ser Asn Gly Ala Ala Gly Val Val Pro Glu His Ser Asp<br>3315              3320              3325 | 10483 |
| tcc gag ctg gcg caa tcc tgc tct tgc act caa acg gag cgt cga<br>Ser Glu Leu Ala Gln Ser Cys Ser Cys Thr Gln Thr Glu Arg Arg<br>3330              3335              3340 | 10528 |
| gtc cgc aac aga ttg caa tcc tgt ctt cct cgc tac atg gtt ccg<br>Val Arg Asn Arg Leu Gln Ser Cys Leu Pro Arg Tyr Met Val Pro<br>3345              3350              3355 | 10573 |
| tcg cga atg gtc ctt ttg gat cga ctg cct gtc aac ccc aat ggt<br>Ser Arg Met Val Leu Leu Asp Arg Leu Pro Val Asn Pro Asn Gly<br>3360              3365              3370 | 10618 |
| aaa gtt gat cga caa gag ctc acg agg cgc gct cag gat ctc cca<br>Lys Val Asp Arg Gln Glu Leu Thr Arg Arg Ala Gln Asp Leu Pro<br>3375              3380              3385 | 10663 |
| ata agc gag tca tcc cca gtg cac gtc aaa ccg cgt act gaa ctg<br>Ile Ser Glu Ser Ser Pro Val His Val Lys Pro Arg Thr Glu Leu<br>3390              3395              3400 | 10708 |
| gaa agg tcg ctg tgc gag gag ttc gcc gat gtt ata ggt ttg gaa<br>Glu Arg Ser Leu Cys Glu Glu Phe Ala Asp Val Ile Gly Leu Glu<br>3405              3410              3415 | 10753 |
| gtc ggc gtt acc gat aat ttc ttc gac cta ggc ggg cac tct ctc<br>Val Gly Val Thr Asp Asn Phe Phe Asp Leu Gly Gly His Ser Leu<br>3420              3425              3430 | 10798 |
| atg gcg atg aaa ctc gca gct cgc atc agc cgt cgt tcg aat gca<br>Met Ala Met Lys Leu Ala Ala Arg Ile Ser Arg Arg Ser Asn Ala<br>3435              3440              3445 | 10843 |
| cat ata tca gtc aag gac att ttc gac cac ccg ctg att gca gat<br>His Ile Ser Val Lys Asp Ile Phe Asp His Pro Leu Ile Ala Asp<br>3450              3455              3460 | 10888 |
| ctc gca atg aaa att cgg gaa ggc tcc gat ctg cac act cca att<br>Leu Ala Met Lys Ile Arg Glu Gly Ser Asp Leu His Thr Pro Ile<br>3465              3470              3475 | 10933 |
| ccc cac agg atg tac gtt gga cct atc cag cta tca ttc gca cag<br>Pro His Arg Met Tyr Val Gly Pro Ile Gln Leu Ser Phe Ala Gln<br>3480              3485              3490 | 10978 |
| gga cgc ttg tgg ttc ctc gac caa ttg aat ttg ggc gca tcg tgg<br>Gly Arg Leu Trp Phe Leu Asp Gln Leu Asn Leu Gly Ala Ser Trp<br>3495              3500              3505 | 11023 |
| tac gtc atg cca ctt gct atg cgc ctc caa ggc tcg ctc cag ctc<br>Tyr Val Met Pro Leu Ala Met Arg Leu Gln Gly Ser Leu Gln Leu<br>3510              3515              3520 | 11068 |
| gac gcg tta gag act gca ctg ttt gct atc gag cag cga cac gaa<br>Asp Ala Leu Glu Thr Ala Leu Phe Ala Ile Glu Gln Arg His Glu<br>3525              3530              3535 | 11113 |
| acc tta cgg atg aca ttt gca gaa caa gac gga gta gct gta caa<br>Thr Leu Arg Met Thr Phe Ala Glu Gln Asp Gly Val Ala Val Gln<br>3540              3545              3550 | 11158 |

```
gta gtg cat gca gcc cac tac aaa cac atc aag atg atc gac aaa      11203
Val Val His Ala Ala His Tyr Lys His Ile Lys Met Ile Asp Lys
            3555            3560            3565 cca ctt aga cag aag att gac gtc ctg aag atg ctg gaa gaa gaa      11248
Pro Leu Arg Gln Lys Ile Asp Val Leu Lys Met Leu Glu Glu Glu
        3570            3575            3580 cgg acg act ccc ttc gag ctg agc cgc gag cct gga tgg agg gta      11293
Arg Thr Thr Pro Phe Glu Leu Ser Arg Glu Pro Gly Trp Arg Val
    3585            3590            3595 gcg ctg ctg cgt ctg gga gat gac gac cac gtc ctc tcc atc gtc      11338
Ala Leu Leu Arg Leu Gly Asp Asp Asp His Val Leu Ser Ile Val
3600            3605            3610 atg cat cac atc atc tcc gac ggt tgg tct gtg gac gtg ctg cgc      11383
Met His His Ile Ile Ser Asp Gly Trp Ser Val Asp Val Leu Arg
            3615            3620            3625 cac gag cta ggt cag ttc tac tcg gcc gcg ctc cgg ggg cag gac      11428
His Glu Leu Gly Gln Phe Tyr Ser Ala Ala Leu Arg Gly Gln Asp
        3630            3635            3640 ccg ttg tcg cag ata agt cct ctg ccg atc cag tat cgt gac ttc      11473
Pro Leu Ser Gln Ile Ser Pro Leu Pro Ile Gln Tyr Arg Asp Phe
    3645            3650            3655 gct ctc tgg cag aga caa gac gag caa gtt gcg gag cat cag cgc      11518
Ala Leu Trp Gln Arg Gln Asp Glu Gln Val Ala Glu His Gln Arg
3660            3665            3670 cag ctg gag cat tgg aca gag cag ttg gca gac agt tca ccc gcc      11563
Gln Leu Glu His Trp Thr Glu Gln Leu Ala Asp Ser Ser Pro Ala
            3675            3680            3685 gag ttg ttg agc gac cac ccg agg cca tcg att ctt tct ggc cag      11608
Glu Leu Leu Ser Asp His Pro Arg Pro Ser Ile Leu Ser Gly Gln
        3690            3695            3700 gcg ggc gct att ccc gtc aat gtt caa ggc tct ctg tat cag gcg      11653
Ala Gly Ala Ile Pro Val Asn Val Gln Gly Ser Leu Tyr Gln Ala
    3705            3710            3715 ctt cgg gcg ttc tgc cgc gct cac cag gtc acc tct ttc gta gtc      11698
Leu Arg Ala Phe Cys Arg Ala His Gln Val Thr Ser Phe Val Val
3720            3725            3730 ctg ctc acg gcg ttc cgc ata gca cac tat cgt ctg acg ggt gcg      11743
Leu Leu Thr Ala Phe Arg Ile Ala His Tyr Arg Leu Thr Gly Ala
            3735            3740            3745 gag gac gca acc att gga act ccc att gca aat cgc aac cgg cca      11788
Glu Asp Ala Thr Ile Gly Thr Pro Ile Ala Asn Arg Asn Arg Pro
        3750            3755            3760 gag ctc gag aac atg atc ggt ttc ttc gtc aat aca caa tgc atg      11833
Glu Leu Glu Asn Met Ile Gly Phe Phe Val Asn Thr Gln Cys Met
    3765            3770            3775 cgc atc gtc att ggc agt gac gac aca ttt gaa ggg ctg gtg cag      11878
Arg Ile Val Ile Gly Ser Asp Asp Thr Phe Glu Gly Leu Val Gln
3780            3785            3790 caa gta cgc tcg ata act gca gct gcc cac gag aac cag gac gtt      11923
Gln Val Arg Ser Ile Thr Ala Ala Ala His Glu Asn Gln Asp Val
            3795            3800            3805 cca ttc gag cgc atc gtg tca gca ctg ctt ccc ggt tct aga gac      11968
Pro Phe Glu Arg Ile Val Ser Ala Leu Leu Pro Gly Ser Arg Asp
        3810            3815            3820 aca tca cgc aat cct ctg gtt cag ctc atg ttt gct gtc cac tcg      12013
Thr Ser Arg Asn Pro Leu Val Gln Leu Met Phe Ala Val His Ser
    3825            3830            3835 caa aga aac ctt ggt cag atc agt cta gaa ggc ctg cag ggt gaa      12058
Gln Arg Asn Leu Gly Gln Ile Ser Leu Glu Gly Leu Gln Gly Glu
3840            3845            3850
```

```
ttg ctg gga gtg gca gcg act acg aga ttc gat gta gag ttc cat          12103
Leu Leu Gly Val Ala Ala Thr Thr Arg Phe Asp Val Glu Phe His
            3855                3860                3865 ctc ttc caa gat gac gac aag ctc agc ggc aac gtg ctc ttc gcg          12148
Leu Phe Gln Asp Asp Asp Lys Leu Ser Gly Asn Val Leu Phe Ala
            3870                3875                3880 acc gag ctc ttc gag cag aag act atg caa ggc atg gtc gac gtg          12193
Thr Glu Leu Phe Glu Gln Lys Thr Met Gln Gly Met Val Asp Val
            3885                3890                3895 ttc cag gaa gtg ctc agc cgg ggc ctt gag cag ccc cag ata cct          12238
Phe Gln Glu Val Leu Ser Arg Gly Leu Glu Gln Pro Gln Ile Pro
            3900                3905                3910 ctg gcg acc ctc ccg ctc acg cac gga ctg gag gag ctc agg acc          12283
Leu Ala Thr Leu Pro Leu Thr His Gly Leu Glu Glu Leu Arg Thr
            3915                3920                3925 atg ggt ctt ctc gac gtg gag aag aca gac tac cct cga gag tcg          12328
Met Gly Leu Leu Asp Val Glu Lys Thr Asp Tyr Pro Arg Glu Ser
            3930                3935                3940 agc gtg gtg gac gtg ttc cgt gag caa gcg gct gcc tgc tcc gag          12373
Ser Val Val Asp Val Phe Arg Glu Gln Ala Ala Ala Cys Ser Glu
            3945                3950                3955 gcg att gcg gtc aaa gac tcg tcg gcg cag ctc acc tac tcg gag          12418
Ala Ile Ala Val Lys Asp Ser Ser Ala Gln Leu Thr Tyr Ser Glu
            3960                3965                3970 ctc gat cga cag tcg gac gag ctt gcc ggc tgg ctg cgc cag caa          12463
Leu Asp Arg Gln Ser Asp Glu Leu Ala Gly Trp Leu Arg Gln Gln
            3975                3980                3985 cgt ctt cct gcg gag tcg ttg gtt gca gtg ctg gca ccc agg tcg          12508
Arg Leu Pro Ala Glu Ser Leu Val Ala Val Leu Ala Pro Arg Ser
            3990                3995                4000 tgc cag acc att gtc gcg ttc ctg ggc atc ctc aag gcg aat ctg          12553
Cys Gln Thr Ile Val Ala Phe Leu Gly Ile Leu Lys Ala Asn Leu
            4005                4010                4015 gca tac ctg ccg cta gac gtc aac gtg ccc gct act cgc ctc gag          12598
Ala Tyr Leu Pro Leu Asp Val Asn Val Pro Ala Thr Arg Leu Glu
            4020                4025                4030 tcg ata ctg tct gcc gtc ggc ggc cgg aag ctg gtc ttg ctt gga          12643
Ser Ile Leu Ser Ala Val Gly Gly Arg Lys Leu Val Leu Leu Gly
            4035                4040                4045 gct gac gtg gcc gac cct ggc ctt cgc ctg gcg gat gtg gag ctc          12688
Ala Asp Val Ala Asp Pro Gly Leu Arg Leu Ala Asp Val Glu Leu
            4050                4055                4060 gtg cgg atc ggc gac aca ctc ggc cgc tgt gta ccc ggg gcg ccc          12733
Val Arg Ile Gly Asp Thr Leu Gly Arg Cys Val Pro Gly Ala Pro
            4065                4070                4075 ggc gac aat gag gca cct gtg gtg cag cct tct gcc aca agc ctt          12778
Gly Asp Asn Glu Ala Pro Val Val Gln Pro Ser Ala Thr Ser Leu
            4080                4085                4090 gcc tac gtc atc ttc act tcc ggc tcg acc ggc aag ccg aag ggt          12823
Ala Tyr Val Ile Phe Thr Ser Gly Ser Thr Gly Lys Pro Lys Gly
            4095                4100                4105 gtc atg gtc gag cac cgt agt atc gtc cgc ttg atg agg cac agc          12868
Val Met Val Glu His Arg Ser Ile Val Arg Leu Met Arg His Ser
            4110                4115                4120 aat gtc tcg agt cgc ctt ctg cta cat ccc cgc atg acc cac ctg          12913
Asn Val Ser Ser Arg Leu Leu Leu His Pro Arg Met Thr His Leu
            4125                4130                4135 tcg aat ctc gcc ttc gat gcg tcg gtg tgg gag att ttc ttg acg          12958
Ser Asn Leu Ala Phe Asp Ala Ser Val Trp Glu Ile Phe Leu Thr
```

-continued

| | | | | | | | | | | | | | | |
|---|---|---|---|---|---|---|---|---|---|---|---|---|---|---|
| ctg | ctc | aac | ggt | gga | aca | ttg | att | tgt | att | gac | tac | ctc | tcg | tca | 13003 |
| Leu | Leu | Asn | Gly | Gly | Thr | Leu | Ile | Cys | Ile | Asp | Tyr | Leu | Ser | Ser | |
| | | | 4155 | | | | 4160 | | | | 4165 | | | | |
| cta | gac | tgt | cgt | gct | ctt | ggg | gta | agt | atc | ctg | gaa | cac | cag | gtt | 13048 |
| Leu | Asp | Cys | Arg | Ala | Leu | Gly | Val | Ser | Ile | Leu | Glu | His | Gln | Val | |
| | | 4170 | | | | 4175 | | | | | 4180 | | | | |
| gac | gca | tcg | gta | ctt | cct | cct | gct | ttg | ctc | aaa | caa | tgc | cta | gca | 13093 |
| Asp | Ala | Ser | Val | Leu | Pro | Pro | Ala | Leu | Leu | Lys | Gln | Cys | Leu | Ala | |
| | | 4185 | | | | 4190 | | | | | 4195 | | | | |
| aat | gtc | cct | gag | gca | ctt | gcg | agc | ctg | caa | gtg | ctc | ttg | tcc | gct | 13138 |
| Asn | Val | Pro | Glu | Ala | Leu | Ala | Ser | Leu | Gln | Val | Leu | Leu | Ser | Ala | |
| | | | 4200 | | | | 4205 | | | | 4210 | | | | |
| gga | gat | cga | ctc | gac | agt | cgt | gat | gct | ata | gag | agt | tgc | gca | ctc | 13183 |
| Gly | Asp | Arg | Leu | Asp | Ser | Arg | Asp | Ala | Ile | Glu | Ser | Cys | Ala | Leu | |
| | | | 4215 | | | | 4220 | | | | 4225 | | | | |
| gtg | cgc | gga | agt | gtc | tac | aat | ggg | tat | ggt | ccc | acg | gag | aat | ggc | 13228 |
| Val | Arg | Gly | Ser | Val | Tyr | Asn | Gly | Tyr | Gly | Pro | Thr | Glu | Asn | Gly | |
| | | 4230 | | | | 4235 | | | | | 4240 | | | | |
| atc | cag | agc | aca | atc | tat | gaa | gtc | aaa | gcg | gac | gct | gag | ttt | gtc | 13273 |
| Ile | Gln | Ser | Thr | Ile | Tyr | Glu | Val | Lys | Ala | Asp | Ala | Glu | Phe | Val | |
| | | | 4245 | | | | 4250 | | | | 4255 | | | | |
| aat | ggt | gtg | cct | atc | ggc | cgc | gct | gtg | agc | aac | tca | ggg | gca | tat | 13318 |
| Asn | Gly | Val | Pro | Ile | Gly | Arg | Ala | Val | Ser | Asn | Ser | Gly | Ala | Tyr | |
| | | | 4260 | | | | 4265 | | | | 4270 | | | | |
| gtc | atg | gac | ccg | cag | cag | caa | ctg | gtg | cct | ctc | ggg | gtg | atg | ggc | 13363 |
| Val | Met | Asp | Pro | Gln | Gln | Gln | Leu | Val | Pro | Leu | Gly | Val | Met | Gly | |
| | | | 4275 | | | | 4280 | | | | 4285 | | | | |
| gag | ctc | gtc | gtc | acc | ggc | gac | ggc | ctg | gcc | cgt | ggt | tac | acc | gac | 13408 |
| Glu | Leu | Val | Val | Thr | Gly | Asp | Gly | Leu | Ala | Arg | Gly | Tyr | Thr | Asp | |
| | | | 4290 | | | | 4295 | | | | 4300 | | | | |
| ccg | tca | ctg | gat | gcg | gac | cgc | ttt | gtg | cag | gtc | tcc | gtc | aac | ggg | 13453 |
| Pro | Ser | Leu | Asp | Ala | Asp | Arg | Phe | Val | Gln | Val | Ser | Val | Asn | Gly | |
| | | | 4305 | | | | 4310 | | | | 4315 | | | | |
| cag | ctc | gtg | aga | gcg | tac | cga | aca | ggc | gat | cgc | gtg | cgc | tgc | agg | 13498 |
| Gln | Leu | Val | Arg | Ala | Tyr | Arg | Thr | Gly | Asp | Arg | Val | Arg | Cys | Arg | |
| | | | 4320 | | | | 4325 | | | | 4330 | | | | |
| cct | tgc | gat | ggc | cag | atc | gag | ttc | ttt | gga | cgt | atg | gac | cgg | caa | 13543 |
| Pro | Cys | Asp | Gly | Gln | Ile | Glu | Phe | Phe | Gly | Arg | Met | Asp | Arg | Gln | |
| | | | 4335 | | | | 4340 | | | | 4345 | | | | |
| gtc | aag | atc | cga | gga | cat | cgc | atc | gag | ctc | gca | gag | gta | gag | cat | 13588 |
| Val | Lys | Ile | Arg | Gly | His | Arg | Ile | Glu | Leu | Ala | Glu | Val | Glu | His | |
| | | | 4350 | | | | 4355 | | | | 4360 | | | | |
| gcg | gtg | ctt | ggc | ttg | gaa | gac | gtg | caa | gac | gct | gcc | gtt | atc | gca | 13633 |
| Ala | Val | Leu | Gly | Leu | Glu | Asp | Val | Gln | Asp | Ala | Ala | Val | Ile | Ala | |
| | | | 4365 | | | | 4370 | | | | 4375 | | | | |
| ttt | gac | aat | gtg | gac | agc | gaa | gag | cca | gaa | atg | gtt | ggg | ttt | gtc | 13678 |
| Phe | Asp | Asn | Val | Asp | Ser | Glu | Glu | Pro | Glu | Met | Val | Gly | Phe | Val | |
| | | | 4380 | | | | 4385 | | | | 4390 | | | | |
| act | att | acc | gaa | gac | aat | cct | gtc | cgt | gag | gac | gaa | acc | agc | ggt | 13723 |
| Thr | Ile | Thr | Glu | Asp | Asn | Pro | Val | Arg | Glu | Asp | Glu | Thr | Ser | Gly | |
| | | | 4395 | | | | 4400 | | | | 4405 | | | | |
| caa | gta | gaa | gac | tgg | gcg | aac | cac | ttc | gag | ata | agt | acc | tac | acc | 13768 |
| Gln | Val | Glu | Asp | Trp | Ala | Asn | His | Phe | Glu | Ile | Ser | Thr | Tyr | Thr | |
| | | | 4410 | | | | 4415 | | | | 4420 | | | | |
| gat | atc | gcg | gcg | atc | gat | cag | ggt | agc | att | gga | agt | gac | ttt | gta | 13813 |
| Asp | Ile | Ala | Ala | Ile | Asp | Gln | Gly | Ser | Ile | Gly | Ser | Asp | Phe | Val | |
| | | | 4425 | | | | 4430 | | | | 4435 | | | | |
| ggt | tgg | act | tct | atg | tac | gac | gga | agc | gag | atc | gac | aag | gca | gag | 13858 |

|  |  |  |  |  |  |  |  |  |  |  |  |  |  |
|---|---|---|---|---|---|---|---|---|---|---|---|---|---|
| Gly | Trp | Thr | Ser | Met | Tyr | Asp | Gly | Ser | Glu | Ile | Asp | Lys | Ala | Glu |
|  |  |  | 4440 |  |  |  | 4445 |  |  |  | 4450 |  |  |

| atg | caa | gaa | tgg | ctt | gcc | gat | acc | atg | gcc | tct | atg | ctc | gac | ggg | 13903 |
|---|---|---|---|---|---|---|---|---|---|---|---|---|---|---|---|
| Met | Gln | Glu | Trp | Leu | Ala | Asp | Thr | Met | Ala | Ser | Met | Leu | Asp | Gly |  |
|  |  |  | 4455 |  |  |  | 4460 |  |  |  | 4465 |  |  |  |  |

| cag | gcg | ccg | ggc | aat | gtg | tta | gag | ata | ggt | aca | ggc | act | ggc | atg | 13948 |
|---|---|---|---|---|---|---|---|---|---|---|---|---|---|---|---|
| Gln | Ala | Pro | Gly | Asn | Val | Leu | Glu | Ile | Gly | Thr | Gly | Thr | Gly | Met |  |
|  |  |  | 4470 |  |  |  | 4475 |  |  |  | 4480 |  |  |  |  |

| gtc | ctc | ttc | aat | ctc | ggc | gac | gga | ctg | cag | agc | tat | gtc | ggc | ctc | 13993 |
|---|---|---|---|---|---|---|---|---|---|---|---|---|---|---|---|
| Val | Leu | Phe | Asn | Leu | Gly | Asp | Gly | Leu | Gln | Ser | Tyr | Val | Gly | Leu |  |
|  |  |  | 4485 |  |  |  | 4490 |  |  |  | 4495 |  |  |  |  |

| gaa | cca | tca | aga | tcg | gcg | gcc | gct | ttt | gtc | aac | cag | acg | att | aag | 14038 |
|---|---|---|---|---|---|---|---|---|---|---|---|---|---|---|---|
| Glu | Pro | Ser | Arg | Ser | Ala | Ala | Ala | Phe | Val | Asn | Gln | Thr | Ile | Lys |  |
|  |  |  | 4500 |  |  |  | 4505 |  |  |  | 4510 |  |  |  |  |

| tcg | ctc | ccc | acc | ctt | gct | ggc | aac | gct | gaa | gta | cac | att | ggc | act | 14083 |
|---|---|---|---|---|---|---|---|---|---|---|---|---|---|---|---|
| Ser | Leu | Pro | Thr | Leu | Ala | Gly | Asn | Ala | Glu | Val | His | Ile | Gly | Thr |  |
|  |  |  | 4515 |  |  |  | 4520 |  |  |  | 4525 |  |  |  |  |

| gcg | acc | gac | gtg | gcc | cgt | cta | gat | ggc | ctc | cgc | ccc | gac | tta | gtg | 14128 |
|---|---|---|---|---|---|---|---|---|---|---|---|---|---|---|---|
| Ala | Thr | Asp | Val | Ala | Arg | Leu | Asp | Gly | Leu | Arg | Pro | Asp | Leu | Val |  |
|  |  |  | 4530 |  |  |  | 4535 |  |  |  | 4540 |  |  |  |  |

| gta | gtc | aat | tcg | gta | gtc | cag | tac | ttc | cca | tca | cca | gag | tac | cta | 14173 |
|---|---|---|---|---|---|---|---|---|---|---|---|---|---|---|---|
| Val | Val | Asn | Ser | Val | Val | Gln | Tyr | Phe | Pro | Ser | Pro | Glu | Tyr | Leu |  |
|  |  |  | 4545 |  |  |  | 4550 |  |  |  | 4555 |  |  |  |  |

| atg | gaa | gtc | gtg | gag | gct | ctt | gca | cgt | ctg | ccg | ggc | gtc | gag | cga | 14218 |
|---|---|---|---|---|---|---|---|---|---|---|---|---|---|---|---|
| Met | Glu | Val | Val | Glu | Ala | Leu | Ala | Arg | Leu | Pro | Gly | Val | Glu | Arg |  |
|  |  |  | 4560 |  |  |  | 4565 |  |  |  | 4570 |  |  |  |  |

| att | ttc | ttc | gga | gac | gta | cgt | tcg | tac | gcc | atc | aac | aga | gat | ttc | 14263 |
|---|---|---|---|---|---|---|---|---|---|---|---|---|---|---|---|
| Ile | Phe | Phe | Gly | Asp | Val | Arg | Ser | Tyr | Ala | Ile | Asn | Arg | Asp | Phe |  |
|  |  |  | 4575 |  |  |  | 4580 |  |  |  | 4585 |  |  |  |  |

| ctg | gct | gcc | aga | gct | cta | cac | gaa | ctt | ggc | gac | aga | gcg | act | aag | 14308 |
|---|---|---|---|---|---|---|---|---|---|---|---|---|---|---|---|
| Leu | Ala | Ala | Arg | Ala | Leu | His | Glu | Leu | Gly | Asp | Arg | Ala | Thr | Lys |  |
|  |  |  | 4590 |  |  |  | 4595 |  |  |  | 4600 |  |  |  |  |

| cac | gag | att | cgg | cga | aag | atg | cta | gag | atg | gaa | gaa | cgc | gaa | gag | 14353 |
|---|---|---|---|---|---|---|---|---|---|---|---|---|---|---|---|
| His | Glu | Ile | Arg | Arg | Lys | Met | Leu | Glu | Met | Glu | Glu | Arg | Glu | Glu |  |
|  |  |  | 4605 |  |  |  | 4610 |  |  |  | 4615 |  |  |  |  |

| gag | ctg | ctc | gtc | gac | cca | gct | ttc | ttc | acc | atg | ttg | acc | agc | agt | 14398 |
|---|---|---|---|---|---|---|---|---|---|---|---|---|---|---|---|
| Glu | Leu | Leu | Val | Asp | Pro | Ala | Phe | Phe | Thr | Met | Leu | Thr | Ser | Ser |  |
|  |  |  | 4620 |  |  |  | 4625 |  |  |  | 4630 |  |  |  |  |

| ctc | cct | ggc | ctg | att | cag | cat | gtc | gag | atc | ttg | ccg | aag | ctg | atg | 14443 |
|---|---|---|---|---|---|---|---|---|---|---|---|---|---|---|---|
| Leu | Pro | Gly | Leu | Ile | Gln | His | Val | Glu | Ile | Leu | Pro | Lys | Leu | Met |  |
|  |  |  | 4635 |  |  |  | 4640 |  |  |  | 4645 |  |  |  |  |

| aga | gcc | act | aat | gag | ctc | agc | gcg | tat | cga | tac | act | gct | gta | gta | 14488 |
|---|---|---|---|---|---|---|---|---|---|---|---|---|---|---|---|
| Arg | Ala | Thr | Asn | Glu | Leu | Ser | Ala | Tyr | Arg | Tyr | Thr | Ala | Val | Val |  |
|  |  |  | 4650 |  |  |  | 4655 |  |  |  | 4660 |  |  |  |  |

| cac | gtg | tgc | cgt | gcc | ggt | caa | gag | cct | cgt | tcc | gtg | cat | acg | atc | 14533 |
|---|---|---|---|---|---|---|---|---|---|---|---|---|---|---|---|
| His | Val | Cys | Arg | Ala | Gly | Gln | Glu | Pro | Arg | Ser | Val | His | Thr | Ile |  |
|  |  |  | 4665 |  |  |  | 4670 |  |  |  | 4675 |  |  |  |  |

| gac | gac | gat | gcc | tgg | gtg | aat | ctt | gga | gct | tct | cgg | ttg | agt | cgc | 14578 |
|---|---|---|---|---|---|---|---|---|---|---|---|---|---|---|---|
| Asp | Asp | Asp | Ala | Trp | Val | Asn | Leu | Gly | Ala | Ser | Arg | Leu | Ser | Arg |  |
|  |  |  | 4680 |  |  |  | 4685 |  |  |  | 4690 |  |  |  |  |

| cct | acc | ctt | tca | agc | ctt | ttg | caa | act | tcc | gag | ggc | gca | tcg | gcc | 14623 |
|---|---|---|---|---|---|---|---|---|---|---|---|---|---|---|---|
| Pro | Thr | Leu | Ser | Ser | Leu | Leu | Gln | Thr | Ser | Glu | Gly | Ala | Ser | Ala |  |
|  |  |  | 4695 |  |  |  | 4700 |  |  |  | 4705 |  |  |  |  |

| gtc | gca | gta | agc | aat | att | cct | tac | agc | aag | acc | atc | aca | gag | cga | 14668 |
|---|---|---|---|---|---|---|---|---|---|---|---|---|---|---|---|
| Val | Ala | Val | Ser | Asn | Ile | Pro | Tyr | Ser | Lys | Thr | Ile | Thr | Glu | Arg |  |
|  |  |  | 4710 |  |  |  | 4715 |  |  |  | 4720 |  |  |  |  |

| gcg | ctc | gtt | agt | gcg | ctc | gat | gag | gat | gat | atg | caa | gac | tca | tcg | 14713 |
|---|---|---|---|---|---|---|---|---|---|---|---|---|---|---|---|
| Ala | Leu | Val | Ser | Ala | Leu | Asp | Glu | Asp | Asp | Met | Gln | Asp | Ser | Ser |  |
|  |  |  | 4725 |  |  |  | 4730 |  |  |  | 4735 |  |  |  |  |

-continued

| | | | | | | | | | | | | | | |
|---|---|---|---|---|---|---|---|---|---|---|---|---|---|---|
| gac | tgg | ctg | ctg | gcc | gtg | cgc | gag | aca | ggc | aga | tct | tgt | tcc | tcc | 14758 |
| Asp | Trp | Leu | Leu | Ala | Val | Arg | Glu | Thr | Gly | Arg | Ser | Cys | Ser | Ser | |
| | 4740 | | | | 4745 | | | | | 4750 | | | | | |
| ttc | tcc | gca | aca | gac | ctt | gtc | gag | ctt | gct | cga | gag | acg | ggc | tgg | 14803 |
| Phe | Ser | Ala | Thr | Asp | Leu | Val | Glu | Leu | Ala | Arg | Glu | Thr | Gly | Trp | |
| | | 4755 | | | | 4760 | | | | | 4765 | | | | |
| cgt | gtg | gag | ctc | agc | tgg | gca | cga | cag | tac | tca | cag | aaa | ggc | gca | 14848 |
| Arg | Val | Glu | Leu | Ser | Trp | Ala | Arg | Gln | Tyr | Ser | Gln | Lys | Gly | Ala | |
| | | 4770 | | | | | 4775 | | | | | 4780 | | | |
| ctc | gat | gct | gtc | ttc | cac | aga | cac | cct | gtt | tcc | gct | ggg | agc | ggg | 14893 |
| Leu | Asp | Ala | Val | Phe | His | Arg | His | Pro | Val | Ser | Ala | Gly | Ser | Gly | |
| | | | 4785 | | | | | 4790 | | | | | 4795 | | |
| cgt | gtc | atg | ttc | cag | ttt | cca | gtt | gag | acc | gaa | gat | cga | ccg | cac | 14938 |
| Arg | Val | Met | Phe | Gln | Phe | Pro | Val | Glu | Thr | Glu | Asp | Arg | Pro | His | |
| | | | 4800 | | | | | 4805 | | | | | 4810 | | |
| atc | tca | cgc | acg | aac | cga | cct | tta | cag | cga | ttg | cag | aag | aag | cga | 14983 |
| Ile | Ser | Arg | Thr | Asn | Arg | Pro | Leu | Gln | Arg | Leu | Gln | Lys | Lys | Arg | |
| | | | 4815 | | | | | 4820 | | | | | 4825 | | |
| acc | gag | aca | cat | gtt | cat | gag | cag | ttg | cgg | gct | ttg | ctt | cca | cga | 15028 |
| Thr | Glu | Thr | His | Val | His | Glu | Gln | Leu | Arg | Ala | Leu | Leu | Pro | Arg | |
| | | 4830 | | | | | 4835 | | | | | 4840 | | | |
| tac | atg | gtt | cct | acg | cgg | att | gtg | gcg | ctt | gat | aag | ctg | ccc | gtc | 15073 |
| Tyr | Met | Val | Pro | Thr | Arg | Ile | Val | Ala | Leu | Asp | Lys | Leu | Pro | Val | |
| | | 4845 | | | | | 4850 | | | | | 4855 | | | |
| aat | gca | aac | ggc | aag | gtt | gat | cgt | caa | cag | ctc | gct | agg | aca | gcc | 15118 |
| Asn | Ala | Asn | Gly | Lys | Val | Asp | Arg | Gln | Gln | Leu | Ala | Arg | Thr | Ala | |
| | | 4860 | | | | | 4865 | | | | | 4870 | | | |
| cag | gtt | ctc | cca | gcg | agc | aag | gcg | ccg | tct | gca | tgc | gtg | gcc | cca | 15163 |
| Gln | Val | Leu | Pro | Ala | Ser | Lys | Ala | Pro | Ser | Ala | Cys | Val | Ala | Pro | |
| | | 4875 | | | | | 4880 | | | | | 4885 | | | |
| cgc | aac | gaa | ttg | gaa | atg | aca | ctg | tgt | gaa | gag | ttc | tcg | cag | gtt | 15208 |
| Arg | Asn | Glu | Leu | Glu | Met | Thr | Leu | Cys | Glu | Glu | Phe | Ser | Gln | Val | |
| | | 4890 | | | | | 4895 | | | | | 4900 | | | |
| ctt | ggc | gtc | gag | gtc | ggc | att | act | gac | aat | ttc | ttc | cac | ctg | ggt | 15253 |
| Leu | Gly | Val | Glu | Val | Gly | Ile | Thr | Asp | Asn | Phe | Phe | His | Leu | Gly | |
| | 4905 | | | | | 4910 | | | | | 4915 | | | | |
| ggc | cac | tct | ctc | atg | gca | aca | aag | ctt | gcc | gct | cgt | atc | agc | cac | 15298 |
| Gly | His | Ser | Leu | Met | Ala | Thr | Lys | Leu | Ala | Ala | Arg | Ile | Ser | His | |
| | | 4920 | | | | | 4925 | | | | | 4930 | | | |
| cgc | ctt | cat | aca | cgc | ata | tcc | gtc | aaa | cac | atc | ttc | gat | cac | cct | 15343 |
| Arg | Leu | His | Thr | Arg | Ile | Ser | Val | Lys | His | Ile | Phe | Asp | His | Pro | |
| | | 4935 | | | | | 4940 | | | | | 4945 | | | |
| ttg | ata | ggc | gat | ttg | tct | gtc | cac | ata | gct | gac | tct | ccg | gtg | cct | 15388 |
| Leu | Ile | Gly | Asp | Leu | Ser | Val | His | Ile | Ala | Asp | Ser | Pro | Val | Pro | |
| | | 4950 | | | | | 4955 | | | | | 4960 | | | |
| ctt | ttg | aca | atc | aca | cgt | gcc | cag | cac | gct | gga | gca | gtg | gag | cag | 15433 |
| Leu | Leu | Thr | Ile | Thr | Arg | Ala | Gln | His | Ala | Gly | Ala | Val | Glu | Gln | |
| | | | 4965 | | | | | 4970 | | | | | 4975 | | |
| tca | ttc | gca | caa | gct | aga | ttg | tgg | ttc | ctt | gtc | cag | cta | gga | ctt | 15478 |
| Ser | Phe | Ala | Gln | Ala | Arg | Leu | Trp | Phe | Leu | Val | Gln | Leu | Gly | Leu | |
| | | | 4980 | | | | | 4985 | | | | | 4990 | | |
| gaa | tct | cct | tcg | tac | atc | ata | cca | att | gta | ttg | cgt | tta | cac | ggt | 15523 |
| Glu | Ser | Pro | Ser | Tyr | Ile | Ile | Pro | Ile | Val | Leu | Arg | Leu | His | Gly | |
| | | | 4995 | | | | | 5000 | | | | | 5005 | | |
| tca | ctc | tca | aag | act | gcc | att | gaa | gga | gct | cta | tca | gcc | ctg | atg | 15568 |
| Ser | Leu | Ser | Lys | Thr | Ala | Ile | Glu | Gly | Ala | Leu | Ser | Ala | Leu | Met | |
| | | | 5010 | | | | | 5015 | | | | | 5020 | | |
| gaa | cgt | cat | gag | gtc | ctt | cgt | acg | acg | ttc | gag | gac | cat | aag | ggt | 15613 |
| Glu | Arg | His | Glu | Val | Leu | Arg | Thr | Thr | Phe | Glu | Asp | His | Lys | Gly | |
| | | | 5025 | | | | | 5030 | | | | | 5035 | | |

```
                                                    -continued atc ggc atg caa gtg gta caa gac cat cgt cac caa gac ttg gtt     15658
Ile Gly Met Gln Val Val Gln Asp His Arg His Gln Asp Leu Val
            5040                5045                5050 gta att gac gtt gca ggt cag ggg tca ctc gac tac aag cag cac     15703
Val Ile Asp Val Ala Gly Gln Gly Ser Leu Asp Tyr Lys Gln His
            5055                5060                5065 tta tac atg gag cac gtg aaa cct ttc gat ctg acc cgg gat cct     15748
Leu Tyr Met Glu His Val Lys Pro Phe Asp Leu Thr Arg Asp Pro
            5070                5075                5080 ggg tgg agg gta gcg ctg ctg cgt ctg gga gat gac gac cac gtc     15793
Gly Trp Arg Val Ala Leu Leu Arg Leu Gly Asp Asp Asp His Val
            5085                5090                5095 ctc tcc atc gta atg cat cac atc atc tcc gat ggc tgg tcg att     15838
Leu Ser Ile Val Met His His Ile Ile Ser Asp Gly Trp Ser Ile
            5100                5105                5110 gat atc ctg ctg cgt gag ttg ggt cag ttc tac tcg gcc gcg ctc     15883
Asp Ile Leu Leu Arg Glu Leu Gly Gln Phe Tyr Ser Ala Ala Leu
            5115                5120                5125 cgg ggg cag gac ccg ttg tca cag aca agt cct ctg ccg atc cag     15928
Arg Gly Gln Asp Pro Leu Ser Gln Thr Ser Pro Leu Pro Ile Gln
            5130                5135                5140 tat cgt gac ttc gct ctc tgg caa aag cag gat cat caa tta gcc     15973
Tyr Arg Asp Phe Ala Leu Trp Gln Lys Gln Asp His Gln Leu Ala
            5145                5150                5155 gat cac gag aag cag ctg cgg tat tgg gaa gag caa ctg gcg gag     16018
Asp His Glu Lys Gln Leu Arg Tyr Trp Glu Glu Gln Leu Ala Glu
            5160                5165                5170 agc tct cca gct gag ctg cta tgt gat cat gca cgt ccg acg acg     16063
Ser Ser Pro Ala Glu Leu Leu Cys Asp His Ala Arg Pro Thr Thr
            5175                5180                5185 ccc tca ggt cag gca ggc tcg att ccc gtc aat gtt caa ggc tct     16108
Pro Ser Gly Gln Ala Gly Ser Ile Pro Val Asn Val Gln Gly Ser
            5190                5195                5200 ctg tat cag gcg ctt cgg gcg ttc tgc cgc gct cac cag gtc acc     16153
Leu Tyr Gln Ala Leu Arg Ala Phe Cys Arg Ala His Gln Val Thr
            5205                5210                5215 tct ttc gta gtc ctg ctc acg gcg ttc cgc ata gca cac tat cgt     16198
Ser Phe Val Val Leu Leu Thr Ala Phe Arg Ile Ala His Tyr Arg
            5220                5225                5230 ctg acg ggt gcg gag gac gca acc att gga act ccc att gca aat     16243
Leu Thr Gly Ala Glu Asp Ala Thr Ile Gly Thr Pro Ile Ala Asn
            5235                5240                5245 cgc aac cgg cca gag ctc gag aac atg atc ggt ttc ttc gtc aat     16288
Arg Asn Arg Pro Glu Leu Glu Asn Met Ile Gly Phe Phe Val Asn
            5250                5255                5260 aca caa tgc atg cgc atc gtc att ggc agt gac gac aca ttt gaa     16333
Thr Gln Cys Met Arg Ile Val Ile Gly Ser Asp Asp Thr Phe Glu
            5265                5270                5275 ggg ctg gtg cag caa gta cgc tcg ata act gca gct gcc cac gag     16378
Gly Leu Val Gln Gln Val Arg Ser Ile Thr Ala Ala Ala His Glu
            5280                5285                5290 aac cag gac gtt cca ttc gag cgc atc gtg tca gca ctg ctt ccc     16423
Asn Gln Asp Val Pro Phe Glu Arg Ile Val Ser Ala Leu Leu Pro
            5295                5300                5305 ggt tct aga gac aca tca cgc aat cct ctg gtg cag ttg ttg ttc     16468
Gly Ser Arg Asp Thr Ser Arg Asn Pro Leu Val Gln Leu Leu Phe
            5310                5315                5320 gct gtt cat gcc tat caa gag gtc gaa aat ttc gcc atc ccc ggt     16513
Ala Val His Ala Tyr Gln Glu Val Glu Asn Phe Ala Ile Pro Gly
```

-continued

```
                 5325                5330                5335
gtg cac tcc gag ttg gtg caa gga acg acc ttt aca aga ttt gat         16558
Val His Ser Glu Leu Val Gln Gly Thr Thr Phe Thr Arg Phe Asp
                 5340                5345                5350 gtc gag ttc cac ctg ctt gaa gac cct gac aag ctc agc ggc aac         16603
Val Glu Phe His Leu Leu Glu Asp Pro Asp Lys Leu Ser Gly Asn
                 5355                5360                5365 gtg ctc ttc gcg acc gag ctc ttc gag cag aag act atg caa ggc         16648
Val Leu Phe Ala Thr Glu Leu Phe Glu Gln Lys Thr Met Gln Gly
                 5370                5375                5380 atg gtc gac gtg ttc cag gaa gtg ctc agc cgg ggc ctt gag cag         16693
Met Val Asp Val Phe Gln Glu Val Leu Ser Arg Gly Leu Glu Gln
                 5385                5390                5395 ccc cag ata cct ctg gcg acc ctc ccg ctc acg cac gga ctg gag         16738
Pro Gln Ile Pro Leu Ala Thr Leu Pro Leu Thr His Gly Leu Glu
                 5400                5405                5410 gag ctc agg acc atg ggt ctt ctc gac gtg gag aag aca gac tac         16783
Glu Leu Arg Thr Met Gly Leu Leu Asp Val Glu Lys Thr Asp Tyr
                 5415                5420                5425 cct cga gag tcg agc gtg gtg gac gtg ttc cgt gag caa gcg gct         16828
Pro Arg Glu Ser Ser Val Val Asp Val Phe Arg Glu Gln Ala Ala
                 5430                5435                5440 gcc tgc tcc gag gcg att gcg gtc aaa gac tcg tcg gcg cag ctc         16873
Ala Cys Ser Glu Ala Ile Ala Val Lys Asp Ser Ser Ala Gln Leu
                 5445                5450                5455 acc tac tcg gag ctc gat cga cag tcg gac gag ctt gcc ggc tgg         16918
Thr Tyr Ser Glu Leu Asp Arg Gln Ser Asp Glu Leu Ala Gly Trp
                 5460                5465                5470 ctg cgc cag caa cgt ctt cct gcg gag tcg ttg gtt gca gtg ctg         16963
Leu Arg Gln Gln Arg Leu Pro Ala Glu Ser Leu Val Ala Val Leu
                 5475                5480                5485 gca ccc agg tcg tgc cag acc att gtc gcg ttc ctg ggc atc ctc         17008
Ala Pro Arg Ser Cys Gln Thr Ile Val Ala Phe Leu Gly Ile Leu
                 5490                5495                5500 aag gcg aat ctg gca tac ctg ccg cta gac gtc aac gtg ccc gct         17053
Lys Ala Asn Leu Ala Tyr Leu Pro Leu Asp Val Asn Val Pro Ala
                 5505                5510                5515 act cgc ctc gag tcg ata ctg tct gcc gtc ggc ggc cgg aag ctg         17098
Thr Arg Leu Glu Ser Ile Leu Ser Ala Val Gly Gly Arg Lys Leu
                 5520                5525                5530 gtc ttg ctt gga gct gac gtg gcc gac cct ggc ctt cgc ctg gcg         17143
Val Leu Leu Gly Ala Asp Val Ala Asp Pro Gly Leu Arg Leu Ala
                 5535                5540                5545 gat gtg gag ctc gtg cgg atc ggc gac aca ctc ggc cgc tgt gta         17188
Asp Val Glu Leu Val Arg Ile Gly Asp Thr Leu Gly Arg Cys Val
                 5550                5555                5560 ccc ggg gcg ccc ggc gac aat gag gca cct gtg gtg cag cct tct         17233
Pro Gly Ala Pro Gly Asp Asn Glu Ala Pro Val Val Gln Pro Ser
                 5565                5570                5575 gcc aca agc ctt gcc tac gtc atc ttc act tcc ggc tcg acc ggc         17278
Ala Thr Ser Leu Ala Tyr Val Ile Phe Thr Ser Gly Ser Thr Gly
                 5580                5585                5590 aag ccg aag ggt gtc atg gtc gag cac cgc agt ata ctc agg gtt         17323
Lys Pro Lys Gly Val Met Val Glu His Arg Ser Ile Leu Arg Val
                 5595                5600                5605 gtc acg tct ccc ccg gcc cgt gct ctg cta ccg tcc aca atc atc         17368
Val Thr Ser Pro Pro Ala Arg Ala Leu Leu Pro Ser Thr Ile Ile
                 5610                5615                5620 atg gcc cac ctg aca aac att gca ttc gat gta tcg cta tgg gag         17413
```

```
                Met Ala His Leu Thr Asn Ile Ala Phe Asp Val Ser Leu Trp Glu
                                 5625                5630                5635 ata tgt aca gct ctt ctt cac ggt ggt acc ctg atc tgt att cag               17458
Ile Cys Thr Ala Leu Leu His Gly Gly Thr Leu Ile Cys Ile Gln
            5640                5645                5650 tat ctt gcc tcg ctc gat gtc agg ggg ctt cag act aca ttc tct               17503
Tyr Leu Ala Ser Leu Asp Val Arg Gly Leu Gln Thr Thr Phe Ser
            5655                5660                5665 cgc gaa gct atc aac gta gct gtg ttt cct cct gcc ttg cta aag               17548
Arg Glu Ala Ile Asn Val Ala Val Phe Pro Pro Ala Leu Leu Lys
            5670                5675                5680 acc tgt ctt gcc aag att cca tct gct cta gca tcg ctg agt gcc               17593
Thr Cys Leu Ala Lys Ile Pro Ser Ala Leu Ala Ser Leu Ser Ala
            5685                5690                5695 atg ttc tcg tcc gga gat cgt ctc gac tca cgc gat gct agc gag               17638
Met Phe Ser Ser Gly Asp Arg Leu Asp Ser Arg Asp Ala Ser Glu
            5700                5705                5710 ggg gcc aca ctt gtg cgg caa ggg ata cac aac gcg tat ggt ccc               17683
Gly Ala Thr Leu Val Arg Gln Gly Ile His Asn Ala Tyr Gly Pro
            5715                5720                5725 acg gag aat ggc atc cag agc aca atc tat gaa gtc aaa gcg gac               17728
Thr Glu Asn Gly Ile Gln Ser Thr Ile Tyr Glu Val Lys Ala Asp
            5730                5735                5740 gct gag ttt gtc aat ggt gtg cct atc ggc cgc gct gtg agc aac               17773
Ala Glu Phe Val Asn Gly Val Pro Ile Gly Arg Ala Val Ser Asn
            5745                5750                5755 tca ggg gca tat gtc atg gac ccg cag cag caa ctg gtg cct ctc               17818
Ser Gly Ala Tyr Val Met Asp Pro Gln Gln Gln Leu Val Pro Leu
            5760                5765                5770 ggg gtg atg ggc gag ctc gtc gtc acc ggc gac ggc ctg gcc cgt               17863
Gly Val Met Gly Glu Leu Val Val Thr Gly Asp Gly Leu Ala Arg
            5775                5780                5785 ggt tac acc gac ccg tca ctg gat gcg gac cgc ttt gtg cag gtc               17908
Gly Tyr Thr Asp Pro Ser Leu Asp Ala Asp Arg Phe Val Gln Val
            5790                5795                5800 tcc gtc aac ggg cag ctc gtg aga gcg tac cga aca ggc gat cgc               17953
Ser Val Asn Gly Gln Leu Val Arg Ala Tyr Arg Thr Gly Asp Arg
            5805                5810                5815 gtg cgc tgc agg cct tgc gat ggc cag atc gag ttc ttt gga cgt               17998
Val Arg Cys Arg Pro Cys Asp Gly Gln Ile Glu Phe Phe Gly Arg
            5820                5825                5830 atg gac cgg caa gtc aag atc cga gga cat cgc atc gag ctc gca               18043
Met Asp Arg Gln Val Lys Ile Arg Gly His Arg Ile Glu Leu Ala
            5835                5840                5845 gag gta gag cat gcg ata ttg tcc ctt gat tat gtg atc gat gca               18088
Glu Val Glu His Ala Ile Leu Ser Leu Asp Tyr Val Ile Asp Ala
            5850                5855                5860 gcc gtc ctt ctg aga cag ctg att gat caa gag cca caa gtg gta               18133
Ala Val Leu Leu Arg Gln Leu Ile Asp Gln Glu Pro Gln Val Val
            5865                5870                5875 gga ttc gtc att gta tcc acc aaa cgg gct tat tcc cga cac aac               18178
Gly Phe Val Ile Val Ser Thr Lys Arg Ala Tyr Ser Arg His Asn
            5880                5885                5890 agc ggc tac gcg tct gaa gtt tcg gca ttc tgc atc aaa gat cag               18223
Ser Gly Tyr Ala Ser Glu Val Ser Ala Phe Cys Ile Lys Asp Gln
            5895                5900                5905 atc gca tgg cgc att cga caa cat ctc tgc agg atg ctg cct tcc               18268
Ile Ala Trp Arg Ile Arg Gln His Leu Cys Arg Met Leu Pro Ser
            5910                5915                5920
```

| | | | | | | | | | | | | | |
|---|---|---|---|---|---|---|---|---|---|---|---|---|---|
| tat | atg | gtt | ccc | tat | caa | att | gca | att | ctt | gat | gaa | atg | cct | atc | 18313 |
| Tyr | Met | Val | Pro | Tyr | Gln | Ile | Ala | Ile | Leu | Asp | Glu | Met | Pro | Ile | |
| | | | 5925 | | | | 5930 | | | | 5935 | | | | |

| aat | gct | aac | ggc | aag | gtg | gat | aga | cag | aat | ctt | gca | agc | aga | act | 18358 |
| Asn | Ala | Asn | Gly | Lys | Val | Asp | Arg | Gln | Asn | Leu | Ala | Ser | Arg | Thr | |
| | | | 5940 | | | | 5945 | | | | 5950 | | | | |

| gtc | aac | gtc | caa | aga | atc | ctc | gcc | gct | cca | tac | atg | gcc | ccg | cgc | 18403 |
| Val | Asn | Val | Gln | Arg | Ile | Leu | Ala | Ala | Pro | Tyr | Met | Ala | Pro | Arg | |
| | | | 5955 | | | | 5960 | | | | 5965 | | | | |

| aat | gaa | gtc | gag | att | tcg | ctt | tgc | gaa | cag | tat | gct | gcc | ctg | ctt | 18448 |
| Asn | Glu | Val | Glu | Ile | Ser | Leu | Cys | Glu | Gln | Tyr | Ala | Ala | Leu | Leu | |
| | | | 5970 | | | | 5975 | | | | 5980 | | | | |

| gaa | cac | gac | gtt | ggc | att | ctt | gac | gac | ttc | ttc | gaa | ctt | ggt | ggt | 18493 |
| Glu | His | Asp | Val | Gly | Ile | Leu | Asp | Asp | Phe | Phe | Glu | Leu | Gly | Gly | |
| | | | 5985 | | | | 5990 | | | | 5995 | | | | |

| cac | tct | ctc | atg | gct | act | aga | ctg | gcc | tcg | cgt | atc | agc | tcc | cga | 18538 |
| His | Ser | Leu | Met | Ala | Thr | Arg | Leu | Ala | Ser | Arg | Ile | Ser | Ser | Arg | |
| | | | 6000 | | | | 6005 | | | | 6010 | | | | |

| ttc | agc | gct | ccg | gtg | tct | gtt | cgt | gat | att | ttc | gac | cat | cca | aga | 18583 |
| Phe | Ser | Ala | Pro | Val | Ser | Val | Arg | Asp | Ile | Phe | Asp | His | Pro | Arg | |
| | | | 6015 | | | | 6020 | | | | 6025 | | | | |

| atc | atg | gac | ctt | gct | agc | atc | att | cgt | gct | gga | gac | att | caa | tgg | 18628 |
| Ile | Met | Asp | Leu | Ala | Ser | Ile | Ile | Arg | Ala | Gly | Asp | Ile | Gln | Trp | |
| | | | 6030 | | | | 6035 | | | | 6040 | | | | |

| tcc | cgg | ata | ctg | cct | tct | gct | tat | gaa | cgt | cca | gtc | gag | caa | tct | 18673 |
| Ser | Arg | Ile | Leu | Pro | Ser | Ala | Tyr | Glu | Arg | Pro | Val | Glu | Gln | Ser | |
| | | | 6045 | | | | 6050 | | | | 6055 | | | | |

| ttc | gca | cag | aat | cgc | ctg | tgg | ttc | ctg | tac | aag | ctt | gac | ata | ggt | 18718 |
| Phe | Ala | Gln | Asn | Arg | Leu | Trp | Phe | Leu | Tyr | Lys | Leu | Asp | Ile | Gly | |
| | | | 6060 | | | | 6065 | | | | 6070 | | | | |

| acg | aca | cag | tat | aat | tta | ccg | ctg | gcg | ata | cac | ctt | cga | gga | cca | 18763 |
| Thr | Thr | Gln | Tyr | Asn | Leu | Pro | Leu | Ala | Ile | His | Leu | Arg | Gly | Pro | |
| | | | 6075 | | | | 6080 | | | | 6085 | | | | |

| cta | gat | ata | tca | gcg | ctg | ttt | atc | gca | ttc | aag | gca | ttg | act | gaa | 18808 |
| Leu | Asp | Ile | Ser | Ala | Leu | Phe | Ile | Ala | Phe | Lys | Ala | Leu | Thr | Glu | |
| | | | 6090 | | | | 6095 | | | | 6100 | | | | |

| aga | cat | gaa | ctt | ttg | cgc | aca | act | ttt | gat | gag | gat | gac | gga | aca | 18853 |
| Arg | His | Glu | Leu | Leu | Arg | Thr | Thr | Phe | Asp | Glu | Asp | Asp | Gly | Thr | |
| | | | 6105 | | | | 6110 | | | | 6115 | | | | |

| tgc | ctg | cag | atg | tta | ttg | cct | gaa | tat | cag | cat | gaa | gta | agg | atc | 18898 |
| Cys | Leu | Gln | Met | Leu | Leu | Pro | Glu | Tyr | Gln | His | Glu | Val | Arg | Ile | |
| | | | 6120 | | | | 6125 | | | | 6130 | | | | |

| acc | gac | ttg | cag | gga | tca | cac | aaa | ggt | agc | ctc | ctg | gat | att | ctc | 18943 |
| Thr | Asp | Leu | Gln | Gly | Ser | His | Lys | Gly | Ser | Leu | Leu | Asp | Ile | Leu | |
| | | | 6135 | | | | 6140 | | | | 6145 | | | | |

| aac | aac | aat | cag | aag | act | ccc | ttc | gag | ctg | agc | cgc | gag | cct | gga | 18988 |
| Asn | Asn | Asn | Gln | Lys | Thr | Pro | Phe | Glu | Leu | Ser | Arg | Glu | Pro | Gly | |
| | | | 6150 | | | | 6155 | | | | 6160 | | | | |

| tgg | agg | gta | gcg | ctg | ctg | cgt | ctg | gga | gat | gac | gac | cac | gtc | ctc | 19033 |
| Trp | Arg | Val | Ala | Leu | Leu | Arg | Leu | Gly | Asp | Asp | Asp | His | Val | Leu | |
| | | | 6165 | | | | 6170 | | | | 6175 | | | | |

| tcc | atc | gtc | atg | cat | cac | atc | atc | tcc | gac | ggt | tgg | tct | gtg | gac | 19078 |
| Ser | Ile | Val | Met | His | His | Ile | Ile | Ser | Asp | Gly | Trp | Ser | Val | Asp | |
| | | | 6180 | | | | 6185 | | | | 6190 | | | | |

| gtg | ctg | cgc | cac | gag | cta | ggt | cag | ttc | tac | tcg | gcc | gcg | ctc | cgg | 19123 |
| Val | Leu | Arg | His | Glu | Leu | Gly | Gln | Phe | Tyr | Ser | Ala | Ala | Leu | Arg | |
| | | | 6195 | | | | 6200 | | | | 6205 | | | | |

| ggg | cag | gac | ccg | ttg | tcg | cag | ata | agt | cct | ctg | ccg | atc | cag | tat | 19168 |
| Gly | Gln | Asp | Pro | Leu | Ser | Gln | Ile | Ser | Pro | Leu | Pro | Ile | Gln | Tyr | |
| | | | 6210 | | | | 6215 | | | | 6220 | | | | |

-continued

| | | | | | | | | | | | | |
|---|---|---|---|---|---|---|---|---|---|---|---|---|
| cgt | gac | ttc | gct | ctc | tgg | cag | aga | caa | gac | gag | caa | gtt | gcg | gag | 19213 |
| Arg | Asp | Phe | Ala | Leu | Trp | Gln | Arg | Gln | Asp | Glu | Gln | Val | Ala | Glu | |
| | | | 6225 | | | | 6230 | | | | 6235 | | | | |

| cat | cag | cgc | cag | ctg | gag | cat | tgg | aca | gag | cag | ttg | gca | gac | agt | 19258 |
| His | Gln | Arg | Gln | Leu | Glu | His | Trp | Thr | Glu | Gln | Leu | Ala | Asp | Ser | |
| | | 6240 | | | | 6245 | | | | 6250 | | | | | |

| tca | ccc | gcc | gag | ttg | ttg | agc | gac | cac | ccg | agg | cca | tcg | att | ctt | 19303 |
| Ser | Pro | Ala | Glu | Leu | Leu | Ser | Asp | His | Pro | Arg | Pro | Ser | Ile | Leu | |
| | | 6255 | | | | 6260 | | | | 6265 | | | | | |

| tct | ggc | cag | gcg | ggc | gct | att | ccc | gtc | aat | gtt | caa | ggc | tct | ctg | 19348 |
| Ser | Gly | Gln | Ala | Gly | Ala | Ile | Pro | Val | Asn | Val | Gln | Gly | Ser | Leu | |
| | | 6270 | | | | 6275 | | | | 6280 | | | | | |

| tat | cag | gcg | ctt | cgg | gcg | ttc | tgc | cgc | gct | cac | cag | gtc | acc | tct | 19393 |
| Tyr | Gln | Ala | Leu | Arg | Ala | Phe | Cys | Arg | Ala | His | Gln | Val | Thr | Ser | |
| | | 6285 | | | | 6290 | | | | 6295 | | | | | |

| ttc | gta | gtc | ctg | ctc | acg | gcg | ttc | cgc | ata | gca | cac | tat | cgt | ctg | 19438 |
| Phe | Val | Val | Leu | Leu | Thr | Ala | Phe | Arg | Ile | Ala | His | Tyr | Arg | Leu | |
| | | 6300 | | | | 6305 | | | | 6310 | | | | | |

| acg | ggt | gcg | gag | gac | gca | acc | att | gga | act | ccc | att | gca | aat | cgc | 19483 |
| Thr | Gly | Ala | Glu | Asp | Ala | Thr | Ile | Gly | Thr | Pro | Ile | Ala | Asn | Arg | |
| | | 6315 | | | | 6320 | | | | 6325 | | | | | |

| aac | cgg | cca | gag | ctc | gag | aac | atg | atc | ggt | ttc | ttc | gtc | aat | aca | 19528 |
| Asn | Arg | Pro | Glu | Leu | Glu | Asn | Met | Ile | Gly | Phe | Phe | Val | Asn | Thr | |
| | | 6330 | | | | 6335 | | | | 6340 | | | | | |

| caa | tgc | atg | cgc | atc | gtc | att | ggc | agt | gac | gac | aca | ttt | gaa | ggg | 19573 |
| Gln | Cys | Met | Arg | Ile | Val | Ile | Gly | Ser | Asp | Asp | Thr | Phe | Glu | Gly | |
| | | 6345 | | | | 6350 | | | | 6355 | | | | | |

| ctg | gtg | cag | caa | gta | cgc | tcg | ata | act | gca | gct | gcc | cac | gag | aac | 19618 |
| Leu | Val | Gln | Gln | Val | Arg | Ser | Ile | Thr | Ala | Ala | Ala | His | Glu | Asn | |
| | | 6360 | | | | 6365 | | | | 6370 | | | | | |

| cag | gac | gtt | cca | ttc | gag | cgc | atc | gtg | tca | gca | ctg | ctt | ccc | ggt | 19663 |
| Gln | Asp | Val | Pro | Phe | Glu | Arg | Ile | Val | Ser | Ala | Leu | Leu | Pro | Gly | |
| | | 6375 | | | | 6380 | | | | 6385 | | | | | |

| tct | aga | gac | aca | tca | cgc | aat | cct | ctg | gtt | cag | ctc | atg | ttt | gct | 19708 |
| Ser | Arg | Asp | Thr | Ser | Arg | Asn | Pro | Leu | Val | Gln | Leu | Met | Phe | Ala | |
| | | 6390 | | | | 6395 | | | | 6400 | | | | | |

| gtc | cac | tcg | caa | aga | aac | ctt | ggt | cag | atc | agt | cta | gaa | ggc | ctg | 19753 |
| Val | His | Ser | Gln | Arg | Asn | Leu | Gly | Gln | Ile | Ser | Leu | Glu | Gly | Leu | |
| | | 6405 | | | | 6410 | | | | 6415 | | | | | |

| cag | ggt | gaa | ttg | ctg | gga | gtg | gca | gcg | act | acg | aga | ttc | gat | gta | 19798 |
| Gln | Gly | Glu | Leu | Leu | Gly | Val | Ala | Ala | Thr | Thr | Arg | Phe | Asp | Val | |
| | | 6420 | | | | 6425 | | | | 6430 | | | | | |

| gag | ttc | cat | ctc | ttc | caa | gat | gac | gac | aag | ctc | agc | ggc | aac | gtg | 19843 |
| Glu | Phe | His | Leu | Phe | Gln | Asp | Asp | Asp | Lys | Leu | Ser | Gly | Asn | Val | |
| | | 6435 | | | | 6440 | | | | 6445 | | | | | |

| ctc | ttc | gcg | acc | gag | ctc | ttc | gag | cag | aag | act | atg | caa | ggc | atg | 19888 |
| Leu | Phe | Ala | Thr | Glu | Leu | Phe | Glu | Gln | Lys | Thr | Met | Gln | Gly | Met | |
| | | 6450 | | | | 6455 | | | | 6460 | | | | | |

| gtc | gac | gtg | ttc | cag | gaa | gtg | ctc | agc | cgg | ggc | ctt | gag | cag | ccc | 19933 |
| Val | Asp | Val | Phe | Gln | Glu | Val | Leu | Ser | Arg | Gly | Leu | Glu | Gln | Pro | |
| | | 6465 | | | | 6470 | | | | 6475 | | | | | |

| cag | ata | cct | ctg | gcg | acc | ctc | ccg | ctc | acg | cac | gga | ctg | gag | gag | 19978 |
| Gln | Ile | Pro | Leu | Ala | Thr | Leu | Pro | Leu | Thr | His | Gly | Leu | Glu | Glu | |
| | | 6480 | | | | 6485 | | | | 6490 | | | | | |

| ctc | agg | acc | atg | ggt | ctt | ctc | gac | gtg | gag | aag | aca | gac | tac | cct | 20023 |
| Leu | Arg | Thr | Met | Gly | Leu | Leu | Asp | Val | Glu | Lys | Thr | Asp | Tyr | Pro | |
| | | 6495 | | | | 6500 | | | | 6505 | | | | | |

| cga | gag | tcg | agc | gtg | gtg | gac | gtg | ttc | cgt | gag | caa | gcg | gct | gcc | 20068 |
| Arg | Glu | Ser | Ser | Val | Val | Asp | Val | Phe | Arg | Glu | Gln | Ala | Ala | Ala | |

-continued

| | | | | | | | | | | | | |
|---|---|---|---|---|---|---|---|---|---|---|---|---|
| | | | | 6510 | | | | 6515 | | | 6520 | |
| tgc | tcc | gag | gcg | att | gcg | gtc | aaa | gac | tcg | tcg | gcg | cag | ctc | acc | 20113 |
| Cys | Ser | Glu | Ala | Ile | Ala | Val | Lys | Asp | Ser | Ser | Ala | Gln | Leu | Thr | |
| | | | | 6525 | | | | 6530 | | | 6535 | |
| tac | tcg | gag | ctc | gat | cga | cag | tcg | gac | gag | ctt | gcc | ggc | tgg | ctg | 20158 |
| Tyr | Ser | Glu | Leu | Asp | Arg | Gln | Ser | Asp | Glu | Leu | Ala | Gly | Trp | Leu | |
| | | | | 6540 | | | | 6545 | | | 6550 | |
| cgc | cag | caa | cgt | ctt | cct | gcg | gag | tcg | ttg | gtt | gca | gtg | ctg | gca | 20203 |
| Arg | Gln | Gln | Arg | Leu | Pro | Ala | Glu | Ser | Leu | Val | Ala | Val | Leu | Ala | |
| | | | | 6555 | | | | 6560 | | | 6565 | |
| ccc | agg | tcg | tgc | cag | acc | att | gtc | gcg | ttc | ctg | ggc | atc | ctc | aag | 20248 |
| Pro | Arg | Ser | Cys | Gln | Thr | Ile | Val | Ala | Phe | Leu | Gly | Ile | Leu | Lys | |
| | | | | 6570 | | | | 6575 | | | 6580 | |
| gcg | aat | ctg | gca | tac | ctg | ccg | cta | gac | gtc | aac | gtg | ccc | gct | act | 20293 |
| Ala | Asn | Leu | Ala | Tyr | Leu | Pro | Leu | Asp | Val | Asn | Val | Pro | Ala | Thr | |
| | | | | 6585 | | | | 6590 | | | 6595 | |
| cgc | ctc | gag | tcg | ata | ctg | tct | gcc | gtc | ggc | ggc | cgg | aag | ctg | gtc | 20338 |
| Arg | Leu | Glu | Ser | Ile | Leu | Ser | Ala | Val | Gly | Gly | Arg | Lys | Leu | Val | |
| | | | | 6600 | | | | 6605 | | | 6610 | |
| ttg | ctt | gga | gct | gac | gtg | gcc | gac | cct | ggc | ctt | cgc | ctg | gcg | gat | 20383 |
| Leu | Leu | Gly | Ala | Asp | Val | Ala | Asp | Pro | Gly | Leu | Arg | Leu | Ala | Asp | |
| | | | | 6615 | | | | 6620 | | | 6625 | |
| gtg | gag | ctc | gtg | cgg | atc | ggc | gac | aca | ctc | ggc | cgc | tgt | gta | ccc | 20428 |
| Val | Glu | Leu | Val | Arg | Ile | Gly | Asp | Thr | Leu | Gly | Arg | Cys | Val | Pro | |
| | | | | 6630 | | | | 6635 | | | 6640 | |
| ggg | gcg | ccc | ggc | gac | aac | gag | gca | cct | gtg | gtg | cag | cct | tct | gcc | 20473 |
| Gly | Ala | Pro | Gly | Asp | Asn | Glu | Ala | Pro | Val | Val | Gln | Pro | Ser | Ala | |
| | | | | 6645 | | | | 6650 | | | 6655 | |
| aca | agc | ctt | gcc | tac | gtc | atc | ttc | act | tcc | ggc | tcg | acc | ggc | aag | 20518 |
| Thr | Ser | Leu | Ala | Tyr | Val | Ile | Phe | Thr | Ser | Gly | Ser | Thr | Gly | Lys | |
| | | | | 6660 | | | | 6665 | | | 6670 | |
| ccg | aag | ggt | gtc | atg | gtc | gag | cac | cgg | ggt | gta | gtg | cga | ctt | gtc | 20563 |
| Pro | Lys | Gly | Val | Met | Val | Glu | His | Arg | Gly | Val | Val | Arg | Leu | Val | |
| | | | | 6675 | | | | 6680 | | | 6685 | |
| aag | cag | agc | aat | gtt | gtc | tac | cat | ctc | ccg | tcc | aca | tct | cgc | gtg | 20608 |
| Lys | Gln | Ser | Asn | Val | Val | Tyr | His | Leu | Pro | Ser | Thr | Ser | Arg | Val | |
| | | | | 6690 | | | | 6695 | | | 6700 | |
| gcc | cac | ctg | tcg | aat | ctc | gcc | ttt | gat | gcc | tcg | gtc | ctc | gag | atc | 20653 |
| Ala | His | Leu | Ser | Asn | Leu | Ala | Phe | Asp | Ala | Ser | Val | Leu | Glu | Ile | |
| | | | | 6705 | | | | 6710 | | | 6715 | |
| tat | gcg | gcc | ctt | ctg | aac | ggt | ggt | act | gtt | tac | tgc | att | gac | tat | 20698 |
| Tyr | Ala | Ala | Leu | Leu | Asn | Gly | Gly | Thr | Val | Tyr | Cys | Ile | Asp | Tyr | |
| | | | | 6720 | | | | 6725 | | | 6730 | |
| ctc | act | acc | ctt | gac | cct | cac | gcg | ctt | gag | tct | gtt | ttc | atc | gat | 20743 |
| Leu | Thr | Thr | Leu | Asp | Pro | His | Ala | Leu | Glu | Ser | Val | Phe | Ile | Asp | |
| | | | | 6735 | | | | 6740 | | | 6745 | |
| gct | gat | ctc | aac | acg | gca | gtc | ctt | cct | ccc | gct | cta | ctt | aaa | cag | 20788 |
| Ala | Asp | Leu | Asn | Thr | Ala | Val | Leu | Pro | Pro | Ala | Leu | Leu | Lys | Gln | |
| | | | | 6750 | | | | 6755 | | | 6760 | |
| gtc | ctt | gct | tcg | agc | cct | tct | acc | ctc | cat | gcc | ctt | gat | tta | ctc | 20833 |
| Val | Leu | Ala | Ser | Ser | Pro | Ser | Thr | Leu | His | Ala | Leu | Asp | Leu | Leu | |
| | | | | 6765 | | | | 6770 | | | 6775 | |
| ttc | ata | gga | gga | gat | cga | ttg | gat | gct | cgt | gac | gcc | ctg | tac | gct | 20878 |
| Phe | Ile | Gly | Gly | Asp | Arg | Leu | Asp | Ala | Arg | Asp | Ala | Leu | Tyr | Ala | |
| | | | | 6780 | | | | 6785 | | | 6790 | |
| aat | cgt | ctg | gtt | cga | ggg | tca | tta | tac | aat | gtc | tat | ggc | ccg | aca | 20923 |
| Asn | Arg | Leu | Val | Arg | Gly | Ser | Leu | Tyr | Asn | Val | Tyr | Gly | Pro | Thr | |
| | | | | 6795 | | | | 6800 | | | 6805 | |
| gag | aac | acc | gtt | ctg | agc | gtc | gtt | tac | ctc | ttt | aat | gat | gac | gat | 20968 |

-continued

| | | | | | | | | | | | | | | |
|---|---|---|---|---|---|---|---|---|---|---|---|---|---|---|
| Glu | Asn | Thr | Val | Leu | Ser | Val | Val | Tyr | Leu | Phe | Asn | Asp | Asp | Asp |
| | | | 6810 | | | | 6815 | | | | 6820 | | | |

| gca | tgc | att | aat | ggc | gtc | cct | atc | ggc | caa | gtc | gtc | agt | aat | tcc | 21013 |
|---|---|---|---|---|---|---|---|---|---|---|---|---|---|---|---|
| Ala | Cys | Ile | Asn | Gly | Val | Pro | Ile | Gly | Gln | Val | Val | Ser | Asn | Ser | |
| | | | 6825 | | | | 6830 | | | | | 6835 | | | |

| ggg | gta | tac | gtc | atg | gac | tca | gaa | cag | aaa | tta | gta | cct | cct | ggg | 21058 |
|---|---|---|---|---|---|---|---|---|---|---|---|---|---|---|---|
| Gly | Val | Tyr | Val | Met | Asp | Ser | Glu | Gln | Lys | Leu | Val | Pro | Pro | Gly | |
| | | | 6840 | | | | 6845 | | | | | 6850 | | | |

| gtc | atg | gga | gaa | atc | gtc | gtg | aca | gga | gac | ggt | ctc | gca | aga | ggg | 21103 |
|---|---|---|---|---|---|---|---|---|---|---|---|---|---|---|---|
| Val | Met | Gly | Glu | Ile | Val | Val | Thr | Gly | Asp | Gly | Leu | Ala | Arg | Gly | |
| | | | 6855 | | | | 6860 | | | | | 6865 | | | |

| tat | act | gac | tca | acc | tta | aat | act | gat | cgt | ttc | gtt | caa | atc | agt | 21148 |
|---|---|---|---|---|---|---|---|---|---|---|---|---|---|---|---|
| Tyr | Thr | Asp | Ser | Thr | Leu | Asn | Thr | Asp | Arg | Phe | Val | Gln | Ile | Ser | |
| | | | 6870 | | | | 6875 | | | | | 6880 | | | |

| gtc | aac | gga | cgt | gta | ctg | caa | gca | tac | cgt | aca | ggc | gat | cgt | ggt | 21193 |
|---|---|---|---|---|---|---|---|---|---|---|---|---|---|---|---|
| Val | Asn | Gly | Arg | Val | Leu | Gln | Ala | Tyr | Arg | Thr | Gly | Asp | Arg | Gly | |
| | | | 6885 | | | | 6890 | | | | | 6895 | | | |

| cgg | tac | cgc | ccg | aca | gac | gct | cgt | ctt | gag | ttc | ttt | ggc | cgt | cta | 21238 |
|---|---|---|---|---|---|---|---|---|---|---|---|---|---|---|---|
| Arg | Tyr | Arg | Pro | Thr | Asp | Ala | Arg | Leu | Glu | Phe | Phe | Gly | Arg | Leu | |
| | | | 6900 | | | | 6905 | | | | | 6910 | | | |

| gat | caa | caa | atc | aag | ctt | cgc | ggg | cat | cgt | gta | gag | ctc | aaa | gaa | 21283 |
|---|---|---|---|---|---|---|---|---|---|---|---|---|---|---|---|
| Asp | Gln | Gln | Ile | Lys | Leu | Arg | Gly | His | Arg | Val | Glu | Leu | Lys | Glu | |
| | | | 6915 | | | | 6920 | | | | | 6925 | | | |

| atc | gag | caa | gcg | atg | ctt | ggc | cac | aat | gct | gtt | gat | gat | gca | gga | 21328 |
|---|---|---|---|---|---|---|---|---|---|---|---|---|---|---|---|
| Ile | Glu | Gln | Ala | Met | Leu | Gly | His | Asn | Ala | Val | Asp | Asp | Ala | Gly | |
| | | | 6930 | | | | 6935 | | | | | 6940 | | | |

| gtt | gtc | gct | ctg | gag | ata | tct | gag | tgc | caa | gag | cta | gag | atg | gtt | 21373 |
|---|---|---|---|---|---|---|---|---|---|---|---|---|---|---|---|
| Val | Val | Ala | Leu | Glu | Ile | Ser | Glu | Cys | Gln | Glu | Leu | Glu | Met | Val | |
| | | | 6945 | | | | 6950 | | | | | 6955 | | | |

| ggc | ttt | gtg | act | cta | cgc | aat | ctt | gga | acc | atg | gaa | gca | act | aac | 21418 |
|---|---|---|---|---|---|---|---|---|---|---|---|---|---|---|---|
| Gly | Phe | Val | Thr | Leu | Arg | Asn | Leu | Gly | Thr | Met | Glu | Ala | Thr | Asn | |
| | | | 6960 | | | | 6965 | | | | | 6970 | | | |

| aat | ctc | gca | cac | aca | agc | tgg | aac | cca | gtg | act | ctc | aaa | acc | cct | 21463 |
|---|---|---|---|---|---|---|---|---|---|---|---|---|---|---|---|
| Asn | Leu | Ala | His | Thr | Ser | Trp | Asn | Pro | Val | Thr | Leu | Lys | Thr | Pro | |
| | | | 6975 | | | | 6980 | | | | | 6985 | | | |

| tta | gca | tca | caa | ata | gtg | gct | gag | gtt | cgg | ggt | aga | ctc | cag | cga | 21508 |
|---|---|---|---|---|---|---|---|---|---|---|---|---|---|---|---|
| Leu | Ala | Ser | Gln | Ile | Val | Ala | Glu | Val | Arg | Gly | Arg | Leu | Gln | Arg | |
| | | | 6990 | | | | 6995 | | | | | 7000 | | | |

| aat | ctg | cca | ctc | tat | atg | gta | ccc | gct | acg | att | gtg | gta | tta | cat | 21553 |
|---|---|---|---|---|---|---|---|---|---|---|---|---|---|---|---|
| Asn | Leu | Pro | Leu | Tyr | Met | Val | Pro | Ala | Thr | Ile | Val | Val | Leu | His | |
| | | | 7005 | | | | 7010 | | | | | 7015 | | | |

| act | atg | cca | gtc | aat | gcc | aac | ggg | aag | ctc | gac | cga | caa | gca | ctt | 21598 |
|---|---|---|---|---|---|---|---|---|---|---|---|---|---|---|---|
| Thr | Met | Pro | Val | Asn | Ala | Asn | Gly | Lys | Leu | Asp | Arg | Gln | Ala | Leu | |
| | | | 7020 | | | | 7025 | | | | | 7030 | | | |

| gtg | aaa | gct | gca | atg | acg | ctt | cca | aaa | act | gct | cca | ctg | gta | tgg | 21643 |
|---|---|---|---|---|---|---|---|---|---|---|---|---|---|---|---|
| Val | Lys | Ala | Ala | Met | Thr | Leu | Pro | Lys | Thr | Ala | Pro | Leu | Val | Trp | |
| | | | 7035 | | | | 7040 | | | | | 7045 | | | |

| atg | gct | ccg | cgc | aat | gaa | gga | gag | aca | tcg | cta | tgt | gag | gag | cta | 21688 |
|---|---|---|---|---|---|---|---|---|---|---|---|---|---|---|---|
| Met | Ala | Pro | Arg | Asn | Glu | Gly | Glu | Thr | Ser | Leu | Cys | Glu | Glu | Leu | |
| | | | 7050 | | | | 7055 | | | | | 7060 | | | |

| aca | gat | atc | ttg | ggg | gtg | aac | gtc | ggg | atc | acc | gat | aac | ttt | ttt | 21733 |
|---|---|---|---|---|---|---|---|---|---|---|---|---|---|---|---|
| Thr | Asp | Ile | Leu | Gly | Val | Asn | Val | Gly | Ile | Thr | Asp | Asn | Phe | Phe | |
| | | | 7065 | | | | 7070 | | | | | 7075 | | | |

| gac | ctt | ggg | ggg | cat | tcc | ctc | ctg | gca | acc | aga | gta | gcc | gcg | cga | 21778 |
|---|---|---|---|---|---|---|---|---|---|---|---|---|---|---|---|
| Asp | Leu | Gly | Gly | His | Ser | Leu | Leu | Ala | Thr | Arg | Val | Ala | Ala | Arg | |
| | | | 7080 | | | | 7085 | | | | | 7090 | | | |

| atc | agc | cga | cgt | ctt | gat | gcc | ctg | gtg | acc | gtc | aaa | caa | ata | ttc | 21823 |
|---|---|---|---|---|---|---|---|---|---|---|---|---|---|---|---|
| Ile | Ser | Arg | Arg | Leu | Asp | Ala | Leu | Val | Thr | Val | Lys | Gln | Ile | Phe | |
| | | | 7095 | | | | 7100 | | | | | 7105 | | | |

-continued

| | | |
|---|---|---|
| gac cat cca gtc att gga gat ctc gca gct gca att caa ggg ggt<br>Asp His Pro Val Ile Gly Asp Leu Ala Ala Ala Ile Gln Gly Gly<br>　　　　　　7110　　　　　　　　　7115　　　　　　　　　7120 | | 21868 |
| tca gta cgg cat tta cca ata act gca agc gag gtc gat gga cct<br>Ser Val Arg His Leu Pro Ile Thr Ala Ser Glu Val Asp Gly Pro<br>　　　　　　7125　　　　　　　　　7130　　　　　　　　　7135 | | 21913 |
| gtt cag cag tcc ttc gcg caa aat cgc ttg tgg ttc cta gag cag<br>Val Gln Gln Ser Phe Ala Gln Asn Arg Leu Trp Phe Leu Glu Gln<br>　　　　　　7140　　　　　　　　　7145　　　　　　　　　7150 | | 21958 |
| atg aat att gga gct act tgg tac atc gta ccg tta gca gtg cgt<br>Met Asn Ile Gly Ala Thr Trp Tyr Ile Val Pro Leu Ala Val Arg<br>　　　　　　7155　　　　　　　　　7160　　　　　　　　　7165 | | 22003 |
| ctg tac ggc aca ctg cga gtt gag gct ctg aat att gcg ttg cgt<br>Leu Tyr Gly Thr Leu Arg Val Glu Ala Leu Asn Ile Ala Leu Arg<br>　　　　　　7170　　　　　　　　　7175　　　　　　　　　7180 | | 22048 |
| acg att cag caa cgc cac gaa aca tta cga acg acc ttc gaa gaa<br>Thr Ile Gln Gln Arg His Glu Thr Leu Arg Thr Thr Phe Glu Glu<br>　　　　　　7185　　　　　　　　　7190　　　　　　　　　7195 | | 22093 |
| cta aat ggg att gcc gtt caa cgt tgt gat tca acc tgc caa ggc<br>Leu Asn Gly Ile Ala Val Gln Arg Cys Asp Ser Thr Cys Gln Gly<br>　　　　　　7200　　　　　　　　　7205　　　　　　　　　7210 | | 22138 |
| caa tta agg gtg gta gat tta gtc ggg cag ggg cca gat cgc tat<br>Gln Leu Arg Val Val Asp Leu Val Gly Gln Gly Pro Asp Arg Tyr<br>　　　　　　7215　　　　　　　　　7220　　　　　　　　　7225 | | 22183 |
| aga gag att ctg gat gtc cag caa act aca cca ttc gag ctg agc<br>Arg Glu Ile Leu Asp Val Gln Gln Thr Thr Pro Phe Glu Leu Ser<br>　　　　　　7230　　　　　　　　　7235　　　　　　　　　7240 | | 22228 |
| cag gag cct gga tgg agg gta gcg ctg ctt cgt ctg gga gat gac<br>Gln Glu Pro Gly Trp Arg Val Ala Leu Leu Arg Leu Gly Asp Asp<br>　　　　　　7245　　　　　　　　　7250　　　　　　　　　7255 | | 22273 |
| gac cac gtc ctc tcc atc gtc atg cat cac atc atc tcc gac ggt<br>Asp His Val Leu Ser Ile Val Met His His Ile Ile Ser Asp Gly<br>　　　　　　7260　　　　　　　　　7265　　　　　　　　　7270 | | 22318 |
| tgg tct gtg gac gtg ctg cta cgt gag ata ggt cag ttc tac tcg<br>Trp Ser Val Asp Val Leu Leu Arg Glu Ile Gly Gln Phe Tyr Ser<br>　　　　　　7275　　　　　　　　　7280　　　　　　　　　7285 | | 22363 |
| gcc gcg ctc cgg ggg cag gac ccg ttg tcg cag ata agt cct ctg<br>Ala Ala Leu Arg Gly Gln Asp Pro Leu Ser Gln Ile Ser Pro Leu<br>　　　　　　7290　　　　　　　　　7295　　　　　　　　　7300 | | 22408 |
| ccg atc cag tat cgt gac ttc gct ctc tgg cag aga caa gac gag<br>Pro Ile Gln Tyr Arg Asp Phe Ala Leu Trp Gln Arg Gln Asp Glu<br>　　　　　　7305　　　　　　　　　7310　　　　　　　　　7315 | | 22453 |
| caa gtt gcg gag cat cag cgc cag ctg gag cat tgg aca gag cag<br>Gln Val Ala Glu His Gln Arg Gln Leu Glu His Trp Thr Glu Gln<br>　　　　　　7320　　　　　　　　　7325　　　　　　　　　7330 | | 22498 |
| ttg gca gac agt tca ccc gcc gag ttg ttg agc gac cac ccg agg<br>Leu Ala Asp Ser Ser Pro Ala Glu Leu Leu Ser Asp His Pro Arg<br>　　　　　　7335　　　　　　　　　7340　　　　　　　　　7345 | | 22543 |
| cca tcg att ctt tct ggc cag gcg ggc gct att ccc gtc aat gtt<br>Pro Ser Ile Leu Ser Gly Gln Ala Gly Ala Ile Pro Val Asn Val<br>　　　　　　7350　　　　　　　　　7355　　　　　　　　　7360 | | 22588 |
| caa ggc tct ctg tat cag gcg ctt cgg gcg ttc tgc cgc gct cac<br>Gln Gly Ser Leu Tyr Gln Ala Leu Arg Ala Phe Cys Arg Ala His<br>　　　　　　7365　　　　　　　　　7370　　　　　　　　　7375 | | 22633 |
| cag gtc acc tct ttc gta gtc ctg ctc acg gcg ttc cgc ata gca<br>Gln Val Thr Ser Phe Val Val Leu Leu Thr Ala Phe Arg Ile Ala<br>　　　　　　7380　　　　　　　　　7385　　　　　　　　　7390 | | 22678 |
| cac tat cgt ctg acg ggt gcg gag gac gca acc att gga act ccc<br>His Tyr Arg Leu Thr Gly Ala Glu Asp Ala Thr Ile Gly Thr Pro<br>　　　　　　7395　　　　　　　　　7400　　　　　　　　　7405 | | 22723 |

```
att gca aat cgc aac cgg cca gag ctc gag aac atg atc ggt ttc      22768
Ile Ala Asn Arg Asn Arg Pro Glu Leu Glu Asn Met Ile Gly Phe
        7410                7415                7420 ttc gtc aat aca caa tgc atg cgc atc gtc att ggc agt gac gac      22813
Phe Val Asn Thr Gln Cys Met Arg Ile Val Ile Gly Ser Asp Asp
        7425                7430                7435 aca ttt gaa ggg ctg gtg cag caa gta cgc tcg ata act gca gct      22858
Thr Phe Glu Gly Leu Val Gln Gln Val Arg Ser Ile Thr Ala Ala
        7440                7445                7450 gcc cac gag aac cag gac gtt cca ttc gag cgc atc gtg tca gca      22903
Ala His Glu Asn Gln Asp Val Pro Phe Glu Arg Ile Val Ser Ala
        7455                7460                7465 ctg ctt ccc ggt tct aga gac aca tca cgc aat cct ctg gtt cag      22948
Leu Leu Pro Gly Ser Arg Asp Thr Ser Arg Asn Pro Leu Val Gln
        7470                7475                7480 ctc atg ttt gct gtc cac tcg caa aga aac ctt ggt cag atc agt      22993
Leu Met Phe Ala Val His Ser Gln Arg Asn Leu Gly Gln Ile Ser
        7485                7490                7495 cta gaa ggc ctg cag ggt gaa ttg ctg gga gtg gca gcg act acg      23038
Leu Glu Gly Leu Gln Gly Glu Leu Leu Gly Val Ala Ala Thr Thr
        7500                7505                7510 aga ttc gat gta gag ttc cat ctc ttc caa gat gac gac aag ctc      23083
Arg Phe Asp Val Glu Phe His Leu Phe Gln Asp Asp Asp Lys Leu
        7515                7520                7525 agc ggc aac gtg ctc ttc gcg acc gag ctc ttc gag cag aag act      23128
Ser Gly Asn Val Leu Phe Ala Thr Glu Leu Phe Glu Gln Lys Thr
        7530                7535                7540 atg caa ggc atg gtc gac gtg ttc cag gaa gtg ctc agc cgg ggc      23173
Met Gln Gly Met Val Asp Val Phe Gln Glu Val Leu Ser Arg Gly
        7545                7550                7555 ctt gag cag ccc cag ata cct ctg gcg acc ctc ccg ctc acg cac      23218
Leu Glu Gln Pro Gln Ile Pro Leu Ala Thr Leu Pro Leu Thr His
        7560                7565                7570 gga ctg gag gag ctc agg acc atg ggt ctt ctc gac gtg gag aag      23263
Gly Leu Glu Glu Leu Arg Thr Met Gly Leu Leu Asp Val Glu Lys
        7575                7580                7585 aca gac tac cct cga gag tcg agc gtg gtg gac gtg ttc cgt gag      23308
Thr Asp Tyr Pro Arg Glu Ser Ser Val Val Asp Val Phe Arg Glu
        7590                7595                7600 caa gcg gct gcc tgc tcc gag gcg att gcg gtc aaa gac tcg tcg      23353
Gln Ala Ala Ala Cys Ser Glu Ala Ile Ala Val Lys Asp Ser Ser
        7605                7610                7615 gcg cag ctc acc tac tcg gag ctc gat cga cag tcg gac gag ctt      23398
Ala Gln Leu Thr Tyr Ser Glu Leu Asp Arg Gln Ser Asp Glu Leu
        7620                7625                7630 gcc ggc tgg ctg cgc cag caa cgt ctt cct gcg gag tcg ttg gtt      23443
Ala Gly Trp Leu Arg Gln Gln Arg Leu Pro Ala Glu Ser Leu Val
        7635                7640                7645 gca gtg ctg gca ccc agg tcg tgc cag acc att gtc gcg ttc ctg      23488
Ala Val Leu Ala Pro Arg Ser Cys Gln Thr Ile Val Ala Phe Leu
        7650                7655                7660 ggc atc ctc aag gcg aat ctg gca tac ctg ccg cta gac gtc aac      23533
Gly Ile Leu Lys Ala Asn Leu Ala Tyr Leu Pro Leu Asp Val Asn
        7665                7670                7675 gtg ccc gct act cgc ctc gag tcg ata ctg tct gcc gtc ggc ggc      23578
Val Pro Ala Thr Arg Leu Glu Ser Ile Leu Ser Ala Val Gly Gly
        7680                7685                7690 cgg aag ctg gtc ttg ctt gga gct gac gtg gcc gac cct ggc ctt      23623
Arg Lys Leu Val Leu Leu Gly Ala Asp Val Ala Asp Pro Gly Leu
```

-continued

```
                   7695                7700                7705
cgc ctg gcg gat gtg gag ctc gtg cgg atc ggc gac aca ctc ggc        23668
Arg Leu Ala Asp Val Glu Leu Val Arg Ile Gly Asp Thr Leu Gly
            7710                7715                7720 cgc tgt gta ccc ggg gcg ccc ggc gac aac gag gca cct gtg gtg        23713
Arg Cys Val Pro Gly Ala Pro Gly Asp Asn Glu Ala Pro Val Val
            7725                7730                7735 cag cct tct gcc aca agc ctt gcc tac gtc atc ttc act tcc ggc        23758
Gln Pro Ser Ala Thr Ser Leu Ala Tyr Val Ile Phe Thr Ser Gly
            7740                7745                7750 tcg acc ggc aag ccg aag ggt gtc atg gtc gag cac cgg ggt gta        23803
Ser Thr Gly Lys Pro Lys Gly Val Met Val Glu His Arg Gly Val
            7755                7760                7765 gtg cga ctt gtc aag cag agc aat gtt gtc tac cat ctc ccg tcc        23848
Val Arg Leu Val Lys Gln Ser Asn Val Val Tyr His Leu Pro Ser
            7770                7775                7780 aca tct cgc gtg gcc cac ctg tcg aat ctc gcc ttt gat gcc tcg        23893
Thr Ser Arg Val Ala His Leu Ser Asn Leu Ala Phe Asp Ala Ser
            7785                7790                7795 gcg tgg gag atc tat gcg gca ctg ctt aat ggc ggt aca ctc atc        23938
Ala Trp Glu Ile Tyr Ala Ala Leu Leu Asn Gly Gly Thr Leu Ile
            7800                7805                7810 tgc att gac tat ttc aca act cta gac tgc tct gct ctc ggc gcc        23983
Cys Ile Asp Tyr Phe Thr Thr Leu Asp Cys Ser Ala Leu Gly Ala
            7815                7820                7825 aaa ttc atc aag gag aag atc gtc gcg acc atg att ccg cca gcg        24028
Lys Phe Ile Lys Glu Lys Ile Val Ala Thr Met Ile Pro Pro Ala
            7830                7835                7840 ctt ctg aag caa tgt ctg gcg atc ttc ccg acc gct ctt agt gaa        24073
Leu Leu Lys Gln Cys Leu Ala Ile Phe Pro Thr Ala Leu Ser Glu
            7845                7850                7855 ctg gtc ctg ctg ttt gct gcc gga gat cga ttc agc agt ggc gat        24118
Leu Val Leu Leu Phe Ala Ala Gly Asp Arg Phe Ser Ser Gly Asp
            7860                7865                7870 gcc gtc gaa gtg cag cgc cac acc aaa ggc gct gtt tgt aac gcg        24163
Ala Val Glu Val Gln Arg His Thr Lys Gly Ala Val Cys Asn Ala
            7875                7880                7885 tac gga ccg aca gaa aac acc att ctt agt acg atc tac gaa gtc        24208
Tyr Gly Pro Thr Glu Asn Thr Ile Leu Ser Thr Ile Tyr Glu Val
            7890                7895                7900 aag cag aat gag aac ttc ccg aac ggt gtg cct atc ggc cgc gct        24253
Lys Gln Asn Glu Asn Phe Pro Asn Gly Val Pro Ile Gly Arg Ala
            7905                7910                7915 gtg agc aac tca ggg gca tat gtc atg gac ccg cag cag caa ctg        24298
Val Ser Asn Ser Gly Ala Tyr Val Met Asp Pro Gln Gln Gln Leu
            7920                7925                7930 gtg cct ctc ggg gtg atg ggc gag ctc gtc gtc acc ggc gac ggc        24343
Val Pro Leu Gly Val Met Gly Glu Leu Val Val Thr Gly Asp Gly
            7935                7940                7945 ctg gcc cgt ggt tac acc gac ccg tca ctg gat gcg gac cgc ttt        24388
Leu Ala Arg Gly Tyr Thr Asp Pro Ser Leu Asp Ala Asp Arg Phe
            7950                7955                7960 gtg cag gtc tcc gtc aac ggg cag ctc gtg aga gcg tac cga aca        24433
Val Gln Val Ser Val Asn Gly Gln Leu Val Arg Ala Tyr Arg Thr
            7965                7970                7975 ggc gat cgc gtg cgc tgc agg cct tgc gat ggc cag atc gag ttc        24478
Gly Asp Arg Val Arg Cys Arg Pro Cys Asp Gly Gln Ile Glu Phe
            7980                7985                7990 ttt gga cgt atg gac cgg caa gtc aag atc cga gga cat cgc atc        24523
```

|  |  |  |  |  |  |  |  |  |  |  |  |  |
|---|---|---|---|---|---|---|---|---|---|---|---|---|
| | Phe | Gly | Arg | Met | Asp | Arg | Gln | Val | Lys | Ile | Arg | Gly | His | Arg | Ile |
| | | | | 7995 | | | | 8000 | | | | 8005 | |

```
gag ctc gca gag gta gag cat gcg gtg ctt ggc ttg gaa gac gtg      24568
Glu Leu Ala Glu Val Glu His Ala Val Leu Gly Leu Glu Asp Val
        8010                8015                8020 caa gac gct gcc gtt atc gca ttt gac aat gtg gac agc gaa gag      24613
Gln Asp Ala Ala Val Ile Ala Phe Asp Asn Val Asp Ser Glu Glu
        8025                8030                8035 cca gaa atg gtt ggg ttt gtc act att acc gaa gac aat cct gtc      24658
Pro Glu Met Val Gly Phe Val Thr Ile Thr Glu Asp Asn Pro Val
        8040                8045                8050 cgt gag gac gaa acc agc ggt caa gta gaa gac tgg gcg aac cac      24703
Arg Glu Asp Glu Thr Ser Gly Gln Val Glu Asp Trp Ala Asn His
        8055                8060                8065 ttc gag ata agt acc tac acc gat atc gcg gcg atc gat cag ggt      24748
Phe Glu Ile Ser Thr Tyr Thr Asp Ile Ala Ala Ile Asp Gln Gly
        8070                8075                8080 agc att gga agt gac ttt gta ggt tgg act tct atg tac gac gga      24793
Ser Ile Gly Ser Asp Phe Val Gly Trp Thr Ser Met Tyr Asp Gly
        8085                8090                8095 agc gag atc gac aag gca gag atg caa gaa tgg ctt gcc gat acc      24838
Ser Glu Ile Asp Lys Ala Glu Met Gln Glu Trp Leu Ala Asp Thr
        8100                8105                8110 atg gcc tct atg ctc gac ggg cag gcg ccg ggc aat gtg tta gag      24883
Met Ala Ser Met Leu Asp Gly Gln Ala Pro Gly Asn Val Leu Glu
        8115                8120                8125 ata ggt aca ggc act ggc atg gtc ctc ttc aat ctc ggc gac gga      24928
Ile Gly Thr Gly Thr Gly Met Val Leu Phe Asn Leu Gly Asp Gly
        8130                8135                8140 ctg cag agc tat gtc ggc ctc gaa cca tca aga tcg gcg gcc gct      24973
Leu Gln Ser Tyr Val Gly Leu Glu Pro Ser Arg Ser Ala Ala Ala
        8145                8150                8155 ttt gtc aac cag acg att aag tcg ctc ccc acc ctt gct ggc aac      25018
Phe Val Asn Gln Thr Ile Lys Ser Leu Pro Thr Leu Ala Gly Asn
        8160                8165                8170 gct gaa gta cac att ggc act gcg acc gac gtg gcc cgt cta gat      25063
Ala Glu Val His Ile Gly Thr Ala Thr Asp Val Ala Arg Leu Asp
        8175                8180                8185 ggc ctc cgc ccc gac tta gtg gta gtc aat tcg gta gtc cag tac      25108
Gly Leu Arg Pro Asp Leu Val Val Val Asn Ser Val Val Gln Tyr
        8190                8195                8200 ttc cca tca cca gag tac cta atg gaa gtc gtg gag gct ctt gca      25153
Phe Pro Ser Pro Glu Tyr Leu Met Glu Val Val Glu Ala Leu Ala
        8205                8210                8215 cgt ctg ccg ggc gtc gag cga att ttc ttc gga gac gta cgt tcg      25198
Arg Leu Pro Gly Val Glu Arg Ile Phe Phe Gly Asp Val Arg Ser
        8220                8225                8230 tac gcc atc aac aga gat ttc ctg gct gcc aga gct cta cac gaa      25243
Tyr Ala Ile Asn Arg Asp Phe Leu Ala Ala Arg Ala Leu His Glu
        8235                8240                8245 ctt ggc gac aga gcg act aag cac gag att cgg cga aag atg cta      25288
Leu Gly Asp Arg Ala Thr Lys His Glu Ile Arg Arg Lys Met Leu
        8250                8255                8260 gag atg gaa gaa cgc gaa gag gag ctg ctc gtc gac cca gct ttc      25333
Glu Met Glu Glu Arg Glu Glu Glu Leu Leu Val Asp Pro Ala Phe
        8265                8270                8275 ttc acc atg ttg acc agc agt ctc cct ggc ctg att cag cat gtc      25378
Phe Thr Met Leu Thr Ser Ser Leu Pro Gly Leu Ile Gln His Val
        8280                8285                8290
```

| | | | | | | | | | | | | |
|---|---|---|---|---|---|---|---|---|---|---|---|---|
| gag | atc | ttg | ccg | aag | ctg | atg | aga | gcc | act | aat | gag | ctc | agc | gcg | 25423 |
| Glu | Ile | Leu | Pro 8295 | Lys | Leu | Met | Arg | Ala 8300 | Thr | Asn | Glu | Leu | Ser 8305 | Ala | |

| tat | cga | tac | act | gct | gta | gta | cac | gtg | tgc | cgt | gcc | ggt | caa | gag | 25468 |
| Tyr | Arg | Tyr | Thr 8310 | Ala | Val | Val | His 8315 | Val | Cys | Arg | Ala | Gly 8320 | Gln | Glu | |

| cct | cgt | tcc | gtg | cat | acg | atc | gac | gac | gat | gcc | tgg | gtg | aat | ctt | 25513 |
| Pro | Arg | Ser | Val 8325 | His | Thr | Ile | Asp 8330 | Asp | Asp | Ala | Trp | Val 8335 | Asn | Leu | |

| gga | gct | tct | cgg | ttg | agt | cgc | cct | acc | ctt | tca | agc | ctt | ttg | caa | 25558 |
| Gly | Ala | Ser | Arg 8340 | Leu | Ser | Arg | Pro 8345 | Thr | Leu | Ser | Ser | Leu 8350 | Leu | Gln | |

| act | tcc | gag | ggc | gca | tcg | gcc | gtc | gca | gta | agc | aat | att | cct | tac | 25603 |
| Thr | Ser | Glu | Gly 8355 | Ala | Ser | Ala | Val 8360 | Ala | Val | Ser | Asn | Ile 8365 | Pro | Tyr | |

| agc | aag | acc | atc | aca | gag | cga | gcg | ctc | gtt | agt | gcg | ctc | gat | gag | 25648 |
| Ser | Lys | Thr | Ile 8370 | Thr | Glu | Arg | Ala 8375 | Leu | Val | Ser | Ala | Leu 8380 | Asp | Glu | |

| gat | gat | atg | caa | gac | tca | tcg | gac | tgg | ctg | ctg | gcc | gtg | cgc | gag | 25693 |
| Asp | Asp | Met | Gln 8385 | Asp | Ser | Ser | Asp 8390 | Trp | Leu | Leu | Ala | Val 8395 | Arg | Glu | |

| aca | ggc | aga | tct | tgt | tcc | tcc | ttc | tcc | gca | aca | gac | ctt | gtc | gag | 25738 |
| Thr | Gly | Arg | Ser 8400 | Cys | Ser | Ser | Phe 8405 | Ser | Ala | Thr | Asp | Leu 8410 | Val | Glu | |

| ctt | gct | cga | gag | acg | ggc | tgg | cgt | gtg | gag | ctc | agc | tgg | gca | cga | 25783 |
| Leu | Ala | Arg | Glu 8415 | Thr | Gly | Trp | Arg 8420 | Val | Glu | Leu | Ser | Trp 8425 | Ala | Arg | |

| cag | tac | tca | cag | aaa | ggc | gca | ctc | gat | gct | gtc | ttc | cac | aga | cac | 25828 |
| Gln | Tyr | Ser | Gln 8430 | Lys | Gly | Ala | Leu 8435 | Asp | Ala | Val | Phe | His 8440 | Arg | His | |

| cct | gtt | tcc | gct | ggg | agc | ggg | cgt | gtc | atg | ttc | cag | ttt | cca | gtt | 25873 |
| Pro | Val | Ser | Ala 8445 | Gly | Ser | Gly | Arg 8450 | Val | Met | Phe | Gln | Phe 8455 | Pro | Val | |

| gag | acc | gaa | gat | cga | ccg | cac | atc | tca | cgc | acg | aac | cga | cct | tta | 25918 |
| Glu | Thr | Glu | Asp 8460 | Arg | Pro | His | Ile 8465 | Ser | Arg | Thr | Asn | Arg 8470 | Pro | Leu | |

| cag | cga | ttg | cag | aag | aag | cga | acc | gag | aca | cat | gtt | cat | gag | cag | 25963 |
| Gln | Arg | Leu | Gln 8475 | Lys | Lys | Arg | Thr 8480 | Glu | Thr | His | Val | His 8485 | Glu | Gln | |

| ttg | cgg | gct | ttg | ctt | cca | cga | tac | atg | gtt | cct | acg | cgg | att | gtg | 26008 |
| Leu | Arg | Ala | Leu 8490 | Leu | Pro | Arg | Tyr 8495 | Met | Val | Pro | Thr | Arg 8500 | Ile | Val | |

| gcg | ctt | gat | aag | ctg | ccc | gtc | aat | gca | aac | ggc | aag | gtt | gat | cgt | 26053 |
| Ala | Leu | Asp | Lys 8505 | Leu | Pro | Val | Asn 8510 | Ala | Asn | Gly | Lys | Val 8515 | Asp | Arg | |

| caa | cag | ctc | gct | agg | aca | gcc | cag | gtt | ctc | cca | gcg | agc | aag | gcg | 26098 |
| Gln | Gln | Leu | Ala 8520 | Arg | Thr | Ala | Gln 8525 | Val | Leu | Pro | Ala | Ser 8530 | Lys | Ala | |

| ccg | tct | gca | tgc | gtg | gcc | cca | cgc | aac | gaa | ttg | gaa | atg | aca | ctg | 26143 |
| Pro | Ser | Ala | Cys 8535 | Val | Ala | Pro | Arg 8540 | Asn | Glu | Leu | Glu | Met 8545 | Thr | Leu | |

| tgt | gaa | gag | ttc | tcg | cag | gtt | ctt | ggc | gtc | gag | gtc | ggc | att | act | 26188 |
| Cys | Glu | Glu | Phe 8550 | Ser | Gln | Val | Leu 8555 | Gly | Val | Glu | Val | Gly 8560 | Ile | Thr | |

| gac | aat | ttc | ttc | cac | ctg | ggt | ggc | cac | tct | ctc | atg | gca | aca | aag | 26233 |
| Asp | Asn | Phe | Phe 8565 | His | Leu | Gly | Gly 8570 | His | Ser | Leu | Met | Ala 8575 | Thr | Lys | |

| ttc | gcc | gct | cgt | atc | agc | cgc | cgg | ctg | aat | gct | atc | gtt | tcg | gtc | 26278 |
| Phe | Ala | Ala | Arg 8580 | Ile | Ser | Arg | Arg 8585 | Leu | Asn | Ala | Ile | Val 8590 | Ser | Val | |

| | | | | | | | | | | | | |
|---|---|---|---|---|---|---|---|---|---|---|---|---|
| aag | aat | gtc | ttc | gac | cac | ccc | gta | cct | atg | gat | ctt | gca | gcg | aca | 26323 |
| Lys | Asn | Val | Phe | Asp | His | Pro | Val | Pro | Met | Asp | Leu | Ala | Ala | Thr | |
| | | | 8595 | | | | 8600 | | | | 8605 | | | | |
| atc | caa | gaa | ggc | tca | aag | ctt | cat | act | cca | atc | cct | cgc | acg | gct | 26368 |
| Ile | Gln | Glu | Gly | Ser | Lys | Leu | His | Thr | Pro | Ile | Pro | Arg | Thr | Ala | |
| | | | 8610 | | | | 8615 | | | | 8620 | | | | |
| tac | agc | ggt | cct | gtc | gaa | cag | tct | ttc | gca | caa | gga | cgt | ctt | tgg | 26413 |
| Tyr | Ser | Gly | Pro | Val | Glu | Gln | Ser | Phe | Ala | Gln | Gly | Arg | Leu | Trp | |
| | | | 8625 | | | | 8630 | | | | 8635 | | | | |
| ttc | ctt | gac | caa | ttc | aat | cct | agc | tcg | att | ggg | tat | gtg | atg | cct | 26458 |
| Phe | Leu | Asp | Gln | Phe | Asn | Pro | Ser | Ser | Ile | Gly | Tyr | Val | Met | Pro | |
| | | | 8640 | | | | 8645 | | | | 8650 | | | | |
| ttc | gct | gcg | cgt | ctt | cat | ggt | caa | cta | caa | atc | gaa | gcg | ctc | aca | 26503 |
| Phe | Ala | Ala | Arg | Leu | His | Gly | Gln | Leu | Gln | Ile | Glu | Ala | Leu | Thr | |
| | | | 8655 | | | | 8660 | | | | 8665 | | | | |
| gca | gca | ttg | ttc | gct | ttg | gaa | cag | cga | cat | gag | atc | ctg | cga | aca | 26548 |
| Ala | Ala | Leu | Phe | Ala | Leu | Glu | Gln | Arg | His | Glu | Ile | Leu | Arg | Thr | |
| | | | 8670 | | | | 8675 | | | | 8680 | | | | |
| acg | ttg | gac | gca | cac | gat | ggt | gta | ggc | atg | cag | atc | gtt | cac | gcg | 26593 |
| Thr | Leu | Asp | Ala | His | Asp | Gly | Val | Gly | Met | Gln | Ile | Val | His | Ala | |
| | | | 8685 | | | | 8690 | | | | 8695 | | | | |
| gaa | cat | ccg | caa | cag | ttg | aga | atc | att | gat | gtg | tca | gca | aag | gcg | 26638 |
| Glu | His | Pro | Gln | Gln | Leu | Arg | Ile | Ile | Asp | Val | Ser | Ala | Lys | Ala | |
| | | | 8700 | | | | 8705 | | | | 8710 | | | | |
| tcg | agc | agt | tat | gct | cag | aca | ctg | cgt | gac | gag | cag | gcg | tca | cct | 26683 |
| Ser | Ser | Ser | Tyr | Ala | Gln | Thr | Leu | Arg | Asp | Glu | Gln | Ala | Ser | Pro | |
| | | | 8715 | | | | 8720 | | | | 8725 | | | | |
| ttc | gac | cta | agc | aag | gaa | cca | ggt | tgg | aga | gtc | tcg | ttg | ctg | cag | 26728 |
| Phe | Asp | Leu | Ser | Lys | Glu | Pro | Gly | Trp | Arg | Val | Ser | Leu | Leu | Gln | |
| | | | 8730 | | | | 8735 | | | | 8740 | | | | |
| ctc | agt | gag | ata | gat | tat | gtt | ctt | tcc | att | gta | atg | cat | cac | acc | 26773 |
| Leu | Ser | Glu | Ile | Asp | Tyr | Val | Leu | Ser | Ile | Val | Met | His | His | Thr | |
| | | | 8745 | | | | 8750 | | | | 8755 | | | | |
| atc | tat | gac | ggt | tgg | tct | ctc | gac | gta | ctc | cgg | cgg | gag | cta | agt | 26818 |
| Ile | Tyr | Asp | Gly | Trp | Ser | Leu | Asp | Val | Leu | Arg | Arg | Glu | Leu | Ser | |
| | | | 8760 | | | | 8765 | | | | 8770 | | | | |
| cag | ttt | tat | gcc | gct | gcc | atc | cgt | ggt | cga | gaa | cct | cta | tcg | aca | 26863 |
| Gln | Phe | Tyr | Ala | Ala | Ala | Ile | Arg | Gly | Arg | Glu | Pro | Leu | Ser | Thr | |
| | | | 8775 | | | | 8780 | | | | 8785 | | | | |
| atc | gag | cca | ttg | cct | atc | caa | tac | cgc | gac | ttt | tct | gtc | tgg | caa | 26908 |
| Ile | Glu | Pro | Leu | Pro | Ile | Gln | Tyr | Arg | Asp | Phe | Ser | Val | Trp | Gln | |
| | | | 8790 | | | | 8795 | | | | 8800 | | | | |
| aag | cag | gaa | gac | caa | gtc | gca | gag | cat | cga | cga | cag | ctc | cat | tat | 26953 |
| Lys | Gln | Glu | Asp | Gln | Val | Ala | Glu | His | Arg | Arg | Gln | Leu | His | Tyr | |
| | | | 8805 | | | | 8810 | | | | 8815 | | | | |
| tgg | ata | gag | cag | cta | gat | ggc | agc | tct | cct | gct | gag | ttc | cta | aac | 26998 |
| Trp | Ile | Glu | Gln | Leu | Asp | Gly | Ser | Ser | Pro | Ala | Glu | Phe | Leu | Asn | |
| | | | 8820 | | | | 8825 | | | | 8830 | | | | |
| gat | aaa | cca | cgg | cct | acg | ttg | ctt | tct | ggc | aag | gca | gga | gtt | gtg | 27043 |
| Asp | Lys | Pro | Arg | Pro | Thr | Leu | Leu | Ser | Gly | Lys | Ala | Gly | Val | Val | |
| | | | 8835 | | | | 8840 | | | | 8845 | | | | |
| gaa | att | gct | gtg | aag | ggc | act | gta | tat | caa | cgt | ctg | cta | gag | ttc | 27088 |
| Glu | Ile | Ala | Val | Lys | Gly | Thr | Val | Tyr | Gln | Arg | Leu | Leu | Glu | Phe | |
| | | | 8850 | | | | 8855 | | | | 8860 | | | | |
| tgc | agg | ctt | cat | cag | gtc | acc | tcg | ttc | atg | gtg | ctg | ctt | gcg | gca | 27133 |
| Cys | Arg | Leu | His | Gln | Val | Thr | Ser | Phe | Met | Val | Leu | Leu | Ala | Ala | |
| | | | 8865 | | | | 8870 | | | | 8875 | | | | |
| ttc | cga | gcg | aca | cac | tat | cgt | ctg | aca | ggc | aca | gag | gac | gcg | act | 27178 |
| Phe | Arg | Ala | Thr | His | Tyr | Arg | Leu | Thr | Gly | Thr | Glu | Asp | Ala | Thr | |

```
                  8880            8885              8890 gtc gga aca ccc atc gcc aat cgc aat cga cct gag ctg gag aac    27223
Val Gly Thr Pro Ile Ala Asn Arg Asn Arg Pro Glu Leu Glu Asn
            8895            8900              8905 atg att gga ttg ttc gtg aat act cag tgt ata cgc ctc aag atc    27268
Met Ile Gly Leu Phe Val Asn Thr Gln Cys Ile Arg Leu Lys Ile
            8910            8915              8920 gag gac aat gat act ctc gag gag cta gta cag cac gtt cgt gcc    27313
Glu Asp Asn Asp Thr Leu Glu Glu Leu Val Gln His Val Arg Ala
            8925            8930              8935 acg atc aca gca tca atc tcg aac cag gat gta ccc ttt gaa cag    27358
Thr Ile Thr Ala Ser Ile Ser Asn Gln Asp Val Pro Phe Glu Gln
            8940            8945              8950 gta gtg tct gca ttg cta cca gga tca cgc gac acc tct agg aac    27403
Val Val Ser Ala Leu Leu Pro Gly Ser Arg Asp Thr Ser Arg Asn
            8955            8960              8965 cca cta gtt cag ctg act ttt gcg gtg cat tct cag cga aat ttg    27448
Pro Leu Val Gln Leu Thr Phe Ala Val His Ser Gln Arg Asn Leu
            8970            8975              8980 gct gac att cag cta gaa aac gtg gag acc aat gct atg cca att    27493
Ala Asp Ile Gln Leu Glu Asn Val Glu Thr Asn Ala Met Pro Ile
            8985            8990              8995 tgc ccc tcg aca cgt ttc gac gct gaa ttc cac ctc ttc caa gag    27538
Cys Pro Ser Thr Arg Phe Asp Ala Glu Phe His Leu Phe Gln Glu
            9000            9005              9010 gag aat atg cta agc gga agg gtg ctg ttt tca gac gat ctt ttc    27583
Glu Asn Met Leu Ser Gly Arg Val Leu Phe Ser Asp Asp Leu Phe
            9015            9020              9025 gag cag aag act atg caa ggc atg gtc gac gtg ttc cag gaa gtg    27628
Glu Gln Lys Thr Met Gln Gly Met Val Asp Val Phe Gln Glu Val
            9030            9035              9040 ctc agc cgg ggc ctt gag cag ccc cag ata cct ctg gcg acc ctc    27673
Leu Ser Arg Gly Leu Glu Gln Pro Gln Ile Pro Leu Ala Thr Leu
            9045            9050              9055 ccg ctc acg cac gga ctg gag gag ctc agg acc atg ggt ctt ctc    27718
Pro Leu Thr His Gly Leu Glu Glu Leu Arg Thr Met Gly Leu Leu
            9060            9065              9070 gac gtg gag aag aca gac tac cct cga gag tcg agc gtg gtg gac    27763
Asp Val Glu Lys Thr Asp Tyr Pro Arg Glu Ser Ser Val Val Asp
            9075            9080              9085 gtg ttc cgt gag caa gcg gct gcc tgc tcc gag gcg att gcg gtc    27808
Val Phe Arg Glu Gln Ala Ala Ala Cys Ser Glu Ala Ile Ala Val
            9090            9095              9100 aaa gac tcg tcg gcg cag ctc acc tac tcg gag ctc gat cga cag    27853
Lys Asp Ser Ser Ala Gln Leu Thr Tyr Ser Glu Leu Asp Arg Gln
            9105            9110              9115 tcg gac gag ctt gcc ggc tgg ctg cgc cag caa cgt ctt cct gcg    27898
Ser Asp Glu Leu Ala Gly Trp Leu Arg Gln Gln Arg Leu Pro Ala
            9120            9125              9130 gag tcg ttg gtt gca gtg ctg gca ccc agg tcg tgc cag acc att    27943
Glu Ser Leu Val Ala Val Leu Ala Pro Arg Ser Cys Gln Thr Ile
            9135            9140              9145 gtc gcg ttc ctg ggc atc ctc aag gcg aat ctg gca tac ctg ccg    27988
Val Ala Phe Leu Gly Ile Leu Lys Ala Asn Leu Ala Tyr Leu Pro
            9150            9155              9160 cta gac gtc aac gtg ccc gct act cgc ctc gag tcg ata ctg tct    28033
Leu Asp Val Asn Val Pro Ala Thr Arg Leu Glu Ser Ile Leu Ser
            9165            9170              9175 gcc gtc ggc ggc cgg aag ctg gtc ttg ctt gga gct gac gtg gcc    28078
```

|  |  |  |  |  |  |  |  |  |  |  |  |  |
|---|---|---|---|---|---|---|---|---|---|---|---|---|
|  | Ala | Val | Gly | Gly | Arg | Lys | Leu | Val | Leu | Leu | Gly | Ala | Asp | Val | Ala |
|  |  |  | 9180 |  |  | 9185 |  |  |  | 9190 |  |

```
gac cct ggc ctt cgc ctg gcg gat gtg gag ctc gtg cgg atc ggc    28123
Asp Pro Gly Leu Arg Leu Ala Asp Val Glu Leu Val Arg Ile Gly
        9195                9200                9205 gac aca ctc ggc cgc tgt gta ccc ggg gcg ccc ggc gac aac gag    28168
Asp Thr Leu Gly Arg Cys Val Pro Gly Ala Pro Gly Asp Asn Glu
        9210                9215                9220 gca cct gtg gtg cag cct tct gcc aca agc ctt gcc tac gtc atc    28213
Ala Pro Val Val Gln Pro Ser Ala Thr Ser Leu Ala Tyr Val Ile
        9225                9230                9235 ttc act tcc ggc tcg acc ggc aag ccg aag ggt gtc atg gtc gag    28258
Phe Thr Ser Gly Ser Thr Gly Lys Pro Lys Gly Val Met Val Glu
        9240                9245                9250 cac cgg ggt gta gtg cga ctt gtc aag cag agc aat gtt gtc tac    28303
His Arg Gly Val Val Arg Leu Val Lys Gln Ser Asn Val Val Tyr
        9255                9260                9265 cat ctc ccg tcc aca tct cgc gtg gcc cac ctg tcg aat ctc gcc    28348
His Leu Pro Ser Thr Ser Arg Val Ala His Leu Ser Asn Leu Ala
        9270                9275                9280 ttt gat gcc tcg gcg tgg gag atc tat gcg gca ctg ctt aat ggc    28393
Phe Asp Ala Ser Ala Trp Glu Ile Tyr Ala Ala Leu Leu Asn Gly
        9285                9290                9295 ggt aca ctc atc tgc att gac tat ttc acc atc ata gac gct cgc    28438
Gly Thr Leu Ile Cys Ile Asp Tyr Phe Thr Ile Ile Asp Ala Arg
        9300                9305                9310 gca ctt ggc gtt atc ttt gcg caa caa agt atc aac gca acc atg    28483
Ala Leu Gly Val Ile Phe Ala Gln Gln Ser Ile Asn Ala Thr Met
        9315                9320                9325 ctg tca cct cta ctc ctc aaa caa ttt ttg tca gat gca cca ttc    28528
Leu Ser Pro Leu Leu Leu Lys Gln Phe Leu Ser Asp Ala Pro Phe
        9330                9335                9340 gtg ctg cga tct ctg cat gcc ctt tat cta ggg ggg gac aga ctt    28573
Val Leu Arg Ser Leu His Ala Leu Tyr Leu Gly Gly Asp Arg Leu
        9345                9350                9355 cag ggt cgt gac gca atc cag gct tgt cgt gta ggt tgc gca ttt    28618
Gln Gly Arg Asp Ala Ile Gln Ala Cys Arg Val Gly Cys Ala Phe
        9360                9365                9370 gtc atc aat gcc tat ggc cca aca gag aat tct gtc atc agt act    28663
Val Ile Asn Ala Tyr Gly Pro Thr Glu Asn Ser Val Ile Ser Thr
        9375                9380                9385 act tac aca ctt gtg aag gga aat gcg gac ttc ccg aac ggt gtg    28708
Thr Tyr Thr Leu Val Lys Gly Asn Ala Asp Phe Pro Asn Gly Val
        9390                9395                9400 cct atc ggc cgc gct gtg agc aac tca ggg gca tat gtc atg gac    28753
Pro Ile Gly Arg Ala Val Ser Asn Ser Gly Ala Tyr Val Met Asp
        9405                9410                9415 ccg cag cag caa ctg gtg cct ctc ggg gtg atg ggc gag ctc gtc    28798
Pro Gln Gln Gln Leu Val Pro Leu Gly Val Met Gly Glu Leu Val
        9420                9425                9430 gtc acc ggc gac ggc ctg gcc cgt ggt tac acc gac ccg tca ctg    28843
Val Thr Gly Asp Gly Leu Ala Arg Gly Tyr Thr Asp Pro Ser Leu
        9435                9440                9445 gat gcg gac cgc ttt gtg cag gtc tcc gtc aac ggg cag ctc gtg    28888
Asp Ala Asp Arg Phe Val Gln Val Ser Val Asn Gly Gln Leu Val
        9450                9455                9460 aga gcg tac cga aca ggc gat cgc gtg cgc tgc agg cct tgc gat    28933
Arg Ala Tyr Arg Thr Gly Asp Arg Val Arg Cys Arg Pro Cys Asp
        9465                9470                9475
```

| | | | | | | | | | | |
|---|---|---|---|---|---|---|---|---|---|---|
| ggc | cag | atc | gag | ttc | ttt | gga | cgt | atg | gac | cgg | caa | gtc | aag | atc | 28978 |
| Gly | Gln | Ile | Glu | Phe | Phe | Gly | Arg | Met | Asp | Arg | Gln | Val | Lys | Ile | |
| | | | 9480 | | | | 9485 | | | | 9490 | | | | |
| cga | gga | cat | cgc | atc | gag | ctc | gca | gag | gta | gag | cat | gcg | gtg | ctt | 29023 |
| Arg | Gly | His | Arg | Ile | Glu | Leu | Ala | Glu | Val | Glu | His | Ala | Val | Leu | |
| | | | 9495 | | | | 9500 | | | | 9505 | | | | |
| ggc | ttg | gaa | gac | gtg | caa | gac | gct | gcc | gtt | ctc | ata | gct | caa | aca | 29068 |
| Gly | Leu | Glu | Asp | Val | Gln | Asp | Ala | Ala | Val | Leu | Ile | Ala | Gln | Thr | |
| | | | 9510 | | | | 9515 | | | | 9520 | | | | |
| gcc | gaa | aat | gaa | gag | cta | gtt | ggc | ttc | ttc | acg | ctt | cga | caa | acc | 29113 |
| Ala | Glu | Asn | Glu | Glu | Leu | Val | Gly | Phe | Phe | Thr | Leu | Arg | Gln | Thr | |
| | | | 9525 | | | | 9530 | | | | 9535 | | | | |
| cag | gct | gtg | cag | tca | aat | ggt | gcc | gct | ggt | gtt | gtg | cca | gag | cac | 29158 |
| Gln | Ala | Val | Gln | Ser | Asn | Gly | Ala | Ala | Gly | Val | Val | Pro | Glu | His | |
| | | | 9540 | | | | 9545 | | | | 9550 | | | | |
| agc | gac | tcc | gag | ctg | gcg | caa | tcc | tgc | tct | tgc | act | caa | acg | gag | 29203 |
| Ser | Asp | Ser | Glu | Leu | Ala | Gln | Ser | Cys | Ser | Cys | Thr | Gln | Thr | Glu | |
| | | | 9555 | | | | 9560 | | | | 9565 | | | | |
| cgt | cga | gtc | cgc | aac | aga | ttg | caa | tcc | tgt | ctt | cct | cgc | tac | atg | 29248 |
| Arg | Arg | Val | Arg | Asn | Arg | Leu | Gln | Ser | Cys | Leu | Pro | Arg | Tyr | Met | |
| | | | 9570 | | | | 9575 | | | | 9580 | | | | |
| gtt | ccg | tcg | cga | atg | gtc | ctt | ttg | gat | cga | ctg | cct | gtc | aac | ccc | 29293 |
| Val | Pro | Ser | Arg | Met | Val | Leu | Leu | Asp | Arg | Leu | Pro | Val | Asn | Pro | |
| | | | 9585 | | | | 9590 | | | | 9595 | | | | |
| aat | ggt | aaa | gtt | gat | cga | caa | gag | ctc | acg | agg | cgc | gct | cag | gat | 29338 |
| Asn | Gly | Lys | Val | Asp | Arg | Gln | Glu | Leu | Thr | Arg | Arg | Ala | Gln | Asp | |
| | | | 9600 | | | | 9605 | | | | 9610 | | | | |
| ctc | cca | ata | agc | gag | tca | tcc | cca | gtg | cac | gtc | aaa | ccg | cgt | act | 29383 |
| Leu | Pro | Ile | Ser | Glu | Ser | Ser | Pro | Val | His | Val | Lys | Pro | Arg | Thr | |
| | | | 9615 | | | | 9620 | | | | 9625 | | | | |
| gaa | ctg | gaa | agg | tcg | ctg | tgc | gag | gag | ttc | gcc | gat | gtt | ata | ggt | 29428 |
| Glu | Leu | Glu | Arg | Ser | Leu | Cys | Glu | Glu | Phe | Ala | Asp | Val | Ile | Gly | |
| | | | 9630 | | | | 9635 | | | | 9640 | | | | |
| ttg | gaa | gtc | ggc | gtt | acc | gat | aat | ttc | ttc | gac | cta | ggc | ggg | cac | 29473 |
| Leu | Glu | Val | Gly | Val | Thr | Asp | Asn | Phe | Phe | Asp | Leu | Gly | Gly | His | |
| | | | 9645 | | | | 9650 | | | | 9655 | | | | |
| tct | ctc | atg | gcg | atg | aaa | ctc | gca | gct | cgc | atc | agc | cgt | cgt | tcg | 29518 |
| Ser | Leu | Met | Ala | Met | Lys | Leu | Ala | Ala | Arg | Ile | Ser | Arg | Arg | Ser | |
| | | | 9660 | | | | 9665 | | | | 9670 | | | | |
| aat | gca | cat | ata | tca | gtc | aag | gac | att | ttc | gac | cac | ccg | ctg | att | 29563 |
| Asn | Ala | His | Ile | Ser | Val | Lys | Asp | Ile | Phe | Asp | His | Pro | Leu | Ile | |
| | | | 9675 | | | | 9680 | | | | 9685 | | | | |
| gca | gat | ctc | gca | atg | aaa | att | cgg | gaa | ggc | tcc | gat | ctg | cac | act | 29608 |
| Ala | Asp | Leu | Ala | Met | Lys | Ile | Arg | Glu | Gly | Ser | Asp | Leu | His | Thr | |
| | | | 9690 | | | | 9695 | | | | 9700 | | | | |
| cca | att | ccc | cac | agg | atg | tac | gtt | gga | cct | atc | cag | cta | tca | ttc | 29653 |
| Pro | Ile | Pro | His | Arg | Met | Tyr | Val | Gly | Pro | Ile | Gln | Leu | Ser | Phe | |
| | | | 9705 | | | | 9710 | | | | 9715 | | | | |
| gca | cag | gga | cgc | ttg | tgg | ttc | ctc | gac | caa | ttg | aat | ttg | ggc | gca | 29698 |
| Ala | Gln | Gly | Arg | Leu | Trp | Phe | Leu | Asp | Gln | Leu | Asn | Leu | Gly | Ala | |
| | | | 9720 | | | | 9725 | | | | 9730 | | | | |
| tcg | tgg | tac | gtc | atg | cca | ctt | gct | atg | cgc | ctc | caa | ggc | tcg | ctc | 29743 |
| Ser | Trp | Tyr | Val | Met | Pro | Leu | Ala | Met | Arg | Leu | Gln | Gly | Ser | Leu | |
| | | | 9735 | | | | 9740 | | | | 9745 | | | | |
| cag | ctc | gac | gcg | tta | gag | act | gca | ctg | ttt | gct | atc | gag | cag | cga | 29788 |
| Gln | Leu | Asp | Ala | Leu | Glu | Thr | Ala | Leu | Phe | Ala | Ile | Glu | Gln | Arg | |
| | | | 9750 | | | | 9755 | | | | 9760 | | | | |
| cac | gaa | acc | tta | cgg | atg | aca | ttt | gca | gaa | caa | gac | gga | gta | gct | 29833 |
| His | Glu | Thr | Leu | Arg | Met | Thr | Phe | Ala | Glu | Gln | Asp | Gly | Val | Ala | |
| | | | 9765 | | | | 9770 | | | | 9775 | | | | |

```
gta caa gta gtg cat gca gcc cac tac aaa cac atc aag atg atc    29878
Val Gln Val Val His Ala Ala His Tyr Lys His Ile Lys Met Ile
            9780            9785            9790 gac aaa cca ctt aga cag aag att gac gtc ctg aag atg ctg gaa    29923
Asp Lys Pro Leu Arg Gln Lys Ile Asp Val Leu Lys Met Leu Glu
            9795            9800            9805 gaa gaa cgg acg act ccc ttc gag ctg agc cgc gag cct gga tgg    29968
Glu Glu Arg Thr Thr Pro Phe Glu Leu Ser Arg Glu Pro Gly Trp
            9810            9815            9820 agg gta gcg ctg ctg cgt ctg gga gat gac gac cac gtc ctc tcc    30013
Arg Val Ala Leu Leu Arg Leu Gly Asp Asp Asp His Val Leu Ser
            9825            9830            9835 atc gtc atg cat cac atc atc tcc gac ggt tgg tct gtg gac gtg    30058
Ile Val Met His His Ile Ile Ser Asp Gly Trp Ser Val Asp Val
            9840            9845            9850 ctg cgc cac gag cta ggt cag ttc tac tcg gcc gcg ctc cgg ggg    30103
Leu Arg His Glu Leu Gly Gln Phe Tyr Ser Ala Ala Leu Arg Gly
            9855            9860            9865 cag gac ccg ttg tcg cag ata agt cct ctg ccg atc cag tat cgt    30148
Gln Asp Pro Leu Ser Gln Ile Ser Pro Leu Pro Ile Gln Tyr Arg
            9870            9875            9880 gac ttc gct ctc tgg cag aga caa gac gag caa gtt gcg gag cat    30193
Asp Phe Ala Leu Trp Gln Arg Gln Asp Glu Gln Val Ala Glu His
            9885            9890            9895 cag cgc cag ctg gag cat tgg aca gag cag ttg gca gac agt tca    30238
Gln Arg Gln Leu Glu His Trp Thr Glu Gln Leu Ala Asp Ser Ser
            9900            9905            9910 ccc gcc gag ttg ttg agc gac cac ccg agg cca tcg att ctt tct    30283
Pro Ala Glu Leu Leu Ser Asp His Pro Arg Pro Ser Ile Leu Ser
            9915            9920            9925 ggc cag gcg ggc gct att ccc gtc aat gtt caa ggc tct ctg tat    30328
Gly Gln Ala Gly Ala Ile Pro Val Asn Val Gln Gly Ser Leu Tyr
            9930            9935            9940 cag gcg ctt cgg gcg ttc tgc cgc gct cac cag gtc acc tct ttc    30373
Gln Ala Leu Arg Ala Phe Cys Arg Ala His Gln Val Thr Ser Phe
            9945            9950            9955 gta gtc ctg ctc acg gcg ttc cgc ata gca cac tat cgt ctg acg    30418
Val Val Leu Leu Thr Ala Phe Arg Ile Ala His Tyr Arg Leu Thr
            9960            9965            9970 ggt gcg gag gac gca acc att gga act ccc att gca aat cgc aac    30463
Gly Ala Glu Asp Ala Thr Ile Gly Thr Pro Ile Ala Asn Arg Asn
            9975            9980            9985 cgg cca gag ctc gag aac atg atc ggt ttc ttc gtc aat aca caa    30508
Arg Pro Glu Leu Glu Asn Met Ile Gly Phe Phe Val Asn Thr Gln
            9990            9995            10000 tgc atg cgc atc gtc att ggc agt gac gac aca ttt gaa ggg ctg    30553
Cys Met Arg Ile Val Ile Gly Ser Asp Asp Thr Phe Glu Gly Leu
            10005           10010           10015 gtg cag caa gta cgc tcg ata act gca gct gcc cac gag aac cag    30598
Val Gln Gln Val Arg Ser Ile Thr Ala Ala Ala His Glu Asn Gln
            10020           10025           10030 gac gtt cca ttc gag cgc atc gtg tca gca ctg ctt ccc ggt tct    30643
Asp Val Pro Phe Glu Arg Ile Val Ser Ala Leu Leu Pro Gly Ser
            10035           10040           10045 aga gac aca tca cgc aat cct ctg gtt cag ctc atg ttt gct gtc    30688
Arg Asp Thr Ser Arg Asn Pro Leu Val Gln Leu Met Phe Ala Val
            10050           10055           10060 cac tcg caa aga aac ctt ggt cag atc agt cta gaa ggc ctg cag    30733
His Ser Gln Arg Asn Leu Gly Gln Ile Ser Leu Glu Gly Leu Gln
```

```
              10065             10070             10075
ggt gaa ttg ctg   gga gtg gca gcg   act acg aga ttc   gat gta   gag   30778
Gly Glu Leu Leu   Gly Val Ala Ala   Thr Thr Arg Phe   Asp Val   Glu
      10080             10085             10090 ttc cat ctc ttc   caa gat gac gac   aag ctc agc ggc   aac gtg   ctc   30823
Phe His Leu Phe   Gln Asp Asp Asp   Lys Leu Ser Gly   Asn Val   Leu
      10095             10100             10105 ttc gcg acc gag   ctc ttc gag cag   aag act atg caa   ggc atg   gtc   30868
Phe Ala Thr Glu   Leu Phe Glu Gln   Lys Thr Met Gln   Gly Met   Val
      10110             10115             10120 gac gtg ttc cag   gaa gtg ctc agc   cgg ggc ctt gag   cag ccc   cag   30913
Asp Val Phe Gln   Glu Val Leu Ser   Arg Gly Leu Glu   Gln Pro   Gln
      10125             10130             10135 ata cct ctg gcg   acc ctc ccg ctc   acg cac gga ctg   gag gag   ctc   30958
Ile Pro Leu Ala   Thr Leu Pro Leu   Thr His Gly Leu   Glu Glu   Leu
      10140             10145             10150 agg acc atg ggt   ctt ctc gac gtg   gag aag aca gac   tac cct   cga   31003
Arg Thr Met Gly   Leu Leu Asp Val   Glu Lys Thr Asp   Tyr Pro   Arg
      10155             10160             10165 gag tcg agc gtg   gtg gac gtg ttc   cgt gag caa gcg   gct gcc   tgc   31048
Glu Ser Ser Val   Val Asp Val Phe   Arg Glu Gln Ala   Ala Ala   Cys
      10170             10175             10180 tcc gag gcg att   gcg gtc aaa gac   tcg tcg gcg cag   ctc acc   tac   31093
Ser Glu Ala Ile   Ala Val Lys Asp   Ser Ser Ala Gln   Leu Thr   Tyr
      10185             10190             10195 tcg gag ctc gat   cga cag tcg gac   gag ctt gcc ggc   tgg ctg   cgc   31138
Ser Glu Leu Asp   Arg Gln Ser Asp   Glu Leu Ala Gly   Trp Leu   Arg
      10200             10205             10210 cag caa cgt ctt   cct gcg gag tcg   ttg gtt gca gtg   ctg gca   ccc   31183
Gln Gln Arg Leu   Pro Ala Glu Ser   Leu Val Ala Val   Leu Ala   Pro
      10215             10220             10225 agg tcg tgc cag   acc att gtc gcg   ttc ctg ggc atc   ctc aag   gcg   31228
Arg Ser Cys Gln   Thr Ile Val Ala   Phe Leu Gly Ile   Leu Lys   Ala
      10230             10235             10240 aat ctg gca tac   ctg ccg cta gac   gtc aac gtg ccc   gct act   cgc   31273
Asn Leu Ala Tyr   Leu Pro Leu Asp   Val Asn Val Pro   Ala Thr   Arg
      10245             10250             10255 ctc gag tcg ata   ctg tct gcc gtc   ggc ggc cgg aag   ctg gtc   ttg   31318
Leu Glu Ser Ile   Leu Ser Ala Val   Gly Gly Arg Lys   Leu Val   Leu
      10260             10265             10270 ctt gga gct gac   gtg gcc gac cct   ggc ctt cgc ctg   gcg gat   gtg   31363
Leu Gly Ala Asp   Val Ala Asp Pro   Gly Leu Arg Leu   Ala Asp   Val
      10275             10280             10285 gag ctc gtg cgg   atc ggc gac aca   ctc ggc cgc tgt   gta ccc   ggg   31408
Glu Leu Val Arg   Ile Gly Asp Thr   Leu Gly Arg Cys   Val Pro   Gly
      10290             10295             10300 gcg ccc ggc gac   aac gag gca cct   gtg gtg cag cct   tct gcc   aca   31453
Ala Pro Gly Asp   Asn Glu Ala Pro   Val Val Gln Pro   Ser Ala   Thr
      10305             10310             10315 agc ctt gcc tac   gtc atc ttc act   tcc ggc tcg acc   ggc aag   ccg   31498
Ser Leu Ala Tyr   Val Ile Phe Thr   Ser Gly Ser Thr   Gly Lys   Pro
      10320             10325             10330 aag ggt gtc atg   gtc gag cac cgg   ggt gta gtg cga   ctt gtc   aag   31543
Lys Gly Val Met   Val Glu His Arg   Gly Val Val Arg   Leu Val   Lys
      10335             10340             10345 cag agc aat gtt   gtc tac cat ctc   ccg tcc aca tct   cgc gtg   gcc   31588
Gln Ser Asn Val   Val Tyr His Leu   Pro Ser Thr Ser   Arg Val   Ala
      10350             10355             10360 cac ctg tcg aat   ctc gcc ttt gat gcc   tcg gcg tgg gag atc   tat   31633
```

|     |     |     |     |     |     |     |     |     |     |     |     |     |       |
|-----|-----|-----|-----|-----|-----|-----|-----|-----|-----|-----|-----|-----|-------|
| His | Leu | Ser | Asn | Leu | Ala | Phe | Asp | Ala | Ser | Ala | Trp | Glu | Ile | Tyr |
|     |     | 10365 |   |     |     |     | 10370 |   |     |     |     | 10375 |     |

```
gcg gca ctg ctt aat ggc ggt aca ctc atc tgc att gac tat ttc   31678
Ala Ala Leu Leu Asn Gly Gly Thr Leu Ile Cys Ile Asp Tyr Phe
        10380           10385               10390 aca act cta gac tgc tct gct ctc ggc gcc aaa ttc atc aag gag   31723
Thr Thr Leu Asp Cys Ser Ala Leu Gly Ala Lys Phe Ile Lys Glu
        10395           10400               10405 aag atc gtc gcg acc atg att ccg cca gcg ctt ctg aag caa tgt   31768
Lys Ile Val Ala Thr Met Ile Pro Pro Ala Leu Leu Lys Gln Cys
        10410           10415               10420 ctg gcg atc ttc ccg acc gct ctt agt gaa ctg gtc ctg ctg ttt   31813
Leu Ala Ile Phe Pro Thr Ala Leu Ser Glu Leu Val Leu Leu Phe
        10425           10430               10435 gct gcc gga gat cga ttc agc agt ggc gat gcc gtc gaa gtg cag   31858
Ala Ala Gly Asp Arg Phe Ser Ser Gly Asp Ala Val Glu Val Gln
        10440           10445               10450 cgc cac acc aaa ggc gct gtt tgt aac gcg tac gga ccg aca gaa   31903
Arg His Thr Lys Gly Ala Val Cys Asn Ala Tyr Gly Pro Thr Glu
        10455           10460               10465 aac acc att ctt agt acg atc tac gaa gtc aag cag aat gag aac   31948
Asn Thr Ile Leu Ser Thr Ile Tyr Glu Val Lys Gln Asn Glu Asn
        10470           10475               10480 ttc ccg aac ggt gtg cct atc ggc cgc gct gtg agc aac tca ggg   31993
Phe Pro Asn Gly Val Pro Ile Gly Arg Ala Val Ser Asn Ser Gly
        10485           10490               10495 gca tat gtc atg gac ccg cag cag caa ctg gtg cct ctc ggg gtg   32038
Ala Tyr Val Met Asp Pro Gln Gln Gln Leu Val Pro Leu Gly Val
        10500           10505               10510 atg ggc gag ctc gtc gtc acc ggc gac ggc ctg gcc cgt ggt tac   32083
Met Gly Glu Leu Val Val Thr Gly Asp Gly Leu Ala Arg Gly Tyr
        10515           10520               10525 acc gac ccg tca ctg gat gcg gac cgc ttt gtg cag gtc tcc gtc   32128
Thr Asp Pro Ser Leu Asp Ala Asp Arg Phe Val Gln Val Ser Val
        10530           10535               10540 aac ggg cag ctc gtg aga gcg tac cga aca ggc gat cgc gtg cgc   32173
Asn Gly Gln Leu Val Arg Ala Tyr Arg Thr Gly Asp Arg Val Arg
        10545           10550               10555 tgc agg cct tgc gat ggc cag atc gag ttc ttt gga cgt atg gac   32218
Cys Arg Pro Cys Asp Gly Gln Ile Glu Phe Phe Gly Arg Met Asp
        10560           10565               10570 cgg caa gtc aag atc cga gga cat cgc atc gag ctc gca gag gta   32263
Arg Gln Val Lys Ile Arg Gly His Arg Ile Glu Leu Ala Glu Val
        10575           10580               10585 gag cat gcg gtg ctt ggc ttg gaa gac gtg caa gac gct gcc gtt   32308
Glu His Ala Val Leu Gly Leu Glu Asp Val Gln Asp Ala Ala Val
        10590           10595               10600 atc gca ttt gac aat gtg gac agc gaa gag cca gaa atg gtt ggg   32353
Ile Ala Phe Asp Asn Val Asp Ser Glu Glu Pro Glu Met Val Gly
        10605           10610               10615 ttt gtc act att acc gaa gac aat cct gtc cgt gag gac gaa acc   32398
Phe Val Thr Ile Thr Glu Asp Asn Pro Val Arg Glu Asp Glu Thr
        10620           10625               10630 agc ggt caa gta gaa gac tgg gcg aac cac ttc gag ata agt acc   32443
Ser Gly Gln Val Glu Asp Trp Ala Asn His Phe Glu Ile Ser Thr
        10635           10640               10645 tac acc gat atc gcg gcg atc gat cag ggt agc att gga agt gac   32488
Tyr Thr Asp Ile Ala Ala Ile Asp Gln Gly Ser Ile Gly Ser Asp
        10650           10655               10660
```

```
ttt gta ggt tgg  act tct atg tac  gac gga agc gag  atc gac aag         32533
Phe Val Gly Trp  Thr Ser Met Tyr  Asp Gly Ser Glu  Ile Asp Lys
        10665             10670             10675 gca gag atg caa  gaa tgg ctt gcc  gat acc atg gcc  tct atg ctc         32578
Ala Glu Met Gln  Glu Trp Leu Ala  Asp Thr Met Ala  Ser Met Leu
        10680             10685             10690 gac ggg cag gcg  ccg ggc aat gtg  tta gag ata ggt  aca ggc act         32623
Asp Gly Gln Ala  Pro Gly Asn Val  Leu Glu Ile Gly  Thr Gly Thr
        10695             10700             10705 ggc atg gtc ctc  ttc aat ctc ggc  gac gga ctg cag  agc tat gtc         32668
Gly Met Val Leu  Phe Asn Leu Gly  Asp Gly Leu Gln  Ser Tyr Val
        10710             10715             10720 ggc ctc gaa cca  tca aga tcg gcg  gcc gct ttt gtc  aac cag acg         32713
Gly Leu Glu Pro  Ser Arg Ser Ala  Ala Ala Phe Val  Asn Gln Thr
        10725             10730             10735 att aag tcg ctc  ccc acc ctt gct  ggc aac gct gaa  gta cac att         32758
Ile Lys Ser Leu  Pro Thr Leu Ala  Gly Asn Ala Glu  Val His Ile
        10740             10745             10750 ggc act gcg acc  gac gtg gcc cgt  cta gat ggc ctc  cgc ccc gac         32803
Gly Thr Ala Thr  Asp Val Ala Arg  Leu Asp Gly Leu  Arg Pro Asp
        10755             10760             10765 tta gtg gta gtc  aat tcg gta gtc  cag tac ttc cca  tca cca gag         32848
Leu Val Val Val  Asn Ser Val Val  Gln Tyr Phe Pro  Ser Pro Glu
        10770             10775             10780 tac cta atg gaa  gtc gtg gag gct  ctt gca cgt ctg  ccg ggc gtc         32893
Tyr Leu Met Glu  Val Val Glu Ala  Leu Ala Arg Leu  Pro Gly Val
        10785             10790             10795 gag cga att ttc  ttc gga gac gta  cgt tcg tac gcc  atc aac aga         32938
Glu Arg Ile Phe  Phe Gly Asp Val  Arg Ser Tyr Ala  Ile Asn Arg
        10800             10805             10810 gat ttc ctg gct  gcc aga gct cta  cac gaa ctt ggc  gac aga gcg         32983
Asp Phe Leu Ala  Ala Arg Ala Leu  His Glu Leu Gly  Asp Arg Ala
        10815             10820             10825 act aag cac gag  att cgg cga aag  atg cta gag atg  gaa gaa cgc         33028
Thr Lys His Glu  Ile Arg Arg Lys  Met Leu Glu Met  Glu Glu Arg
        10830             10835             10840 gaa gag gag ctg  ctc gtc gac cca  gct ttc ttc acc  atg ttg acc         33073
Glu Glu Glu Leu  Leu Val Asp Pro  Ala Phe Phe Thr  Met Leu Thr
        10845             10850             10855 agc agt ctc cct  ggc ctg att cag  cat gtc gag atc  ttg ccg aag         33118
Ser Ser Leu Pro  Gly Leu Ile Gln  His Val Glu Ile  Leu Pro Lys
        10860             10865             10870 ctg atg aga gcc  act aat gag ctc  agc gcg tat cga  tac act gct         33163
Leu Met Arg Ala  Thr Asn Glu Leu  Ser Ala Tyr Arg  Tyr Thr Ala
        10875             10880             10885 gta gta cac gtg  tgc cgt gcc ggt  caa gag cct cgt  tcc gtg cat         33208
Val Val His Val  Cys Arg Ala Gly  Gln Glu Pro Arg  Ser Val His
        10890             10895             10900 acg atc gac gac  gat gcc tgg gtg  aat ctt gga gct  tct cgg ttg         33253
Thr Ile Asp Asp  Asp Ala Trp Val  Asn Leu Gly Ala  Ser Arg Leu
        10905             10910             10915 agt cgc cct acc  ctt tca agc ctt  ttg caa act tcc  gag ggc gca         33298
Ser Arg Pro Thr  Leu Ser Ser Leu  Leu Gln Thr Ser  Glu Gly Ala
        10920             10925             10930 tcg gcc gtc gca  gta agc aat att  cct tac agc aag  acc atc aca         33343
Ser Ala Val Ala  Val Ser Asn Ile  Pro Tyr Ser Lys  Thr Ile Thr
        10935             10940             10945 gag cga gcg ctc  gtt agt gcg ctc  gat gag gat gat  atg caa gac         33388
Glu Arg Ala Leu  Val Ser Ala Leu  Asp Glu Asp Asp  Met Gln Asp
        10950             10955             10960
```

| | | | | | | | | | | | | | |
|---|---|---|---|---|---|---|---|---|---|---|---|---|---|
| tca | tcg | gac | tgg | ctg | ctg | gcc | gtg | cgc | gag | aca | ggc | aga | tct | tgt | 33433 |
| Ser | Ser | Asp | Trp | Leu | Leu | Ala | Val | Arg | Glu | Thr | Gly | Arg | Ser | Cys |
| | | | 10965 | | | | 10970 | | | | | 10975 | | |
| tcc | tcc | ttc | tcc | gca | aca | gac | ctt | gtc | gag | ctt | gct | cga | gag | acg | 33478 |
| Ser | Ser | Phe | Ser | Ala | Thr | Asp | Leu | Val | Glu | Leu | Ala | Arg | Glu | Thr |
| | | | 10980 | | | | 10985 | | | | | 10990 | | |
| ggc | tgg | cgt | gtg | gag | ctc | agc | tgg | gca | cga | cag | tac | tca | cag | aaa | 33523 |
| Gly | Trp | Arg | Val | Glu | Leu | Ser | Trp | Ala | Arg | Gln | Tyr | Ser | Gln | Lys |
| | | | 10995 | | | | 11000 | | | | | 11005 | | |
| ggc | gca | ctc | gat | gct | gtc | ttc | cac | aga | cac | cct | gtt | tcc | gct | ggg | 33568 |
| Gly | Ala | Leu | Asp | Ala | Val | Phe | His | Arg | His | Pro | Val | Ser | Ala | Gly |
| | | | 11010 | | | | 11015 | | | | | 11020 | | |
| agc | ggg | cgt | gtc | atg | ttc | cag | ttt | cca | gtt | gag | acc | gaa | gat | cga | 33613 |
| Ser | Gly | Arg | Val | Met | Phe | Gln | Phe | Pro | Val | Glu | Thr | Glu | Asp | Arg |
| | | | 11025 | | | | 11030 | | | | | 11035 | | |
| ccg | cac | atc | tca | cgc | acg | aac | cga | cct | tta | cag | cga | ttg | cag | aag | 33658 |
| Pro | His | Ile | Ser | Arg | Thr | Asn | Arg | Pro | Leu | Gln | Arg | Leu | Gln | Lys |
| | | | 11040 | | | | 11045 | | | | | 11050 | | |
| aag | cga | acc | gag | aca | cat | gtt | cat | gag | cag | ttg | cgg | gct | ttg | ctt | 33703 |
| Lys | Arg | Thr | Glu | Thr | His | Val | His | Glu | Gln | Leu | Arg | Ala | Leu | Leu |
| | | | 11055 | | | | 11060 | | | | | 11065 | | |
| cca | cga | tac | atg | gtt | cct | acg | cgg | att | gtg | gcg | ctt | gat | aag | ctg | 33748 |
| Pro | Arg | Tyr | Met | Val | Pro | Thr | Arg | Ile | Val | Ala | Leu | Asp | Lys | Leu |
| | | | 11070 | | | | 11075 | | | | | 11080 | | |
| ccc | gtc | aat | gca | aac | ggc | aag | gtt | gat | cgt | caa | cag | ctc | gct | agg | 33793 |
| Pro | Val | Asn | Ala | Asn | Gly | Lys | Val | Asp | Arg | Gln | Gln | Leu | Ala | Arg |
| | | | 11085 | | | | 11090 | | | | | 11095 | | |
| aca | gcc | cag | gtt | ctc | cca | gcg | agc | aag | gcg | ccg | tct | gca | tgc | gtg | 33838 |
| Thr | Ala | Gln | Val | Leu | Pro | Ala | Ser | Lys | Ala | Pro | Ser | Ala | Cys | Val |
| | | | 11100 | | | | 11105 | | | | | 11110 | | |
| gcc | cca | cgc | aac | gaa | ttg | gaa | atg | aca | ctg | tgt | gaa | gag | ttc | tcg | 33883 |
| Ala | Pro | Arg | Asn | Glu | Leu | Glu | Met | Thr | Leu | Cys | Glu | Glu | Phe | Ser |
| | | | 11115 | | | | 11120 | | | | | 11125 | | |
| cag | gtt | ctt | ggc | gtc | gag | gtc | ggc | att | act | gac | aat | ttc | ttc | cac | 33928 |
| Gln | Val | Leu | Gly | Val | Glu | Val | Gly | Ile | Thr | Asp | Asn | Phe | Phe | His |
| | | | 11130 | | | | 11135 | | | | | 11140 | | |
| ctg | ggt | ggc | cac | tct | ctc | atg | gca | aca | aag | ctt | gcc | gct | cgt | atc | 33973 |
| Leu | Gly | Gly | His | Ser | Leu | Met | Ala | Thr | Lys | Leu | Ala | Ala | Arg | Ile |
| | | | 11145 | | | | 11150 | | | | | 11155 | | |
| agc | cgt | caa | cta | aat | atc | caa | gtc | tca | gtc | cga | gac | atc | ttt | gac | 34018 |
| Ser | Arg | Gln | Leu | Asn | Ile | Gln | Val | Ser | Val | Arg | Asp | Ile | Phe | Asp |
| | | | 11160 | | | | 11165 | | | | | 11170 | | |
| tat | ccc | gtt | ata | gtc | gac | ctc | aca | gac | aga | ttg | aga | ctc | cat | cat | 34063 |
| Tyr | Pro | Val | Ile | Val | Asp | Leu | Thr | Asp | Arg | Leu | Arg | Leu | His | His |
| | | | 11175 | | | | 11180 | | | | | 11185 | | |
| acg | cgt | atc | ctt | act | cat | gat | cat | gga | caa | cat | gga | cag | cca | gac | 34108 |
| Thr | Arg | Ile | Leu | Thr | His | Asp | His | Gly | Gln | His | Gly | Gln | Pro | Asp |
| | | | 11190 | | | | 11195 | | | | | 11200 | | |
| ctc | aag | cca | ttc | acc | ttg | cta | cca | acc | aac | aat | cct | caa | gaa | ttc | 34153 |
| Leu | Lys | Pro | Phe | Thr | Leu | Leu | Pro | Thr | Asn | Asn | Pro | Gln | Glu | Phe |
| | | | 11205 | | | | 11210 | | | | | 11215 | | |
| cta | cag | cat | cac | att | ttg | cca | caa | ctt | gtt | ccc | gat | cat | gcg | aag | 34198 |
| Leu | Gln | His | His | Ile | Leu | Pro | Gln | Leu | Val | Pro | Asp | His | Ala | Lys |
| | | | 11220 | | | | 11225 | | | | | 11230 | | |
| atc | ctc | gat | gtg | tat | ccc | gtt | aca | aga | ata | cag | aga | agg | ttt | ctt | 34243 |
| Ile | Leu | Asp | Val | Tyr | Pro | Val | Thr | Arg | Ile | Gln | Arg | Arg | Phe | Leu |
| | | | 11235 | | | | 11240 | | | | | 11245 | | |
| cat | cat | ccg | aag | cgc | ggc | ctc | cct | cgt | ttt | ccc | tcc | atg | gtc | ttc | 34288 |
| His | His | Pro | Lys | Arg | Gly | Leu | Pro | Arg | Phe | Pro | Ser | Met | Val | Phe |

-continued

|  |  |  |  |
|---|---|---|---|
| 11250 | 11255 | 11260 |  | ttt gac ttc cct cct ggt tca gac cca cac aag cta aga tta gct 34333
Phe Asp Phe Pro Pro Gly Ser Asp Pro His Lys Leu Arg Leu Ala
11265           11270               11275 tgt atg gca tta gtc cag cgt ttc gac att ctt cgc aca atc ttc 34378
Cys Met Ala Leu Val Gln Arg Phe Asp Ile Leu Arg Thr Ile Phe
11280           11285               11290 ctt tct gtt tcg ggt caa ttc ttc caa gtg gtc ctg gat gga tat 34423
Leu Ser Val Ser Gly Gln Phe Phe Gln Val Val Leu Asp Gly Tyr
11295           11300               11305 ggg att gtc ata ccg gtc atc gag gtt gac gaa gag cta gac gac 34468
Gly Ile Val Ile Pro Val Ile Glu Val Asp Glu Glu Leu Asp Asp
11310           11315               11320 gcc acc cgt aaa tta cac gat tcc gat att cag cag ccc tta cgg 34513
Ala Thr Arg Lys Leu His Asp Ser Asp Ile Gln Gln Pro Leu Arg
11325           11330               11335 ttg gga aaa ccg tta ata cgc att gct gtc ttg aaa agg cag cac 34558
Leu Gly Lys Pro Leu Ile Arg Ile Ala Val Leu Lys Arg Gln His
11340           11345               11350 tcc aga gta cga gca gtc ttg cgc ttg tcg cat gct ctc tat gat 34603
Ser Arg Val Arg Ala Val Leu Arg Leu Ser His Ala Leu Tyr Asp
11355           11360               11365 ggt ttg agc ttt gag cat atc atc caa tct ctt cat gcc ctt tat 34648
Gly Leu Ser Phe Glu His Ile Ile Gln Ser Leu His Ala Leu Tyr
11370           11375               11380 ctc gat atc acc ctt tcg gcc cca ccg aag ttt gga ctc tac gta 34693
Leu Asp Ile Thr Leu Ser Ala Pro Pro Lys Phe Gly Leu Tyr Val
11385           11390               11395 caa cat atg ata caa agt cgc gca gaa ggt tat gct ttc tgg cgg 34738
Gln His Met Ile Gln Ser Arg Ala Glu Gly Tyr Ala Phe Trp Arg
11400           11405               11410 tct gtc ttg aag ggc tcg tcg atg aca att ctc gag cgt tct agc 34783
Ser Val Leu Lys Gly Ser Ser Met Thr Ile Leu Glu Arg Ser Ser
11415           11420               11425 acc ctt caa tcg cgg cag ccg cat ctt gga cgt ttt ctc tct gcg 34828
Thr Leu Gln Ser Arg Gln Pro His Leu Gly Arg Phe Leu Ser Ala
11430           11435               11440 gag aaa att att aag gct cct tta cac gcc aac aag tct gga atc 34873
Glu Lys Ile Ile Lys Ala Pro Leu His Ala Asn Lys Ser Gly Ile
11445           11450               11455 aca cag gca aca gtg ttc gcg gcc gca aac gca ctc atg ctt gcg 34918
Thr Gln Ala Thr Val Phe Ala Ala Ala Asn Ala Leu Met Leu Ala
11460           11465               11470 aat ctt act ggt act aat gac gtt gtg ttt gcc cgc att gtc tct 34963
Asn Leu Thr Gly Thr Asn Asp Val Val Phe Ala Arg Ile Val Ser
11475           11480               11485 gga cgt caa tct ttg cct aag aac ttt cag cac gtt gtg gga cct 35008
Gly Arg Gln Ser Leu Pro Lys Asn Phe Gln His Val Val Gly Pro
11490           11495               11500 tgc acg aac gat gtg ccc gtt cgc gta cgc atg gag cct ggc gtg 35053
Cys Thr Asn Asp Val Pro Val Arg Val Arg Met Glu Pro Gly Val
11505           11510               11515 gga cca aaa gct tta ctc aga cag gtg caa gac cag tat gtt cat 35098
Gly Pro Lys Ala Leu Leu Arg Gln Val Gln Asp Gln Tyr Val His
11520           11525               11530 agc ttc cct ttc gaa aca cta gga ttc gac gag atc aag gag aac 35143
Ser Phe Pro Phe Glu Thr Leu Gly Phe Asp Glu Ile Lys Glu Asn
11535           11540               11545 tgt acg gac tgg cca gaa aga atc acg aat ttt ggg tgt tct aca 35188

-continued

| | | | | | | | | | | | | |
|---|---|---|---|---|---|---|---|---|---|---|---|---|
|Cys|Thr|Asp|Trp 11550|Pro|Glu|Arg|Ile 11555|Asn|Phe|Gly|Cys Ser 11560|Thr|

```
act tac cag aac ttt gac att ttt ccc aaa agt cag att gac    cac       35233
Thr Tyr Gln Asn Phe Asp Ile Phe Pro Lys Ser Gln Ile Asp    His
            11565               11570               11575 cag cag att caa atg gct agc ttg gca agc gag tat cag aat    cga       35278
Gln Gln Ile Gln Met Ala Ser Leu Ala Ser Glu Tyr Gln Asn    Arg
            11580               11585               11590 gaa acc tgg gac gaa gcg ccg cta tac gac ctc aat gtc aca    gga       35323
Glu Thr Trp Asp Glu Ala Pro Leu Tyr Asp Leu Asn Val Thr    Gly
            11595               11600               11605 gta cct cag cct gac gga cgt cat atc aag ata tac gtg ggt    gta       35368
Val Pro Gln Pro Asp Gly Arg His Ile Lys Ile Tyr Val Gly    Val
            11610               11615               11620 gac ggg cag ctt tgc gat gaa agc acg ctt gat tgc att ctc    tcg       35413
Asp Gly Gln Leu Cys Asp Glu Ser Thr Leu Asp Cys Ile Leu    Ser
            11625               11630               11635 gat att tgt gag ggt gtg gtc tcg ctc aca gac gct ttg caa    gaa       35458
Asp Ile Cys Glu Gly Val Val Ser Leu Thr Asp Ala Leu Gln    Glu
            11640               11645               11650 ctt ccc gct gct   agc att act gag tag aatcccaaga gagcaacacc          35505
Leu Pro Ala Ala   Ser Ile Thr Glu
            11655 ctatcatgat agcgacagca cgttttcagt tcgtcagagc ttgactgaaa tgcttttcgt    35565 ctactacatc tagcgtgtca taccagctag tagctacaac ggagcaacga ttggctgatg    35625 agccaggacc tgaaaagaag aagaagatgg aaatatagcc ttggaatcta taataaag      35683
```

<210> SEQ ID NO 6
<211> LENGTH: 11659
<212> TYPE: PRT
<213> ORGANISM: Aureobasidium pullulans strain BP-1938

<400> SEQUENCE: 6

```
Met Ser Arg Met Pro Gln Gly Ala Ala Arg Arg Asn Asp Cys Val Ser
1               5                   10                  15

Glu His Gln Gly Thr Thr Asp Leu Glu Asp Ile Val Arg Phe Trp Glu
            20                  25                  30

Arg His Leu Asp Gly Val Asn Ala Ser Ala Phe Pro Ala Leu Ser Ser
        35                  40                  45

Ser Leu Val Val Pro Lys Pro Lys Leu Gln Thr Glu His Arg Ile Ser
    50                  55                  60

Leu Gly Thr Ala Val Ser Asp Gln Trp Ser Asp Ala Val Ile Cys Arg
65                  70                  75                  80

Ala Ala Leu Ala Val Ile Leu Ala Arg Tyr Thr His Ala Thr Glu Ala
                85                  90                  95

Leu Tyr Gly Ile Val Val Glu Gln Pro Ser Val Ser Asn Ala Gln Lys
            100                 105                 110

Arg Ser Ala Asp Asp Ala Ser Ser Ile Val Pro Ile Arg Val Gln
        115                 120                 125

Cys Ala Ser Gly Gln Phe Gly Asn Asp Ile Leu Ala Ala Ile Ala Thr
    130                 135                 140

His Asp Ala Ser Cys Arg Ser Leu Ser Ala Ile Gly Leu Asp Gly Ile
145                 150                 155                 160

Arg Cys Leu Asp Asp Ala Lys Thr Val Ala Arg Gly Leu Gln Thr Val
                165                 170                 175

Leu Thr Val Thr Ser Arg Lys Ser Val Asp Ala Ser Ser Pro Asn Ile
```

-continued

```
                180                 185                 190
Leu Asp Leu Glu Asn Ile Ala Ser Ser His Gly Arg Ala Leu Met Ile
            195                 200                 205
Glu Cys Gln Met Ser Thr Thr Ser Ala Cys Leu Arg Ala Gln Tyr Asp
        210                 215                 220
Ala Gly Ile Leu Arg Asn Glu Gln Val Val Arg Leu Leu Lys Gln Leu
225                 230                 235                 240
Ala Leu Ser Ile Gln His Phe Arg Gly Asn Ala Ala Asn Asp Leu Leu
                245                 250                 255
Arg Asp Phe Cys Phe Ile Ser Pro Gly Glu Glu Met Glu Ile Ala Tyr
            260                 265                 270
Trp Asn Arg Arg Ser Ile Arg Thr Asn Glu Val Cys Ile His Asp Val
        275                 280                 285
Ile Phe Lys Arg Ala Thr Tyr Met Pro Thr Asp Thr Ala Val Ser Ala
    290                 295                 300
Trp Asp Gly Glu Trp Thr Tyr Ala Asp Leu Asp Val Val Ser Ser Cys
305                 310                 315                 320
Leu Ala Asp Tyr Val Arg Ser Leu Asp Leu Arg Ser Gly Gln Ala Ile
                325                 330                 335
Pro Leu Cys Phe Glu Lys Ser Arg Asn Thr Ile Ala Ala Met Val Ala
            340                 345                 350
Val Leu Lys Ala Gly His Pro Phe Cys Leu Ile Asp Pro Ser Thr Pro
        355                 360                 365
Ser Ala Arg Ile Thr Gln Met Cys Glu Gln Met Ser Ala Thr Val Ala
    370                 375                 380
Phe Ala Ser Arg Ala Leu Cys Ser Ile Met Gln Ala Gly Val Ser Arg
385                 390                 395                 400
Cys Ile Ala Val Asp Asp Leu Phe Gln Ser Leu Ser Ser Val Ile
                405                 410                 415
Gly Cys Pro Gln Met Ser Met Thr Arg Pro Gln Asp Leu Ala Tyr Val
            420                 425                 430
Ile Phe Thr Ser Gly Ser Thr Gly Ile Pro Lys Gly Ser Met Ile Glu
        435                 440                 445
His Arg Gly Phe Ala Ser Cys Ala Leu Glu Phe Gly Pro Gln Leu Leu
    450                 455                 460
Ile Asp Arg Asn Thr Arg Ala Leu Gln Phe Ala Ser His Ala Phe Gly
465                 470                 475                 480
Ala Cys Leu Leu Glu Val Leu Val Thr Leu Met Leu Gly Gly Cys Val
                485                 490                 495
Cys Val Pro Ser Glu Asn Asp Arg Leu Asn Asn Leu Ser Gly Phe Ile
            500                 505                 510
Glu Gln Ser Gly Val Asn Trp Thr Leu Phe Thr Pro Ser Phe Ile Gly
        515                 520                 525
Ala Leu Thr Pro Glu Thr Ile Arg Gly Val His Thr Val Val Leu Gly
    530                 535                 540
Gly Glu Pro Met Thr Pro Phe Ile Arg Asp Val Trp Ala Ser Lys Val
545                 550                 555                 560
Gln Leu Leu Ser Ile Tyr Gly Gln Ser Glu Ser Ser Thr Val Cys Ser
                565                 570                 575
Val Val Lys Ile Lys Pro Asp Thr Thr Asp Leu Ser Ser Leu Gly His
            580                 585                 590
Ala Ile Gly Ala Arg Phe Trp Ile Val Asp Ala Glu Asn Pro Ser Arg
        595                 600                 605
```

-continued

```
Leu Ala Pro Ile Gly Cys Ile Gly Glu Leu Met Val Glu Ser Pro Gly
610                 615                 620

Ile Ala Arg Glu Tyr Leu Ser Ala Gln Glu Ala Gln Met Ser Pro Phe
625                 630                 635                 640

Ile Thr Lys Thr Pro Ala Trp Tyr Pro Met Lys Gln Arg Cys Ser Pro
            645                 650                 655

Val Lys Phe Tyr Met Thr Gly Asp Leu Ala Cys Tyr Gly Arg Asp Gly
            660                 665                 670

Thr Val Met Asn Leu Gly Arg Lys Asp Ser Gln Val Lys Ile Arg Gly
                675                 680                 685

Gln Arg Val Glu Leu Gly Asp Val Glu Thr Asn Leu Arg Ser Val Leu
690                 695                 700

Pro Lys His Ile Ile Pro Val Glu Ala Ile Asp Ser Ile His Ala
705                 710                 715                 720

Ser Gly Ser Lys Phe Leu Val Ala Ile Leu Ile Gly Ala Asn His Gly
                725                 730                 735

Met Lys Asn Glu Phe Asp Thr Glu Pro Arg Arg Glu Val Ser Ile Leu
                740                 745                 750

Asp Glu Thr Ala Val Ile Arg Ile Arg Lys Ser Met Gln Asp Leu Val
                755                 760                 765

Pro Ser Tyr Cys Ile Pro Thr Gln Tyr Ile Cys Met Glu Arg Leu Leu
770                 775                 780

Thr Thr Thr Thr Gly Lys Ala Asp Arg Lys Arg Leu Arg Ala Ile Cys
785                 790                 795                 800

Val Asp Leu Leu Lys Pro Ser Arg Arg Ala Met Val Pro Glu Ser Ser
                805                 810                 815

Asp Gly Pro Thr Leu Lys Leu Thr Ala Gly Gln Val Leu Asp Glu Ala
                820                 825                 830

Trp His Arg Tyr Leu Arg Phe Asp Ser Val Leu Asp Gly Ser Lys Ser
                835                 840                 845

Lys Phe Phe Asp Leu Asn Gly Asp Ser Ile Thr Ala Ile Lys Ile Ala
850                 855                 860

Asn Ala Ala Arg Lys His Gly Val Met Leu Lys Val Ala Asp Ile Leu
865                 870                 875                 880

Ala Asn Pro Thr Leu Ala Asp Leu Arg Ala Gln Phe Gln Ile Asp Phe
                885                 890                 895

Thr Pro Gln Asn Ser Ile Leu Arg Thr Ser Tyr Arg Gly Pro Ile Gln
                900                 905                 910

Gln Ser Phe Ala Gln Asn Arg Leu Trp Phe Leu Asp Gln Leu Asn Val
                915                 920                 925

Gly Ala Ser Trp Tyr Ile Val Pro Val Ala Val Arg Leu Gln Gly Thr
                930                 935                 940

Val His Val Asp Ala Leu Val Thr Ala Leu Cys Ala Leu Glu Gln Arg
945                 950                 955                 960

His Glu Thr Leu Arg Thr Thr Phe Glu Glu Ser Asp Gly Glu Gly Ile
                965                 970                 975

Gln Arg Ile Gln Pro Ser Gly Leu Glu Gln Leu Arg Leu Ile Asp Val
                980                 985                 990

Asp Cys Val Asp Ser Arg Asp Tyr  Gln Arg Val Leu Glu  Glu Glu Gln
            995                 1000                1005

Thr Thr  Pro Phe Glu Leu Ser  Arg Glu Pro Gly Trp  Arg Val Ala
    1010                1015                1020
```

```
Leu Leu Arg Leu Gly Asp Asp Asp His Val Leu Ser Ile Val Met
    1025                1030                1035

His His Ile Ile Ser Asp Gly Trp Ser Val Asp Val Leu Arg His
    1040                1045                1050

Glu Leu Gly Gln Phe Tyr Ser Ala Ala Leu Arg Gly Gln Asp Pro
    1055                1060                1065

Leu Ser Gln Ile Ser Pro Leu Pro Ile Gln Tyr Arg Asp Phe Ala
    1070                1075                1080

Leu Trp Gln Arg Gln Asp Glu Gln Val Ala Glu His Gln Arg Gln
    1085                1090                1095

Leu Glu His Trp Thr Glu Gln Leu Ala Asp Ser Ser Pro Ala Glu
    1100                1105                1110

Leu Leu Ser Asp His Pro Arg Pro Ser Ile Leu Ser Gly Gln Ala
    1115                1120                1125

Gly Ala Ile Pro Val Asn Val Gln Gly Ser Leu Tyr Gln Ala Leu
    1130                1135                1140

Arg Ala Phe Cys Arg Ala His Gln Val Thr Ser Phe Val Val Leu
    1145                1150                1155

Leu Thr Ala Phe Arg Ile Ala His Tyr Arg Leu Thr Gly Ala Glu
    1160                1165                1170

Asp Ala Thr Ile Gly Thr Pro Ile Ala Asn Arg Asn Arg Pro Glu
    1175                1180                1185

Leu Glu Asn Met Ile Gly Phe Phe Val Asn Thr Gln Cys Met Arg
    1190                1195                1200

Ile Val Ile Gly Ser Asp Asp Thr Phe Glu Gly Leu Val Gln Gln
    1205                1210                1215

Val Arg Ser Ile Thr Ala Ala Ala His Glu Asn Gln Asp Val Pro
    1220                1225                1230

Phe Glu Arg Ile Val Ser Ala Leu Leu Pro Gly Ser Arg Asp Thr
    1235                1240                1245

Ser Arg Asn Pro Leu Val Gln Leu Met Phe Ala Val His Ser Gln
    1250                1255                1260

Arg Asn Leu Gly Gln Ile Ser Leu Glu Gly Leu Gln Gly Glu Leu
    1265                1270                1275

Leu Gly Val Ala Ser Pro Thr Arg Phe Asp Val Glu Phe His Leu
    1280                1285                1290

Phe Gln Glu Glu Asn Met Leu Ser Gly Arg Val Leu Phe Ser Asp
    1295                1300                1305

Asp Leu Phe Glu Gln Lys Thr Met Gln Gly Met Val Asp Val Phe
    1310                1315                1320

Gln Glu Val Leu Ser Arg Gly Leu Glu Gln Pro Gln Ile Pro Leu
    1325                1330                1335

Ala Thr Leu Pro Leu Thr His Gly Leu Glu Glu Leu Arg Thr Met
    1340                1345                1350

Gly Leu Leu Asp Val Glu Lys Thr Asp Tyr Pro Arg Glu Ser Ser
    1355                1360                1365

Val Val Asp Val Phe Arg Glu Gln Ala Ala Ala Cys Ser Glu Ala
    1370                1375                1380

Ile Ala Val Lys Asp Ser Ser Ala Gln Leu Thr Tyr Ser Glu Leu
    1385                1390                1395

Asp Arg Gln Ser Asp Glu Leu Ala Gly Trp Leu Arg Gln Gln Arg
    1400                1405                1410

Leu Pro Ala Glu Ser Leu Val Ala Val Leu Ala Pro Arg Ser Cys
```

```
             1415                1420                1425
Gln Thr Ile Val Ala Phe Leu Gly Ile Leu Lys Ala Asn Leu Ala
         1430                1435                1440

Tyr Leu Pro Leu Asp Val Asn Val Pro Ala Thr Arg Leu Glu Ser
         1445                1450                1455

Ile Leu Ser Ala Val Gly Gly Arg Lys Leu Val Leu Leu Gly Ala
         1460                1465                1470

Asp Val Ala Asp Pro Gly Leu Arg Leu Ala Asp Val Glu Leu Val
         1475                1480                1485

Arg Ile Gly Asp Thr Leu Gly Arg Cys Val Pro Gly Ala Pro Gly
         1490                1495                1500

Asp Asn Glu Ala Pro Val Val Gln Pro Ser Ala Thr Ser Leu Ala
         1505                1510                1515

Tyr Val Ile Phe Thr Ser Gly Ser Thr Gly Lys Pro Lys Gly Val
         1520                1525                1530

Met Val Glu His Arg Gly Val Val Arg Leu Val Lys Gln Ser Asn
         1535                1540                1545

Val Val Tyr His Leu Pro Ser Thr Ser Arg Val Ala His Leu Ser
         1550                1555                1560

Asn Leu Ala Phe Asp Ala Ser Ala Trp Glu Ile Tyr Ala Ala Leu
         1565                1570                1575

Leu Asn Gly Gly Thr Leu Ile Cys Ile Asp Tyr Phe Thr Thr Leu
         1580                1585                1590

Asp Cys Ser Ala Leu Gly Ala Lys Phe Ile Lys Glu Lys Ile Val
         1595                1600                1605

Ala Thr Met Ile Pro Pro Ala Leu Leu Lys Gln Cys Leu Ala Ile
         1610                1615                1620

Phe Pro Thr Ala Leu Ser Glu Leu Val Leu Leu Phe Ala Ala Gly
         1625                1630                1635

Asp Arg Phe Ser Ser Gly Asp Ala Val Glu Val Gln Arg His Thr
         1640                1645                1650

Lys Gly Ala Val Cys Asn Ala Tyr Gly Pro Thr Glu Asn Thr Ile
         1655                1660                1665

Leu Ser Thr Ile Tyr Glu Val Lys Gln Asn Glu Asn Phe Pro Asn
         1670                1675                1680

Gly Val Pro Ile Gly Arg Ala Val Ser Asn Ser Gly Ala Tyr Val
         1685                1690                1695

Met Asp Pro Gln Gln Gln Leu Val Pro Leu Gly Val Met Gly Glu
         1700                1705                1710

Leu Val Val Thr Gly Asp Gly Leu Ala Arg Gly Tyr Thr Asp Pro
         1715                1720                1725

Ser Leu Asp Ala Asp Arg Phe Val Gln Val Ser Val Asn Gly Gln
         1730                1735                1740

Leu Val Arg Ala Tyr Arg Thr Gly Asp Arg Val Arg Cys Arg Pro
         1745                1750                1755

Cys Asp Gly Gln Ile Glu Phe Phe Gly Arg Met Asp Arg Gln Val
         1760                1765                1770

Lys Ile Arg Gly His Arg Ile Glu Leu Ala Glu Val Glu His Ala
         1775                1780                1785

Val Leu Gly Leu Glu Asp Val Gln Asp Ala Ala Val Ile Ala Phe
         1790                1795                1800

Asp Asn Val Asp Ser Glu Glu Pro Glu Met Val Gly Phe Val Thr
         1805                1810                1815
```

```
Ile Thr Glu Asp Asn Pro Val Arg Glu Asp Glu Thr Ser Gly Gln
    1820            1825                1830

Val Glu Asp Trp Ala Asn His Phe Glu Ile Ser Thr Tyr Thr Asp
    1835            1840                1845

Ile Ala Ala Ile Asp Gln Gly Ser Ile Gly Ser Asp Phe Val Gly
    1850            1855                1860

Trp Thr Ser Met Tyr Asp Gly Ser Glu Ile Asp Lys Ala Glu Met
    1865            1870                1875

Gln Glu Trp Leu Ala Asp Thr Met Ala Ser Met Leu Asp Gly Gln
    1880            1885                1890

Ala Pro Gly Asn Val Leu Glu Ile Gly Thr Gly Thr Gly Met Val
    1895            1900                1905

Leu Phe Asn Leu Gly Asp Gly Leu Gln Ser Tyr Val Gly Leu Glu
    1910            1915                1920

Pro Ser Arg Ser Ala Ala Ala Phe Val Asn Gln Thr Ile Lys Ser
    1925            1930                1935

Leu Pro Thr Leu Ala Gly Asn Ala Glu Val His Ile Gly Thr Ala
    1940            1945                1950

Thr Asp Val Ala Arg Leu Asp Gly Leu Arg Pro Asp Leu Val Val
    1955            1960                1965

Val Asn Ser Val Val Gln Tyr Phe Pro Ser Pro Glu Tyr Leu Met
    1970            1975                1980

Glu Val Val Glu Ala Leu Ala Arg Leu Pro Gly Val Glu Arg Ile
    1985            1990                1995

Phe Phe Gly Asp Val Arg Ser Tyr Ala Ile Asn Arg Asp Phe Leu
    2000            2005                2010

Ala Ala Arg Ala Leu His Glu Leu Gly Asp Arg Ala Thr Lys His
    2015            2020                2025

Glu Ile Arg Arg Lys Met Leu Glu Met Glu Glu Arg Glu Glu Glu
    2030            2035                2040

Leu Leu Val Asp Pro Ala Phe Phe Thr Met Leu Thr Ser Ser Leu
    2045            2050                2055

Pro Gly Leu Ile Gln His Val Glu Ile Leu Pro Lys Leu Met Arg
    2060            2065                2070

Ala Thr Asn Glu Leu Ser Ala Tyr Arg Tyr Thr Ala Val Val His
    2075            2080                2085

Val Cys Arg Ala Gly Gln Glu Pro Arg Ser Val His Thr Ile Asp
    2090            2095                2100

Asp Asp Ala Trp Val Asn Leu Gly Ala Ser Arg Leu Ser Arg Pro
    2105            2110                2115

Thr Leu Ser Ser Leu Leu Gln Thr Ser Glu Gly Ala Ser Ala Val
    2120            2125                2130

Ala Val Ser Asn Ile Pro Tyr Ser Lys Thr Ile Thr Glu Arg Ala
    2135            2140                2145

Leu Val Ser Ala Leu Asp Glu Asp Asp Met Gln Asp Ser Ser Asp
    2150            2155                2160

Trp Leu Leu Ala Val Arg Glu Thr Gly Arg Ser Cys Ser Ser Phe
    2165            2170                2175

Ser Ala Thr Asp Leu Val Glu Leu Ala Arg Glu Thr Gly Trp Arg
    2180            2185                2190

Val Glu Leu Ser Trp Ala Arg Gln Tyr Ser Gln Lys Gly Ala Leu
    2195            2200                2205
```

```
Asp Ala Val Phe His Arg His Pro Val Ser Ala Gly Ser Gly Arg
    2210                2215                2220
Val Met Phe Gln Phe Pro Val Glu Thr Glu Asp Arg Pro His Ile
    2225                2230                2235
Ser Arg Thr Asn Arg Pro Leu Gln Arg Leu Gln Lys Lys Arg Thr
    2240                2245                2250
Glu Thr His Val His Glu Gln Leu Arg Ala Leu Leu Pro Arg Tyr
    2255                2260                2265
Met Val Pro Thr Arg Ile Val Ala Leu Asp Lys Leu Pro Val Asn
    2270                2275                2280
Ala Asn Gly Lys Val Asp Arg Gln Gln Leu Ala Arg Thr Ala Gln
    2285                2290                2295
Val Leu Pro Ala Ser Lys Ala Pro Ser Ala Cys Val Ala Pro Arg
    2300                2305                2310
Asn Glu Leu Glu Met Thr Leu Cys Glu Glu Phe Ser Gln Val Leu
    2315                2320                2325
Gly Val Glu Val Gly Ile Thr Asp Asn Phe Phe His Leu Gly Gly
    2330                2335                2340
His Ser Leu Met Ala Thr Lys Phe Ala Ala Arg Ile Ser Arg Arg
    2345                2350                2355
Leu Asn Ala Ile Val Ser Val Lys Asn Val Phe Asp His Pro Val
    2360                2365                2370
Pro Met Asp Leu Ala Ala Thr Ile Gln Glu Gly Ser Lys Leu His
    2375                2380                2385
Thr Pro Ile Pro Arg Thr Ala Tyr Ser Gly Pro Val Glu Gln Ser
    2390                2395                2400
Phe Ala Gln Gly Arg Leu Trp Phe Leu Asp Gln Phe Asn Pro Ser
    2405                2410                2415
Ser Ile Gly Tyr Val Met Pro Phe Ala Ala Arg Leu His Gly Gln
    2420                2425                2430
Leu Gln Ile Glu Ala Leu Thr Ala Ala Leu Phe Ala Leu Glu Gln
    2435                2440                2445
Arg His Glu Ile Leu Arg Thr Thr Leu Asp Ala His Asp Gly Val
    2450                2455                2460
Gly Met Gln Ile Val His Ala Glu His Pro Gln Gln Leu Arg Ile
    2465                2470                2475
Ile Asp Val Ser Ala Lys Ala Ser Ser Ser Tyr Ala Gln Thr Leu
    2480                2485                2490
Arg Asp Glu Gln Ala Ser Pro Phe Asp Leu Ser Lys Glu Pro Gly
    2495                2500                2505
Trp Arg Val Ser Leu Leu Gln Leu Ser Glu Ile Asp Tyr Val Leu
    2510                2515                2520
Ser Ile Val Met His His Thr Ile Tyr Asp Gly Trp Ser Leu Asp
    2525                2530                2535
Val Leu Arg Arg Glu Leu Ser Gln Phe Tyr Ala Ala Ala Ile Arg
    2540                2545                2550
Gly Arg Glu Pro Leu Ser Thr Ile Glu Pro Leu Pro Ile Gln Tyr
    2555                2560                2565
Arg Asp Phe Ser Val Trp Gln Lys Gln Glu Asp Gln Val Ala Glu
    2570                2575                2580
His Arg Arg Gln Leu His Tyr Trp Ile Glu Gln Leu Asp Gly Ser
    2585                2590                2595
Ser Pro Ala Glu Phe Leu Asn Asp Lys Pro Arg Pro Thr Leu Leu
```

```
                2600                     2605                    2610
Ser  Gly  Lys  Ala  Gly  Val  Val  Glu  Ile  Ala  Val  Lys  Gly  Thr  Val
     2615                     2620                    2625

Tyr  Gln  Arg  Leu  Leu  Glu  Phe  Cys  Arg  Leu  His  Gln  Val  Thr  Ser
     2630                     2635                    2640

Phe  Met  Val  Leu  Leu  Ala  Ala  Phe  Arg  Ala  Thr  His  Tyr  Arg  Leu
     2645                     2650                    2655

Thr  Gly  Thr  Glu  Asp  Ala  Thr  Val  Gly  Thr  Pro  Ile  Ala  Asn  Arg
     2660                     2665                    2670

Asn  Arg  Pro  Glu  Leu  Glu  Asn  Met  Ile  Gly  Leu  Phe  Val  Asn  Thr
     2675                     2680                    2685

Gln  Cys  Ile  Arg  Leu  Lys  Ile  Glu  Asp  Asn  Asp  Thr  Leu  Glu  Glu
     2690                     2695                    2700

Leu  Val  Gln  His  Val  Arg  Ala  Thr  Ile  Thr  Ala  Ser  Ile  Ser  Asn
     2705                     2710                    2715

Gln  Asp  Val  Pro  Phe  Glu  Gln  Val  Val  Ser  Ala  Leu  Leu  Pro  Gly
     2720                     2725                    2730

Ser  Arg  Asp  Thr  Ser  Arg  Asn  Pro  Leu  Val  Gln  Leu  Thr  Phe  Ala
     2735                     2740                    2745

Val  His  Ser  Gln  Arg  Asn  Leu  Ala  Asp  Ile  Gln  Leu  Glu  Asn  Val
     2750                     2755                    2760

Glu  Thr  Asn  Ala  Met  Pro  Ile  Cys  Pro  Ser  Thr  Arg  Phe  Asp  Ala
     2765                     2770                    2775

Glu  Phe  His  Leu  Phe  Gln  Glu  Glu  Asn  Met  Leu  Ser  Gly  Arg  Val
     2780                     2785                    2790

Leu  Phe  Ser  Asp  Asp  Leu  Phe  Glu  Gln  Lys  Thr  Met  Gln  Gly  Met
     2795                     2800                    2805

Val  Asp  Val  Phe  Gln  Glu  Val  Leu  Ser  Arg  Gly  Leu  Glu  Gln  Pro
     2810                     2815                    2820

Gln  Ile  Pro  Leu  Ala  Thr  Leu  Pro  Leu  Thr  His  Gly  Leu  Glu  Glu
     2825                     2830                    2835

Leu  Arg  Thr  Met  Gly  Leu  Leu  Asp  Val  Glu  Lys  Thr  Asp  Tyr  Pro
     2840                     2845                    2850

Arg  Glu  Ser  Ser  Val  Val  Asp  Val  Phe  Arg  Glu  Gln  Ala  Ala  Ala
     2855                     2860                    2865

Cys  Ser  Glu  Ala  Ile  Ala  Val  Lys  Asp  Ser  Ser  Ala  Gln  Leu  Thr
     2870                     2875                    2880

Tyr  Ser  Glu  Leu  Asp  Arg  Gln  Ser  Asp  Glu  Leu  Ala  Gly  Trp  Leu
     2885                     2890                    2895

Arg  Gln  Gln  Arg  Leu  Pro  Ala  Glu  Ser  Leu  Val  Ala  Val  Leu  Ala
     2900                     2905                    2910

Pro  Arg  Ser  Cys  Gln  Thr  Ile  Val  Ala  Phe  Leu  Gly  Ile  Leu  Lys
     2915                     2920                    2925

Ala  Asn  Leu  Ala  Tyr  Leu  Pro  Leu  Asp  Val  Asn  Val  Pro  Ala  Thr
     2930                     2935                    2940

Arg  Leu  Glu  Ser  Ile  Leu  Ser  Ala  Val  Gly  Gly  Arg  Lys  Leu  Val
     2945                     2950                    2955

Leu  Leu  Gly  Ala  Asp  Val  Ala  Asp  Pro  Gly  Leu  Arg  Leu  Ala  Asp
     2960                     2965                    2970

Val  Glu  Leu  Val  Arg  Ile  Gly  Asp  Thr  Leu  Gly  Arg  Cys  Val  Pro
     2975                     2980                    2985

Gly  Ala  Pro  Gly  Asp  Asn  Glu  Ala  Pro  Val  Val  Gln  Pro  Ser  Ala
     2990                     2995                    3000
```

-continued

Thr Ser Leu Ala Tyr Val Ile Phe Thr Ser Gly Ser Thr Gly Lys
3005              3010              3015

Pro Lys Gly Val Met Val Glu His Arg Ser Ile Val Arg Leu Met
3020              3025              3030

Arg His Ser Asn Val Ser Ser Arg Leu Leu Leu His Pro Arg Met
3035              3040              3045

Thr His Leu Ser Asn Leu Ala Phe Asp Ala Ser Val Trp Glu Ile
3050              3055              3060

Phe Leu Thr Leu Leu Asn Gly Gly Thr Leu Ile Cys Ile Asp Tyr
3065              3070              3075

Leu Ser Ser Leu Asp Cys Arg Ala Leu Gly Val Ser Ile Leu Glu
3080              3085              3090

His Gln Val Asp Ala Ser Val Leu Pro Pro Ala Leu Leu Lys Gln
3095              3100              3105

Cys Leu Ala Asn Val Pro Glu Ala Leu Ala Ser Leu Gln Val Leu
3110              3115              3120

Leu Ser Ala Gly Asp Arg Leu Asp Ser Arg Asp Ala Ile Glu Ser
3125              3130              3135

Cys Ala Leu Val Arg Gly Ser Val Tyr Asn Gly Tyr Gly Pro Thr
3140              3145              3150

Glu Asn Gly Ile Gln Ser Thr Ile Tyr Glu Val Lys Ala Asp Ala
3155              3160              3165

Glu Phe Val Asn Gly Val Pro Ile Gly Arg Ala Val Ser Asn Ser
3170              3175              3180

Gly Ala Tyr Val Met Asp Pro Gln Gln Gln Leu Val Pro Leu Gly
3185              3190              3195

Val Met Gly Glu Leu Val Val Thr Gly Asp Gly Leu Ala Arg Gly
3200              3205              3210

Tyr Thr Asp Pro Ser Leu Asp Ala Asp Arg Phe Val Gln Val Ser
3215              3220              3225

Val Asn Gly Gln Leu Val Arg Ala Tyr Arg Thr Gly Asp Arg Val
3230              3235              3240

Arg Cys Arg Pro Cys Asp Gly Gln Ile Glu Phe Phe Gly Arg Met
3245              3250              3255

Asp Arg Gln Val Lys Ile Arg Gly His Arg Ile Glu Leu Ala Glu
3260              3265              3270

Val Glu His Ala Val Leu Gly Leu Glu Asp Val Gln Asp Ala Ala
3275              3280              3285

Val Leu Ile Ala Gln Thr Ala Glu Asn Glu Glu Leu Val Gly Phe
3290              3295              3300

Phe Thr Leu Arg Gln Thr Gln Ala Val Gln Ser Asn Gly Ala Ala
3305              3310              3315

Gly Val Val Pro Glu His Ser Asp Ser Glu Leu Ala Gln Ser Cys
3320              3325              3330

Ser Cys Thr Gln Thr Glu Arg Arg Val Arg Asn Arg Leu Gln Ser
3335              3340              3345

Cys Leu Pro Arg Tyr Met Val Pro Ser Arg Met Val Leu Leu Asp
3350              3355              3360

Arg Leu Pro Val Asn Pro Asn Gly Lys Val Asp Arg Gln Glu Leu
3365              3370              3375

Thr Arg Arg Ala Gln Asp Leu Pro Ile Ser Glu Ser Ser Pro Val
3380              3385              3390

| | | | | | | | | | | |
|---|---|---|---|---|---|---|---|---|---|---|
| His | Val | Lys | Pro | Arg | Thr | Glu | Leu | Glu | Arg | Ser | Leu | Cys | Glu | Glu |
| 3395 | | | | | 3400 | | | | | 3405 | | | | |

Phe Ala Asp Val Ile Gly Leu Glu Val Gly Val Thr Asp Asn Phe
3410                    3415                    3420

Phe Asp Leu Gly Gly His Ser Leu Met Ala Met Lys Leu Ala Ala
3425                    3430                    3435

Arg Ile Ser Arg Arg Ser Asn Ala His Ile Ser Val Lys Asp Ile
3440                    3445                    3450

Phe Asp His Pro Leu Ile Ala Asp Leu Ala Met Lys Ile Arg Glu
3455                    3460                    3465

Gly Ser Asp Leu His Thr Pro Ile Pro His Arg Met Tyr Val Gly
3470                    3475                    3480

Pro Ile Gln Leu Ser Phe Ala Gln Gly Arg Leu Trp Phe Leu Asp
3485                    3490                    3495

Gln Leu Asn Leu Gly Ala Ser Trp Tyr Val Met Pro Leu Ala Met
3500                    3505                    3510

Arg Leu Gln Gly Ser Leu Gln Leu Asp Ala Leu Glu Thr Ala Leu
3515                    3520                    3525

Phe Ala Ile Glu Gln Arg His Glu Thr Leu Arg Met Thr Phe Ala
3530                    3535                    3540

Glu Gln Asp Gly Val Ala Val Gln Val Val His Ala Ala His Tyr
3545                    3550                    3555

Lys His Ile Lys Met Ile Asp Lys Pro Leu Arg Gln Lys Ile Asp
3560                    3565                    3570

Val Leu Lys Met Leu Glu Glu Glu Arg Thr Thr Pro Phe Glu Leu
3575                    3580                    3585

Ser Arg Glu Pro Gly Trp Arg Val Ala Leu Leu Arg Leu Gly Asp
3590                    3595                    3600

Asp Asp His Val Leu Ser Ile Val Met His His Ile Ile Ser Asp
3605                    3610                    3615

Gly Trp Ser Val Asp Val Leu Arg His Glu Leu Gly Gln Phe Tyr
3620                    3625                    3630

Ser Ala Ala Leu Arg Gly Gln Asp Pro Leu Ser Gln Ile Ser Pro
3635                    3640                    3645

Leu Pro Ile Gln Tyr Arg Asp Phe Ala Leu Trp Gln Arg Gln Asp
3650                    3655                    3660

Glu Gln Val Ala Glu His Gln Arg Gln Leu Glu His Trp Thr Glu
3665                    3670                    3675

Gln Leu Ala Asp Ser Ser Pro Ala Glu Leu Leu Ser Asp His Pro
3680                    3685                    3690

Arg Pro Ser Ile Leu Ser Gly Gln Ala Gly Ala Ile Pro Val Asn
3695                    3700                    3705

Val Gln Gly Ser Leu Tyr Gln Ala Leu Arg Ala Phe Cys Arg Ala
3710                    3715                    3720

His Gln Val Thr Ser Phe Val Val Leu Leu Thr Ala Phe Arg Ile
3725                    3730                    3735

Ala His Tyr Arg Leu Thr Gly Ala Glu Asp Ala Thr Ile Gly Thr
3740                    3745                    3750

Pro Ile Ala Asn Arg Asn Arg Pro Glu Leu Glu Asn Met Ile Gly
3755                    3760                    3765

Phe Phe Val Asn Thr Gln Cys Met Arg Ile Val Ile Gly Ser Asp
3770                    3775                    3780

Asp Thr Phe Glu Gly Leu Val Gln Gln Val Arg Ser Ile Thr Ala

-continued

```
               3785                3790                3795
Ala Ala His Glu Asn Gln Asp Val Pro Phe Glu Arg Ile Val Ser
    3800                3805                3810

Ala Leu Leu Pro Gly Ser Arg Asp Thr Ser Arg Asn Pro Leu Val
    3815                3820                3825

Gln Leu Met Phe Ala Val His Ser Gln Arg Asn Leu Gly Gln Ile
    3830                3835                3840

Ser Leu Glu Gly Leu Gln Gly Glu Leu Leu Gly Val Ala Ala Thr
    3845                3850                3855

Thr Arg Phe Asp Val Glu Phe His Leu Phe Gln Asp Asp Asp Lys
    3860                3865                3870

Leu Ser Gly Asn Val Leu Phe Ala Thr Glu Leu Phe Glu Gln Lys
    3875                3880                3885

Thr Met Gln Gly Met Val Asp Val Phe Gln Glu Val Leu Ser Arg
    3890                3895                3900

Gly Leu Glu Gln Pro Gln Ile Pro Leu Ala Thr Leu Pro Leu Thr
    3905                3910                3915

His Gly Leu Glu Glu Leu Arg Thr Met Gly Leu Leu Asp Val Glu
    3920                3925                3930

Lys Thr Asp Tyr Pro Arg Glu Ser Ser Val Val Asp Val Phe Arg
    3935                3940                3945

Glu Gln Ala Ala Ala Cys Ser Glu Ala Ile Ala Val Lys Asp Ser
    3950                3955                3960

Ser Ala Gln Leu Thr Tyr Ser Glu Leu Asp Arg Gln Ser Asp Glu
    3965                3970                3975

Leu Ala Gly Trp Leu Arg Gln Gln Arg Leu Pro Ala Glu Ser Leu
    3980                3985                3990

Val Ala Val Leu Ala Pro Arg Ser Cys Gln Thr Ile Val Ala Phe
    3995                4000                4005

Leu Gly Ile Leu Lys Ala Asn Leu Ala Tyr Leu Pro Leu Asp Val
    4010                4015                4020

Asn Val Pro Ala Thr Arg Leu Glu Ser Ile Leu Ser Ala Val Gly
    4025                4030                4035

Gly Arg Lys Leu Val Leu Leu Gly Ala Asp Val Ala Asp Pro Gly
    4040                4045                4050

Leu Arg Leu Ala Asp Val Glu Leu Val Arg Ile Gly Asp Thr Leu
    4055                4060                4065

Gly Arg Cys Val Pro Gly Ala Pro Gly Asp Asn Glu Ala Pro Val
    4070                4075                4080

Val Gln Pro Ser Ala Thr Ser Leu Ala Tyr Val Ile Phe Thr Ser
    4085                4090                4095

Gly Ser Thr Gly Lys Pro Lys Gly Val Met Val Glu His Arg Ser
    4100                4105                4110

Ile Val Arg Leu Met Arg His Ser Asn Val Ser Ser Arg Leu Leu
    4115                4120                4125

Leu His Pro Arg Met Thr His Leu Ser Asn Leu Ala Phe Asp Ala
    4130                4135                4140

Ser Val Trp Glu Ile Phe Leu Thr Leu Leu Asn Gly Gly Thr Leu
    4145                4150                4155

Ile Cys Ile Asp Tyr Leu Ser Ser Leu Asp Cys Arg Ala Leu Gly
    4160                4165                4170

Val Ser Ile Leu Glu His Gln Val Asp Ala Ser Val Leu Pro Pro
    4175                4180                4185
```

Ala Leu Leu Lys Gln Cys Leu Ala Asn Val Pro Glu Ala Leu Ala
4190                4195                4200

Ser Leu Gln Val Leu Leu Ser Ala Gly Asp Arg Leu Asp Ser Arg
4205                4210                4215

Asp Ala Ile Glu Ser Cys Ala Leu Val Arg Gly Ser Val Tyr Asn
4220                4225                4230

Gly Tyr Gly Pro Thr Glu Asn Gly Ile Gln Ser Thr Ile Tyr Glu
4235                4240                4245

Val Lys Ala Asp Ala Glu Phe Val Asn Gly Val Pro Ile Gly Arg
4250                4255                4260

Ala Val Ser Asn Ser Gly Ala Tyr Val Met Asp Pro Gln Gln Gln
4265                4270                4275

Leu Val Pro Leu Gly Val Met Gly Glu Leu Val Val Thr Gly Asp
4280                4285                4290

Gly Leu Ala Arg Gly Tyr Thr Asp Pro Ser Leu Asp Ala Asp Arg
4295                4300                4305

Phe Val Gln Val Ser Val Asn Gly Gln Leu Val Arg Ala Tyr Arg
4310                4315                4320

Thr Gly Asp Arg Val Arg Cys Arg Pro Cys Asp Gly Gln Ile Glu
4325                4330                4335

Phe Phe Gly Arg Met Asp Arg Gln Val Lys Ile Arg Gly His Arg
4340                4345                4350

Ile Glu Leu Ala Glu Val Glu His Ala Val Leu Gly Leu Glu Asp
4355                4360                4365

Val Gln Asp Ala Ala Val Ile Ala Phe Asp Asn Val Asp Ser Glu
4370                4375                4380

Glu Pro Glu Met Val Gly Phe Val Thr Ile Thr Glu Asp Asn Pro
4385                4390                4395

Val Arg Glu Asp Glu Thr Ser Gly Gln Val Glu Asp Trp Ala Asn
4400                4405                4410

His Phe Glu Ile Ser Thr Tyr Thr Asp Ile Ala Ala Ile Asp Gln
4415                4420                4425

Gly Ser Ile Gly Ser Asp Phe Val Gly Trp Thr Ser Met Tyr Asp
4430                4435                4440

Gly Ser Glu Ile Asp Lys Ala Glu Met Gln Glu Trp Leu Ala Asp
4445                4450                4455

Thr Met Ala Ser Met Leu Asp Gly Gln Ala Pro Gly Asn Val Leu
4460                4465                4470

Glu Ile Gly Thr Gly Thr Gly Met Val Leu Phe Asn Leu Gly Asp
4475                4480                4485

Gly Leu Gln Ser Tyr Val Gly Leu Glu Pro Ser Arg Ser Ala Ala
4490                4495                4500

Ala Phe Val Asn Gln Thr Ile Lys Ser Leu Pro Thr Leu Ala Gly
4505                4510                4515

Asn Ala Glu Val His Ile Gly Thr Ala Thr Asp Val Ala Arg Leu
4520                4525                4530

Asp Gly Leu Arg Pro Asp Leu Val Val Val Asn Ser Val Val Gln
4535                4540                4545

Tyr Phe Pro Ser Pro Glu Tyr Leu Met Glu Val Val Glu Ala Leu
4550                4555                4560

Ala Arg Leu Pro Gly Val Glu Arg Ile Phe Phe Gly Asp Val Arg
4565                4570                4575

```
Ser Tyr Ala Ile Asn Arg Asp Phe Leu Ala Ala Arg Ala Leu His
    4580                4585                4590

Glu Leu Gly Asp Arg Ala Thr Lys His Glu Ile Arg Arg Lys Met
    4595                4600                4605

Leu Glu Met Glu Glu Arg Glu Glu Leu Leu Val Asp Pro Ala
    4610                4615                4620

Phe Phe Thr Met Leu Thr Ser Ser Leu Pro Gly Leu Ile Gln His
    4625                4630                4635

Val Glu Ile Leu Pro Lys Leu Met Arg Ala Thr Asn Glu Leu Ser
    4640                4645                4650

Ala Tyr Arg Tyr Thr Ala Val Val His Val Cys Arg Ala Gly Gln
    4655                4660                4665

Glu Pro Arg Ser Val His Thr Ile Asp Asp Ala Trp Val Asn
    4670                4675                4680

Leu Gly Ala Ser Arg Leu Ser Arg Pro Thr Leu Ser Ser Leu Leu
    4685                4690                4695

Gln Thr Ser Glu Gly Ala Ser Ala Val Ala Val Ser Asn Ile Pro
    4700                4705                4710

Tyr Ser Lys Thr Ile Thr Glu Arg Ala Leu Val Ser Ala Leu Asp
    4715                4720                4725

Glu Asp Asp Met Gln Asp Ser Ser Asp Trp Leu Leu Ala Val Arg
    4730                4735                4740

Glu Thr Gly Arg Ser Cys Ser Ser Phe Ser Ala Thr Asp Leu Val
    4745                4750                4755

Glu Leu Ala Arg Glu Thr Gly Trp Arg Val Glu Leu Ser Trp Ala
    4760                4765                4770

Arg Gln Tyr Ser Gln Lys Gly Ala Leu Asp Ala Val Phe His Arg
    4775                4780                4785

His Pro Val Ser Ala Gly Ser Gly Arg Val Met Phe Gln Phe Pro
    4790                4795                4800

Val Glu Thr Glu Asp Arg Pro His Ile Ser Arg Thr Asn Arg Pro
    4805                4810                4815

Leu Gln Arg Leu Gln Lys Lys Arg Thr Glu Thr His Val His Glu
    4820                4825                4830

Gln Leu Arg Ala Leu Leu Pro Arg Tyr Met Val Pro Thr Arg Ile
    4835                4840                4845

Val Ala Leu Asp Lys Leu Pro Val Asn Ala Asn Gly Lys Val Asp
    4850                4855                4860

Arg Gln Gln Leu Ala Arg Thr Ala Gln Val Leu Pro Ala Ser Lys
    4865                4870                4875

Ala Pro Ser Ala Cys Val Ala Pro Arg Asn Glu Leu Glu Met Thr
    4880                4885                4890

Leu Cys Glu Glu Phe Ser Gln Val Leu Gly Val Glu Val Gly Ile
    4895                4900                4905

Thr Asp Asn Phe Phe His Leu Gly Gly His Ser Leu Met Ala Thr
    4910                4915                4920

Lys Leu Ala Ala Arg Ile Ser His Arg Leu His Thr Arg Ile Ser
    4925                4930                4935

Val Lys His Ile Phe Asp His Pro Leu Ile Gly Asp Leu Ser Val
    4940                4945                4950

His Ile Ala Asp Ser Pro Val Pro Leu Leu Thr Ile Thr Arg Ala
    4955                4960                4965

Gln His Ala Gly Ala Val Glu Gln Ser Phe Ala Gln Ala Arg Leu
```

```
                    4970                4975                4980
Trp Phe Leu Val Gln Leu Gly Leu Glu Ser Pro Ser Tyr Ile Ile
        4985                4990                4995

Pro Ile Val Leu Arg Leu His Gly Ser Leu Ser Lys Thr Ala Ile
        5000                5005                5010

Glu Gly Ala Leu Ser Ala Leu Met Glu Arg His Glu Val Leu Arg
        5015                5020                5025

Thr Thr Phe Glu Asp His Lys Gly Ile Gly Met Gln Val Val Gln
        5030                5035                5040

Asp His Arg His Gln Asp Leu Val Val Ile Asp Val Ala Gly Gln
        5045                5050                5055

Gly Ser Leu Asp Tyr Lys Gln His Leu Tyr Met Glu His Val Lys
        5060                5065                5070

Pro Phe Asp Leu Thr Arg Asp Pro Gly Trp Arg Val Ala Leu Leu
        5075                5080                5085

Arg Leu Gly Asp Asp His Val Leu Ser Ile Val Met His His
        5090                5095                5100

Ile Ile Ser Asp Gly Trp Ser Ile Asp Ile Leu Leu Arg Glu Leu
        5105                5110                5115

Gly Gln Phe Tyr Ser Ala Ala Leu Arg Gly Gln Asp Pro Leu Ser
        5120                5125                5130

Gln Thr Ser Pro Leu Pro Ile Gln Tyr Arg Asp Phe Ala Leu Trp
        5135                5140                5145

Gln Lys Gln Asp His Gln Leu Ala Asp His Glu Lys Gln Leu Arg
        5150                5155                5160

Tyr Trp Glu Glu Gln Leu Ala Glu Ser Ser Pro Ala Glu Leu Leu
        5165                5170                5175

Cys Asp His Ala Arg Pro Thr Thr Pro Ser Gly Gln Ala Gly Ser
        5180                5185                5190

Ile Pro Val Asn Val Gln Gly Ser Leu Tyr Gln Ala Leu Arg Ala
        5195                5200                5205

Phe Cys Arg Ala His Gln Val Thr Ser Phe Val Val Leu Leu Thr
        5210                5215                5220

Ala Phe Arg Ile Ala His Tyr Arg Leu Thr Gly Ala Glu Asp Ala
        5225                5230                5235

Thr Ile Gly Thr Pro Ile Ala Asn Arg Asn Arg Pro Glu Leu Glu
        5240                5245                5250

Asn Met Ile Gly Phe Phe Val Asn Thr Gln Cys Met Arg Ile Val
        5255                5260                5265

Ile Gly Ser Asp Asp Thr Phe Glu Gly Leu Val Gln Gln Val Arg
        5270                5275                5280

Ser Ile Thr Ala Ala Ala His Glu Asn Gln Asp Val Pro Phe Glu
        5285                5290                5295

Arg Ile Val Ser Ala Leu Leu Pro Gly Ser Arg Asp Thr Ser Arg
        5300                5305                5310

Asn Pro Leu Val Gln Leu Leu Phe Ala Val His Ala Tyr Gln Glu
        5315                5320                5325

Val Glu Asn Phe Ala Ile Pro Gly Val His Ser Glu Leu Val Gln
        5330                5335                5340

Gly Thr Thr Phe Thr Arg Pro Asp Val Glu Phe His Leu Leu Glu
        5345                5350                5355

Asp Pro Asp Lys Leu Ser Gly Asn Val Leu Phe Ala Thr Glu Leu
        5360                5365                5370
```

```
Phe Glu Gln Lys Thr Met Gln Gly Met Val Asp Val Phe Gln Glu
    5375            5380                5385
Val Leu Ser Arg Gly Leu Glu Gln Pro Gln Ile Pro Leu Ala Thr
    5390            5395                5400
Leu Pro Leu Thr His Gly Leu Glu Glu Leu Arg Thr Met Gly Leu
    5405            5410                5415
Leu Asp Val Glu Lys Thr Asp Tyr Pro Arg Glu Ser Ser Val Val
    5420            5425                5430
Asp Val Phe Arg Glu Gln Ala Ala Cys Ser Glu Ala Ile Ala
    5435            5440                5445
Val Lys Asp Ser Ser Ala Gln Leu Thr Tyr Ser Glu Leu Asp Arg
    5450            5455                5460
Gln Ser Asp Glu Leu Ala Gly Trp Leu Arg Gln Gln Arg Leu Pro
    5465            5470                5475
Ala Glu Ser Leu Val Ala Val Leu Ala Pro Arg Ser Cys Gln Thr
    5480            5485                5490
Ile Val Ala Phe Leu Gly Ile Leu Lys Ala Asn Leu Ala Tyr Leu
    5495            5500                5505
Pro Leu Asp Val Asn Val Pro Ala Thr Arg Leu Glu Ser Ile Leu
    5510            5515                5520
Ser Ala Val Gly Gly Arg Lys Leu Val Leu Leu Gly Ala Asp Val
    5525            5530                5535
Ala Asp Pro Gly Leu Arg Leu Ala Asp Val Glu Leu Val Arg Ile
    5540            5545                5550
Gly Asp Thr Leu Gly Arg Cys Val Pro Gly Ala Pro Gly Asp Asn
    5555            5560                5565
Glu Ala Pro Val Val Gln Pro Ser Ala Thr Ser Leu Ala Tyr Val
    5570            5575                5580
Ile Phe Thr Ser Gly Ser Thr Gly Lys Pro Lys Gly Val Met Val
    5585            5590                5595
Glu His Arg Ser Ile Leu Arg Val Val Thr Ser Pro Pro Ala Arg
    5600            5605                5610
Ala Leu Leu Pro Ser Thr Ile Ile Met Ala His Leu Thr Asn Ile
    5615            5620                5625
Ala Phe Asp Val Ser Leu Trp Glu Ile Cys Thr Ala Leu Leu His
    5630            5635                5640
Gly Gly Thr Leu Ile Cys Ile Gln Tyr Leu Ala Ser Leu Asp Val
    5645            5650                5655
Arg Gly Leu Gln Thr Thr Phe Ser Arg Glu Ala Ile Asn Val Ala
    5660            5665                5670
Val Phe Pro Pro Ala Leu Leu Lys Thr Cys Leu Ala Lys Ile Pro
    5675            5680                5685
Ser Ala Leu Ala Ser Leu Ser Ala Met Phe Ser Ser Gly Asp Arg
    5690            5695                5700
Leu Asp Ser Arg Asp Ala Ser Glu Gly Ala Thr Leu Val Arg Gln
    5705            5710                5715
Gly Ile His Asn Ala Tyr Gly Pro Thr Glu Asn Gly Ile Gln Ser
    5720            5725                5730
Thr Ile Tyr Glu Val Lys Ala Asp Ala Glu Phe Val Asn Gly Val
    5735            5740                5745
Pro Ile Gly Arg Ala Val Ser Asn Ser Gly Ala Tyr Val Met Asp
    5750            5755                5760
```

```
Pro Gln Gln Gln Leu Val Pro Leu Gly Val Met Gly Glu Leu Val
5765                5770                5775

Val Thr Gly Asp Gly Leu Ala Arg Gly Tyr Thr Asp Pro Ser Leu
5780                5785                5790

Asp Ala Asp Arg Phe Val Gln Val Ser Val Asn Gly Gln Leu Val
5795                5800                5805

Arg Ala Tyr Arg Thr Gly Asp Arg Val Arg Cys Arg Pro Cys Asp
5810                5815                5820

Gly Gln Ile Glu Phe Phe Gly Arg Met Asp Arg Gln Val Lys Ile
5825                5830                5835

Arg Gly His Arg Ile Glu Leu Ala Glu Val Glu His Ala Ile Leu
5840                5845                5850

Ser Leu Asp Tyr Val Ile Asp Ala Ala Val Leu Leu Arg Gln Leu
5855                5860                5865

Ile Asp Gln Glu Pro Gln Val Val Gly Phe Val Ile Val Ser Thr
5870                5875                5880

Lys Arg Ala Tyr Ser Arg His Asn Ser Gly Tyr Ala Ser Glu Val
5885                5890                5895

Ser Ala Phe Cys Ile Lys Asp Gln Ile Ala Trp Arg Ile Arg Gln
5900                5905                5910

His Leu Cys Arg Met Leu Pro Ser Tyr Met Val Pro Tyr Gln Ile
5915                5920                5925

Ala Ile Leu Asp Glu Met Pro Ile Asn Ala Asn Gly Lys Val Asp
5930                5935                5940

Arg Gln Asn Leu Ala Ser Arg Thr Val Asn Val Gln Arg Ile Leu
5945                5950                5955

Ala Ala Pro Tyr Met Ala Pro Arg Asn Glu Val Glu Ile Ser Leu
5960                5965                5970

Cys Glu Gln Tyr Ala Ala Leu Leu Glu His Asp Val Gly Ile Leu
5975                5980                5985

Asp Asp Phe Phe Glu Leu Gly Gly His Ser Leu Met Ala Thr Arg
5990                5995                6000

Leu Ala Ser Arg Ile Ser Ser Arg Phe Ser Ala Pro Val Ser Val
6005                6010                6015

Arg Asp Ile Phe Asp His Pro Arg Ile Met Asp Leu Ala Ser Ile
6020                6025                6030

Ile Arg Ala Gly Asp Ile Gln Trp Ser Arg Ile Leu Pro Ser Ala
6035                6040                6045

Tyr Glu Arg Pro Val Glu Gln Ser Phe Ala Gln Asn Arg Leu Trp
6050                6055                6060

Phe Leu Tyr Lys Leu Asp Ile Gly Thr Thr Gln Tyr Asn Leu Pro
6065                6070                6075

Leu Ala Ile His Leu Arg Gly Pro Leu Asp Ile Ser Ala Leu Phe
6080                6085                6090

Ile Ala Phe Lys Ala Leu Thr Glu Arg His Glu Leu Leu Arg Thr
6095                6100                6105

Thr Phe Asp Glu Asp Asp Gly Thr Cys Leu Gln Met Leu Leu Pro
6110                6115                6120

Glu Tyr Gln His Glu Val Arg Ile Thr Asp Leu Gln Gly Ser His
6125                6130                6135

Lys Gly Ser Leu Leu Asp Ile Leu Asn Asn Asn Gln Lys Thr Pro
6140                6145                6150

Phe Glu Leu Ser Arg Glu Pro Gly Trp Arg Val Ala Leu Leu Arg
```

Leu Gly Asp Asp Asp His Val Leu Ser Ile Val Met His His Ile
6170                6175                6180

Ile Ser Asp Gly Trp Ser Val Asp Val Leu Arg His Glu Leu Gly
6185                6190                6195

Gln Phe Tyr Ser Ala Ala Leu Arg Gly Gln Asp Pro Leu Ser Gln
6200                6205                6210

Ile Ser Pro Leu Pro Ile Gln Tyr Arg Asp Phe Ala Leu Trp Gln
6215                6220                6225

Arg Gln Asp Glu Gln Val Ala Glu His Gln Arg Gln Leu Glu His
6230                6235                6240

Trp Thr Glu Gln Leu Ala Asp Ser Ser Pro Ala Glu Leu Leu Ser
6245                6250                6255

Asp His Pro Arg Pro Ser Ile Leu Ser Gly Gln Ala Gly Ala Ile
6260                6265                6270

Pro Val Asn Val Gln Gly Ser Leu Tyr Gln Ala Leu Arg Ala Phe
6275                6280                6285

Cys Arg Ala His Gln Val Thr Ser Phe Val Val Leu Leu Thr Ala
6290                6295                6300

Phe Arg Ile Ala His Tyr Arg Leu Thr Gly Ala Glu Asp Ala Thr
6305                6310                6315

Ile Gly Thr Pro Ile Ala Asn Arg Asn Arg Pro Glu Leu Glu Asn
6320                6325                6330

Met Ile Gly Phe Phe Val Asn Thr Gln Cys Met Arg Ile Val Ile
6335                6340                6345

Gly Ser Asp Asp Thr Phe Glu Gly Leu Val Gln Gln Val Arg Ser
6350                6355                6360

Ile Thr Ala Ala Ala His Glu Asn Gln Asp Val Pro Phe Glu Arg
6365                6370                6375

Ile Val Ser Ala Leu Leu Pro Gly Ser Arg Asp Thr Ser Arg Asn
6380                6385                6390

Pro Leu Val Gln Leu Met Phe Ala Val His Ser Gln Arg Asn Leu
6395                6400                6405

Gly Gln Ile Ser Leu Glu Gly Leu Gln Gly Glu Leu Leu Gly Val
6410                6415                6420

Ala Ala Thr Thr Arg Phe Asp Val Glu Phe His Leu Phe Gln Asp
6425                6430                6435

Asp Asp Lys Leu Ser Gly Asn Val Leu Phe Ala Thr Glu Leu Phe
6440                6445                6450

Glu Gln Lys Thr Met Gln Gly Met Val Asp Val Phe Gln Glu Val
6455                6460                6465

Leu Ser Arg Gly Leu Glu Gln Pro Gln Ile Pro Leu Ala Thr Leu
6470                6475                6480

Pro Leu Thr His Gly Leu Glu Glu Leu Arg Thr Met Gly Leu Leu
6485                6490                6495

Asp Val Glu Lys Thr Asp Tyr Pro Arg Glu Ser Ser Val Val Asp
6500                6505                6510

Val Phe Arg Glu Gln Ala Ala Ala Cys Ser Glu Ala Ile Ala Val
6515                6520                6525

Lys Asp Ser Ser Ala Gln Leu Thr Tyr Ser Glu Leu Asp Arg Gln
6530                6535                6540

Ser Asp Glu Leu Ala Gly Trp Leu Arg Gln Gln Arg Leu Pro Ala
6545                6550                6555

```
Glu Ser Leu Val Ala Val Leu Ala Pro Arg Ser Cys Gln Thr Ile
    6560                6565                6570

Val Ala Phe Leu Gly Ile Leu Lys Ala Asn Leu Ala Tyr Leu Pro
    6575                6580                6585

Leu Asp Val Asn Val Pro Ala Thr Arg Leu Glu Ser Ile Leu Ser
    6590                6595                6600

Ala Val Gly Gly Arg Lys Leu Val Leu Leu Gly Ala Asp Val Ala
    6605                6610                6615

Asp Pro Gly Leu Arg Leu Ala Asp Val Glu Leu Val Arg Ile Gly
    6620                6625                6630

Asp Thr Leu Gly Arg Cys Val Pro Gly Ala Pro Gly Asp Asn Glu
    6635                6640                6645

Ala Pro Val Val Gln Pro Ser Ala Thr Ser Leu Ala Tyr Val Ile
    6650                6655                6660

Phe Thr Ser Gly Ser Thr Gly Lys Pro Lys Gly Val Met Val Glu
    6665                6670                6675

His Arg Gly Val Val Arg Leu Val Lys Gln Ser Asn Val Val Tyr
    6680                6685                6690

His Leu Pro Ser Thr Ser Arg Val Ala His Leu Ser Asn Leu Ala
    6695                6700                6705

Phe Asp Ala Ser Val Leu Glu Ile Tyr Ala Ala Leu Leu Asn Gly
    6710                6715                6720

Gly Thr Val Tyr Cys Ile Asp Tyr Leu Thr Thr Leu Asp Pro His
    6725                6730                6735

Ala Leu Glu Ser Val Phe Ile Asp Ala Asp Leu Asn Thr Ala Val
    6740                6745                6750

Leu Pro Pro Ala Leu Leu Lys Gln Val Leu Ala Ser Ser Pro Ser
    6755                6760                6765

Thr Leu His Ala Leu Asp Leu Leu Phe Ile Gly Gly Asp Arg Leu
    6770                6775                6780

Asp Ala Arg Asp Ala Leu Tyr Ala Asn Arg Leu Val Arg Gly Ser
    6785                6790                6795

Leu Tyr Asn Val Tyr Gly Pro Thr Glu Asn Thr Val Leu Ser Val
    6800                6805                6810

Val Tyr Leu Phe Asn Asp Asp Ala Cys Ile Asn Gly Val Pro
    6815                6820                6825

Ile Gly Gln Val Val Ser Asn Ser Gly Val Tyr Val Met Asp Ser
    6830                6835                6840

Glu Gln Lys Leu Val Pro Pro Gly Val Met Gly Glu Ile Val Val
    6845                6850                6855

Thr Gly Asp Gly Leu Ala Arg Gly Tyr Thr Asp Ser Thr Leu Asn
    6860                6865                6870

Thr Asp Arg Phe Val Gln Ile Ser Val Asn Gly Arg Val Leu Gln
    6875                6880                6885

Ala Tyr Arg Thr Gly Asp Arg Gly Arg Tyr Arg Pro Thr Asp Ala
    6890                6895                6900

Arg Leu Glu Phe Phe Gly Arg Leu Asp Gln Gln Ile Lys Leu Arg
    6905                6910                6915

Gly His Arg Val Glu Leu Lys Glu Ile Glu Gln Ala Met Leu Gly
    6920                6925                6930

His Asn Ala Val Asp Asp Ala Gly Val Val Ala Leu Glu Ile Ser
    6935                6940                6945
```

```
Glu Cys Gln Glu Leu Glu Met Val Gly Phe Val Thr Leu Arg Asn
6950                6955                6960

Leu Gly Thr Met Glu Ala Thr Asn Asn Leu Ala His Thr Ser Trp
6965                6970                6975

Asn Pro Val Thr Leu Lys Thr Pro Leu Ala Ser Gln Ile Val Ala
6980                6985                6990

Glu Val Arg Gly Arg Leu Gln Arg Asn Leu Pro Leu Tyr Met Val
6995                7000                7005

Pro Ala Thr Ile Val Val Leu His Thr Met Pro Val Asn Ala Asn
7010                7015                7020

Gly Lys Leu Asp Arg Gln Ala Leu Val Lys Ala Ala Met Thr Leu
7025                7030                7035

Pro Lys Thr Ala Pro Leu Val Trp Met Ala Pro Arg Asn Glu Gly
7040                7045                7050

Glu Thr Ser Leu Cys Glu Glu Leu Thr Asp Ile Leu Gly Val Asn
7055                7060                7065

Val Gly Ile Thr Asp Asn Phe Phe Asp Leu Gly Gly His Ser Leu
7070                7075                7080

Leu Ala Thr Arg Val Ala Ala Arg Ile Ser Arg Arg Leu Asp Ala
7085                7090                7095

Leu Val Thr Val Lys Gln Ile Phe Asp His Pro Val Ile Gly Asp
7100                7105                7110

Leu Ala Ala Ala Ile Gln Gly Gly Ser Val Arg His Leu Pro Ile
7115                7120                7125

Thr Ala Ser Glu Val Asp Gly Pro Val Gln Gln Ser Phe Ala Gln
7130                7135                7140

Asn Arg Leu Trp Phe Leu Glu Gln Met Asn Ile Gly Ala Thr Trp
7145                7150                7155

Tyr Ile Val Pro Leu Ala Val Arg Leu Tyr Gly Thr Leu Arg Val
7160                7165                7170

Glu Ala Leu Asn Ile Ala Leu Arg Thr Ile Gln Gln Arg His Glu
7175                7180                7185

Thr Leu Arg Thr Thr Phe Glu Glu Leu Asn Gly Ile Ala Val Gln
7190                7195                7200

Arg Cys Asp Ser Thr Cys Gln Gly Gln Leu Arg Val Val Asp Leu
7205                7210                7215

Val Gly Gln Gly Pro Asp Arg Tyr Arg Glu Ile Leu Asp Val Gln
7220                7225                7230

Gln Thr Thr Pro Phe Glu Leu Ser Gln Glu Pro Gly Trp Arg Val
7235                7240                7245

Ala Leu Leu Arg Leu Gly Asp Asp Asp His Val Leu Ser Ile Val
7250                7255                7260

Met His His Ile Ile Ser Asp Gly Trp Ser Val Asp Val Leu Leu
7265                7270                7275

Arg Glu Ile Gly Gln Phe Tyr Ser Ala Ala Leu Arg Gly Gln Asp
7280                7285                7290

Pro Leu Ser Gln Ile Ser Pro Leu Pro Ile Gln Tyr Arg Asp Phe
7295                7300                7305

Ala Leu Trp Gln Arg Gln Asp Glu Gln Val Ala Glu His Gln Arg
7310                7315                7320

Gln Leu Glu His Trp Thr Glu Gln Leu Ala Asp Ser Ser Pro Ala
7325                7330                7335

Glu Leu Leu Ser Asp His Pro Arg Pro Ser Ile Leu Ser Gly Gln
```

```
                 7340              7345                 7350
Ala Gly Ala Ile Pro Val Asn Val Gln Gly Ser Leu Tyr Gln Ala
         7355              7360                 7365
Leu Arg Ala Phe Cys Arg Ala His Gln Val Thr Ser Phe Val Val
         7370              7375                 7380
Leu Leu Thr Ala Phe Arg Ile Ala His Tyr Arg Leu Thr Gly Ala
         7385              7390                 7395
Glu Asp Ala Thr Ile Gly Thr Pro Ile Ala Asn Arg Asn Arg Pro
         7400              7405                 7410
Glu Leu Glu Asn Met Ile Gly Phe Phe Val Asn Thr Gln Cys Met
         7415              7420                 7425
Arg Ile Val Ile Gly Ser Asp Asp Thr Phe Glu Gly Leu Val Gln
         7430              7435                 7440
Gln Val Arg Ser Ile Thr Ala Ala Ala His Glu Asn Gln Asp Val
         7445              7450                 7455
Pro Phe Glu Arg Ile Val Ser Ala Leu Leu Pro Gly Ser Arg Asp
         7460              7465                 7470
Thr Ser Arg Asn Pro Leu Val Gln Leu Met Phe Ala Val His Ser
         7475              7480                 7485
Gln Arg Asn Leu Gly Gln Ile Ser Leu Glu Gly Leu Gln Gly Glu
         7490              7495                 7500
Leu Leu Gly Val Ala Ala Thr Thr Arg Phe Asp Val Glu Phe His
         7505              7510                 7515
Leu Phe Gln Asp Asp Lys Leu Ser Gly Asn Val Leu Phe Ala
         7520              7525                 7530
Thr Glu Leu Phe Glu Gln Lys Thr Met Gln Gly Met Val Asp Val
         7535              7540                 7545
Phe Gln Glu Val Leu Ser Arg Gly Leu Glu Gln Pro Gln Ile Pro
         7550              7555                 7560
Leu Ala Thr Leu Pro Leu Thr His Gly Leu Glu Glu Leu Arg Thr
         7565              7570                 7575
Met Gly Leu Leu Asp Val Glu Lys Thr Asp Tyr Pro Arg Glu Ser
         7580              7585                 7590
Ser Val Val Asp Val Phe Arg Glu Gln Ala Ala Ala Cys Ser Glu
         7595              7600                 7605
Ala Ile Ala Val Lys Asp Ser Ser Ala Gln Leu Thr Tyr Ser Glu
         7610              7615                 7620
Leu Asp Arg Gln Ser Asp Glu Leu Ala Gly Trp Leu Arg Gln Gln
         7625              7630                 7635
Arg Leu Pro Ala Glu Ser Leu Val Ala Val Leu Ala Pro Arg Ser
         7640              7645                 7650
Cys Gln Thr Ile Val Ala Phe Leu Gly Ile Leu Lys Ala Asn Leu
         7655              7660                 7665
Ala Tyr Leu Pro Leu Asp Val Asn Val Pro Ala Thr Arg Leu Glu
         7670              7675                 7680
Ser Ile Leu Ser Ala Val Gly Gly Arg Lys Leu Val Leu Leu Gly
         7685              7690                 7695
Ala Asp Val Ala Asp Pro Gly Leu Arg Leu Ala Asp Val Glu Leu
         7700              7705                 7710
Val Arg Ile Gly Asp Thr Leu Gly Arg Cys Val Pro Gly Ala Pro
         7715              7720                 7725
Gly Asp Asn Glu Ala Pro Val Val Gln Pro Ser Ala Thr Ser Leu
         7730              7735                 7740
```

```
Ala Tyr Val Ile Phe Thr Ser Gly Ser Thr Gly Lys Pro Lys Gly
            7745              7750              7755

Val Met Val Glu His Arg Gly Val Val Arg Leu Val Lys Gln Ser
            7760              7765              7770

Asn Val Val Tyr His Leu Pro Ser Thr Ser Arg Val Ala His Leu
            7775              7780              7785

Ser Asn Leu Ala Phe Asp Ala Ser Ala Trp Glu Ile Tyr Ala Ala
            7790              7795              7800

Leu Leu Asn Gly Gly Thr Leu Ile Cys Ile Asp Tyr Phe Thr Thr
            7805              7810              7815

Leu Asp Cys Ser Ala Leu Gly Ala Lys Phe Ile Lys Glu Lys Ile
            7820              7825              7830

Val Ala Thr Met Ile Pro Pro Ala Leu Leu Lys Gln Cys Leu Ala
            7835              7840              7845

Ile Phe Pro Thr Ala Leu Ser Glu Leu Val Leu Leu Phe Ala Ala
            7850              7855              7860

Gly Asp Arg Phe Ser Ser Gly Asp Ala Val Glu Val Gln Arg His
            7865              7870              7875

Thr Lys Gly Ala Val Cys Asn Ala Tyr Gly Pro Thr Glu Asn Thr
            7880              7885              7890

Ile Leu Ser Thr Ile Tyr Glu Val Lys Gln Asn Glu Asn Phe Pro
            7895              7900              7905

Asn Gly Val Pro Ile Gly Arg Ala Val Ser Asn Ser Gly Ala Tyr
            7910              7915              7920

Val Met Asp Pro Gln Gln Gln Leu Val Pro Leu Gly Val Met Gly
            7925              7930              7935

Glu Leu Val Val Thr Gly Asp Gly Leu Ala Arg Gly Tyr Thr Asp
            7940              7945              7950

Pro Ser Leu Asp Ala Asp Arg Phe Val Gln Val Ser Val Asn Gly
            7955              7960              7965

Gln Leu Val Arg Ala Tyr Arg Thr Gly Asp Arg Val Arg Cys Arg
            7970              7975              7980

Pro Cys Asp Gly Gln Ile Glu Phe Phe Gly Arg Met Asp Arg Gln
            7985              7990              7995

Val Lys Ile Arg Gly His Arg Ile Glu Leu Ala Glu Val Glu His
            8000              8005              8010

Ala Val Leu Gly Leu Glu Asp Val Gln Asp Ala Ala Val Ile Ala
            8015              8020              8025

Phe Asp Asn Val Asp Ser Glu Glu Pro Glu Met Val Gly Phe Val
            8030              8035              8040

Thr Ile Thr Glu Asp Asn Pro Val Arg Glu Asp Glu Thr Ser Gly
            8045              8050              8055

Gln Val Glu Asp Trp Ala Asn His Phe Glu Ile Ser Thr Tyr Thr
            8060              8065              8070

Asp Ile Ala Ala Ile Asp Gln Gly Ser Ile Gly Ser Asp Phe Val
            8075              8080              8085

Gly Trp Thr Ser Met Tyr Asp Gly Ser Glu Ile Asp Lys Ala Glu
            8090              8095              8100

Met Gln Glu Trp Leu Ala Asp Thr Met Ala Ser Met Leu Asp Gly
            8105              8110              8115

Gln Ala Pro Gly Asn Val Leu Glu Ile Gly Thr Gly Thr Gly Met
            8120              8125              8130
```

| | | | | | | | | | | | |
|---|---|---|---|---|---|---|---|---|---|---|---|
|Val|Leu|Phe|Asn|Leu|Gly|Asp|Gly|Leu|Gln|Ser|Tyr|Val|Gly|Leu|
| |8135| | | | |8140| | | | |8145| | | |
|Glu|Pro|Ser|Arg|Ser|Ala|Ala|Ala|Phe|Val|Asn|Gln|Thr|Ile|Lys|
| |8150| | | | |8155| | | | |8160| | | |
|Ser|Leu|Pro|Thr|Leu|Ala|Gly|Asn|Ala|Glu|Val|His|Ile|Gly|Thr|
| |8165| | | | |8170| | | | |8175| | | |
|Ala|Thr|Asp|Val|Ala|Arg|Leu|Asp|Gly|Leu|Arg|Pro|Asp|Leu|Val|
| |8180| | | | |8185| | | | |8190| | | |
|Val|Val|Asn|Ser|Val|Val|Gln|Tyr|Phe|Pro|Ser|Pro|Glu|Tyr|Leu|
| |8195| | | | |8200| | | | |8205| | | |
|Met|Glu|Val|Val|Glu|Ala|Leu|Ala|Arg|Leu|Pro|Gly|Val|Glu|Arg|
| |8210| | | | |8215| | | | |8220| | | |
|Ile|Phe|Phe|Gly|Asp|Val|Arg|Ser|Tyr|Ala|Ile|Asn|Arg|Asp|Phe|
| |8225| | | | |8230| | | | |8235| | | |
|Leu|Ala|Ala|Arg|Ala|Leu|His|Glu|Leu|Gly|Asp|Arg|Ala|Thr|Lys|
| |8240| | | | |8245| | | | |8250| | | |
|His|Glu|Ile|Arg|Arg|Lys|Met|Leu|Glu|Met|Glu|Glu|Arg|Glu|Glu|
| |8255| | | | |8260| | | | |8265| | | |
|Glu|Leu|Leu|Val|Asp|Pro|Ala|Phe|Phe|Thr|Met|Leu|Thr|Ser|Ser|
| |8270| | | | |8275| | | | |8280| | | |
|Leu|Pro|Gly|Leu|Ile|Gln|His|Val|Glu|Ile|Leu|Pro|Lys|Leu|Met|
| |8285| | | | |8290| | | | |8295| | | |
|Arg|Ala|Thr|Asn|Glu|Leu|Ser|Ala|Tyr|Arg|Tyr|Thr|Ala|Val|Val|
| |8300| | | | |8305| | | | |8310| | | |
|His|Val|Cys|Arg|Ala|Gly|Gln|Glu|Pro|Arg|Ser|Val|His|Thr|Ile|
| |8315| | | | |8320| | | | |8325| | | |
|Asp|Asp|Asp|Ala|Trp|Val|Asn|Leu|Gly|Ala|Ser|Arg|Leu|Ser|Arg|
| |8330| | | | |8335| | | | |8340| | | |
|Pro|Thr|Leu|Ser|Ser|Leu|Leu|Gln|Thr|Ser|Glu|Gly|Ala|Ser|Ala|
| |8345| | | | |8350| | | | |8355| | | |
|Val|Ala|Val|Ser|Asn|Ile|Pro|Tyr|Ser|Lys|Thr|Ile|Thr|Glu|Arg|
| |8360| | | | |8365| | | | |8370| | | |
|Ala|Leu|Val|Ser|Ala|Leu|Asp|Glu|Asp|Met|Gln|Asp|Ser|Ser|
| |8375| | | | |8380| | | | |8385| | | |
|Asp|Trp|Leu|Leu|Ala|Val|Arg|Glu|Thr|Gly|Arg|Ser|Cys|Ser|Ser|
| |8390| | | | |8395| | | | |8400| | | |
|Phe|Ser|Ala|Thr|Asp|Leu|Val|Glu|Leu|Ala|Arg|Glu|Thr|Gly|Trp|
| |8405| | | | |8410| | | | |8415| | | |
|Arg|Val|Glu|Leu|Ser|Trp|Ala|Arg|Gln|Tyr|Ser|Gln|Lys|Gly|Ala|
| |8420| | | | |8425| | | | |8430| | | |
|Leu|Asp|Ala|Val|Phe|His|Arg|His|Pro|Val|Ser|Ala|Gly|Ser|Gly|
| |8435| | | | |8440| | | | |8445| | | |
|Arg|Val|Met|Phe|Gln|Phe|Pro|Val|Glu|Thr|Glu|Asp|Arg|Pro|His|
| |8450| | | | |8455| | | | |8460| | | |
|Ile|Ser|Arg|Thr|Asn|Arg|Pro|Leu|Gln|Arg|Leu|Gln|Lys|Lys|Arg|
| |8465| | | | |8470| | | | |8475| | | |
|Thr|Glu|Thr|His|Val|His|Glu|Gln|Leu|Arg|Ala|Leu|Leu|Pro|Arg|
| |8480| | | | |8485| | | | |8490| | | |
|Tyr|Met|Val|Pro|Thr|Arg|Ile|Val|Ala|Leu|Asp|Lys|Leu|Pro|Val|
| |8495| | | | |8500| | | | |8505| | | |
|Asn|Ala|Asn|Gly|Lys|Val|Asp|Arg|Gln|Gln|Leu|Ala|Arg|Thr|Ala|
| |8510| | | | |8515| | | | |8520| | | |
|Gln|Val|Leu|Pro|Ala|Ser|Lys|Ala|Pro|Ser|Ala|Cys|Val|Ala|Pro|

-continued

```
            8525                8530                8535
Arg Asn Glu Leu Glu Met Thr Leu Cys Glu Glu Phe Ser Gln Val
            8540                8545                8550
Leu Gly Val Glu Val Gly Ile Thr Asp Asn Phe Phe His Leu Gly
            8555                8560                8565
Gly His Ser Leu Met Ala Thr Lys Phe Ala Ala Arg Ile Ser Arg
            8570                8575                8580
Arg Leu Asn Ala Ile Val Ser Val Lys Asn Val Phe Asp His Pro
            8585                8590                8595
Val Pro Met Asp Leu Ala Ala Thr Ile Gln Glu Gly Ser Lys Leu
            8600                8605                8610
His Thr Pro Ile Pro Arg Thr Ala Tyr Ser Gly Pro Val Glu Gln
            8615                8620                8625
Ser Phe Ala Gln Gly Arg Leu Trp Phe Leu Asp Gln Phe Asn Pro
            8630                8635                8640
Ser Ser Ile Gly Tyr Val Met Pro Phe Ala Ala Arg Leu His Gly
            8645                8650                8655
Gln Leu Gln Ile Glu Ala Leu Thr Ala Ala Leu Phe Ala Leu Glu
            8660                8665                8670
Gln Arg His Glu Ile Leu Arg Thr Thr Leu Asp Ala His Asp Gly
            8675                8680                8685
Val Gly Met Gln Ile Val His Ala Glu His Pro Gln Gln Leu Arg
            8690                8695                8700
Ile Ile Asp Val Ser Ala Lys Ala Ser Ser Ser Tyr Ala Gln Thr
            8705                8710                8715
Leu Arg Asp Glu Gln Ala Ser Pro Phe Asp Leu Ser Lys Glu Pro
            8720                8725                8730
Gly Trp Arg Val Ser Leu Leu Gln Leu Ser Glu Ile Asp Tyr Val
            8735                8740                8745
Leu Ser Ile Val Met His His Thr Ile Tyr Asp Gly Trp Ser Leu
            8750                8755                8760
Asp Val Leu Arg Arg Glu Leu Ser Gln Phe Tyr Ala Ala Ala Ile
            8765                8770                8775
Arg Gly Arg Glu Pro Leu Ser Thr Ile Glu Pro Leu Pro Ile Gln
            8780                8785                8790
Tyr Arg Asp Phe Ser Val Trp Gln Lys Gln Glu Asp Gln Val Ala
            8795                8800                8805
Glu His Arg Arg Gln Leu His Tyr Trp Ile Glu Gln Leu Asp Gly
            8810                8815                8820
Ser Ser Pro Ala Glu Phe Leu Asn Asp Lys Pro Arg Pro Thr Leu
            8825                8830                8835
Leu Ser Gly Lys Ala Gly Val Val Glu Ile Ala Val Lys Gly Thr
            8840                8845                8850
Val Tyr Gln Arg Leu Leu Glu Phe Cys Arg Leu His Gln Val Thr
            8855                8860                8865
Ser Phe Met Val Leu Leu Ala Ala Phe Arg Ala Thr His Tyr Arg
            8870                8875                8880
Leu Thr Gly Thr Glu Asp Ala Thr Val Gly Thr Pro Ile Ala Asn
            8885                8890                8895
Arg Asn Arg Pro Glu Leu Glu Asn Met Ile Gly Leu Phe Val Asn
            8900                8905                8910
Thr Gln Cys Ile Arg Leu Lys Ile Glu Asp Asn Asp Thr Leu Glu
            8915                8920                8925
```

```
Glu Leu Val Gln His Val Arg Ala Thr Ile Thr Ala Ser Ile Ser
8930                8935                8940

Asn Gln Asp Val Pro Phe Glu Gln Val Val Ser Ala Leu Leu Pro
8945                8950                8955

Gly Ser Arg Asp Thr Ser Arg Asn Pro Leu Val Gln Leu Thr Phe
8960                8965                8970

Ala Val His Ser Gln Arg Asn Leu Ala Asp Ile Gln Leu Glu Asn
8975                8980                8985

Val Glu Thr Asn Ala Met Pro Ile Cys Pro Ser Thr Arg Phe Asp
8990                8995                9000

Ala Glu Phe His Leu Phe Gln Glu Glu Asn Met Leu Ser Gly Arg
9005                9010                9015

Val Leu Phe Ser Asp Asp Leu Phe Glu Gln Lys Thr Met Gln Gly
9020                9025                9030

Met Val Asp Val Phe Gln Glu Val Leu Ser Arg Gly Leu Glu Gln
9035                9040                9045

Pro Gln Ile Pro Leu Ala Thr Leu Pro Leu Thr His Gly Leu Glu
9050                9055                9060

Glu Leu Arg Thr Met Gly Leu Leu Asp Val Glu Lys Thr Asp Tyr
9065                9070                9075

Pro Arg Glu Ser Ser Val Val Asp Val Phe Arg Glu Gln Ala Ala
9080                9085                9090

Ala Cys Ser Glu Ala Ile Ala Val Lys Asp Ser Ser Ala Gln Leu
9095                9100                9105

Thr Tyr Ser Glu Leu Asp Arg Gln Ser Asp Glu Leu Ala Gly Trp
9110                9115                9120

Leu Arg Gln Gln Arg Leu Pro Ala Glu Ser Leu Val Ala Val Leu
9125                9130                9135

Ala Pro Arg Ser Cys Gln Thr Ile Val Ala Phe Leu Gly Ile Leu
9140                9145                9150

Lys Ala Asn Leu Ala Tyr Leu Pro Leu Asp Val Asn Val Pro Ala
9155                9160                9165

Thr Arg Leu Glu Ser Ile Leu Ser Ala Val Gly Gly Arg Lys Leu
9170                9175                9180

Val Leu Leu Gly Ala Asp Val Ala Asp Pro Gly Leu Arg Leu Ala
9185                9190                9195

Asp Val Glu Leu Val Arg Ile Gly Asp Thr Leu Gly Arg Cys Val
9200                9205                9210

Pro Gly Ala Pro Gly Asp Asn Glu Ala Pro Val Gln Pro Ser
9215                9220                9225

Ala Thr Ser Leu Ala Tyr Val Ile Phe Thr Ser Gly Ser Thr Gly
9230                9235                9240

Lys Pro Lys Gly Val Met Val Glu His Arg Gly Val Val Arg Leu
9245                9250                9255

Val Lys Gln Ser Asn Val Val Tyr His Leu Pro Ser Thr Ser Arg
9260                9265                9270

Val Ala His Leu Ser Asn Leu Ala Phe Asp Ala Ser Ala Trp Glu
9275                9280                9285

Ile Tyr Ala Ala Leu Leu Asn Gly Gly Thr Leu Ile Cys Ile Asp
9290                9295                9300

Tyr Phe Thr Ile Ile Asp Ala Arg Ala Leu Gly Val Ile Phe Ala
9305                9310                9315
```

```
Gln Gln Ser Ile Asn Ala Thr Met Leu Ser Pro Leu Leu Leu Lys
9320                9325                9330

Gln Phe Leu Ser Asp Ala Pro Phe Val Leu Arg Ser Leu His Ala
9335                9340                9345

Leu Tyr Leu Gly Gly Asp Arg Leu Gln Gly Arg Asp Ala Ile Gln
9350                9355                9360

Ala Cys Arg Val Gly Cys Ala Phe Val Ile Asn Ala Tyr Gly Pro
9365                9370                9375

Thr Glu Asn Ser Val Ile Ser Thr Thr Tyr Thr Leu Val Lys Gly
9380                9385                9390

Asn Ala Asp Phe Pro Asn Gly Val Pro Ile Gly Arg Ala Val Ser
9395                9400                9405

Asn Ser Gly Ala Tyr Val Met Asp Pro Gln Gln Leu Val Pro
9410                9415                9420

Leu Gly Val Met Gly Glu Leu Val Val Thr Gly Asp Gly Leu Ala
9425                9430                9435

Arg Gly Tyr Thr Asp Pro Ser Leu Asp Ala Asp Arg Phe Val Gln
9440                9445                9450

Val Ser Val Asn Gly Gln Leu Val Arg Ala Tyr Arg Thr Gly Asp
9455                9460                9465

Arg Val Arg Cys Arg Pro Cys Asp Gly Gln Ile Glu Phe Phe Gly
9470                9475                9480

Arg Met Asp Arg Gln Val Lys Ile Arg Gly His Arg Ile Glu Leu
9485                9490                9495

Ala Glu Val Glu His Ala Val Leu Gly Leu Glu Asp Val Gln Asp
9500                9505                9510

Ala Ala Val Leu Ile Ala Gln Thr Ala Glu Asn Glu Glu Leu Val
9515                9520                9525

Gly Phe Phe Thr Leu Arg Gln Thr Gln Ala Val Gln Ser Asn Gly
9530                9535                9540

Ala Ala Gly Val Val Pro Glu His Ser Asp Ser Glu Leu Ala Gln
9545                9550                9555

Ser Cys Ser Cys Thr Gln Thr Glu Arg Arg Val Arg Asn Arg Leu
9560                9565                9570

Gln Ser Cys Leu Pro Arg Tyr Met Val Pro Ser Arg Met Val Leu
9575                9580                9585

Leu Asp Arg Leu Pro Val Asn Pro Asn Gly Lys Val Asp Arg Gln
9590                9595                9600

Glu Leu Thr Arg Arg Ala Gln Asp Leu Pro Ile Ser Glu Ser Ser
9605                9610                9615

Pro Val His Val Lys Pro Arg Thr Glu Leu Glu Arg Ser Leu Cys
9620                9625                9630

Glu Glu Phe Ala Asp Val Ile Gly Leu Glu Val Gly Val Thr Asp
9635                9640                9645

Asn Phe Phe Asp Leu Gly Gly His Ser Leu Met Ala Met Lys Leu
9650                9655                9660

Ala Ala Arg Ile Ser Arg Arg Ser Asn Ala His Ile Ser Val Lys
9665                9670                9675

Asp Ile Phe Asp His Pro Leu Ile Ala Asp Leu Ala Met Lys Ile
9680                9685                9690

Arg Glu Gly Ser Asp Leu His Thr Pro Ile Pro His Arg Met Tyr
9695                9700                9705

Val Gly Pro Ile Gln Leu Ser Phe Ala Gln Gly Arg Leu Trp Phe
```

-continued

```
            9710                9715                9720
Leu Asp Gln Leu Asn Leu Gly Ala Ser Trp Tyr Val Met Pro Leu
        9725                9730                9735
Ala Met Arg Leu Gln Gly Ser Leu Gln Leu Asp Ala Leu Glu Thr
        9740                9745                9750
Ala Leu Phe Ala Ile Glu Gln Arg His Glu Thr Leu Arg Met Thr
        9755                9760                9765
Phe Ala Glu Gln Asp Gly Val Ala Val Gln Val Val His Ala Ala
        9770                9775                9780
His Tyr Lys His Ile Lys Met Ile Asp Lys Pro Leu Arg Gln Lys
        9785                9790                9795
Ile Asp Val Leu Lys Met Leu Glu Glu Arg Thr Thr Pro Phe
        9800                9805                9810
Glu Leu Ser Arg Glu Pro Gly Trp Arg Val Ala Leu Leu Arg Leu
        9815                9820                9825
Gly Asp Asp Asp His Val Leu Ser Ile Val Met His His Ile Ile
        9830                9835                9840
Ser Asp Gly Trp Ser Val Asp Val Leu Arg His Glu Leu Gly Gln
        9845                9850                9855
Phe Tyr Ser Ala Ala Leu Arg Gly Gln Asp Pro Leu Ser Gln Ile
        9860                9865                9870
Ser Pro Leu Pro Ile Gln Tyr Arg Asp Phe Ala Leu Trp Gln Arg
        9875                9880                9885
Gln Asp Glu Gln Val Ala Glu His Gln Arg Gln Leu Glu His Trp
        9890                9895                9900
Thr Glu Gln Leu Ala Asp Ser Ser Pro Ala Glu Leu Leu Ser Asp
        9905                9910                9915
His Pro Arg Pro Ser Ile Leu Ser Gly Gln Ala Gly Ala Ile Pro
        9920                9925                9930
Val Asn Val Gln Gly Ser Leu Tyr Gln Ala Leu Arg Ala Phe Cys
        9935                9940                9945
Arg Ala His Gln Val Thr Ser Phe Val Val Leu Leu Thr Ala Phe
        9950                9955                9960
Arg Ile Ala His Tyr Arg Leu Thr Gly Ala Glu Asp Ala Thr Ile
        9965                9970                9975
Gly Thr Pro Ile Ala Asn Arg Asn Arg Pro Glu Leu Glu Asn Met
        9980                9985                9990
Ile Gly Phe Phe Val Asn Thr Gln Cys Met Arg Ile Val Ile Gly
        9995               10000               10005
Ser Asp Asp Thr Phe Glu Gly Leu Val Gln Gln Val Arg Ser Ile
       10010               10015               10020
Thr Ala Ala Ala His Glu Asn Gln Asp Val Pro Phe Glu Arg Ile
       10025               10030               10035
Val Ser Ala Leu Leu Pro Gly Ser Arg Asp Thr Ser Arg Asn Pro
       10040               10045               10050
Leu Val Gln Leu Met Phe Ala Val His Ser Gln Arg Asn Leu Gly
       10055               10060               10065
Gln Ile Ser Leu Glu Gly Leu Gln Gly Glu Leu Leu Gly Val Ala
       10070               10075               10080
Ala Thr Thr Arg Phe Asp Val Glu Phe His Leu Phe Gln Asp Asp
       10085               10090               10095
Asp Lys Leu Ser Gly Asn Val Leu Phe Ala Thr Glu Leu Phe Glu
       10100               10105               10110
```

```
Gln Lys Thr Met Gln Gly Met Val Asp Val Phe Gln Glu Val Leu
    10115           10120               10125

Ser Arg Gly Leu Glu Gln Pro Gln Ile Pro Leu Ala Thr Leu Pro
    10130           10135               10140

Leu Thr His Gly Leu Glu Glu Leu Arg Thr Met Gly Leu Leu Asp
    10145           10150               10155

Val Glu Lys Thr Asp Tyr Pro Arg Glu Ser Ser Val Val Asp Val
    10160           10165               10170

Phe Arg Glu Gln Ala Ala Ala Cys Ser Glu Ala Ile Ala Val Lys
    10175           10180               10185

Asp Ser Ser Ala Gln Leu Thr Tyr Ser Glu Leu Asp Arg Gln Ser
    10190           10195               10200

Asp Glu Leu Ala Gly Trp Leu Arg Gln Gln Arg Leu Pro Ala Glu
    10205           10210               10215

Ser Leu Val Ala Val Leu Ala Pro Arg Ser Cys Gln Thr Ile Val
    10220           10225               10230

Ala Phe Leu Gly Ile Leu Lys Ala Asn Leu Ala Tyr Leu Pro Leu
    10235           10240               10245

Asp Val Asn Val Pro Ala Thr Arg Leu Glu Ser Ile Leu Ser Ala
    10250           10255               10260

Val Gly Gly Arg Lys Leu Val Leu Leu Gly Ala Asp Val Ala Asp
    10265           10270               10275

Pro Gly Leu Arg Leu Ala Asp Val Glu Leu Val Arg Ile Gly Asp
    10280           10285               10290

Thr Leu Gly Arg Cys Val Pro Gly Ala Pro Gly Asp Asn Glu Ala
    10295           10300               10305

Pro Val Val Gln Pro Ser Ala Thr Ser Leu Ala Tyr Val Ile Phe
    10310           10315               10320

Thr Ser Gly Ser Thr Gly Lys Pro Lys Gly Val Met Val Glu His
    10325           10330               10335

Arg Gly Val Val Arg Leu Val Lys Gln Ser Asn Val Val Tyr His
    10340           10345               10350

Leu Pro Ser Thr Ser Arg Val Ala His Leu Ser Asn Leu Ala Phe
    10355           10360               10365

Asp Ala Ser Ala Trp Glu Ile Tyr Ala Ala Leu Leu Asn Gly Gly
    10370           10375               10380

Thr Leu Ile Cys Ile Asp Tyr Phe Thr Thr Leu Asp Cys Ser Ala
    10385           10390               10395

Leu Gly Ala Lys Phe Ile Lys Glu Lys Ile Val Ala Thr Met Ile
    10400           10405               10410

Pro Pro Ala Leu Leu Lys Gln Cys Leu Ala Ile Phe Pro Thr Ala
    10415           10420               10425

Leu Ser Glu Leu Val Leu Leu Phe Ala Ala Gly Asp Arg Phe Ser
    10430           10435               10440

Ser Gly Asp Ala Val Glu Val Gln Arg His Thr Lys Gly Ala Val
    10445           10450               10455

Cys Asn Ala Tyr Gly Pro Thr Glu Asn Thr Ile Leu Ser Thr Ile
    10460           10465               10470

Tyr Glu Val Lys Gln Asn Glu Asn Phe Pro Asn Gly Val Pro Ile
    10475           10480               10485

Gly Arg Ala Val Ser Asn Ser Gly Ala Tyr Val Met Asp Pro Gln
    10490           10495               10500
```

-continued

| | | | | | | | | | | |
|---|---|---|---|---|---|---|---|---|---|---|
| Gln | Gln | Leu | Val | Pro | Leu | Gly | Val | Met | Gly | Glu | Leu | Val | Val | Thr |
| | 10505 | | | | 10510 | | | | 10515 | |
| Gly | Asp | Gly | Leu | Ala | Arg | Gly | Tyr | Thr | Asp | Pro | Ser | Leu | Asp | Ala |
| 10520 | | | | | 10525 | | | | | 10530 |
| Asp | Arg | Phe | Val | Gln | Val | Ser | Val | Asn | Gly | Gln | Leu | Val | Arg | Ala |
| 10535 | | | | | 10540 | | | | | 10545 |
| Tyr | Arg | Thr | Gly | Asp | Arg | Val | Arg | Cys | Arg | Pro | Cys | Asp | Gly | Gln |
| 10550 | | | | | 10555 | | | | | 10560 |
| Ile | Glu | Phe | Phe | Gly | Arg | Met | Asp | Arg | Gln | Val | Lys | Ile | Arg | Gly |
| 10565 | | | | | 10570 | | | | | 10575 |
| His | Arg | Ile | Glu | Leu | Ala | Glu | Val | Glu | His | Ala | Val | Leu | Gly | Leu |
| 10580 | | | | | 10585 | | | | | 10590 |
| Glu | Asp | Val | Gln | Asp | Ala | Ala | Val | Ile | Ala | Phe | Asp | Asn | Val | Asp |
| 10595 | | | | | 10600 | | | | | 10605 |
| Ser | Glu | Glu | Pro | Glu | Met | Val | Gly | Phe | Val | Thr | Ile | Thr | Glu | Asp |
| 10610 | | | | | 10615 | | | | | 10620 |
| Asn | Pro | Val | Arg | Glu | Asp | Glu | Thr | Ser | Gly | Gln | Val | Glu | Asp | Trp |
| 10625 | | | | | 10630 | | | | | 10635 |
| Ala | Asn | His | Phe | Glu | Ile | Ser | Thr | Tyr | Thr | Asp | Ile | Ala | Ala | Ile |
| 10640 | | | | | 10645 | | | | | 10650 |
| Asp | Gln | Gly | Ser | Ile | Gly | Ser | Asp | Phe | Val | Gly | Trp | Thr | Ser | Met |
| 10655 | | | | | 10660 | | | | | 10665 |
| Tyr | Asp | Gly | Ser | Glu | Ile | Asp | Lys | Ala | Glu | Met | Gln | Glu | Trp | Leu |
| 10670 | | | | | 10675 | | | | | 10680 |
| Ala | Asp | Thr | Met | Ala | Ser | Met | Leu | Asp | Gly | Gln | Ala | Pro | Gly | Asn |
| 10685 | | | | | 10690 | | | | | 10695 |
| Val | Leu | Glu | Ile | Gly | Thr | Gly | Thr | Gly | Met | Val | Leu | Phe | Asn | Leu |
| 10700 | | | | | 10705 | | | | | 10710 |
| Gly | Asp | Gly | Leu | Gln | Ser | Tyr | Val | Gly | Leu | Glu | Pro | Ser | Arg | Ser |
| 10715 | | | | | 10720 | | | | | 10725 |
| Ala | Ala | Ala | Phe | Val | Asn | Gln | Thr | Ile | Lys | Ser | Leu | Pro | Thr | Leu |
| 10730 | | | | | 10735 | | | | | 10740 |
| Ala | Gly | Asn | Ala | Glu | Val | His | Ile | Gly | Thr | Ala | Thr | Asp | Val | Ala |
| 10745 | | | | | 10750 | | | | | 10755 |
| Arg | Leu | Asp | Gly | Leu | Arg | Pro | Asp | Leu | Val | Val | Asn | Ser | Val |
| 10760 | | | | | 10765 | | | | | 10770 |
| Val | Gln | Tyr | Phe | Pro | Ser | Pro | Glu | Tyr | Leu | Met | Glu | Val | Val | Glu |
| 10775 | | | | | 10780 | | | | | 10785 |
| Ala | Leu | Ala | Arg | Leu | Pro | Gly | Val | Glu | Arg | Ile | Phe | Phe | Gly | Asp |
| 10790 | | | | | 10795 | | | | | 10800 |
| Val | Arg | Ser | Tyr | Ala | Ile | Asn | Arg | Asp | Phe | Leu | Ala | Ala | Arg | Ala |
| 10805 | | | | | 10810 | | | | | 10815 |
| Leu | His | Glu | Leu | Gly | Asp | Arg | Ala | Thr | Lys | His | Glu | Ile | Arg | Arg |
| 10820 | | | | | 10825 | | | | | 10830 |
| Lys | Met | Leu | Glu | Met | Glu | Glu | Arg | Glu | Glu | Leu | Leu | Val | Asp |
| 10835 | | | | | 10840 | | | | | 10845 |
| Pro | Ala | Phe | Phe | Thr | Met | Leu | Thr | Ser | Ser | Leu | Pro | Gly | Leu | Ile |
| 10850 | | | | | 10855 | | | | | 10860 |
| Gln | His | Val | Glu | Ile | Leu | Pro | Lys | Leu | Met | Arg | Ala | Thr | Asn | Glu |
| 10865 | | | | | 10870 | | | | | 10875 |
| Leu | Ser | Ala | Tyr | Arg | Tyr | Thr | Ala | Val | Val | His | Val | Cys | Arg | Ala |
| 10880 | | | | | 10885 | | | | | 10890 |
| Gly | Gln | Glu | Pro | Arg | Ser | Val | His | Thr | Ile | Asp | Asp | Asp | Ala | Trp |

```
            10895              10900              10905

Val Asn Leu Gly Ala Ser Arg Leu Ser Arg Pro Thr Leu Ser Ser
        10910              10915              10920

Leu Leu Gln Thr Ser Glu Gly Ala Ser Ala Val Ala Val Ser Asn
        10925              10930              10935

Ile Pro Tyr Ser Lys Thr Ile Thr Glu Arg Ala Leu Val Ser Ala
        10940              10945              10950

Leu Asp Glu Asp Asp Met Gln Asp Ser Ser Asp Trp Leu Leu Ala
        10955              10960              10965

Val Arg Glu Thr Gly Arg Ser Cys Ser Ser Phe Ser Ala Thr Asp
        10970              10975              10980

Leu Val Glu Leu Ala Arg Glu Thr Gly Trp Arg Val Glu Leu Ser
        10985              10990              10995

Trp Ala Arg Gln Tyr Ser Gln Lys Gly Ala Leu Asp Ala Val Phe
        11000              11005              11010

His Arg His Pro Val Ser Ala Gly Ser Gly Arg Val Met Phe Gln
        11015              11020              11025

Phe Pro Val Glu Thr Glu Asp Arg Pro His Ile Ser Arg Thr Asn
        11030              11035              11040

Arg Pro Leu Gln Arg Leu Gln Lys Lys Arg Thr Glu Thr His Val
        11045              11050              11055

His Glu Gln Leu Arg Ala Leu Leu Pro Arg Tyr Met Val Pro Thr
        11060              11065              11070

Arg Ile Val Ala Leu Asp Lys Leu Pro Val Asn Ala Asn Gly Lys
        11075              11080              11085

Val Asp Arg Gln Gln Leu Ala Arg Thr Ala Gln Val Leu Pro Ala
        11090              11095              11100

Ser Lys Ala Pro Ser Ala Cys Val Ala Pro Arg Asn Glu Leu Glu
        11105              11110              11115

Met Thr Leu Cys Glu Glu Phe Ser Gln Val Leu Gly Val Glu Val
        11120              11125              11130

Gly Ile Thr Asp Asn Phe Phe His Leu Gly Gly His Ser Leu Met
        11135              11140              11145

Ala Thr Lys Leu Ala Ala Arg Ile Ser Arg Gln Leu Asn Ile Gln
        11150              11155              11160

Val Ser Val Arg Asp Ile Phe Asp Tyr Pro Val Ile Val Asp Leu
        11165              11170              11175

Thr Asp Arg Leu Arg Leu His His Thr Arg Ile Leu Thr His Asp
        11180              11185              11190

His Gly Gln His Gly Gln Pro Asp Leu Lys Pro Phe Thr Leu Leu
        11195              11200              11205

Pro Thr Asn Asn Pro Gln Glu Phe Leu Gln His His Ile Leu Pro
        11210              11215              11220

Gln Leu Val Pro Asp His Ala Lys Ile Leu Asp Val Tyr Pro Val
        11225              11230              11235

Thr Arg Ile Gln Arg Arg Phe Leu His His Pro Lys Arg Gly Leu
        11240              11245              11250

Pro Arg Phe Pro Ser Met Val Phe Phe Asp Phe Pro Gly Ser
        11255              11260              11265

Asp Pro His Lys Leu Arg Leu Ala Cys Met Ala Leu Val Gln Arg
        11270              11275              11280

Phe Asp Ile Leu Arg Thr Ile Phe Leu Ser Val Ser Gly Gln Phe
        11285              11290              11295
```

```
Phe Gln Val Val Leu Asp Gly Tyr Gly Ile Val Ile Pro Val Ile
    11300           11305               11310

Glu Val Asp Glu Glu Leu Asp Asp Ala Thr Arg Lys Leu His Asp
    11315           11320               11325

Ser Asp Ile Gln Gln Pro Leu Arg Leu Gly Lys Pro Leu Ile Arg
    11330           11335               11340

Ile Ala Val Leu Lys Arg Gln His Ser Arg Val Arg Ala Val Leu
    11345           11350               11355

Arg Leu Ser His Ala Leu Tyr Asp Gly Leu Ser Phe Glu His Ile
    11360           11365               11370

Ile Gln Ser Leu His Ala Leu Tyr Leu Asp Ile Thr Leu Ser Ala
    11375           11380               11385

Pro Pro Lys Phe Gly Leu Tyr Val Gln His Met Ile Gln Ser Arg
    11390           11395               11400

Ala Glu Gly Tyr Ala Phe Trp Arg Ser Val Leu Lys Gly Ser Ser
    11405           11410               11415

Met Thr Ile Leu Glu Arg Ser Ser Thr Leu Gln Ser Arg Gln Pro
    11420           11425               11430

His Leu Gly Arg Phe Leu Ser Ala Glu Lys Ile Ile Lys Ala Pro
    11435           11440               11445

Leu His Ala Asn Lys Ser Gly Ile Thr Gln Ala Thr Val Phe Ala
    11450           11455               11460

Ala Ala Asn Ala Leu Met Leu Ala Asn Leu Thr Gly Thr Asn Asp
    11465           11470               11475

Val Val Phe Ala Arg Ile Val Ser Gly Arg Gln Ser Leu Pro Lys
    11480           11485               11490

Asn Phe Gln His Val Val Gly Pro Cys Thr Asn Asp Val Pro Val
    11495           11500               11505

Arg Val Arg Met Glu Pro Gly Val Gly Pro Lys Ala Leu Leu Arg
    11510           11515               11520

Gln Val Gln Asp Gln Tyr Val His Ser Phe Pro Phe Glu Thr Leu
    11525           11530               11535

Gly Phe Asp Glu Ile Lys Glu Asn Cys Thr Asp Trp Pro Glu Arg
    11540           11545               11550

Ile Thr Asn Phe Gly Cys Ser Thr Thr Tyr Gln Asn Phe Asp Ile
    11555           11560               11565

Phe Pro Lys Ser Gln Ile Asp His Gln Gln Ile Gln Met Ala Ser
    11570           11575               11580

Leu Ala Ser Glu Tyr Gln Asn Arg Glu Thr Trp Asp Glu Ala Pro
    11585           11590               11595

Leu Tyr Asp Leu Asn Val Thr Gly Val Pro Gln Pro Asp Gly Arg
    11600           11605               11610

His Ile Lys Ile Tyr Val Gly Val Asp Gly Gln Leu Cys Asp Glu
    11615           11620               11625

Ser Thr Leu Asp Cys Ile Leu Ser Asp Ile Cys Glu Gly Val Val
    11630           11635               11640

Ser Leu Thr Asp Ala Leu Gln Glu Leu Pro Ala Ala Ser Ile Thr
    11645           11650               11655

Glu
```

<210> SEQ ID NO 7
<211> LENGTH: 2103
<212> TYPE: DNA

<213> ORGANISM: Aureobasidium melanogenum strain W5-2

<400> SEQUENCE: 7

```
atggcttcat ctaatggccc gatgaattcc ccctttgaat tgatcccaa ggtcgtcaat        60
aagaagaatt actatactga cttcttgaag cgcgatgagc aattcctcgc atttcgcctt       120
caaggcgagg agaaccgtaa tcgcatgatc aaagctgcgc gcgataagga ccgcgcaatg       180
gctcaggctg cttctaatgg agtctcagct gatgctgcgc aagctgagat tgacgatgat       240
gccgccgagg atgaagctgc tgaagctgaa gcctttggct caaagacgat tgtcattcat       300
cctggcagtc gcaacctacg tattggtctt gcaacagacg cccttcccaa gacaatcccg       360
atggtgattg cacgcaaggc ttcacatgca gaagacgagg agcctggcgc tgaaccgcgg       420
ccaaagcgag tcaagatgca ggatggtacg gcagagcctg ctggcgagag tgcgttcggc       480
gaagatttcg caaggaata cagtagcatg gcagctgact tcaaaatcta ccgtcgcaac        540
aacaaacgta gagtcttgcc caactcgcgt gaactggtcg tcaactggaa ctcgcgcaat       600
gctccggaaa ccatttctga acataacgat cctcagcgtg ttgactggac agaaattgtg       660
tcacctgcac ccgaaatctt cactggacat gcagctctgc gaataccaca gcattccaaa       720
ccccgataca gactctactg gccactcaaa tgtggttggc tcaatgaaca agactattcg       780
agcaaatcta gcttatttcg cgacttcttc agcatcatcg aagaggccat caagaacgag       840
cttcacctga accgtaagag agactgggca cagtactctt gcgtgttcat cattcccgat       900
ctgtacgaga aagttttcgt gacatccatc ctcgaggaaa tgttcagaga cttcggtttc       960
cagcgtgttt gcttcatcca agaaagtctg gcagcaacct ttggagctgg atactcgagc      1020
agttgtattg ttgatgttgg tgcacaaaag acttctatct gctgcgttga ggaaggcatg      1080
tgcgtcgaga ctcccgcat gaacctgaag tttggcggag aagatgttac agaaacattc       1140
atcaagatga tgctgtacga ccacttcaat tatgccaaca tggatctgct gaggagacat      1200
gactaccttc ttgcggaaga gctgaagcaa aagttctgca cgctcgagga tgcacatatc      1260
agcgtacagc tttatgagtt ccatctccgt gcgttcggcc aagacactcg caaataccag      1320
ttcaagacgt atgatgaagt catgctggca cctatgggtt tcttcaggcc aacaatattt      1380
gatcattcag acaagctcgc tggcagacgc aagctcatcg gtcgctcaac tgacacttac      1440
gatgataaac ctaatgatcc catgtcactc gctcaactgc aggtctacaa gtactcgtcc      1500
gataatgttc cctcagctgt agcagaatca agtacaccgg cacctggtgg cgtgcctgca      1560
acacccagca aacccttgaa cctggaccgc taacgcatc ttgccgatgt agcggaaagt       1620
acacctcgtt cctctccagc aggatcgcct gctcctgacg cacggcaac accagtacca       1680
ggagctggag acgcaacacc agccgtagca ggtggcggga tcgaaggtgc acagccaaat      1740
actgaagatg tgctgcctgt gatgcccttg gatcaagcaa tcgtcacatg catcaccgaa      1800
ggcgccaagg gtgatgagaa gaagacgcgt gacttcttcg gtggtatcat ggtgatcgga      1860
ggcggtagca agacttacaa tttcaacgtc tatctcgagc agagacttcg cgcgctacag      1920
ccaaacttcc agaaggaaat cttggttgga cctccgccta gagagctcga tcctcaggtt      1980
ctggtgtgga agggcggtag tgtgtttggc aagatgagag gcactaatga cagctggatc      2040
ggacagttgg agtttgacag actgggtgcc agaatcttga accagaagtg tatgtgggca      2100
tac                                                                    2103
```

<210> SEQ ID NO 8
<211> LENGTH: 1377

```
<212> TYPE: DNA
<213> ORGANISM: Aureobasidium melanogenum strain W5-2

<400> SEQUENCE: 8
atgggtaagg aaaagtccca cattaacgtc gtcgttatcg gccacgtcga ctccggtaag      60
tcgaccacca ccggtcactt gatctacaag tgcggtggta tcgacaagcg taccatcgag     120
aagttcgaga aggaagccgc cgaactcggc aagggttcct tcaagtacgc ctgggtcctc     180
gacaagctga agtctgagcg tgagcgtggt atcactatcg atatcgccct gtggaagttc     240
gagaccccca agtacatggt caccgtcatc gacgcccccg gtcaccgtga tttcatcaag     300
aacatgatca ctggtacctc gcaggctgac tgcgccattc tcatcattgc cgccggtact     360
ggtgagttcg aggctggtat ctccaaggat ggccagaccc gtgagcacgc ccttctcgcc     420
tacaccctcg gtgtcaagca gctcatcgtt gccatcaaca gatggacac caccaagtgg     480
tccgaggccc gttaccagga gatcatcaag gagacctccg gtttcatcaa gaaggtcggc     540
tacaaccca agcacgttcc cttcgtcccc atctccggtt caacggtga caacatgatc     600
gaggtttcca ccaactgccc ctggtacaag ggttgggaga aggagaccaa ggccaaggcc     660
accggcaaga ctctcctcga agccattgac gccatcgacc tcctacccg ccccaccgac     720
aagcccctcc gtcttcccct ccaggatgtc tacaagatcg gtggtattgg cacggtgccc     780
gtcggccgtg tcgagaccgg taccatcaag gtggtatgg tcgtcacctt cgcccccgct     840
ggtgtcacca ctgaggtcaa gtccgtcgag atgcaccacg agcagctcgc cgagggtctt     900
cccggtgaca acgtcggctt caacgtcaag aacgtctccg tcaaggagat ccgtcgtggt     960
aacgttgccg gtgactccaa gaacgacccc ccaagggtt gtgactcctt caacgcccag    1020
gtcatcgtcc tgaaccaccc cggtcaggtc ggtgctggtt acgcacccgt cctcgactgc    1080
cacactgccc acatcgcctg caagttctcc gagcttgttg agaagatcga ccgccgtacc    1140
ggcaagtccg ttgaggccgc ccccaagttc atcaagtctg gtgacgccgc cattgtcaag    1200
atggttccct ccaagcccat gtgtgttgag gccttcactg actaccctcc tctcggtcgt    1260
ttcgccgtcc gtgacatgag acagaccgtc gccgtcggtg tcatcaagtc tgtcgccaag    1320
tccgacaagg gtggtgccgg taaggtcact aaggccgccg tcaaggctgg caagaag       1377

<210> SEQ ID NO 9
<211> LENGTH: 1341
<212> TYPE: DNA
<213> ORGANISM: Aureobasidium melanogenum strain W5-2

<400> SEQUENCE: 9
atgcgtgaga ttgtccacct ccagaccggc caatgcggta accaagttgg tgctgccttc      60
tggcagacca tctctggcga gcacggcctt gacggtgctg tgtctacaa cggtacctca     120
gatctccagc tggagcgcat gaacgtctac ttcaacgagg cctctggtaa caaatatgtt     180
ccccgtgccg tcctcgtcga cttggagcct ggtaccatgg acgccgtccg tgctggtcct     240
ttcggtcagc tcttccgtcc cgacaacttc gtcttcggtc agtccggtgc tggcaacaac     300
tgggccaagg tcactacac tgagggtgcc gagttggtcg accaggtctt ggatgtcgtt     360
cgtcgtgagg ccgagagctg tgactgcctc caaggtttcc agatcactca ctcgctcggt     420
ggtggtaccg gtgccggtat gggaacgctc tcatctcca gatccgtga ggagttcccc     480
gaccgtatga tggccacctt ctccgtcatg ccctccccca ggtctccga caccgttgtc     540
gagccttaca acgctaccct ctccgtccac cagctggtcg agaactctga cgagaccttc     600
```

| | |
|---|---|
| tgtatcgaca accaggctct ctacgacatc tgcatgagca ccctcaagct caacaacccc | 660 |
| tcctacggcg acctgaacta cctcgtctcc gccgtcatgt ccggtgttac cgtctcgctc | 720 |
| cgtttccctg ccagctcaa ctccgacttg cgcaagctcg ccgtcaacat ggtcccttc | 780 |
| ccccgtctcc acttcttcat ggtcggtttt gctcctctca ccagccgtaa cgcccactcg | 840 |
| ttccgcgccg tctcggttcc cgagctcacc cagcaaatct tcgaccccaa gaacatgatg | 900 |
| gccgccaccg atttccgcaa cggccgctac ctgacctgct ctgccatctt ccgtggtaag | 960 |
| gtctccatga aggaggtcga ggaccagatg cgcaacgtcc agaacaagaa ctccgcctac | 1020 |
| ttcgttgagt ggatcccaa caacgtccag accgccctct gctccattcc tcctcgtggt | 1080 |
| cttaagatgt catcgacctt cgtcggtaac tcgacctcga tccaggagct gttcaagcgt | 1140 |
| gtcggtgacc agttctctgc catgttccgt cgcaaggctt tcttgcactg gtacactggt | 1200 |
| gagggtatgg acgagatgga gttcactgag gctgagtcta acatgaacga cttggtcagc | 1260 |
| gagtaccagc agtaccagga ggcttccatc tccgagggtg aggaggagta cgacgaggag | 1320 |
| gctcctatgg aggctgagga g | 1341 |

<210> SEQ ID NO 10
<211> LENGTH: 6093
<212> TYPE: DNA
<213> ORGANISM: Aureobasidium melanogenum strain W5-2

<400> SEQUENCE: 10

| | |
|---|---|
| cggccggcgc cttgcaacat caacgcccgt catatcctcg acctcaccct tgctgctacc | 60 |
| acgccctcac caaccgcatc gccgcgcatc acctccattg cgcgcaatcg ccgtctcgag | 120 |
| tcgcgtcgct ccttcatcgc ctgtcgattt ctctgtttcg ccgctgtccg cctgcgcgcg | 180 |
| cgccgttcga aaggccagtc gctcgacacg cgctcttccg ccagaggcaa ccctcttaca | 240 |
| tccacaatca tccaccttat caccactttc atctgtcctg gagatccacg ctcaacctct | 300 |
| ccgtcgacag cgccctgaag gcggcagccg ctgatacgat tcttacacaa tttctcttag | 360 |
| ctattgctat caacatccgc caccatgaac atccactctt ttccctattc cagcgctccg | 420 |
| ctgaagacca ttcaggagat tcagtttggt ctcttctctc ctgaggagat caagaacatg | 480 |
| agtgtgtgtc acatcgagta cccagagacc atggacgagc aacggatgcg tccgcgagag | 540 |
| aagggcttaa cgaccccaa gctgggctct atcgatcgct cagttgcctg tggtacctgc | 600 |
| ggtgaagaca tgctggagtg tcccggtcac tttggtcata ttgagcttgc tgtgcccgtc | 660 |
| ttccacgtcg gttttgtcac caagatcaag aagattctcg aaaccgtctg ccacaactgt | 720 |
| ggcaaagtct tgcttgatga aagcattcct gccttcgccc aagctgtccg cataagagat | 780 |
| cccaagcgcc gcttcgatgc tgttcacaga ctgtgcaagg ccaagacgac ctgcgatccc | 840 |
| gatgaggctg gtgacgatgg agaagacccg aaagacgcct tgaagaaggg caagcgatca | 900 |
| cacggtggct gcggtaaacct gcaacccaca attcgcaagg acggtcttaa gcttaccggc | 960 |
| acctacacat accccaagga cgccgataca gaacaaaagc ccgtggagaa gaaggtcatc | 1020 |
| accctcaga tggcactgaa cgttttccgc aacatttcga catacgactt ggccagaatg | 1080 |
| ggcctcaacg cagactacgc tcgtcccgaa tggatgatcc tgaccgtgtt gcccgtaccg | 1140 |
| ccaccagctg ttcgtcccag tgtttcggtc gatggaacca accaaggaat gcgttccgag | 1200 |
| gatgatttga ctttcaaact cagtgatatt atccgcgcca atgccaacgt tcgcaagtgt | 1260 |
| gagctcgagg gctctccaca ccacgttatt gcagagtttg aggctttgct gcagttccac | 1320 |
| gtcgctacat acatggacaa cgatattgca ggacagccta aggctctgca aaaatccggt | 1380 |

```
agacctgtca aggctattcg tgcgcgcctg aagtccaagg agggtcgtct tcgtggtaac   1440
cttatgggca agcgtgtcga tttctccgct cgtacagtca tcactggtga cccgaacttg   1500
tctctggatg aagtaggtgt tcctagaagt accgcccgca tccttacctt ccccgagacc   1560
gtcaacgctt tcaacatcga caagctacaa caactcgtcc gcaacggtcc caacgaacac   1620
cctggagcaa agtatgtcat tcgagacact ggcgagcgca tcgatttgcg ccatcacaag   1680
cgcgctggcg agattcaact gcaatatggc tacaaagtcg aaagacatat cgtcgatggt   1740
gatgttatta tcttcaaccg tcaaccttcg ctgcacaagg agtctatgat gggtcacaga   1800
gtccgtgtca tgccctactc tactttccgt ctcaaccttt ccgttacttc gccatacaac   1860
gccgatttcg atggtgatga gatgaacttg cacgttcctc agagtcacga aactcgctca   1920
gaagtcatga acctttgcat ggttcccctc aacatcgtct ctcctcagcg taacggtccc   1980
ttgatgggta tcgtgcaaga cactctttgt ggtatctaca agatgtgccg tcgtgatgtt   2040
ttcctggacc aggaacacgt catgaacatt ctcatgtggg tgcctgattg ggacggtgtc   2100
atcccaccac cttctatcct caaacctcgc cctagatgga ctggtaagca gattatcagc   2160
ttgatcgtcc ccactggttt gaaccttgtt cgtggtgatg ctgagggcat gcatcccctc   2220
aacgacaacg gtttgatggt acatggtggc gagctcatgt acggtctgtt cagcaagaag   2280
tccgtcggtg ccagtggagg tggtatcatc cacatcgtct acaacgaaaa gggctgggaa   2340
gctgctgtca gtttcttcaa cggagctcag cgtgtcgtca actactggct gctccacaac   2400
ggtttcagta tcggtattgg tgacacagtt cctgacgagg cgactgccga ggccatcaca   2460
gacgcagtca atgagcagaa ggcagaagta gctgtcatca ccgaggctgc tactgctaac   2520
gagcttgaag ctctgcctgg tatgaacgtt cgtgagacgt tcgagagcag agtgtccaag   2580
gctttgaaca gtgctcgtga caacgctggt gaccgtacgg aaaagagttt gaaggatttg   2640
aacaacgcca ttcagatggc tcgttcaggt tccaagggtt cggctatcaa catttcgcag   2700
atgaccgctg tcgtcggcca acaatccgtc gagggaaagc gtattccttt cggcttcaag   2760
tacagatcgc ttccccactt caccaaggac gattactctc ccgagtctcg tggtttcgtc   2820
gagaactcct atctccgcgg attgacacct tcagaattct tcttccacgc catggctggt   2880
cgtgagggtc tgatcgatac tgctgtcaag actgccgaaa ctggttacat tcagcgtcgt   2940
ctcgtcaagg ctcttgaaga agtcatggcc aagtatgatg cactgttcg taactccttg   3000
ggcgatatcg tgcaattcgt ctacggtgaa gatggtttgg atgctgtgca tatcgaaggt   3060
caaaagttgg atatcatcaa ctgctccgac agtcaattcg agaagaagtt ccgtattgat   3120
gtcatggacc ccaagatgtc tctttcaccc gacattctcg agcaagcaca cgagattgct   3180
ggagatgttg aggtccagcg tcacctcgac gctgagtatg aagcattgtt ggctgacaga   3240
gctctgctca gagatggccg taccgatgac gaagaaaccc accaacttcc tcttaacatc   3300
acccgtatcg tcgagagtgc taagaccaga ttccgcatca aggatggcgc tcgcagtgat   3360
cttcacccgt ccgacgttat tcccaaggtt cagaacttgc ttgaccagat tgttgttgtt   3420
cgtggtgacg accctctttc ccaagaagca caatacaacg ccactatcct cttcaaggcc   3480
ctgctcagat cacgtctcgc ttttaagcgt ctggtcaagg agtactcttt gaacaagctc   3540
gcgcttgaca acattcttgg tgatattctg aacagattct caagatcgct tgtcagtccc   3600
ggtgaaatgg ttggtgtctt ggccgcacag tctattggag aacccgcaac acagatgacg   3660
ctcaacactt tccatttcgc tggtgtctcg tccaagaacg ttaccctcgg tgtgccccgt   3720
```

```
ctgaaggaaa ttctgaacgt tgctaccaac atcaagacac cttccatgac tgtctaccaa      3780
tctgccgaaa accgccttga tcaggaagct tgcaagcgac ttcgtagtct ggttgagtac      3840
accagtttgc gctccattac tgagaagacc gaaatttggt tcgaccctga cattcaatca      3900
accgttgttg aacaagacag ggatatggtc gagtcttact tcatcatccc cgaagagaat      3960
gcagagagtc ccgagactta ctccaagtgg ttgctgcgta tcgttcttgg tcgtagacag      4020
cttttggaca agggtctttc ggtcgctgat gtcgccgctg ctatcaagaa tgtctaccac      4080
caggagatgt ctattatctt cagtgacgac aacgctgatg agcttgttat tcgtatcaga      4140
ccttcgaacg tgcttatgga gtccaaagaa gacgatgata ccgctcttga ggccgatctg      4200
atcatcggaa gactcgaaac tcatctgttg gacgagacca gacttcgtgg tgtcttgggc      4260
gtcgatcgtg ctttcgtcaa cttcaaggaa cgtctgcgcg tcaaggaaga cggtgctctt      4320
actatgtcca agagcgatcc tctttgcaag gaatggttct tggataccag cggaactgct      4380
ctcaaggaag ttcttactgt tgagggcact gatcctaccc gcacttacac taaccacttc      4440
attgacatct tcagtgtgtt cggtattgag gctactagat ccgcattgat gagagaactc      4500
aagcaagtgc tttcgttcga cggttcttat gtcaaccatc gccatcttgc cctcctggtc      4560
gatattatga ccgctcgcgg taaccttatg gctgtcaccc gtcacggtat caaccgtgct      4620
gacactggtg cactgatgcg ttgttcgttc gaagagacgg tcgagattct gttcgaagct      4680
gcctcctcag gtgaacttga cgactgccgt ggtgtttccg aaaacatcat tcttggtcag      4740
cttgcacctt cgggtactgg tgagtttgat gttcttttgg accagcagat gctcagcact      4800
gttgtctctc gtcaccatgg tatgggtgct ggtactcaag ctggcgccgc tcctcttgac      4860
ggtgctatga ctccctacga tatgggctct cctcttgccg agggcgacta cggtactgcg      4920
gactatggtg cttccttctc tcctatggtc caggcaggtg cgacgagat gggtggtttc      4980 tctgcctacc aaggtggaag cttcagccct tacagtggcg gtcagagccc tggttacgca      5040
cctaccagtc cattcagcat gggtacaagc ccatcatctc ccggatatgc ctcgccatct      5100
tctcctggct attcacccag atcacctggt gcagctcttg gcagcccgg ctacggcatg      5160 ggttcacctg ccagtccggc gtacaaccca acatcgccca cttactcgcc tacatctcct      5220
gcctacggca agggctctcc cacctcacct tcttactctc ctacatctcc cagctattcg      5280
ccaacttcac ccagctactc gcctacgtcg cctagctact ctcctacctc tccttcatac      5340
agccccactt ctcctgctca cagaggatcg ggcatttctc caacctctcc acgatacagc      5400
ccgacatctc cggcttactc gcccacttca cctgcataca gcccgaccag ccctcctac      5460 aaccctggcg gagcctcgca ctcgcctacg tcgcccagct acagcccgac gtcgccagtg      5520
tacagcccaa ccagtccggc acagcagggc tattctccta cctcaccaca gtacactccc      5580
aactctcctg gtcaagcttc gcctaagtat tcacctacta gccccaagta ctcgcccaac      5640
tcgcctggcc aataagcgaa tgaagcgagc agttacccaa ctgggacgta ccctttgctg      5700
ggcccacgtc ttgtcatggg ctagggttaa tatcaaggtc accaacattc gaaacaact       5760 cgtagtctgg gttttggttc acgaagacga tgcacgagcg ataagagcac aagcaggtac      5820
attgcgggag atttttacaag gcgttcttct tttttcttttt ctgctagtct tgttttttgag     5880 agaaggaaag ttctccaagg tttgtttttc aggctcacaa aattgcatat ggagaacgag      5940
```

```
ccaagtgtag tatcagagag gatttttcga ggcaaagata aaccaaagat gagataacac    6000
aaatgcgaac aagcaagtcc aaatttctgc tttcgttgaa agtgactgct ggccgagggc    6060
aaaaagcaag tgtaatattt ttttatgtag tcg                                 6093
```